US012630554B2

(12) United States Patent
Su et al.

(10) Patent No.: US 12,630,554 B2
(45) Date of Patent: May 19, 2026

(54) PYRIMIDINONE COMPOUNDS AND USES THEREOF

(71) Applicant: HUTCHISON MEDIPHARMA LIMITED, Shanghai (CN)

(72) Inventors: Wei-Guo Su, Shanghai (CN); Weihan Zhang, Shanghai (CN); Wei Deng, Shanghai (CN); Haibin Yang, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 589 days.

(21) Appl. No.: 18/042,091

(22) PCT Filed: Aug. 17, 2021

(86) PCT No.: PCT/CN2021/113038

§ 371 (c)(1),
(2) Date: Feb. 17, 2023

(87) PCT Pub. No.: WO2022/037585

PCT Pub. Date: Feb. 24, 2022

(65) Prior Publication Data

US 2024/0002388 A1 Jan. 4, 2024

(30) Foreign Application Priority Data

Aug. 18, 2020 (CN) ........................ 202010840261.X
Aug. 5, 2021 (CN) ........................ 202110894582.2
Aug. 13, 2021 (CN) ........................ 202110928029.6

(51) Int. Cl.

| | |
|---|---|
| *A61K 45/06* | (2006.01) |
| *C07D 239/47* | (2006.01) |
| *C07D 403/12* | (2006.01) |
| *C07D 413/12* | (2006.01) |
| *C07D 471/04* | (2006.01) |
| *C07D 487/04* | (2006.01) |

(52) U.S. Cl.

CPC ............ *C07D 487/04* (2013.01); *A61K 45/06* (2013.01); *C07D 239/47* (2013.01); *C07D 403/12* (2013.01); *C07D 413/12* (2013.01); *C07D 471/04* (2013.01)

(58) Field of Classification Search

CPC .............................. C07D 487/04; A61K 45/06
See application file for complete search history.

(56) References Cited

U.S. PATENT DOCUMENTS

| | | | |
|---|---|---|---|
| 2004/0254158 | A1 | 12/2004 | Qiao et al. |
| 2006/0052358 | A1 | 3/2006 | Ruah et al. |
| 2009/0005359 | A1 | 1/2009 | Cossrow et al. |
| 2009/0318518 | A1 | 12/2009 | Boyd et al. |
| 2012/0270870 | A1 | 10/2012 | Cook et al. |
| 2012/0316197 | A1 | 12/2012 | Kanazawa et al. |
| 2013/0072679 | A1 | 3/2013 | Aebi et al. |
| 2016/0096834 | A1 | 4/2016 | Gaillard et al. |
| 2017/0183332 | A1 | 6/2017 | Jeong |
| 2017/0266199 | A1 | 9/2017 | Berger et al. |
| 2018/0194762 | A1 | 7/2018 | Atallah et al. |
| 2019/0071431 | A1 | 3/2019 | Mainolfi |
| 2019/0144433 | A1 | 5/2019 | Han et al. |
| 2019/0241566 | A1 | 8/2019 | Hirayama et al. |
| 2020/0216443 | A1 | 7/2020 | Zhou et al. |
| 2020/0277252 | A1 | 9/2020 | McGowan et al. |
| 2021/0079013 | A1 | 3/2021 | Zhou et al. |
| 2023/0026425 | A1 | 1/2023 | Qiang et al. |

FOREIGN PATENT DOCUMENTS

| | | | |
|---|---|---|---|
| CN | 112047877 | 12/2020 | |
| WO | WO 2003/010141 A2 | 2/2003 | |
| WO | WO 2006/136829 A2 | 12/2006 | |
| WO | WO 2008/017164 | 2/2008 | |
| WO | WO 2012/076063 | 6/2012 | |
| WO | WO 2012/082817 | 6/2012 | |
| WO | WO 2019/079614 A1 | 4/2019 | |
| WO | WO 2019/099294 | 5/2019 | |
| WO | WO 2019/152982 A1 | 8/2019 | |
| WO | 2019/204537 A1 | 10/2019 | |
| WO | 2019/213445 A1 | 11/2019 | |
| WO | 2019/224773 A1 | 11/2019 | |
| WO | WO 2020/228823 | 11/2020 | |
| WO | WO-2020228823 A1 * | 11/2020 | ........... C07D 213/71 |

* cited by examiner

*Primary Examiner* — Sarah Pihonak
*Assistant Examiner* — Mikhail O'Donnel Robinson
(74) *Attorney, Agent, or Firm* — Hoxie & Associates LLC

(57) ABSTRACT

The present invention relates to pyrimidinone compounds and uses thereof. In particular, the present invention relates to pyrimidinone compounds of formula (I), pharmaceutical compositions comprising same, methods for preparing same, and uses thereof, wherein the variables are as defined in the description.

(I)

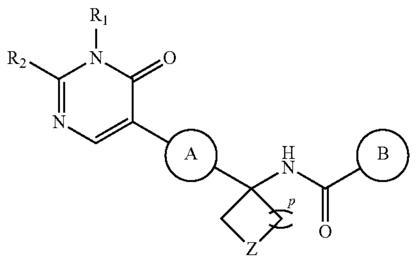

19 Claims, No Drawings

Specification includes a Sequence Listing.

SEQUENCE LISTING

```
<160> NUMBER OF SEQ ID NOS: 1

<210> SEQ ID NO 1
<211> LENGTH: 618
<212> TYPE: PRT
<213> ORGANISM: Artificial
<220> FEATURE:
<223> OTHER INFORMATION: Construct

<400> SEQUENCE: 1

Met His His His His His His His His His His Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Ser Asp Leu Val Pro Arg Gly Ser Glu Asn Leu Tyr
225                 230                 235                 240

Phe Gln Gly Met Gln Pro Asp Met Ser Leu Asn Val Ile Lys Met Lys
                245                 250                 255

Ser Ser Asp Phe Leu Glu Ser Ala Glu Leu Asp Ser Gly Gly Phe Gly
            260                 265                 270

Lys Val Ser Leu Cys Phe His Arg Thr Gln Gly Leu Met Ile Met Lys
        275                 280                 285

Thr Val Tyr Lys Gly Pro Asn Cys Ile Glu His Asn Glu Ala Leu Leu
    290                 295                 300
```

```
Glu Glu Ala Lys Met Met Asn Arg Leu Arg His Ser Arg Val Val Lys
305                 310                 315                 320

Leu Leu Gly Val Ile Ile Glu Glu Gly Lys Tyr Ser Leu Val Met Glu
                325                 330                 335

Tyr Met Glu Lys Gly Asn Leu Met His Val Leu Lys Ala Glu Met Ser
            340                 345                 350

Thr Pro Leu Ser Val Lys Gly Arg Ile Ile Leu Glu Ile Ile Glu Gly
        355                 360                 365

Met Cys Tyr Leu His Gly Lys Gly Val Ile His Lys Asp Leu Lys Pro
    370                 375                 380

Glu Asn Ile Leu Val Asp Asn Asp Phe His Ile Lys Ile Ala Asp Leu
385                 390                 395                 400

Gly Leu Ala Ser Phe Lys Met Trp Ser Lys Leu Asn Asn Glu Glu His
                405                 410                 415

Asn Glu Leu Arg Glu Val Asp Gly Thr Ala Lys Lys Asn Gly Gly Thr
            420                 425                 430

Leu Tyr Tyr Met Ala Pro Glu His Leu Asn Asp Val Asn Ala Lys Pro
        435                 440                 445

Thr Glu Lys Ser Asp Val Tyr Ser Phe Ala Val Val Leu Trp Ala Ile
    450                 455                 460

Phe Ala Asn Lys Glu Pro Tyr Glu Asn Ala Ile Cys Glu Gln Gln Leu
465                 470                 475                 480

Ile Met Cys Ile Lys Ser Gly Asn Arg Pro Asp Val Asp Asp Ile Thr
                485                 490                 495

Glu Tyr Cys Pro Arg Glu Ile Ile Ser Leu Met Lys Leu Cys Trp Glu
            500                 505                 510

Ala Asn Pro Glu Ala Arg Pro Thr Phe Pro Gly Ile Glu Glu Lys Phe
        515                 520                 525

Arg Pro Phe Tyr Leu Ser Gln Leu Glu Glu Ser Val Glu Glu Asp Val
    530                 535                 540

Lys Ser Leu Lys Lys Glu Tyr Ser Asn Glu Asn Ala Val Val Lys Arg
545                 550                 555                 560

Met Gln Ser Leu Gln Leu Asp Cys Val Ala Val Pro Ser Ser Arg Ser
                565                 570                 575

Asn Ser Ala Thr Glu Gln Pro Gly Ser Leu His Ser Ser Gln Gly Leu
            580                 585                 590

Gly Met Gly Pro Val Glu Glu Ser Trp Phe Ala Pro Ser Leu Glu His
        595                 600                 605

Pro Gln Glu Glu Asn Glu Pro Ser Leu Gln
    610                 615
```

PYRIMIDINONE COMPOUNDS AND USES THEREOF

CROSS-REFERENCE TO RELATED APPLICATIONS

This application is a United States Application under 35 U.S.C. § 371 claiming priority to, and the benefit of, International Application No. PCT/CN2021/113038, filed on Aug. 17, 2021, which claims priority to, and the benefit of, Chinese Application No. 202010840261.X, filed on Aug. 18, 2020, Chinese Application No. 202110894582.2, filed on Aug. 5, 2021, and Chinese Application No. 202110928029.6, filed on Aug. 13, 2021, the contents of each of which are hereby incorporated by reference in their entireties.

TECHNICAL FIELD

The present invention relates to pyrimidinone compounds, pharmaceutical compositions comprising same, methods for preparing same, and uses thereof.

BACKGROUND ART

RIPK1 (receptor-interacting protein 1 kinase), a serine/threonine protein kinase, is an important cell signal transduction molecule. RIPK1, the first member of the RIP kinase family, was initially identified by Stanger et al. in 1995 through yeast two-hybrid experiments. The C terminal domain of RIPK1 is a death domain (DD), which can interact with Fas, a member of the death receptor family so that it was designated as receptor-interacting protein (Stanger B Z. et al., Cell. 1995, 81: 513-523). The N-terminal serine/threonine-specific kinase domain, meditates autophosphorylation of RIPK1 at serine/threonine residue sites; while the C-terminal death domain, interacts with other death domain-containing proteins; the intermediate domain with RIP homotypic interaction motif (RHIM), is required for the interaction of RIPK1 and RIPK3 (Grootjans S, et al., Cell Death Differ. 2017, 24(7): 1184-1195).

Necroptosis as a new form of programmed cell death, regulated and controlled by intracellular signal factors are critical process in the organismal development and viability. Dysfunction of this process can result in a pathological mechanism that leads to a disease state. Necrosis can be triggered by a variety of triggers, including tumor necrosis factor (TNFα), Fas, TNF-related apoptosis-inducing ligand (TRAIL), interferon (IFN), lipopolysaccharide (LPS), double-stranded RNA and DNA damage, endoplasmic reticulum stress, viral infection, and anti-cancer drugs. RIPK1 as the key molecule regulates apoptosis, necroptosis and inflammatory signaling pathways, and participates in many important biological processes such as embryonic development, hematopoietic system development, and maintenance of immune homeostasis (Ofengeim D, et al., Nat Rev Mol Cell Biol. 2013, 14: 727-736). As in the necroptosis caused by TNFα, once TNFα binds to TNFR1, cytoplasmic domain of trimerized TNFR1 recruits multiple molecules including RIPK1, to activate the NF-κB signaling pathway, leading to the production of multiple cytokines and promoting cell survival (Kelliher M A, et al., Immunity. 1998, 8: 297-303). In the context of various cell types and microenvironments, RIPK1 recruits Fas-associated protein with death domain (FADD) and caspase 8 precursor to trigger apoptosis (Feoktistova M, et al., Mol Cell. 2011, 43: 449-463). When the apoptosis pathway is inhibited, RIPK1 interacts with RIPK3 via the RHIM domain to facilitate the autophosphorylation of RIPK3. The autophosphorylated RIPK3, in turn, phosphorylates MLKL, thereby prompting MLKL to form trimers and to be translocated to the plasma membrane, causing cell membrane to swell and burst and the leakage of contents, leading to the initiation of necroptosis (Cai Z, et al., Nat Cell Biol. 2014, 16: 55-65). Therefore, regulating and controlling the kinase activity of RIPK1 can affect the inflammatory response triggered by apoptosis, programmed cell necrosis, and intracellular substances released after cell disruption.

Given the important roles RIPK1 plays in regulating and controlling cell death and in inflammation, RIPK1 has elicited significant interest in studying the potential therapeutic benefit of selective RIPK1 inhibitors in a variety of diseases. Current studies have shown that RIPK1 inhibitors have potential therapeutic effects on a variety of diseases, such as central nervous system degenerative diseases, peripheral inflammation and autoimmune diseases. These diseases include multiple sclerosis (Ofengeim D, et al., Cell Rep. 2015, 10: 1836-1849), Huntington's disease (Zhu S, et al., Cell Death Dis. 2011, 2: e115-24), Alzheimer's disease (Caccamo A, et al., Nat Neurosci. 2017, 20: 1236-1246), Parkinson's disease (Lin Q S, et al., Lab Invest. 2020, 100(3): 503-511), amyotrophic lateral sclerosis (Re D B, et al. Neuron. 2014, 81(5): 1001-1008), retinitis pigmentosa (Murakami Y, et al., Proc Natl Acad Sci USA. 2012, 109(36): 14598-603), retinal degeneration (Jang K H, et al., Exp Eye Res. 2019, 180: 8-17), age-related macular degeneration (AMD) (Murakami Y, et al., Cell Death Differ. 2013, 21: 270-7), inflammatory bowel disease including Crohn's disease and ulcerative colitis (Liu Z Y, et al., Am J Cancer Res. 2015, 5(10): 3174-85), psoriasis (Duan X, et al., Cell Death Dis. 2020, 11(2): 134), rheumatoid arthritis (Jhun J, et al., J Transl Med. 2019, 17(1): 84), ischemia reperfusion injury of parenchymatous organs such as heart (Oerlemans M I F J, et al., Basic Res Cardiol. 2012, 107: 270), brain (Degterev A, et al., Nat. Chem. Biol. 2005, 1: 112-119) and kidney (Linkermann A, et al., Kidney Int. 2012, 81: 751-61), renal transplant rejection (Lau A, et al., Am J Transplant. 2013, 13: 2805-18), asthma (Zhang H, et al., J Cell Physiol. 2019, 234(9): 15080-15088), chronic obstructive pulmonary disease (Mizumura K, et al., Respir Investig. 2016, 54(6): 407-412), non-alcoholic fatty liver disease (Majdi A, et al., J Hepatol. 2020, 72(4): 627-635), alcohol fatty liver disease (Wang S, et al., Oncotarget. 2016, 7: 17681-17698), arterosclerosis (Lin J, et al., Cell Rep. 2013, 3: 200-10; Karunakaran D, et al., FASEB J. 2018, 32(supplement): 38.1-38.1), sepsis/systemic inflammatory response syndrome (Duprez L, et al., Immunity. 2011, 908-18), chemotherapy drugs induced organ injury (Xu Y, et al., J Am Soc Nephrol. 2015, 26(11): 2647-58), Gaucher's Disease (Vitter E B, et al., Nat Med. 2014, 204-208), and malignancies (Wang W, et al., Cancer Cell. 2018, 34(5): 757-774; Strilic B, et al., Nature. 2016, 536(7615): 215-8). There are needs for new RIPK1 inhibitors for use in the treatment of these diseases, especially inflammatory diseases or autoimmune diseases. The present invention addresses such needs.

SUMMARY OF THE INVENTION

Provided is a compound of formula (I):

(I)

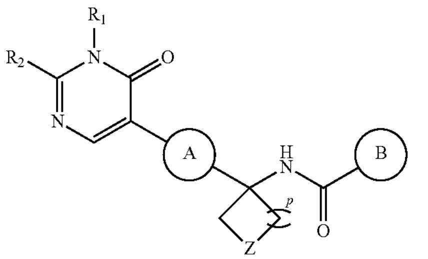

or a pharmaceutically acceptable salt thereof, or a solvate, a racemic mixture, an enantiomer, a diastereomer or a tautomer thereof, wherein $R_1$ is hydrogen, $C_{1-6}$ alkyl, $C_{1-6}$ haloalkyl, cyano-substituted $C_{1-6}$ alkyl, —$(C_{1-6}$ alkylene$)_n$-$C_{3-6}$ cycloalkyl, —$(C_{1-6}$ alkylene$)_n$-phenyl, —$(C_{1-6}$ alkylene$)_n$-4-6 membered heterocyclyl or —$(C_{1-6}$ alkylene$)_n$-5-6 membered heteroaryl; wherein the $C_{3-6}$ cycloalkyl, phenyl, 4-6 membered heterocyclyl and 5-6 membered heteroaryl are each optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl) and —N$(C_{1-6}$ alkyl$)_2$;

$R_2$ is hydrogen, halogen, —CN, —$NH_2$, $C_{1-6}$ alkyl, $C_{1-6}$ haloalkyl, —O($C_{1-6}$ alkyl), —O($C_{1-6}$ haloalkyl), —NH ($C_{1-6}$ alkyl) or —N$(C_{1-6}$ alkyl$)_2$;

Z is O, $NR_3$ or $CR_4R_5$;

$R_3$ is hydrogen or $C_{1-6}$ alkyl;

$R_4$ and $R_5$ are each independently chosen from: hydrogen, halogen, —CN, —OH, $C_{1-6}$ alkyl, $C_{1-6}$ haloalkyl, —O($C_{1-6}$ alkyl), —O($C_{1-6}$ haloalkyl) and $C_{3-6}$ cycloalkyl;

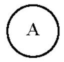

is phenyl or 5-6 membered heteroaryl, each of which is optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl) and —N$(C_{1-6}$ alkyl$)_2$;

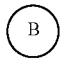

is 5-12 membered heteroaryl, which is optionally substituted with one or more groups independently chosen from: halogen, —CN, —OH, oxo, —$NH_2$, $C_{1-6}$ alkyl, $C_{1-6}$ haloalkyl, $C_{2-6}$ alkenyl, $C_{2-6}$ alkynyl, —O($C_{1-6}$ alkyl), —O($C_{1-6}$ haloalkyl), —NH($C_{1-6}$ alkyl), —N$(C_{1-6}$ alkyl$)_2$, —$(C_{1-6}$ alkylene$)_n$-$C_{3-6}$ cycloalkyl, —$(C_{1-6}$ alkylene$)_n$-phenyl, —$(C_{1-6}$ alkylene$)_n$-4-6 membered heterocyclyl and —$(C_{1-6}$ alkylene$)_n$-5-6 membered heteroaryl; wherein the phenyl, $C_{3-6}$ cycloalkyl, 4-6 membered heterocyclyl and 5-6 membered heteroaryl are each optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl), —N$(C_{1-6}$ alkyl$)_2$ and $C_{3-6}$ cycloalkyl;

n is 0 or 1;

and p is 0 or 1.

Also provided is a pharmaceutical composition, comprising the compound of formula (I) of the present invention (e.g., a compound of any of the examples as described herein) or a pharmaceutically acceptable salt thereof, and optionally comprising a pharmaceutically acceptable carrier.

Also provided is a method of in vivo or in vitro inhibiting the activity of RIPK1, comprising contacting RIPK1 with an effective amount of the compound of formula (I) of the present invention (e.g., a compound of any of the examples as described herein) or a pharmaceutically acceptable salt thereof.

Also provided is a method of treating a disease partially or completely mediated by RIPK1 in a subject, comprising administering to the subject in need thereof an effective amount of the compound of formula (I) of the present invention (e.g., the compound of formula (I-1) or a compound of any of the examples as described herein) or a pharmaceutically acceptable salt thereof.

Also provided is a method of treating an autoimmune disease, an inflammatory disease, a neurodegenerative disease, or cancer in a subject, comprising administering to the subject in need thereof an effective amount of the compound of formula (I) of the present invention (e.g., the compound of formula (I-1) or a compound of any of the examples as described herein) or a pharmaceutically acceptable salt thereof.

Also provided is the use of the compound of formula (I) of the present invention (e.g., the compound of formula (I-1) or a compound of any of the examples as described herein) or a pharmaceutically acceptable salt thereof in the treatment of a disease partially or completely mediated by RIPK1 in a subject.

Also provided is the use of the compound of formula (I) of the present invention (e.g., the compound of formula (I-1) or a compound of any of the examples as described herein) or a pharmaceutically acceptable salt thereof in the treatment of an autoimmune disease, an inflammatory disease, a neurodegenerative disease or cancer in a subject.

Also provided is the use of the compound of formula (I) of the present invention (e.g., the compound of formula (I-1) or a compound of any of the examples as described herein) or a pharmaceutically acceptable salt thereof in the manufacture of a medicament for treating a disease partially or completely mediated by RIPK1 in a subject.

Also provided is the use of the compound of formula (I) of the present invention (e.g., the compound of formula (I-1) or a compound of any of the examples as described herein) or a pharmaceutically acceptable salt thereof in the manufacture of a medicament for treating an autoimmune disease, an inflammatory disease, a neurodegenerative disease or cancer in a subject.

DETAILED DESCRIPTION OF THE INVENTION

Definitions

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —O($C_{1-6}$ alkyl) refers to the attachment of $C_{1-6}$ alkyl to the rest of the molecule through an oxygen atom.

The term "alkyl" as used herein refers to a straight or branched saturated hydrocarbon radical containing 1-18 carbon atoms, preferably 1-10 carbon atoms, particularly preferably 1-6 carbon atoms, further preferably 1-4 carbon atoms. For example, "$C_{1-6}$ alkyl" refers to an alkyl containing 1-6 carbon atoms. Examples of alkyl include, but are not limited to, methyl, ethyl, n-propyl, i-propyl, n-butyl, i-butyl, s-butyl, and t-butyl.

The term "alkylene" as used herein refers to a straight or branched saturated divalent hydrocarbon radical containing 1-18 carbon atoms, preferably 1-10 carbon atoms, particularly preferably 1-6 carbon atoms, further preferably 1-4 carbon atoms. For example, "$C_{1-6}$ alkylene" refers to a straight or branched alkylene containing 1-6 carbon atoms, for example, straight alkylene-$(CH_2)_n$—, wherein n is an integer from 1 to 6, such as —$CH_2$—, —$CH_2$—$CH_2$—, —$CH_2$—$CH_2$—$CH_2$— etc., or branched alkylene, such as —$CH_2$—$CH(CH_3)$—$CH_2$—, —$CH(CH_3)$—$CH_2$—, —CH ($CH_3$)— and the like.

The term "alkenyl" as used herein refers to a straight or branched unsaturated hydrocarbon radical having one or more, for example 1, 2, or 3 carbon-carbon double bonds (C═C) and 2-10 carbon atoms, preferably 2-6 carbon atoms, more preferably 2-4 carbon atoms. For example, "$C_{2-6}$ alkenyl" refers to an alkenyl radical containing 1, 2 or 3, preferably 1 or 2 carbon-carbon double bonds, and 2-6 carbon atoms. Examples of alkenyl include, but are not limited to, vinyl, propenyl, allyl and 2-butenyl. The point of attachment for the alkenyl can be on or not on the double bonds.

The term "alkynyl" as used herein refers to a straight or branched unsaturated hydrocarbon radical having one or more, for example 1, 2, or 3, carbon-carbon triple bonds (C≡C) and 2-10 carbon atoms, preferably 2-6 carbon atoms, more preferably 2-4 carbon atoms. For example, "$C_{2-6}$ alkynyl" refers to an alkynyl radical containing 1, 2 or 3, preferably 1 or 2 carbon-carbon triple bonds, and 2-6 carbon atoms. Examples of alkynyl include, but are not limited to, ethynyl, 2-propynyl and 2-butynyl. The point of attachment for the alkynyl can be on or not on the triple bonds.

The term "halogen" or "halo" as used herein refers to fluoro, chloro, bromo, and iodo, preferably fluoro, chloro and bromo, more preferably fluoro and chloro.

The term "haloalkyl" as used herein refers to an alkyl radical, as defined herein, in which one or more, for example 1, 2, 3, 4, 5 or 6, hydrogen atoms are replaced with halogen atoms, and when more than one hydrogen atoms are replaced with halogen atoms, the halogen atoms may be the same or different from each other. $C_{1-6}$ haloalkyl refers to an alkyl radical having 1-6 carbon atoms, in which one or more hydrogen atoms, for example 1, 2, 3, 4, 5 or 6 hydrogen atoms are replaced with halogen atoms. Examples of haloalkyl include, but are not limited to, —$CF_3$, —$CHF_2$, —$CH_2CF_3$, —$CH(CH_3)CF_3$, —$CH(CF_3)$ 2 and the like.

The term "cyano-substituted alkyl" as used herein refers to an alkyl radical, as defined herein, in which one or more hydrogen atoms, for example 1, 2 or 3 hydrogen atoms are replaced with cyano. For example, "cyano-substituted $C_{1-6}$ alkyl" refers to a straight or branched saturated hydrocarbon radical having 1-6 carbon atoms, in which one or more hydrogen atoms, for example 1, 2 or 3 hydrogen atoms are replaced with cyano. Examples of cyano-substituted alkyl include, but are not limited to, cyanomethyl, 1-cyanoethyl, 1-cyanopropyl and the like.

The term "cycloalkyl" as used herein refers to a saturated or partially unsaturated cyclic hydrocarbon radical having 3-12, such as 3-8 or 3-6 ring carbon atoms; which may have one or more rings, such as 1, 2 or 3 rings, preferably 1 or 2 rings, most preferably 1 ring (i.e. monocyclic). The cycloalkyl includes a fused or bridged ring, or a spirocyclic ring. The rings of the cycloalkyl may be saturated or have one or more, for example, one or two double bonds (i.e. partially unsaturated), but not fully conjugated, and not an aryl as defined herein. "$C_{3-12}$ cycloalkyl" refers to monocyclic or bicyclic cycloalkyl having 3-12 ring carbon atoms, more preferably saturated monocyclic or bicyclic cycloalkyl having 3-12 ring carbon atoms. "$C_{3-6}$ cycloalkyl" refers to monocyclic cycloalkyl having 3-6 ring carbon atoms, more preferably saturated monocyclic cycloalkyl having 3-6 ring carbon atoms. Examples of cycloalkyl include, but are not limited to, cyclopropyl, cyclobutyl, cyclopentyl, cyclohexyl, cycloheptyl, cyclooctyl, bicyclo[4.1.0]heptanyl, bicyclo [3.1.1]heptanyl, spiro[3.3]heptanyl, spiro[2.2]pentanyl, cyclopropenyl, cyclobutenyl, cyclopentenyl, cyclopentadienyl, cyclohexenyl, cycloheptenyl, cyclooctenyl and bicyclo [3.1.1]hept-2-ene.

The term "heterocyclyl" or "heterocycle" as used herein refers to: saturated or partially unsaturated cyclic radicals having 3-12 ring atoms, such as 3-8 ring atoms, 4-7 ring atoms or 4-6 ring atoms, and containing one or more, for example 1, 2 or 3, preferably 1 or 2 heteroatoms independently chosen from N, O and S in the rings, with the remaining ring atoms being carbon; it may have one or more rings, for example 1, 2 or 3, preferably 1 or 2 rings. Preferably, "3-12 membered heterocyclyl" refers to monocyclic or bicyclic heterocycloalkyl having 3-12 ring atoms, which is saturated or partially unsaturated, preferably saturated, has 1, 2 or 3, preferably 1 or 2 ring heteroatoms chosen from N, O and S, with the remaining ring atoms being carbon atoms; "4-6 membered heterocyclyl" refers to monocyclic heterocyclyl having 4-6 ring atoms, which is saturated or partially unsaturated, preferably saturated, and has 1, 2 or 3, preferably 1 or 2 ring heteroatoms chosen from N, O and S, with the remaining ring atoms being carbon atoms. N and S in heterocyclyl may be optionally oxidized. The point of attachment of heterocyclyl can be on the N heteroatom or carbon. The heterocyclyl includes a fused or bridged ring, or a spirocyclic ring. The rings of heterocyclyl may be saturated or have one or more, for example, one or two double bonds (i.e. partially unsaturated), but not fully conjugated, and not a heteroaryl as defined herein. Examples of heterocyclyl include, but are not limited to: oxiranyl, aziridinyl, oxetanyl, azetidinyl, pyrrolidyl, tetrahydrofuranyl, tetrahydropyranyl, dioxolanyl, dioxanyl, morpholinyl, thiomorpholinyl, piperidyl, piperazinyl, pyrazolidinyl, and oxaspiro[3.3]heptanyl.

The term "aryl" or "aromatic ring" as used herein refers to carbocyclic hydrocarbon radical of 6 to 14 carbon atoms consisting of one ring or more fused rings, wherein at least one ring is an aromatic ring. Examples of aryl include, but are not limited to: phenyl, naphthyl, 1,2,3,4-tetrahydronaphthyl, indenyl, indanyl, azulenyl, preferably phenyl and naphthyl, most preferably phenyl.

The term "heteroaryl" or "heteroaromatic ring" as used herein refers to aromatic hydrocarbon radical having 5-12 ring atoms (e.g., 5-10 ring atoms, 5-9 ring atoms, 5-6 ring atoms or 6 ring atoms) (i.e., 5-12 membered heteroaryl, 5-10 membered heteroaryl, 5-9 membered heteroaryl, 5-6 membered heteroaryl or 6 membered heteroaryl), and containing one or more (e.g., 1, 2, 3 or 4, preferably 1, 2 or 3) ring heteroatoms independently chosen from N, O and S in the rings, with the remaining ring atoms being carbon atoms; which may have one or more rings, such as 1, 2, or 3 rings, preferably 1 or 2 rings. Preferably, the heteroaryl is:

- monocyclic aromatic hydrocarbyl having 5, 6 or 7 ring atoms (namely, 5-7 membered monocyclic heteroaryl) (preferably monocyclic aromatic hydrocarbyl having 5 or 6 ring atoms (namely, 5-6 membered monocyclic heteroaryl)), and containing one or more, for example 1, 2, 3 or 4, preferably 1, 2 or 3 ring heteroatoms independently chosen from N, O and S (preferably N and O) in the ring, with the remaining ring atoms being carbon atoms; or
- bicyclic aromatic hydrocarbyl having 8-12 ring atoms (namely, 8-12 membered bicyclic heteroaryl) (preferably bicyclic aromatic hydrocarbyl having 8, 9, 10 ring atoms (namely, 8-10 membered bicyclic heteroaryl), more preferably bicyclic aromatic hydrocarbyl having 8 or 9 ring atoms (namely, 8-9 membered bicyclic heteroaryl)), and containing one or more, for example 1, 2, 3 or 4, preferably 2, 3 or 4 ring heteroatoms independently chosen from N, O and S (preferably N) in the ring, with the remaining ring atoms being carbon atoms, wherein at least one ring is an aromatic ring. For example, bicyclic heteroaryl includes a 5-6 membered heteroaryl ring fused with a 5-6 membered cycloalkyl ring; bicyclic heteroaryl also includes a 5-6 membered heteroaryl ring fused with a 5-6 membered heterocyclyl ring.

When the total number of S and O atoms in the heteroaryl group exceeds 1, said S and O heteroatoms are not adjacent to one another.

Examples of monocyclic heteroaryl include, but are not limited to, pyridyl, N-oxide pyridyl, pyrazinyl, pyrimidyl, triazinyl (e.g., 1,3,5-triazinyl), pyrazolyl, imidazolyl, oxazolyl, isoxazolyl, oxadiazolyl (e.g., 1,2,4-oxadiazolyl, 1,2,5-oxadiazolyl and 1,3,4-oxadiazolyl), thiazolyl, isothiazolyl, thiadiazolyl, tetrazolyl, triazolyl (e.g., 1,2,3-triazolyl and 1,2,4-triazolyl), thienyl, furanyl, pyranyl, pyrrolyl, and pyridazinyl. Examples of bicyclic heteroaryl include, but are not limited to, benzodioxolyl, benzoxazolyl, benzoisoxazolyl, benzothienyl, benzothiazolyl, benzoisothiazolyl, imidazopyridyl (e.g., imidazo[1,2-a]pyridyl), imidazopyridazinyl (e.g., imidazo[1,2-b]pyridazinyl), pyrrolopyridyl (e.g., 1H-pyrrolo[2,3-b]pyridyl), pyrrolopyrimidyl (e.g., pyrrolo[3,4-d]pyrimidyl), pyrrolotriazolyl (e.g., pyrrolo[1,2-b][1,2,4]triazolyl), dihydropyrrolotriazolyl (e.g., 6,7-dihydro-5H-pyrrolo[1,2-b][1,2,4]triazolyl), pyrazolopyridyl (e.g., 1H-pyrazolo[3,4-b]pyridyl and pyrazolo[4,3-c]pyridyl), pyrazolopyrimidyl (e.g., pyrazolo[3,4-d]pyrimidyl and pyrazolo[1,5-a]pyrimidyl), triazolopyridyl (e.g., [1,2,4]triazolo[4,3-a]pyridyl and [1,2,4]triazolo[1,5-a]pyridyl), tetrazolopyridyl (e.g., tetrazolo[1,5-a]pyridyl), benzofuranyl, benzoimidazolinyl, indolyl, indazolyl, purinyl, quinolinyl, isoquinolinyl, and quinazolinyl.

The term "hydroxyl" as used herein refers to —OH group.

The term "oxo" as used herein refers to =O group.

The term "cyano" as used herein refers to —CN group.

When a structural formula herein contains an asterisk "*", it means that the chiral center at the "*" mark in the compound is a single configuration of (R) configuration or (S) configuration; wherein the content of the single-configuration compound marked with "*" is at least 90% (e.g., 90%, 91%, 92%, 93%, 94%, 95%, 96%, 97%, 98%, 99%, 99.5%, 99.9%, 100%, or any value between these listed values).

When a structural formula herein contains "(RS)", it means that the chiral center at the "(RS)" mark in the compound contains two configurations (R) and (S), that is, the compound is a mixture of the two configurations.

The term "optional" or "optionally" as used herein means that the subsequently described event or circumstance may or may not occur, and the description includes instances wherein the event or circumstance occur and instances in which it does not occur. For example, "optionally substituted alkyl" includes "unsubstituted alkyl" and "substituted alkyl" defined herein. It will be understood by the POSITA, with respect to any group containing one or more substituents, that such groups are not intended to introduce any substitution or substitution patterns that are sterically impractical, chemically incorrect, synthetically non-feasible and/or inherently unstable.

The term "substituted" or "substituted with . . . ", as used herein, means that one or more hydrogen atoms on the designated atom or group are replaced with one or more substituents chosen from the indicated group of substituents, provided that the designated atom's normal valence is not exceeded. When a substituent is oxo (i.e., =O), then two hydrogens on a single atom are replaced by the oxo. Combinations of substituents and/or variables are permitted only when they result in chemically correct and stable compounds. A chemically correct and stable compound is meant to imply a compound that is sufficiently robust to survive sufficient isolation from a reaction mixture, and then can be formulated into a formulation having at least practical utility.

Unless otherwise specified, substituents are named into the core structure. For example, it is to be understood that when (cycloalkyl)alkyl is listed as a possible substituent, the point of attachment of this substituent to the core structure is in the alkyl portion.

The term "substituted with one or more groups" as used herein means that one or more hydrogens on the designated atom or group are independently replaced with one or more substituents chosen from indicated group. In some embodiments, "substituted with one or more groups" means the designated atom or group is replaced with 1, 2, 3, 4, 5 or 6, preferably 1, 2, 3 or 4 substituents independently chosen from designated group.

It will be understood by the POSITA that some of the compounds of formula (I) may contain one or more chiral centers and therefore exist in two or more stereoisomeric forms. The racemates of these isomers, the individual isomers and mixtures enriched in one enantiomer, as well as diastereomers when there are two chiral centers, and mixtures enriched with specific diastereomers are within the scope of the present invention. It will be further understood by the POSITA that the present invention includes all the individual stereoisomers (e g enantiomers), racemic mixtures or partially resolved mixtures of the compounds of formula (I) and, where appropriate, the individual tautomeric forms thereof.

The term "stereoisomers" as used herein refers to compounds that have the same chemical constitution but differ in the arrangement of atoms or groups in space. Stereoisomers include enantiomers, diastereomers and the like.

The terms "enantiomers" and "enantiomeric forms" as used herein can be used interchangeably and refer to two stereoisomers of a compound that are non-superimposable mirror images of each other.

The terms "diastereomers" and "diastereomeric forms" as used herein can be used interchangeably and refer to stereoisomers that have two or more chiral centers and whose molecules are not mirror images of each other. Diastereomers have different physical properties, such as melting points, boiling points, spectral properties, or biological activities. A mixture of diastereomers can be separated by high-resolution analytical methods such as electrophoresis and chromatography such as HPLC.

Stereochemical definitions and conventions can follow: S. P. Parker edit, McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, that is, they have the ability to rotate the plane of plane-polarized light. When describing optically active compounds, the prefixes D and L or R and S are used to indicate the absolute configuration of the molecule with respect to its chiral center. The prefixes d and l or (+) and (−) are used to denote the symbols for the rotation of plane-polarized light of the compound, where (−) or 1 indicates that the compound is levorotatory. The compound prefixed with (+) or d is dextrorotatory. For a given chemical structure, these stereoisomers are the same except that they are mirror images of each other. Specific stereoisomers can also be referred to as enantiomers, and a mixture of such isomers are usually called an enantiomeric mixture. A mixture of enantiomers at 50:50 is called a racemic mixture or racemate, which can occur in situations where there is no stereoselectivity or stereospecificity in a chemical reaction or method. The terms "racemic mixture" and "racemate" refer to an equimolar mixture of two enantiomers that are not optically active.

In some embodiments, the present invention provides compounds of various stereoisomeric purities, that is, enantiomeric or diastereomeric purity expressed in different "ee" or "de" values. In some embodiments, the compound of formula (I) described herein has an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9% ee, or any value between these listed values). In some embodiments, the compound of formula (I) described herein has an enantiomeric purity of greater than 99.9% ee. In some embodiments, the compound of formula (I) described herein has a diastereomeric purity of at least 60% de (e.g., 60%, 65%, 70%, 75%, 80%, 85%, 90%, 91%, 92%, 93%, 94%, 95%, 96%, 97%, 98%, 99%, 99.5%, 99.9% de, or any value between these listed values). In some embodiments, the compound of formula (I) described herein has a diastereomeric purity of greater than 99.9% de.

The term "enantiomeric excess" or "ee" refers to the amount of one enantiomer relative to the other. For a mixture of R and S enantiomers, the percentage of enantiomeric excess is defined as $|R-S|*100$, where R and S are the mole or weight fractions of the respective enantiomers in the mixture, $R+S=1$. If the optical rotation of a chiral substance is known, the percentage of enantiomeric excess is defined as ([a]obs/[a]max)*100, wherein [a]obs is the optical rotation of the enantiomeric mixture, and [a]max is the optical rotation of the pure enantiomer.

The term "diastereomeric excess" or "de" refers to the amount of one diastereomer relative to the other, and is defined by analogy based on the enantiomeric excess. Therefore, for a mixture of diastereomers D1 and D2, the percentage of diastereomeric excess is defined as $|D1-D2|*100$, wherein D1 and D2 are the mole or weight fractions of the respective diastereomers in the mixture, $D1+D2=1$.

The diastereomeric excess and enantiomeric excess can be measured by a number of analytical techniques (including nuclear magnetic resonance spectroscopy, chiral column chromatography and/or optical polarimetry) according to conventional protocols well known to a person skilled in the art.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively, individual isomers can be separated chemically through the following process: forming diastereomeric salts with a mixture and a chiral acid (e.g., the individual enantiomers of 10-camphorsulfonic acid, camphoric acid, alpha-bromocamphoric acid, tartaric acid, diacetyltartaric acid, malic acid, pyrrolidone-5-carboxylic acid, and the like), fractionally crystallizing the salts, and then freeing one or both of the resolved bases, optionally repeating the process, so as obtain either or both substantially free of the other; i.e., in a form having an optical purity of >95%. Alternatively, the racemates can be covalently linked to a chiral compound (auxiliary) to produce diastereomers which can be separated by chromatography or by fractional crystallization after which time the chiral auxiliary is chemically removed to afford the pure enantiomers.

The term "tautomer" as used herein refers to constitutional isomers of compounds generated by rapid movement of an atom in two positions in a molecule. Tautomers readily interconvert into each other, e.g., enol form and ketone form are tipical tautomers.

A "pharmaceutically acceptable salt" is intended to mean a salt of a free acid or base of a compound of formula (I) that is non-toxic, biologically tolerable, or otherwise biologically suitable for administration to the subject. For example, the pharmaceutically acceptable salt is an acid addition salt including such as a salt derived from an inorganic acid and an organic acid. Said inorganic acid includes such as hydrochloric acid, hydrobromic acid, hydroiodic acid, sulfuric acid, phosphoric acid, and nitric acid; said organic acid includes such as p-toluenesulfonic acid, salicylic acid, methanesulfonic acid, oxalic acid, succinic acid, citric acid, malic acid, lactic acid, fumaric acid, and the like. For examples, see, generally, S. M. Berge et. al., "Pharmaceutical Salts", J. Pharm. Sci., 1977, 66:1-19, and Handbook of Pharmaceutical Salts, Properties, Selection, and Use, edited by Stahl and Wermuth, Wiley-VCH and VHCA, Zurich, 2002.

In addition, if a compound of the present invention herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts or base addition salts.

The term "solvates" means solvent addition forms that contain either stoichiometric or non-stoichiometric amounts of solvent. Some compounds have a tendency to trap a fixed molar ratio of solvent molecules in the solid state, thus forming a solvate. When the solvent is water, the formed solvate is a hydrate, and when the solvent is alcohol, the formed solvate is an alcoholate. Hydrates are formed by the combination of one or more molecules of water, with one molecule of the substances in which the water retains its molecular state as $H_2O$, such combination being able to form one or more hydrates, for example, hemihydrate, monohydrate, and dihydrate.

The term "deuterate" means the compound formed by replacing one or more, for example, 1, 2 or 3 hydrogen atoms in a compound with its isotope deuterium, wherein at the substitution position, the abundance of isotope deuterium (i.e., the deuteration degree) of the element deuterium is at least greater than the natural abundance. In some embodiments, the deuterate in the compound of formula (I) or in the compound of its sub-formula (I-1) has a deuteration degree of at least 50% (e.g., 50%, 60%, 65%, 70%, 75%, 80%, 85%, 90%, 91%, 92%, 93%, 94%, 95%, 96%, 97%, 98%, 99%, 99.5%, 99.9%, or any value therebetween). In some embodiments, the compound of formula (I) or the compound of its sub-formula (I-1) has a deuteration degree of greater than 99.9% or up to 100%.

As used herein, the terms "group(s)" and "radical(s)" are synonymous and are intended to indicate functional groups or fragments of molecules attachable to other fragments of molecules.

The term "active ingredient" is used herein to refer to a chemical substance with biological activity, such as the compound of formula (I) of the present invention (e.g., a compound of any of the examples as described herein) or a pharmaceutically acceptable salt thereof. In some embodiments, the "active ingredient" is a chemical substance having pharmaceutical use, and its pharmaceutical activity can be determined by appropriate in vitro or in vivo trials (for example, preclinical or clinical trials).

The terms "treating" or "treatment" of a disease or disorder, in the context of achieving therapeutic benefit, refer to administering one or more pharmaceutical substances, especially the compound of formula (I) described herein or a pharmaceutically acceptable salt thereof to a subject that has the disease or disorder, or has a symptom of a disease or disorder, or has a predisposition toward a disease or disorder, with the purpose to cure, alleviate, relieve, alter, remedy, ameliorate, improve, or affect the disease or disorder, the symptoms of the disease or disorder, or the predisposition toward the disease or disorder. Therefore, the "treatment" described herein includes preventive treatment, curative treatment and palliative treatment. In some embodiment, the disease or disorder is an autoimmune disease or inflammatory disease.

The terms "treating", "contacting" and "reacting", in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount of the RIPK1 inhibitor sufficient to generally bring about a therapeutic benefit in patients in need of treatment for a disease or disorder mediated partially or completely by RIPK1 activity. Effective amounts or doses of the active ingredient of the present disclosure may be ascertained by methods such as modeling, dose escalation studies or clinical trials, and by taking into consideration factors, e.g., the route of administration, the pharmacokinetics of the agent, the severity of the disease or disorder, the subject's previous or ongoing therapy, the subject's health status and response to drugs, and the judgment of the attending physician.

An exemplary dose is in the range of from about 0.0001 to about 200 mg of active ingredient/kg body weight/day, for example from about 0.001 to 100 mg/kg body weight/day, or about 0.01 to 35 mg/kg body weight/day, or about 0.1 to 10 mg/kg body weight/day, daily in single or divided dosage units (e.g., BID, TID, QID). For a 70 kg person, a suitable dose is from about 0.05 to about 7 g/day, or from about 0.2 to about 5 g/day.

The term "inhibition" or "inhibiting" refers to a decrease in the baseline activity of a biological activity. The term "inhibition of RIPK1 activity" refers to a decrease in the activity of RIPK1 as a direct or indirect response to the presence of the compound of formula (I) and/or a pharmaceutically acceptable salt thereof, relative to the activity of RIPK1 in the absence of the compound of formula (I) and/or a pharmaceutically acceptable salt thereof described herein. The decrease in activity may be due to the direct interaction of the compound of formula (I) and/or a pharmaceutically acceptable salt thereof described herein with RIPK1, or due to the interaction of the compound of formula (I) and/or a pharmaceutically acceptable salt thereof described herein, with one or more other factors that in turn affect the RIPK1 activity. For example, the presence of the compound of formula (I) and/or a pharmaceutically acceptable salt thereof described herein may decrease the RIPK1 activity by directly binding to the RIPK1, by directly or indirectly influencing another factor, or by directly or indirectly decreasing the amount of RIPK1 present in the cell or organism.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

The term "pharmaceutically acceptable" refers to that the substances defined following the term can be used to prepare a pharmaceutical composition, which are generally safe, non-toxic, and have no undesirable biological or other properties, especially for human pharmaceutical use.

The term "about" as used herein means approximately, in the region of, roughly, or around. When the term "about" is used in conjunction with a numerical range, it adjusts the range by extending the limit above or below the numerical value given. In general, the term "about" is used herein to modify a numerical value above or below the stated value by a variance of 20%.

Technical and scientific terms used herein and not specifically defined have the meaning commonly understood by the POSITA to which the present disclosure pertains.

DETAILED DESCRIPTION OF EMBODIMENTS

Embodiment 1. A compound of formula (I):

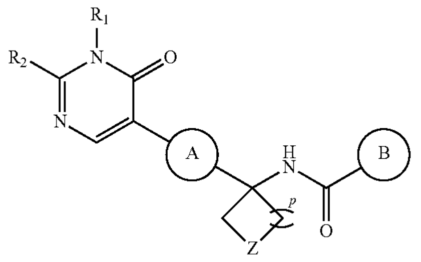

(I)

or a pharmaceutically acceptable salt thereof, or a solvate, a racemic mixture, an enantiomer, a diastereomer or a tautomer thereof, wherein $R_1$ is hydrogen, $C_{1-6}$ alkyl, $C_{1-6}$ haloalkyl, cyano-substituted $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl or —($C_{1-6}$ alkylene)$_n$-5-6 membered heteroaryl; wherein the $C_{3-6}$ cycloalkyl, phenyl, 4-6 membered heterocyclyl and 5-6 membered heteroaryl are each optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl) and —N($C_{1-6}$ alkyl)$_2$;

$R_2$ is hydrogen, halogen, —CN, —$NH_2$, $C_{1-6}$ alkyl, $C_{1-6}$ haloalkyl, —O($C_{1-6}$ alkyl), —O($C_{1-6}$ haloalkyl), —NH ($C_{1-6}$ alkyl) or —N($C_{1-6}$ alkyl)$_2$;

Z is O, $NR_3$ or $CR_4R_5$;

$R_3$ is hydrogen or $C_{1-6}$ alkyl;

$R_4$ and $R_5$ are each independently chosen from: hydrogen, halogen, —CN, —OH, $C_{1-6}$ alkyl, $C_{1-6}$ haloalkyl, —O($C_{1-6}$ alkyl), —O($C_{1-6}$ haloalkyl) and $C_{3-6}$ cycloalkyl;

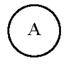

is phenyl or 5-6 membered heteroaryl, each of which is optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl) and —N($C_{1-6}$ alkyl)$_2$;

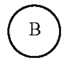

is 5-12 membered heteroaryl, which is optionally substituted with one or more groups independently chosen from: halogen, —CN, —OH, oxo, —$NH_2$, $C_{1-6}$ alkyl, $C_{1-6}$ haloalkyl, $C_{2-6}$ alkenyl, $C_{2-6}$ alkynyl, —O($C_{1-6}$ alkyl), —O($C_{1-6}$ haloalkyl), —NH($C_{1-6}$ alkyl), —N($C_{1-6}$ alkyl)$_2$, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl), —N($C_{1-6}$ alkyl)$_2$ and $C_{3-6}$ cycloalkyl;

n is 0 or 1;

and p is 0 or 1.

Embodiment 2. The compound of formula (I), or a pharmaceutically acceptable salt thereof, or a solvate, a racemic mixture, an enantiomer, a diastereomer or a tautomer thereof according to embodiment 1, wherein $R_1$ is $C_{1-6}$ alkyl, $C_{1-6}$ haloalkyl, cyano-substituted $C_{1-6}$ alkyl, —($C_{1-6}$ alkylene)$_n$-$C_{3-6}$ cycloalkyl or —($C_{1-6}$ alkylene)$_n$-4-6 membered heterocyclyl; and wherein the $C_{3-6}$ cycloalkyl and 4-6 membered heterocyclyl are each optionally substituted with one or more groups independently chosen from: halogen, —CN, —OH, —$NH_2$, $C_{1-6}$ alkyl, $C_{1-6}$ haloalkyl, —O($C_{1-6}$ alkyl), —O($C_{1-6}$ haloalkyl), —NH($C_{1-6}$ alkyl) and —N($C_{1-6}$ alkyl)$_2$.

Embodiment 3. The compound of formula (I), or a pharmaceutically acceptable salt thereof, or a solvate, a racemic mixture, an enantiomer, a diastereomer or a tautomer thereof according to embodiment 2, wherein $R_1$ is $C_{1-6}$ alkyl, $C_{1-6}$ haloalkyl, cyano-substituted $C_{1-6}$ alkyl, —($C_{1-6}$ alkylene)$_n$-$C_{3-6}$ cycloalkyl or —($C_{1-6}$ alkylene)$_n$-4-6 membered heterocyclyl; wherein the $C_{3-6}$ cycloalkyl and 4-6 membered heterocyclyl are each optionally substituted with one or more groups independently chosen from: halogen and $C_{1-6}$ alkyl.

Embodiment 4. The compound of formula (I), or a pharmaceutically acceptable salt thereof, or a solvate, a racemic mixture, an enantiomer, a diastereomer or a tautomer thereof according to embodiment 3, wherein $R_1$ is $C_{1-6}$ alkyl, and preferably, $R_1$ is methyl or i-propyl.

Embodiment 5. The compound of formula (I), or a pharmaceutically acceptable salt thereof, or a solvate, a racemic mixture, an enantiomer, a diastereomer or a tautomer thereof according to embodiment 3, wherein $R_1$ is $C_{1-6}$ haloalkyl, —($C_{1-6}$ alkylene)$_n$-$C_{3-6}$ cycloalkyl or —($C_{1-6}$ alkylene)$_n$-4-6 membered heterocyclyl; wherein the $C_{3-6}$ cycloalkyl is optionally substituted with one or more groups independently chosen from: halogen and $C_{1-6}$ alkyl;

preferably, $R_1$ is —($C_{1-6}$ alkylene)$_n$-$C_{3-6}$ cycloalkyl, wherein the $C_{3-6}$ cycloalkyl is optionally substituted with one or more halogen, and n is 0 or 1; or $R_1$ is 4-6 membered heterocyclyl, wherein the 4-6 membered heterocyclyl is oxetanyl, tetrahydrofuranyl or tetrahydropyranyl.

Embodiment 6. The compound of formula (I), or a pharmaceutically acceptable salt thereof, or a solvate, a racemic mixture, an enantiomer, a diastereomer or a tautomer thereof according to any one of embodiments 1-5, wherein $R_2$ is hydrogen, —$NH_2$, $C_{1-6}$ alkyl, —NH($C_{1-6}$ alkyl) or —N($C_{1-6}$ alkyl)$_2$; preferably, $R_2$ is hydrogen, —$NH_2$ or $C_{1-6}$ alkyl; and more preferably, $R_2$ is hydrogen.

Embodiment 7. The compound of formula (I), or a pharmaceutically acceptable salt thereof, or a solvate, a racemic mixture, an enantiomer, a diastereomer or a tautomer thereof according to any one of embodiments 1-6, wherein p is 0, and Z is $CR_4R_5$; more preferably, p is 0, and Z is $CH_2$.

Embodiment 8. The compound of formula (I), or a pharmaceutically acceptable salt thereof, or a solvate, a racemic mixture, an enantiomer, a diastereomer or a tautomer thereof according to any one of embodiments 1-7, wherein

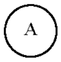

is phenyl or 5-6 membered heteroaryl, each of which is optionally substituted with one or more groups independently chosen from: halogen, $C_{1-6}$ alkyl and $C_{1-6}$ haloalkyl;

preferably,

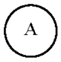

is phenyl or pyridyl, each of which is optionally substituted with one or more groups independently chosen from: halogen, $C_{1-6}$ alkyl and $C_{1-6}$ haloalkyl;

more preferably,

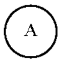

is phenyl, which is optionally substituted with one or more groups independently chosen from: halogen, $C_{1-6}$ alkyl or $C_{1-6}$ haloalkyl; or

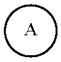

is pyridyl.

Embodiment 9. The compound of formula (I), or a pharmaceutically acceptable salt thereof, or a solvate, a racemic mixture, an enantiomer, a diastereomer or a tautomer thereof according to any one of embodiments 1-8, wherein

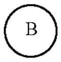

is 5-12 membered heteroaryl, preferably 5-10 membered heteroaryl, more preferably 5-9 membered heteroaryl, which is optionally substituted with one or more groups independently chosen from: halogen, $C_{1-6}$ alkyl, —$(C_{1-6}$ alkylene$)_n$-$C_{3-6}$ cycloalkyl, —$(C_{1-6}$ alkylene$)_n$-phenyl, —$(C_{1-6}$ alkylene$)_n$-4-6 membered heterocyclyl and —$(C_{1-6}$ alkylene$)_n$-5-6 membered heteroaryl; and wherein the phenyl, $C_{3-6}$ cycloalkyl, 4-6 membered heterocyclyl and 5-6 membered heteroaryl are each optionally substituted with one or more halogen.

Embodiment 10. The compound of formula (I), or a pharmaceutically acceptable salt thereof, or a solvate, a racemic mixture, an enantiomer, a diastereomer or a tautomer thereof according to embodiment 1, wherein the compound of formula (I) is the compound of formula (I-1):

(I-1)

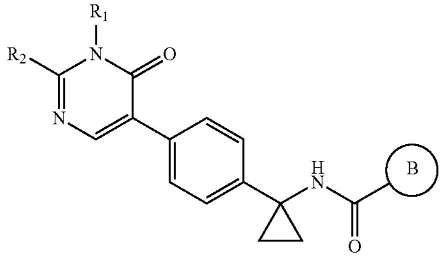

wherein $R_1$ is $C_{1-6}$ alkyl, $C_{1-6}$ haloalkyl, cyano-substituted $C_{1-6}$ alkyl, —$(C_{1-6}$ alkylene$)_n$-$C_{3-6}$ cycloalkyl or —$(C_{1-6}$ alkylene$)_n$-4-6 membered heterocyclyl; wherein the $C_{3-6}$ cycloalkyl and 4-6 membered heterocyclyl are each optionally substituted with one or more groups independently chosen from: halogen and $C_{1-6}$ alkyl; preferably, $R_1$ is $C_{1-6}$ alkyl, $C_{1-6}$ haloalkyl, —$(C_{1-6}$ alkylene$)_n$-$C_{3-6}$ cycloalkyl or —$(C_{1-6}$ alkylene$)_n$-4-6 membered heterocyclyl; wherein the $C_{3-6}$ cycloalkyl is optionally substituted with one or more groups independently chosen from: halogen and $C_{1-6}$ alkyl;

$R_2$ is hydrogen, —$NH_2$, $C_{1-6}$ alkyl, —$NH(C_{1-6}$ alkyl) or —$N(C_{1-6}$ alkyl$)_2$; preferably, $R_2$ is hydrogen, —$NH_2$ or $C_{1-6}$ alkyl; and more preferably, $R_2$ is hydrogen;

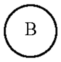

is 5-12 membered heteroaryl, preferably 5-10 membered heteroaryl, more preferably 5-9 membered heteroaryl, which is optionally substituted with one or more groups independently chosen from: halogen, $C_{1-6}$ alkyl, —$(C_{1-6}$ alkylene$)_n$-$C_{3-6}$ cycloalkyl, —$(C_{1-6}$ alkylene$)_n$-phenyl, —$(C_{1-6}$ alkylene$)_n$-4-6 membered heterocyclyl and —$(C_{1-6}$ alkylene$)_n$-5-6 membered heteroaryl; wherein the phenyl, $C_{3-6}$ cycloalkyl, 4-6 membered heterocyclyl and 5-6 membered heteroaryl are each optionally substituted with one or more halogen; and n is 0 or 1.

Embodiment 11. The compound of formula (I), or a pharmaceutically acceptable salt thereof, or a solvate, a racemic mixture, an enantiomer, a diastereomer or a tautomer thereof according to any one of embodiments 1-10, wherein

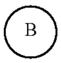

is triazolyl, oxazolyl, isoxazolyl, oxadiazolyl, pyrimidyl, pyrazolopyrimidyl, pyrazolopyridyl or dihydropyrrolotriazolyl, each of which is optionally substituted with one or more groups independently chosen from: halogen, $C_{1-6}$ alkyl, —$(C_{1-6}$ alkylene$)_n$-$C_{3-6}$ cycloalkyl, —$(C_{1-6}$ alkylene$)_n$-phenyl, —$(C_{1-6}$ alkylene$)_n$-4-6 membered heterocyclyl and —$(C_{1-6}$ alkylene$)_n$-5-6 membered heteroaryl; and wherein the phenyl, $C_{3-6}$ cycloalkyl, 4-6 membered heterocyclyl and 5-6 membered heteroaryl are each optionally substituted with one or more halogen.

Embodiment 12. The compound of formula (I), or a pharmaceutically acceptable salt thereof, or a solvate, a racemic mixture, an enantiomer, a diastereomer or a tautomer thereof according to embodiment 11, wherein

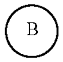

is chosen from

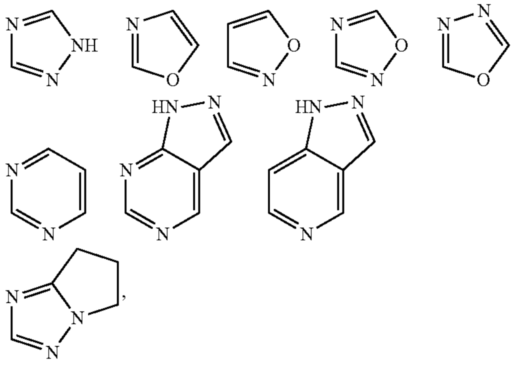
, each of which is optionally substituted with one or more groups independently chosen from: halogen, $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more halogen;

preferably,

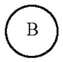

is chosen from

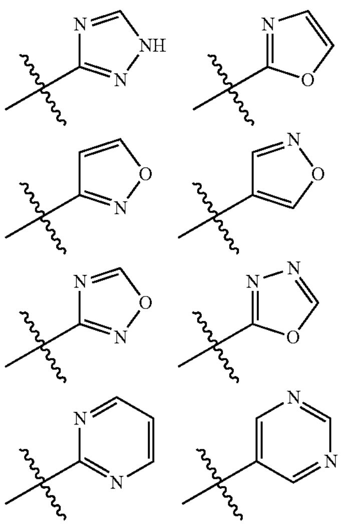

-continued

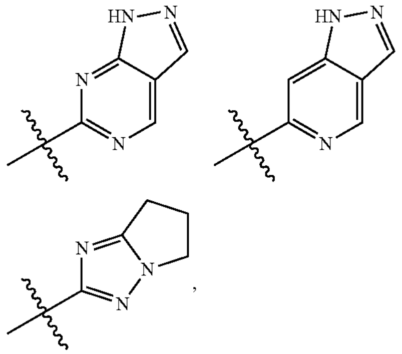
, each of which is optionally substituted with one or more groups independently chosen from: halogen, $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more halogen.

Embodiment 13. The compound of formula (I), or a pharmaceutically acceptable salt thereof, or a solvate, a racemic mixture, an enantiomer, a diastereomer or a tautomer thereof according to embodiment 12, wherein

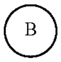 is 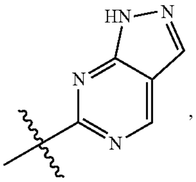, which is optionally substituted with one or more groups independently chosen from: $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; and wherein the $C_{3-6}$ cycloalkyl, 4-6 membered heterocyclyl and 5-6 membered heteroaryl are each optionally substituted with one or more halogen, and n is 0 or 1.

Embodiment 14. The compound of formula (I), or a pharmaceutically acceptable salt thereof, or a solvate, a racemic mixture, an enantiomer, a diastereomer or a tautomer thereof according to embodiment 13, wherein

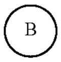 is 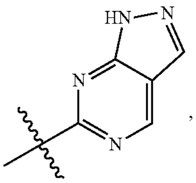, which is optionally substituted with one or more groups independently chosen from: $C_{1-6}$ alkyl;

or

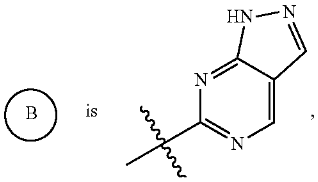, which is optionally substituted with one or more groups independently chosen from: —$(C_{1-6}$ alkylene$)_n$-$C_{3-6}$ cycloalkyl, wherein n is 0 or 1; wherein the $C_{3-6}$ cycloalkyl is optionally substituted with one or more halogen;

or

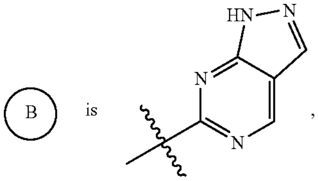, which is optionally substituted with one or more groups independently chosen from: —$(C_{1-6}$ alkylene$)_n$-phenyl, wherein n is 0 or 1;

or

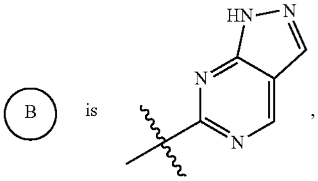, which is optionally substituted with one or more groups independently chosen from: 4-6 membered heterocyclyl; wherein the 4-6 membered heterocyclyl is oxetanyl;

or

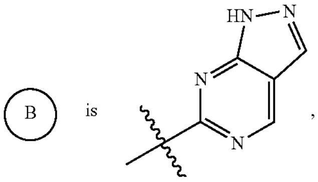, which is optionally substituted with one or more groups independently chosen from: 5-6 membered heteroaryl; wherein the 5-6 membered heteroaryl is pyridyl.

Embodiment 15. The compound of formula (I), or a pharmaceutically acceptable salt thereof according to embodiment 1, wherein the compound of formula (I) is chosen from compounds 1-19, 22-48 and 53-95:

| Compound No. | Structure |
|---|---|
| 1 | 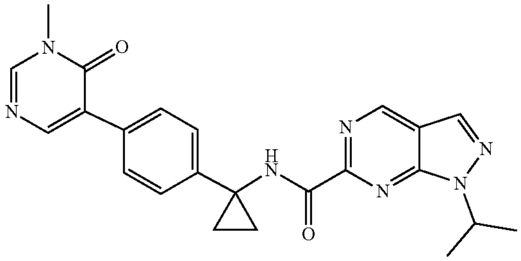 |
| 2 | 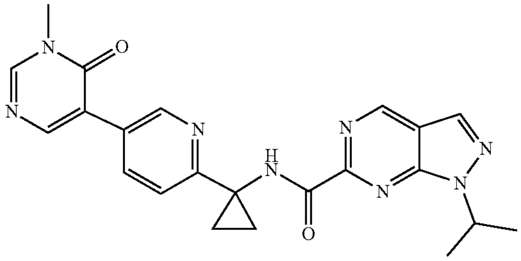 [SMILES: CC(C)n1ncc2cnc(C(=O)NC3(c4ccc(-c5cncn(C)c5=O)cn4)CC3)nc21] |

-continued
| Compound No. | Structure |
|---|---|
| 3 | 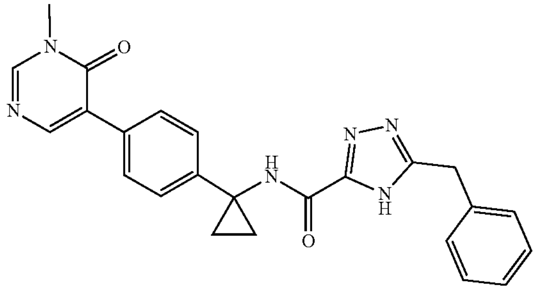 [SMILES: Cn1cncc(-c2ccc(C3(NC(=O)c4nnc(Cc5ccccc5)[nH]4)CC3)cc2)c1=O] |
| 4 | 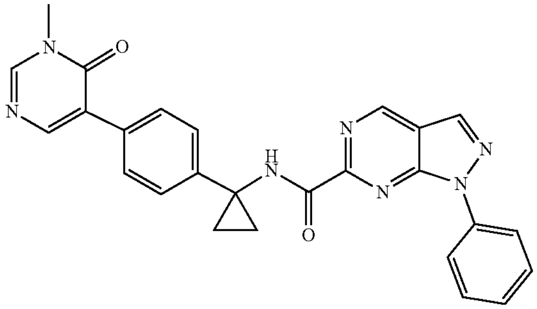 [SMILES: Cn1cncc(-c2ccc(C3(NC(=O)c4ncc5cnn(-c6ccccc6)c5n4)CC3)cc2)c1=O] |
| 5 | 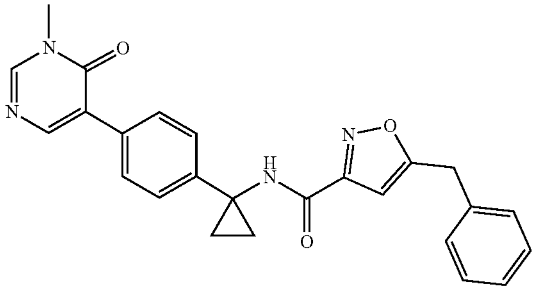 [SMILES: Cn1cncc(-c2ccc(C3(NC(=O)c4cc(Cc5ccccc5)on4)CC3)cc2)c1=O] |
| 6 | 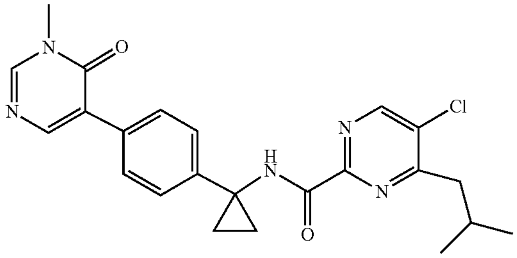 [SMILES: CC(C)Cc1nc(C(=O)NC2(c3ccc(-c4cncn(C)c4=O)cc3)CC2)ncc1Cl] |
| 7 | 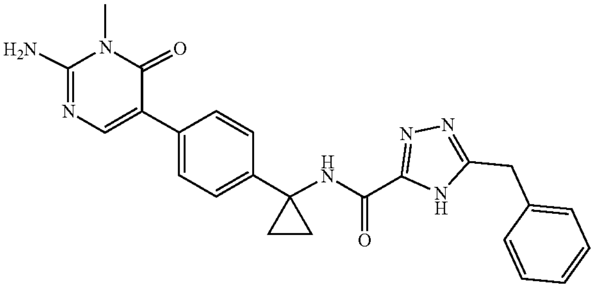 [SMILES: Cn1c(N)ncc(-c2ccc(C3(NC(=O)c4nnc(Cc5ccccc5)[nH]4)CC3)cc2)c1=O] |

-continued
| Compound No. | Structure |
|---|---|
| 8 | 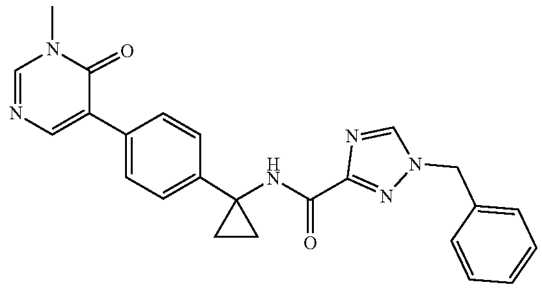 [SMILES: Cn1cncc(-c2ccc(C3(NC(=O)c4ncn(Cc5ccccc5)n4)CC3)cc2)c1=O] |
| 9 | 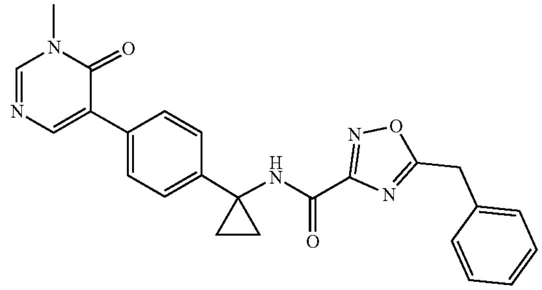 [SMILES: Cn1cncc(-c2ccc(C3(NC(=O)c4noc(Cc5ccccc5)n4)CC3)cc2)c1=O] |
| 10 | 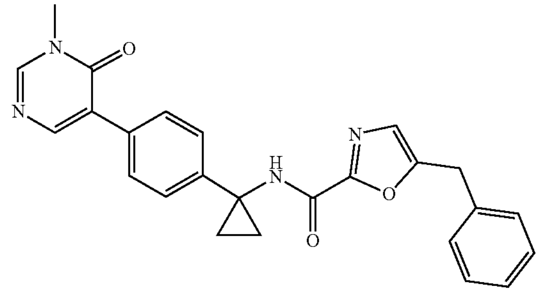 [SMILES: Cn1cncc(-c2ccc(C3(NC(=O)c4ncc(Cc5ccccc5)o4)CC3)cc2)c1=O] |
| 11 | 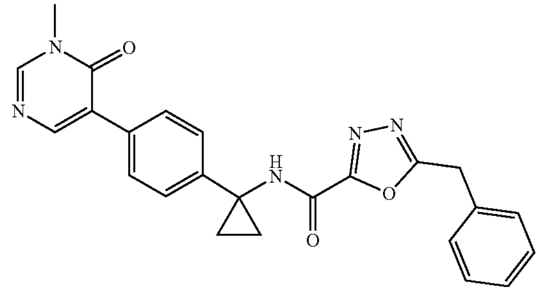 [SMILES: Cn1cncc(-c2ccc(C3(NC(=O)c4nnc(Cc5ccccc5)o4)CC3)cc2)c1=O] |
| 12 | 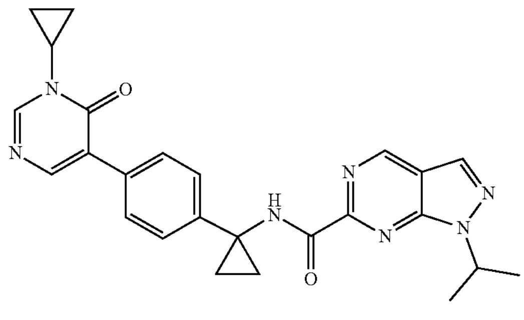 [SMILES: CC(C)n1ncc2cnc(C(=O)NC3(c4ccc(-c5cncn(C6CC6)c5=O)cc4)CC3)nc21] |

-continued
| Compound No. | Structure |
| --- | --- |
| 13 | 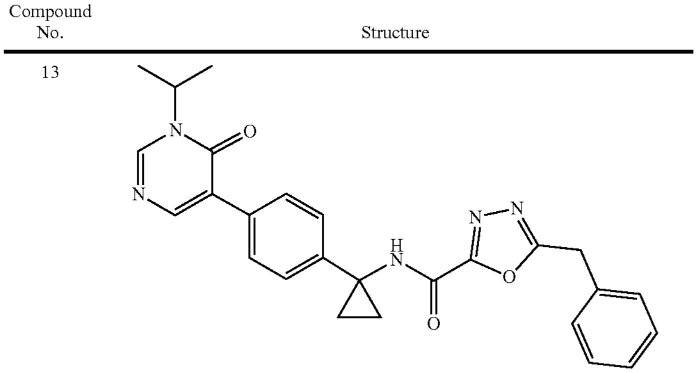 |
| 14 | 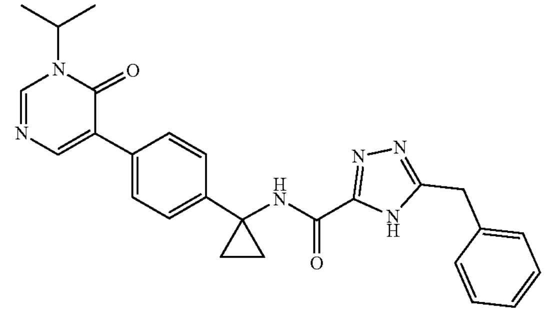 [SMILES: CC(C)n1cncc(-c2ccc(C3(NC(=O)c4nnc(Cc5ccccc5)[nH]4)CC3)cc2)c1=O] |
| 15 and 16 | 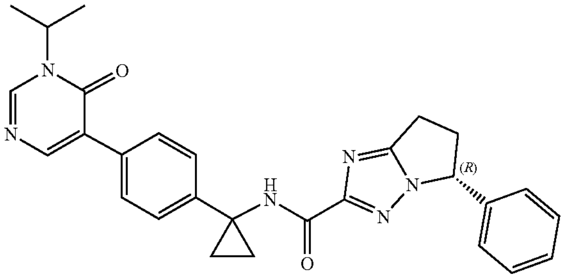 and 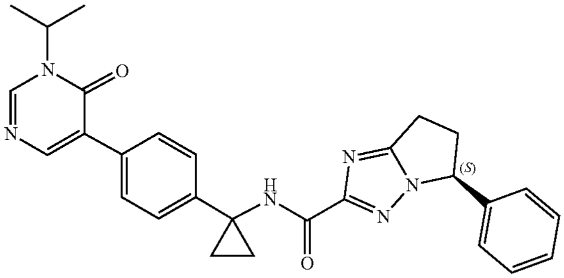 |
| 17 | 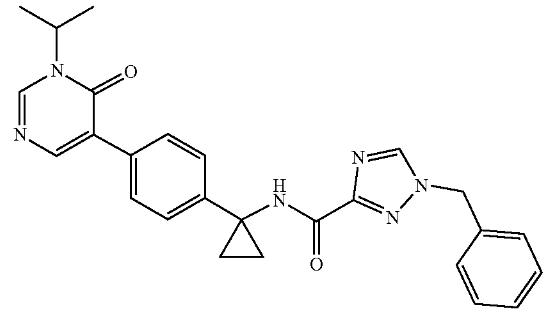 [SMILES: CC(C)n1cncc(-c2ccc(C3(NC(=O)c4ncn(Cc5ccccc5)n4)CC3)cc2)c1=O] |

-continued
| Compound No. | Structure |
|---|---|
| 18 | 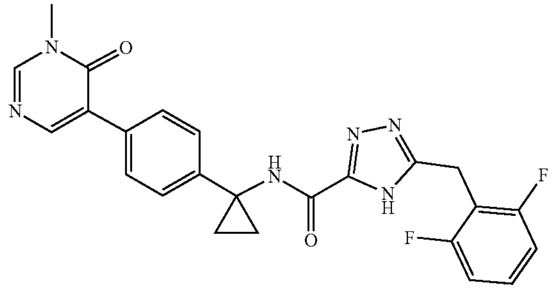 [SMILES: Cn1cncc(-c2ccc(C3(NC(=O)c4nnc(Cc5c(F)cccc5F)[nH]4)CC3)cc2)c1=O] |
| 19 | 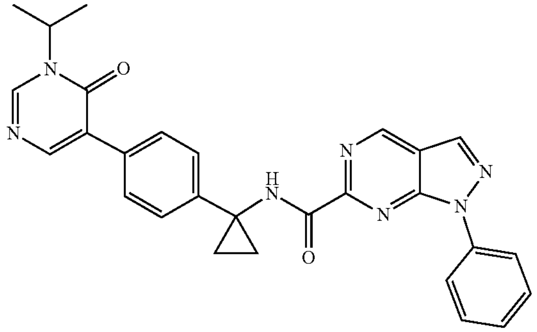 [SMILES: CC(C)n1cncc(-c2ccc(C3(NC(=O)c4ncc5cnn(-c6ccccc6)c5n4)CC3)cc2)c1=O] |
| 22 | 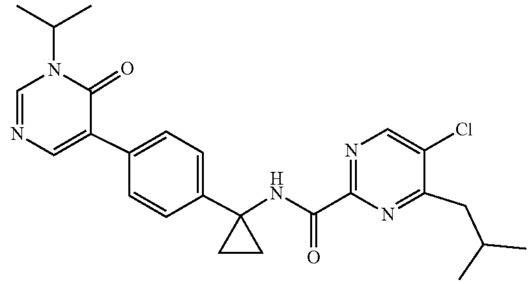 [SMILES: CC(C)Cc1nc(C(=O)NC2(c3ccc(-c4cncn(C(C)C)c4=O)cc3)CC2)ncc1Cl] |
| 23 | 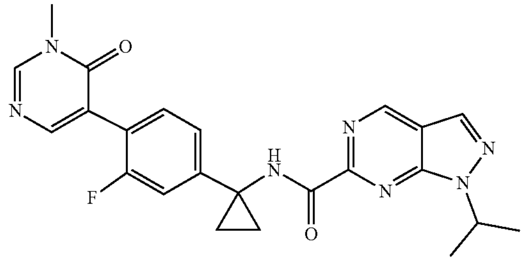 [SMILES: CC(C)n1ncc2cnc(C(=O)NC3(c4ccc(-c5cncn(C)c5=O)c(F)c4)CC3)nc21] |
| 24 | 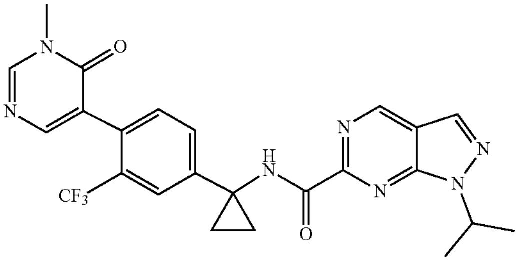 [SMILES: CC(C)n1ncc2cnc(C(=O)NC3(c4ccc(-c5cncn(C)c5=O)c(C(F)(F)F)c4)CC3)nc21] |

-continued
| Compound No. | Structure |
|---|---|
| 25 | 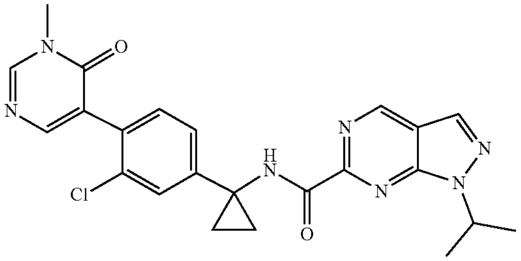 [SMILES: CC(C)n1ncc2cnc(C(=O)NC3(c4ccc(-c5cncn(C)c5=O)c(Cl)c4)CC3)nc21] |
| 26 | 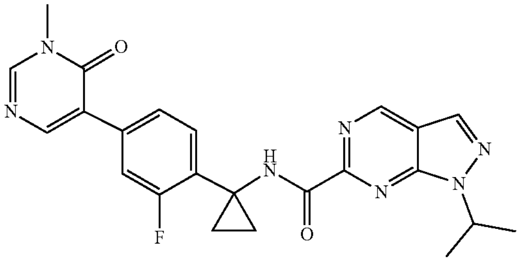 [SMILES: CC(C)n1ncc2cnc(C(=O)NC3(c4ccc(-c5cncn(C)c5=O)cc4F)CC3)nc21] |
| 27 | 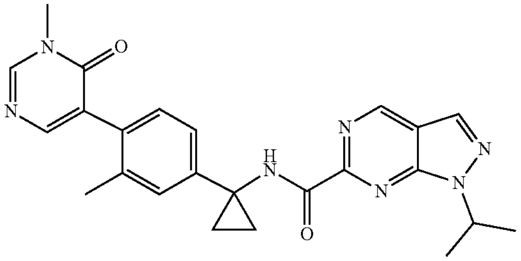 [SMILES: Cc1cc(C2(NC(=O)c3ncc4cnn(C(C)C)c4n3)CC2)ccc1-c1cncn(C)c1=O] |
| 28 | 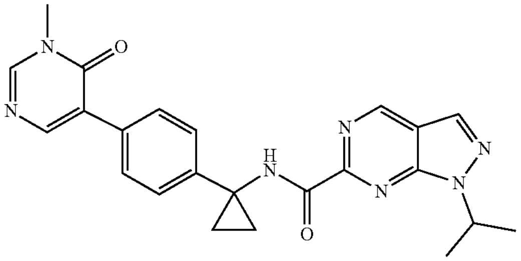 [SMILES: CC(C)n1ncc2cnc(C(=O)NC3(c4ccc(-c5cncn(C)c5=O)cc4)CC3)nc21] |
| 29 | 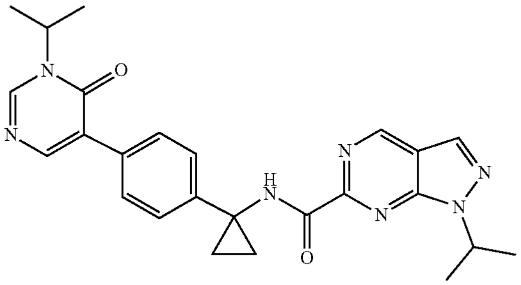 [SMILES: CC(C)n1cncc(-c2ccc(C3(NC(=O)c4ncc5cnn(C(C)C)c5n4)CC3)cc2)c1=O] |

-continued
| Compound No. | Structure |
|---|---|
| 30 | 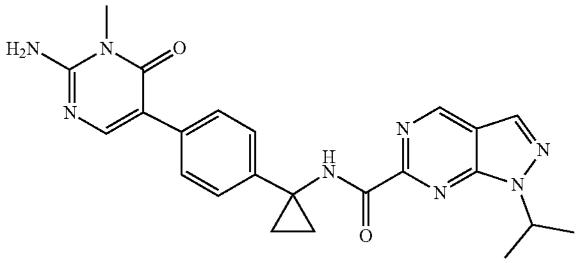 [SMILES: CC(C)n1ncc2cnc(C(=O)NC3(c4ccc(-c5cnc(N)n(C)c5=O)cc4)CC3)nc21] |
| 31 | 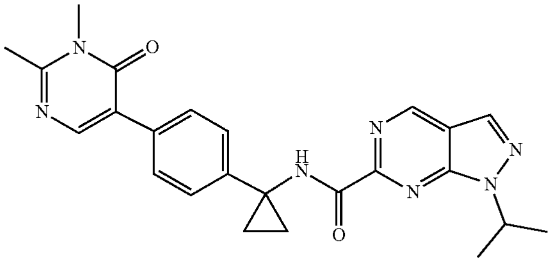 [SMILES: Cc1ncc(-c2ccc(C3(NC(=O)c4ncc5cnn(C(C)C)c5n4)CC3)cc2)c(=O)n1C] |
| 32 | 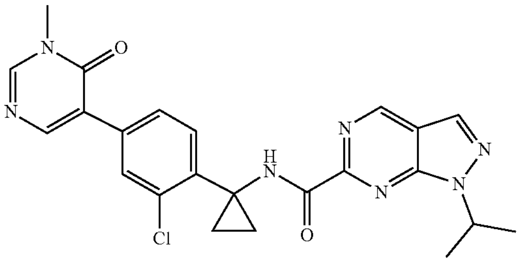 [SMILES: CC(C)n1ncc2cnc(C(=O)NC3(c4ccc(-c5cncn(C)c5=O)cc4Cl)CC3)nc21] |
| 33 | 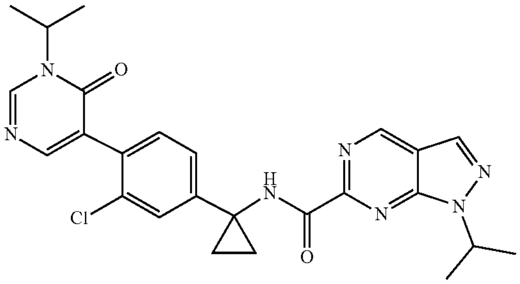 [SMILES: CC(C)n1cncc(-c2ccc(C3(NC(=O)c4ncc5cnn(C(C)C)c5n4)CC3)cc2Cl)c1=O] |
| 34 | 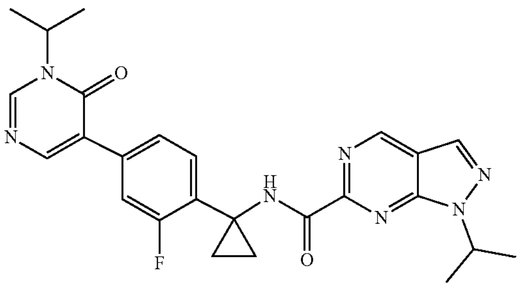 [SMILES: CC(C)n1cncc(-c2ccc(C3(NC(=O)c4ncc5cnn(C(C)C)c5n4)CC3)c(F)c2)c1=O] |

-continued
| Compound No. | Structure |
|---|---|
| 35 | 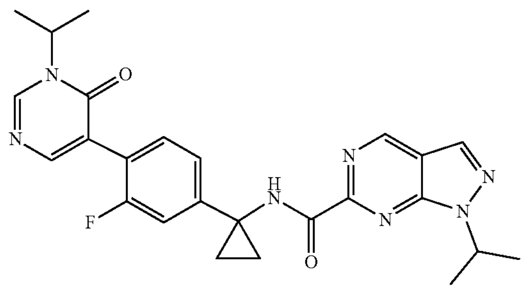 [SMILES: CC(C)n1cncc(-c2ccc(C3(NC(=O)c4ncc5cnn(C(C)C)c5n4)CC3)cc2F)c1=O] |
| 36 | 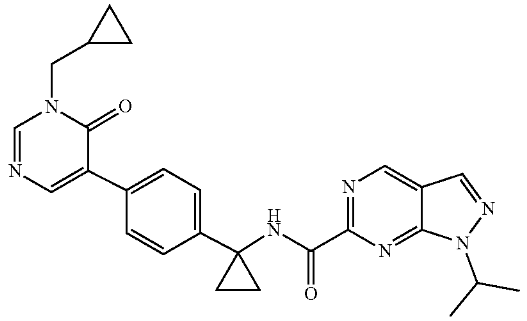 [SMILES: CC(C)n1ncc2cnc(C(=O)NC3(c4ccc(-c5cncn(CC6CC6)c5=O)cc4)CC3)nc21] |
| 37 | 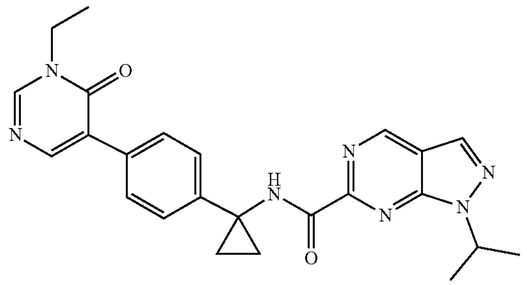 [SMILES: CCn1cncc(-c2ccc(C3(NC(=O)c4ncc5cnn(C(C)C)c5n4)CC3)cc2)c1=O] |
| 38 | 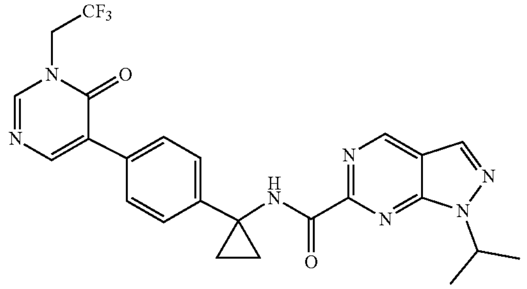 [SMILES: CC(C)n1ncc2cnc(C(=O)NC3(c4ccc(-c5cncn(CC(F)(F)F)c5=O)cc4)CC3)nc21] |
| 39 | 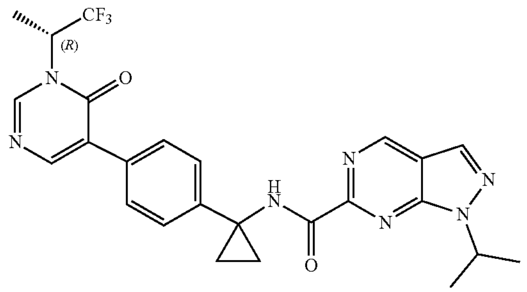 |

-continued
| Compound No. | Structure |
|---|---|
| 40 | 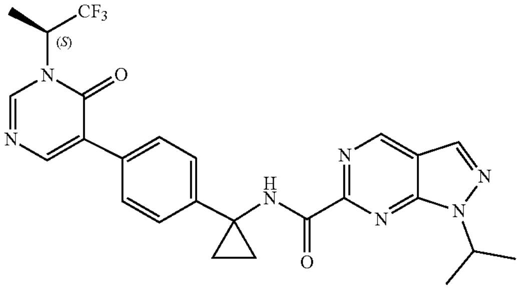 |
| 41 | 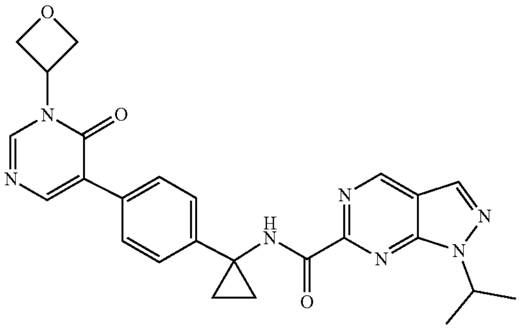 [SMILES: CC(C)n1ncc2cnc(C(=O)NC3(c4ccc(-c5cncn(C6COC6)c5=O)cc4)CC3)nc21] |
| 42 | 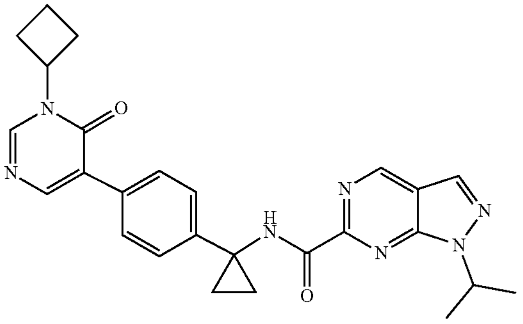 [SMILES: CC(C)n1ncc2cnc(C(=O)NC3(c4ccc(-c5cncn(C6CCC6)c5=O)cc4)CC3)nc21] |
| 43 | 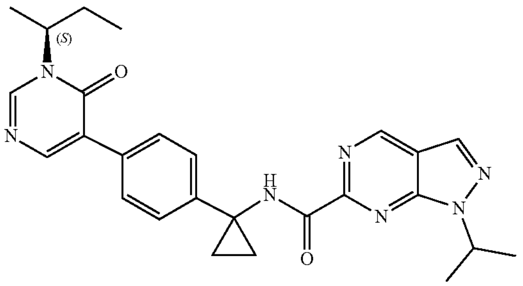 |
| 44 | 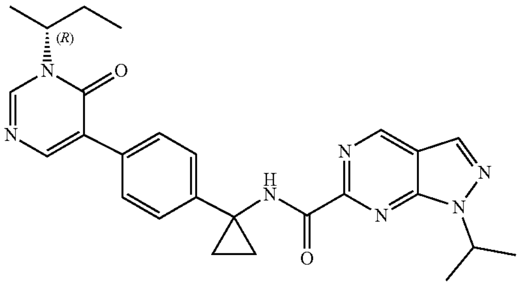 |

-continued
| Compound No. | Structure |
|---|---|
| 45 | 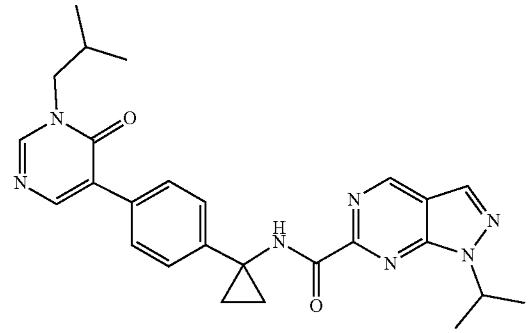 [SMILES: CC(C)Cn1cncc(-c2ccc(C3(NC(=O)c4ncc5cnn(C(C)C)c5n4)CC3)cc2)c1=O] |
| 46 | 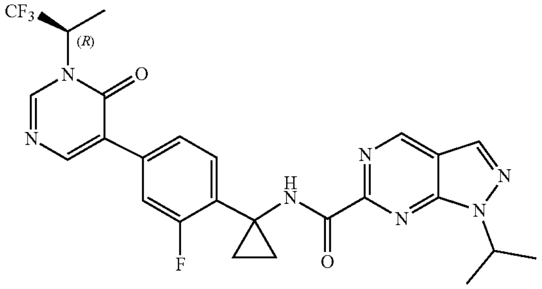 |
| 47 | 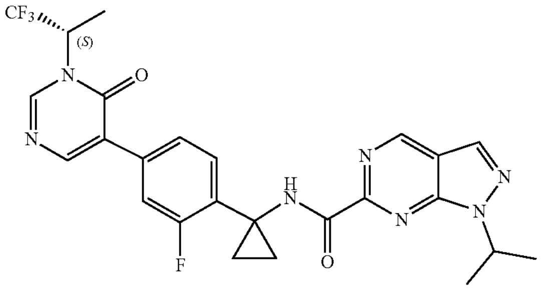 |
| 48 | 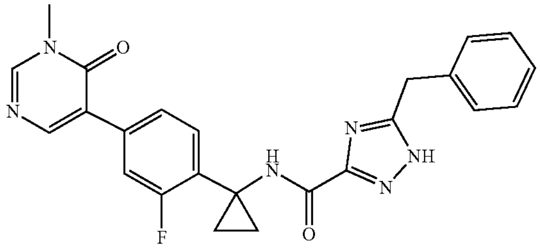 [SMILES: Cn1cncc(-c2ccc(C3(NC(=O)c4n[nH]c(Cc5ccccc5)n4)CC3)c(F)c2)c1=O] |
| 53 and 54 | 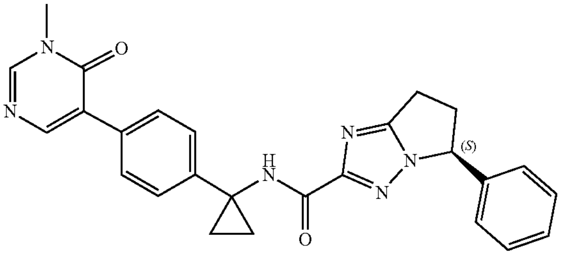 |

-continued
| Compound No. | Structure |
| --- | --- |
| | and |
| | 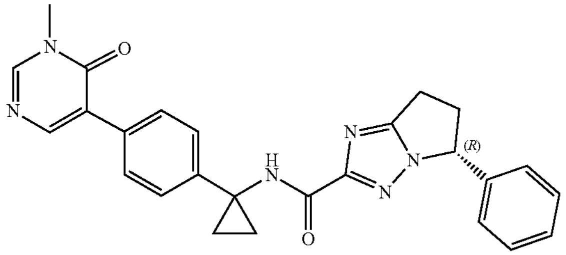 |
| 55 and 56 | 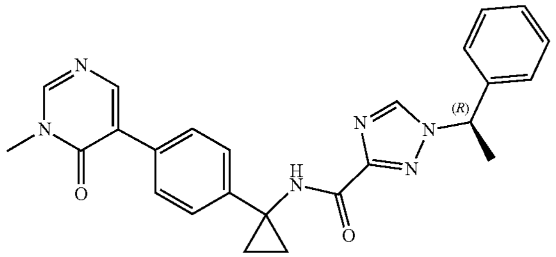 |
| | and |
| | 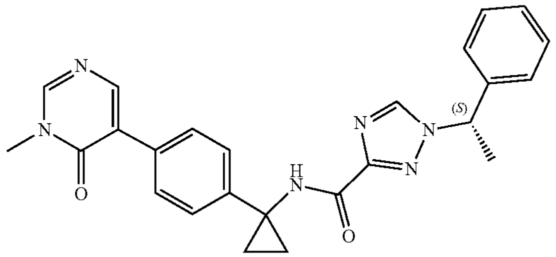 |
| 57 and 58 | 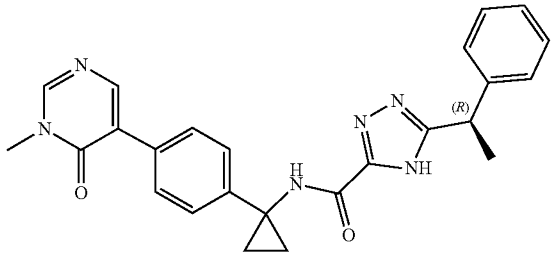 |
| | and |
| | 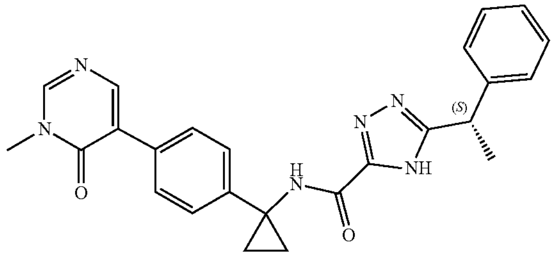 |

-continued
| Compound No. | Structure |
|---|---|
| 59 | 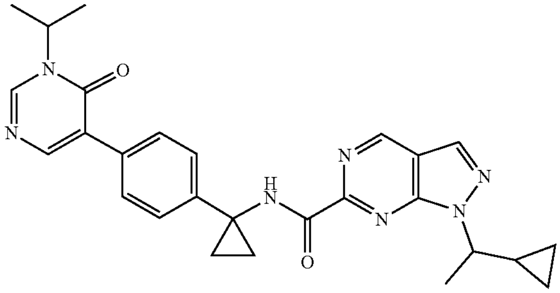 [SMILES: CC(C)n1cncc(-c2ccc(C3(NC(=O)c4ncc5cnn(C(C)C6CC6)c5n4)CC3)cc2)c1=O] |
| 60 | 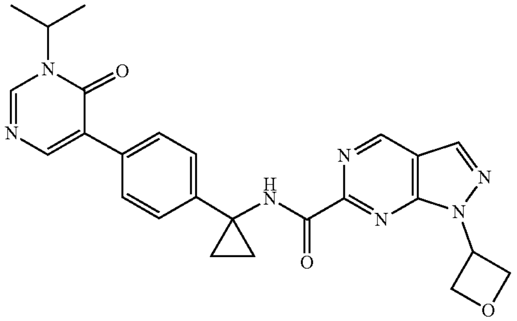 [SMILES: CC(C)n1cncc(-c2ccc(C3(NC(=O)c4ncc5cnn(C6COC6)c5n4)CC3)cc2)c1=O] |
| 61 | 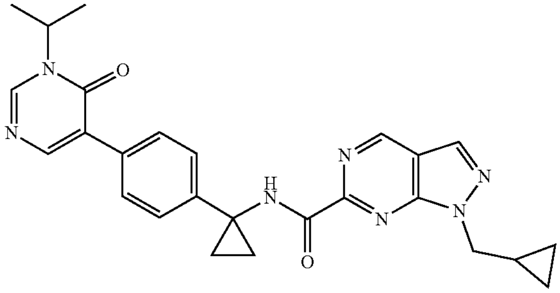 [SMILES: CC(C)n1cncc(-c2ccc(C3(NC(=O)c4ncc5cnn(CC6CC6)c5n4)CC3)cc2)c1=O] |
| 62 | 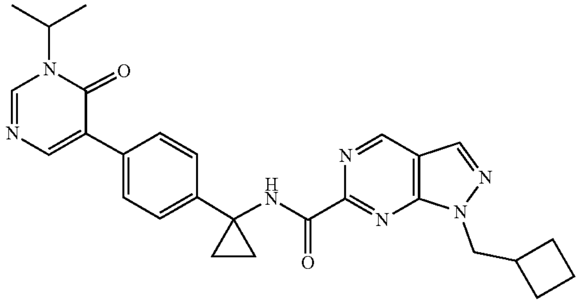 [SMILES: CC(C)n1cncc(-c2ccc(C3(NC(=O)c4ncc5cnn(CC6CCC6)c5n4)CC3)cc2)c1=O] |
| 63 | 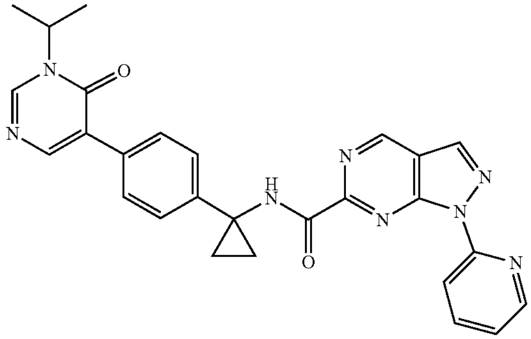 [SMILES: CC(C)n1cncc(-c2ccc(C3(NC(=O)c4ncc5cnn(-c6ccccn6)c5n4)CC3)cc2)c1=O] |

-continued
| Compound No. | Structure |
|---|---|
| 64 | 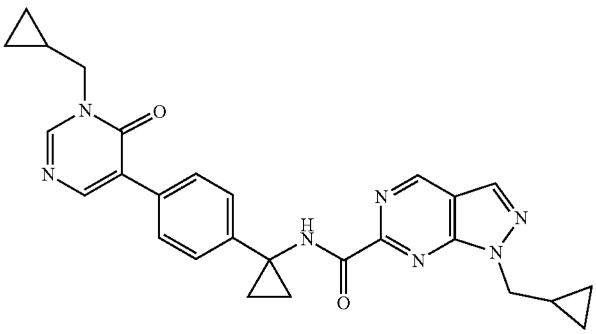 [SMILES: O=C(NC1(c2ccc(-c3cncn(CC4CC4)c3=O)cc2)CC1)c1ncc2cnn(CC3CC3)c2n1] |
| 65 | 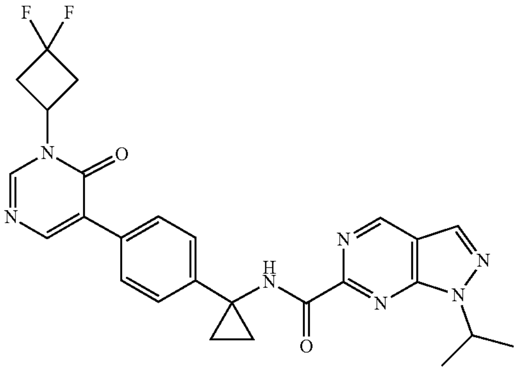 [SMILES: CC(C)n1ncc2cnc(C(=O)NC3(c4ccc(-c5cncn(C6CC(F)(F)C6)c5=O)cc4)CC3)nc21] |
| 66 | 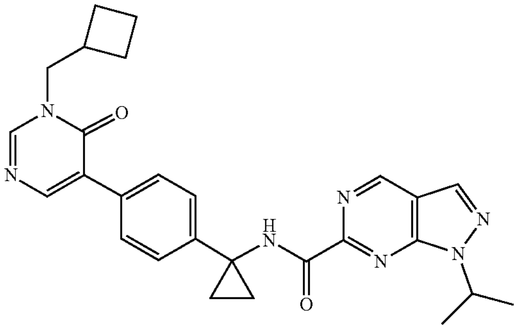 [SMILES: CC(C)n1ncc2cnc(C(=O)NC3(c4ccc(-c5cncn(CC6CCC6)c5=O)cc4)CC3)nc21] |
| 67 | 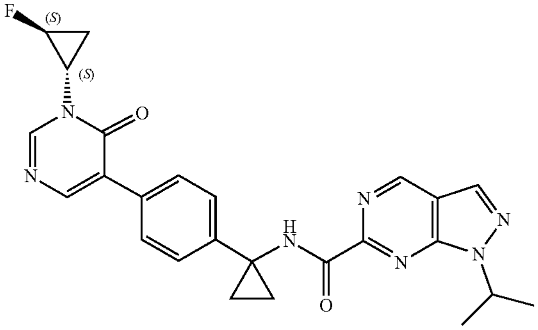 |

-continued
| Compound No. | Structure |
| --- | --- |
| 68 | 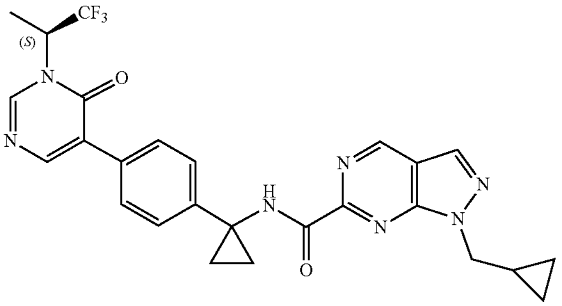 |
| 69 | 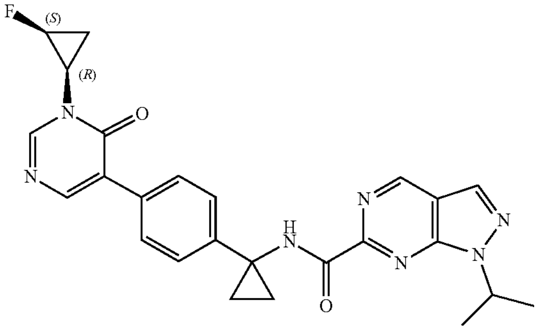 |
| 70 | 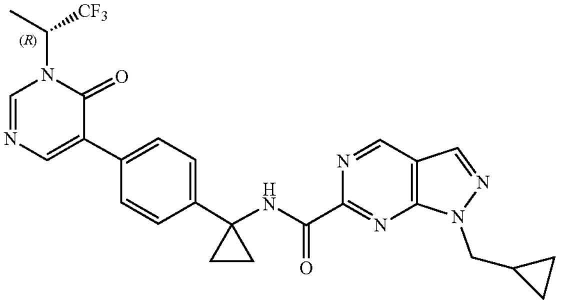 |
| 71 | 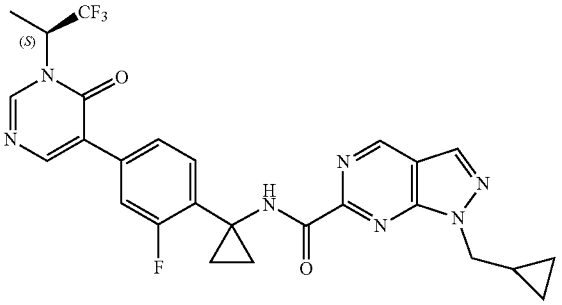 |
| 72 | 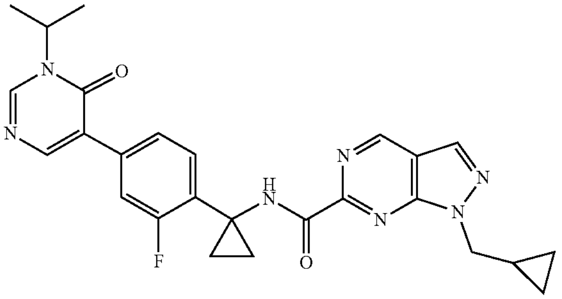 [SMILES: CC(C)n1cncc(-c2ccc(C3(NC(=O)c4ncc5cnn(CC6CC6)c5n4)CC3)c(F)c2)c1=O] |

-continued
| Compound No. | Structure |
| --- | --- |
| 73 | 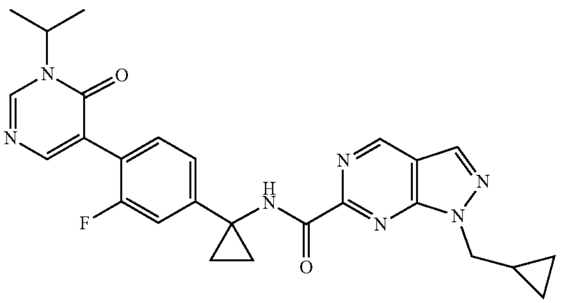 [SMILES: CC(C)n1cncc(-c2ccc(C3(NC(=O)c4ncc5cnn(CC6CC6)c5n4)CC3)cc2F)c1=O] |
| 74 | 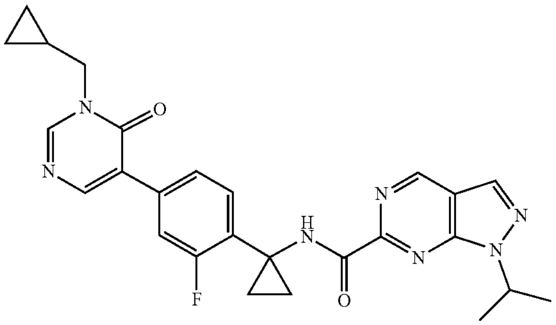 [SMILES: CC(C)n1ncc2cnc(C(=O)NC3(c4ccc(-c5cncn(CC6CC6)c5=O)cc4F)CC3)nc21] |
| 75 | 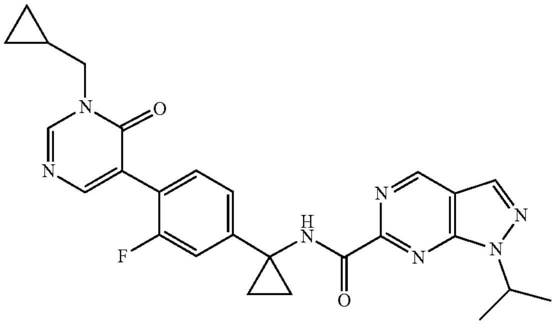 [SMILES: CC(C)n1ncc2cnc(C(=O)NC3(c4ccc(-c5cncn(CC6CC6)c5=O)c(F)c4)CC3)nc21] |
| 76 | 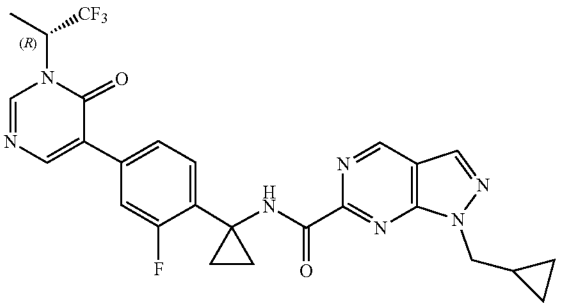 |

-continued
| Compound No. | Structure |
|---|---|
| 77 | 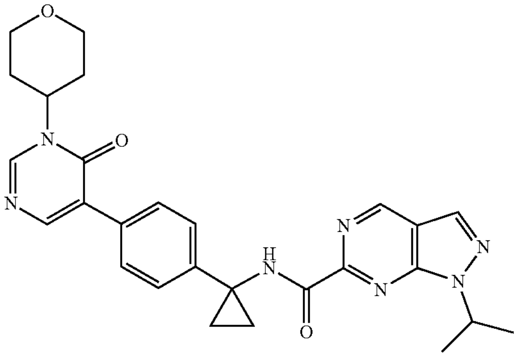 [SMILES: CC(C)n1ncc2cnc(C(=O)NC3(c4ccc(-c5cncn(C6CCOCC6)c5=O)cc4)CC3)nc21] |
| 78 | 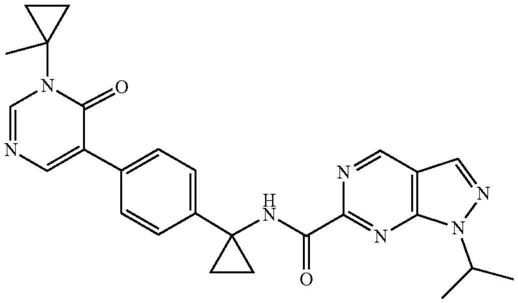 [SMILES: CC(C)n1ncc2cnc(C(=O)NC3(c4ccc(-c5cncn(C6(C)CC6)c5=O)cc4)CC3)nc21] |
| 79 | 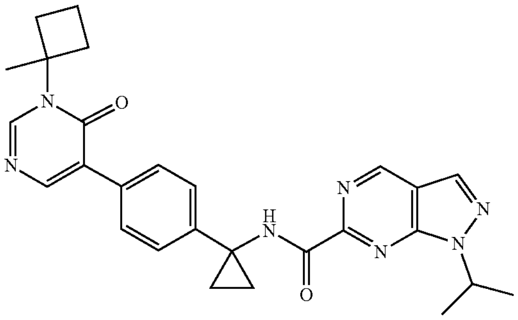 [SMILES: CC(C)n1ncc2cnc(C(=O)NC3(c4ccc(-c5cncn(C6(C)CCC6)c5=O)cc4)CC3)nc21] |
| 80 and 81 | 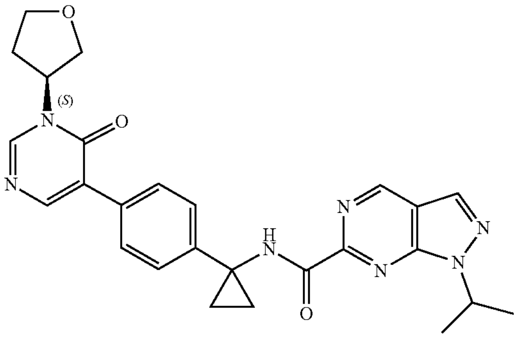 |

-continued
| Compound No. | Structure |
|---|---|
| | and<br>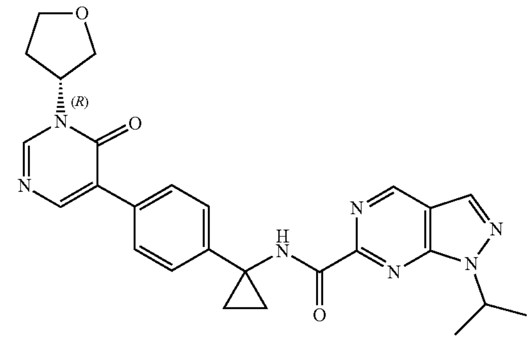 |
| 82 and 83 | 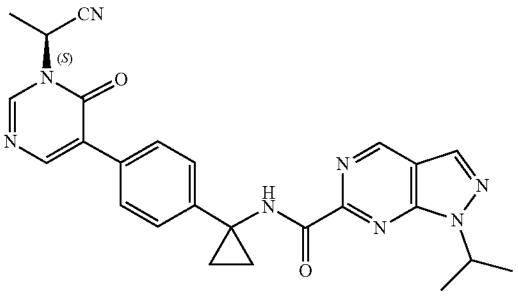<br>and<br>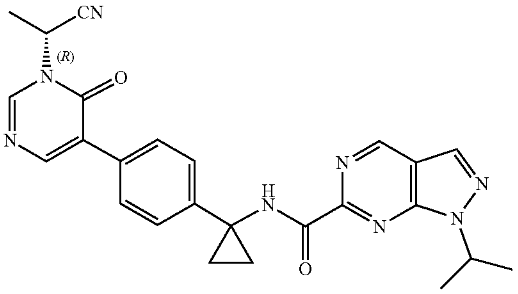 |
| 84 and 85 | 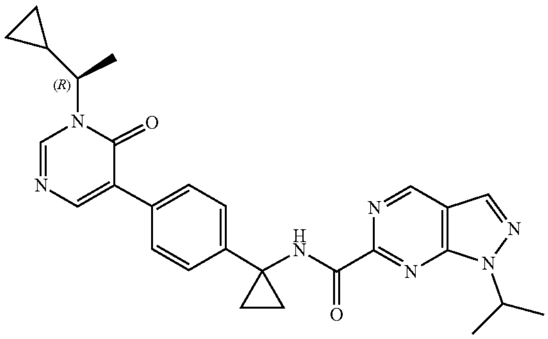 |

-continued
| Compound No. | Structure |
|---|---|
| | and |
| | 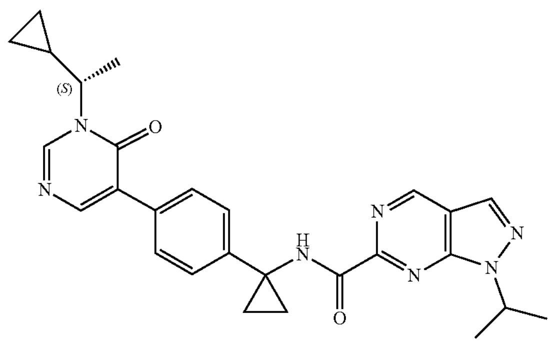 |
| 86 | 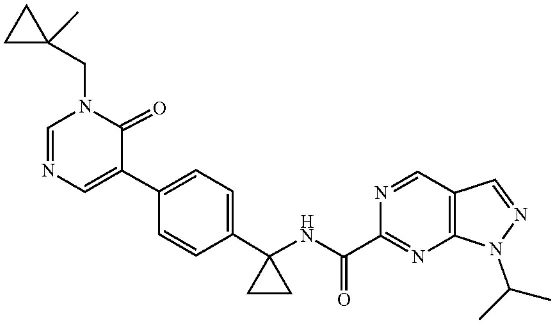 [SMILES: CC(C)n1ncc2cnc(C(=O)NC3(c4ccc(-c5cncn(CC6(C)CC6)c5=O)cc4)CC3)nc21] |
| 87 and 88 | 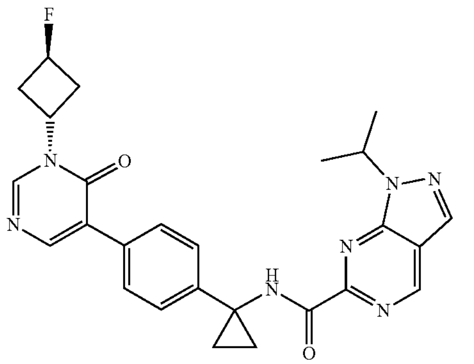 |
| | and |
| | 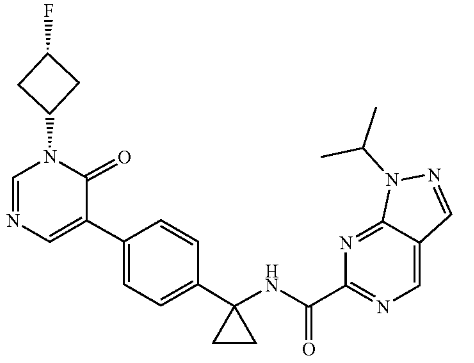 |

-continued
| Compound No. | Structure |
|---|---|
| 89 and 90 | 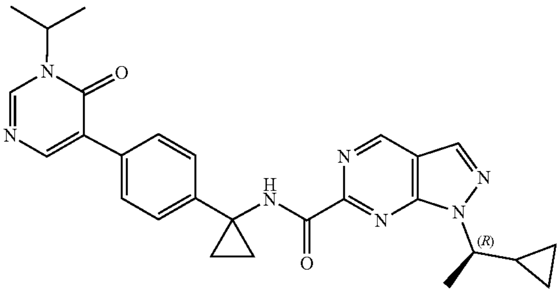 and 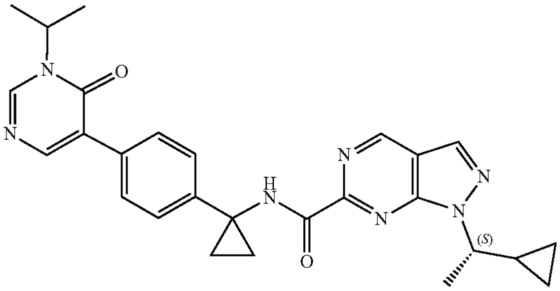 |
| 91 | 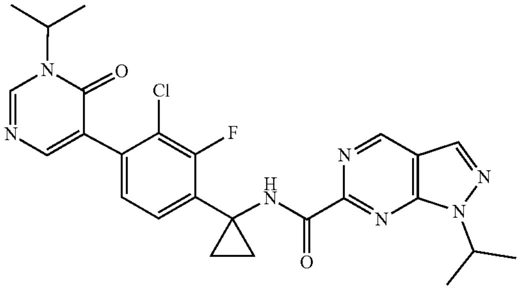 [SMILES: CC(C)n1cncc(-c2ccc(C3(NC(=O)c4ncc5cnn(C(C)C)c5n4)CC3)c(F)c2Cl)c1=O] |
| 92 | 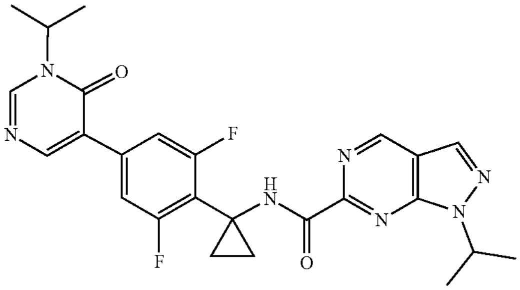 [SMILES: CC(C)n1cncc(-c2cc(F)c(C3(NC(=O)c4ncc5cnn(C(C)C)c5n4)CC3)c(F)c2)c1=O] |
| 93 | 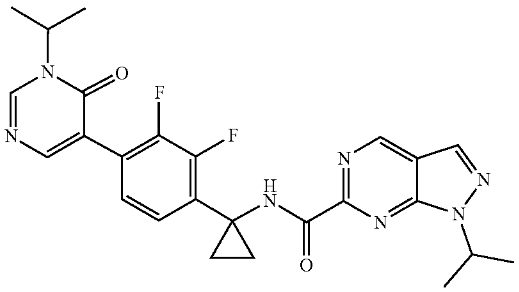 [SMILES: CC(C)n1cncc(-c2ccc(C3(NC(=O)c4ncc5cnn(C(C)C)c5n4)CC3)c(F)c2F)c1=O] |

-continued

| Compound No. | Structure |
|---|---|
| 94 | 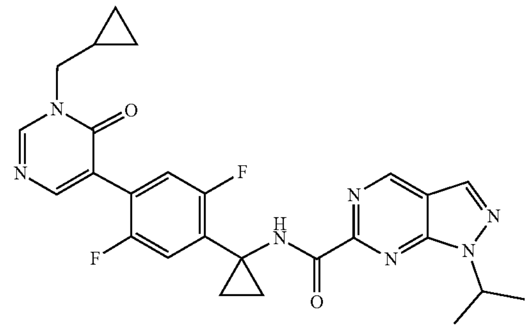 [SMILES: CC(C)n1ncc2cnc(C(=O)NC3(c4cc(F)c(-c5cncn(CC6CC6)c5=O)cc4F)CC3)nc21] |
| 95 | 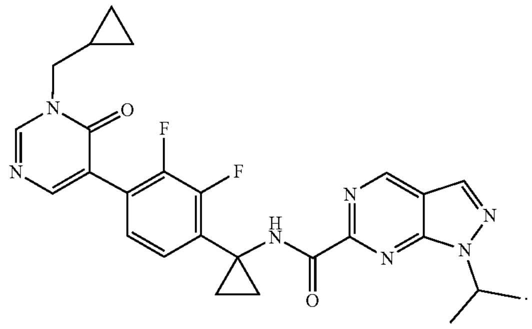 [SMILES: CC(C)n1ncc2cnc(C(=O)NC3(c4ccc(-c5cncn(CC6CC6)c5=O)c(F)c4F)CC3)nc21] |

Embodiment 16. A pharmaceutical composition, comprising the compound or a pharmaceutically acceptable salt thereof according to any one of embodiments 1-15, and optionally comprising a pharmaceutically acceptable carrier.

Embodiment 17. A method of in vivo or in vitro inhibiting the activity of RIPK1, comprising contacting RIPK1 with an effective amount of the compound or a pharmaceutically acceptable salt thereof according to any one of embodiments 1-15.

Embodiment 18. A method of treating a disease partially or completely mediated by RIPK1 in a subject, comprising administering to the subject an effective amount of the compound or a pharmaceutically acceptable salt thereof according to any one of embodiments 1-15.

Embodiment 19. The method according to embodiment 18, wherein the disease is chosen from an autoimmune disease, an inflammatory disease, a neurodegenerative disease and cancer.

Embodiment 20. The compound or a pharmaceutically acceptable salt thereof according to any one of embodiments 1-15, for use as a medicament.

Embodiment 21. The compound or a pharmaceutically acceptable salt thereof according to any one of embodiments 1-15, for use in the treatment of a disease partially or completely mediated by RIPK1 in a subject.

Embodiment 22. The compound or a pharmaceutically acceptable salt thereof according to embodiment 21, wherein the disease is chosen from an autoimmune disease, an inflammatory disease, a neurodegenerative disease and cancer.

Embodiment 23. Use of the compound or a pharmaceutically acceptable salt thereof according to any one of embodiments 1-15 in the manufacture of a medicament for treating a disease partially or completely mediated by RIPK1 in a subject.

Embodiment 24. The use according to embodiment 23, wherein the disease is chosen from an autoimmune disease, an inflammatory disease, a neurodegenerative disease and cancer.

Embodiment 25. A pharmaceutical combination, comprising the compound or a pharmaceutically acceptable salt thereof according to any one of embodiments 1-15, and at least one additional therapeutic agent.

Embodiment 26. The pharmaceutical combination according to embodiment 25, wherein the therapeutic agent is an anti-inflammatory agent or an anti-neoplastic agent; preferably, the anti-neoplastic agent is chosen from a radiotherapeutic agent, a chemotherapeutic agent, an immunotherapeutic agent and a targeted therapeutic agent.

The diseases partially or completely mediated by RIPK1 described herein can be more specifically selected from multiple sclerosis, systemic scleroderma, inflammatory bowel diseases (including Crohn's disease, ulcerative colitis), psoriasis, atopic dermatitis, asthma, chronic obstructive pulmonary disease, Behcet's disease, rheumatoid arthritis, spinal arthritis, osteoarthritis, systemic juvenile idiopathic arthritis (SoJIA), retinitis pigmentosa, retinal degeneration, age-related macular degeneration, pancreatitis, ischemia reperfusion injury of parenchymatous organs, organ-graft rejection, septicemia, systemic inflammatory response syndrome, chemotherapy drugs induced organ injury, non-alcoholic fatty liver disease, alcohol fatty liver disease, atherosclerosis, Gaucher's Disease, Huntington's disease, Alzheimer's disease, Parkinson's disease, amyotrophic lateral sclerosis (ALS) and spinal muscular atrophy (SMA).

The autoimmune disease or inflammatory disease described herein can be more specifically chosen from multiple sclerosis, systemic scleroderma, inflammatory bowel diseases (including Crohn's disease, ulcerative colitis), psoriasis, atopic dermatitis, asthma, chronic obstructive pulmonary disease, Behcet's disease, rheumatoid arthritis, spinal arthritis, osteoarthritis, systemic juvenile idiopathic arthritis (SoJIA), ischemia reperfusion injury of parenchymatous organs, organ-graft rejection, septicemia, systemic inflammatory response syndrome, systemic lupus erythematosus and autoimmune nephritis.

The neurodegenerative diseases described herein can be more specifically chosen from Parkinson's disease (PD), multiple system atrophy (MSA), Alzheimer's disease (AD), frontotemporal lobar dementia, Huntington's disease (HD), corticobasal degeneration, spinocerebellar ataxia (SCA), amyotrophic lateral sclerosis (ALS), spinal muscular atrophy (SMA), hereditary motor and sensory neuropathy (CMT), etc.

The cancer described herein can be solid tumor or hematologic malignancy (e.g., leukemia, lymphoma or myeloma).

General Synthetic Methods

The compound of formula (I) or a pharmaceutically acceptable salt thereof described herein can be synthesized using commercially available materials, by methods known in the art, or methods disclosed in the application. The synthetic methods shown in routes 1 and 2 illustrate the general synthetic methods for preparing the compounds of the present invention.

Route 1

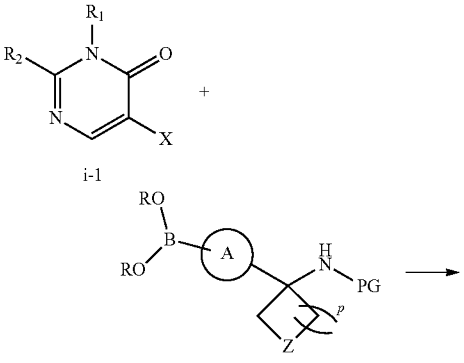

i-1 i-2

-continued

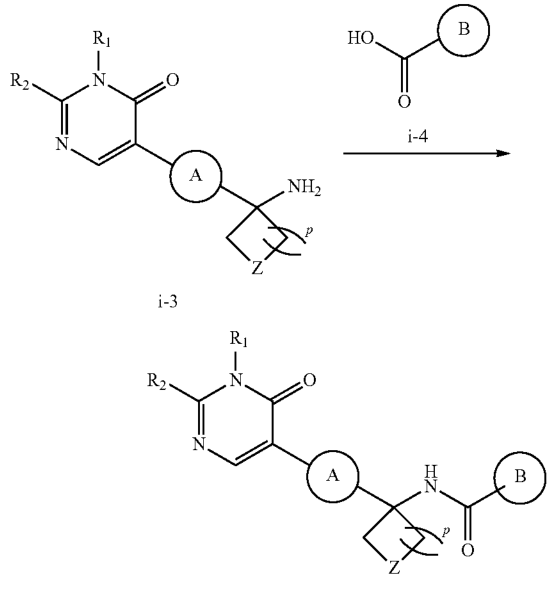

i-3 i-4

(I)

As shown in route 1, a compound of formula i-1 is subjected to coupling reaction and deprotection reaction with a compound of formula i-2 to give an amino compound of formula i-3, which is subjected to condensation reaction with a carboxylic acid compound of formula i-4 to give a compound of formula (I), wherein $R_1$, $R_2$, Z, p,

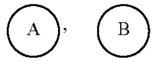

are as defined above; X is halogen; PG is a protecting group; $B(OR)_2$ is boronic acid or borate.

Route 2

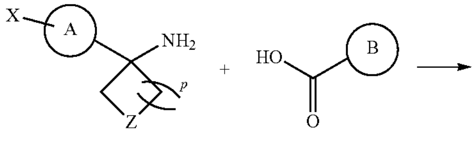

ii-1 ii-2

-continued

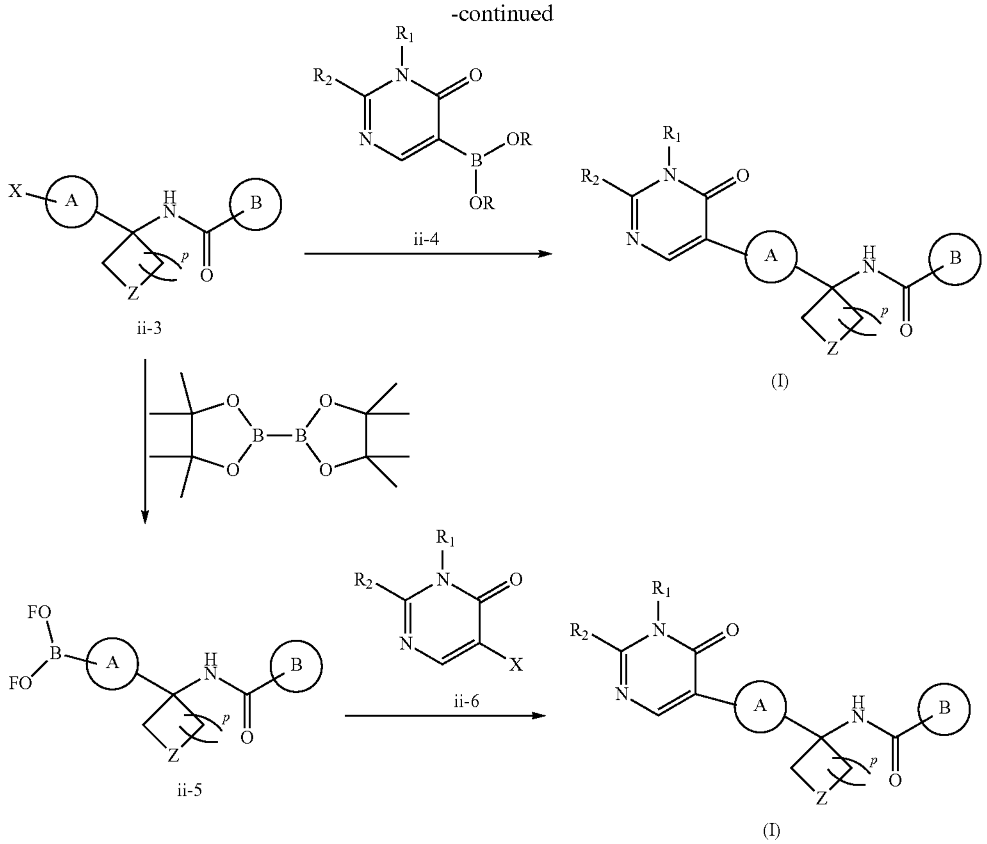

As shown in route 2, a compound of formula ii-1 is subjected to condensation reaction with a compound of formula ii-2 to give a compound of formula ii-3, then which is subjected to coupling reaction with boronic acid or borate of formula ii-4 to give the compound of formula (I); or the compound of formula ii-3 is reacted with bis(pinacolato) diboron to give a compound of formula ii-5, then which is subjected to coupling reaction with a halogenated compound of formula ii-6 to give the compound of formula (I), wherein $R_1$, $R_2$, Z, p,

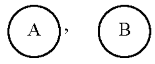

are as defined above; X is halogen; $B(OR)_2$ is boronic acid or borate.

The substituents of the compounds thus obtained can be further modified to provide other desired compounds. Synthetic chemistry transformations are described, for example, in R. Larock, *Comprehensive Organic Transformations*, VCH Publishers (1989); L. Fieser and M. Fieser, *Fieser and Fieser's Reagents for Organic Synthesis*, John Wiley and Sons (1994); *Encyclopedia of Reagents for Organic Synthesis*, edited by L. Paquette, John Wiley and Sons (1995) and subsequent editions thereof.

Before use, the compound of formula (I) or a pharmaceutically acceptable salt thereof described herein can be purified by column chromatography, high performance liquid chromatography, crystallization or other suitable methods.

Pharmaceutical Compositions and Utility

A composition comprising the compound of formula (I) or a pharmaceutically acceptable salt thereof described herein can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, pills, powder, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (e.g., Tween 80) and suspending agents. The sterile injectable composition can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, and natural pharmaceutically acceptable oils, such as olive oil or castor oil, especially in their polyoxyethylated versions, are often used in the preparation of an injectable composition. These oil solutions or suspensions can also contain a long-chain alcohol diluent or dispersant or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compound of formula (I) or a pharmaceutically acceptable salt thereof described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

In some embodiments, the compound of formula (I) or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a tablet. In some embodiments, the compound of formula (I) or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

Suitable in vitro assays can be used to evaluate the practical utility of the compound of formula (I) or a pharmaceutically acceptable salt thereof described herein in inhibiting the activity of RIPK1. The compound of formula (I) or a pharmaceutically acceptable salt thereof described herein can further be examined for the utility in treating autoimmune diseases, inflammatory diseases, neurodegenerative diseases or cancers by in vivo assays. For example, the compound of formula (I) or a pharmaceutically acceptable salt thereof described herein can be administered to an animal (e.g., a mouse model) having an autoimmune disease or an inflammatory disease and its therapeutic effects can be accessed. If the pre-clinical results are successful, the dosage range and administration route for animals, such as humans, can be projected.

The compound of formula (I) or a pharmaceutically acceptable salt thereof described herein can be used to achieve a beneficial therapeutic or prophylactic effect, for example, in subjects with an autoimmune disease or inflammatory disease.

The term "autoimmune disease" refers to a disease or disorder arising from or directed against an individual's own tissues or organs, or a co-segregate or manifestation thereof, or resulting condition therefrom. Examples of autoimmune diseases include, but are not limited to: chronic obstructive pulmonary disease (COPD), allergic rhinitis, lupus erythematosus, myasthenia gravis, multiple sclerosis (MS), rheumatoid arthritis (RA), collagen-induced arthritis, psoriasis, inflammatory bowel disease (IBD), asthma, idiopathic thrombocytopenic purpura (ITP), and myeloproliferative disease, such as myelofibrosis, post-polycythemia vera/essential thrombocytosis myelofibrosis (post-PV/ET myelofibrosis).

The term "inflammatory disease" or "inflammatory disorder" refers to a pathological state that leads to inflammation, especially due to neutrophil chemotaxis. Non-limiting examples of inflammatory diseases include systemic inflammation and local inflammation, inflammation associated with immunosuppression, organ-graft rejection, allergic disease, inflammatory skin disease (including psoriasis and atopic dermatitis); systemic scleroderma and sclerosis; reactions associated with inflammatory bowel diseases (IBD, such as Crohn's disease and ulcerative colitis); ischemia reperfusion injury, including reperfusion injury of tissue caused by surgery, myocardial ischemia, such as myocardial infarction, cardiac arrest, reperfusion after heart operation and abnormal contractile response of coronary vessel after percutaneous transluminal coronary angioplasty, surgical tissue reperfusion injury of stroke and abdominal aortic aneurysm; cerebral edema secondary to stroke; cranial trauma, and hemorrhagic shock; asphyxia; adult respiratory distress syndrome; acute lung injury; Behcet's disease; dermatomyositis; polymyositis; multiple sclerosis (MS); dermatitis; meningitis; encephalitis; uveitis; osteoarthritis; lupus nephritis; autoimmune disease such as rheumatoid arthritis (RA), Sjorgen's syndrome, and vasculitis; diseases involving leukopedesis; central nervous system (CNS) inflammatory disease and multiple organ injury syndrome secondary to septicemia or trauma; alcoholic hepatitis; bacterial pneumonia; antigen-antibody complex mediated disease, including glomerulonephritis; pyaemia; sarcoidosis; immunopathologic responses to tissue/organ transplantation; lung inflammation, including pleurisy, alveolitis, vasculitis, pneumonia, chronic bronchitis, bronchiectasia, diffuse pantothcnic bronchiolitis, hypersensitivity pneumonitis, idiopathic pulmonary fibrosis (IPF), cystic fibrosis, etc. Preferably indications include, but are not limited to, chronic inflammation, autoimmune diabetes, rheumatoid arthritis (RA), rheumatoid spondylitis, gouty arthritis and other arthrosis conditions, multiple sclerosis (MS), asthma, systemic lupus erythematosus, adult respiratory distress syndrome, Behcet's disease, psoriasis, chronic pulmonary inflammatory disease, graft versus host reaction, Crohn's disease, ulcerative colitis, inflammatory bowel disease (IBD), Alzheimer's disease and pyresis, and any diseases associated with inflammation and related conditions.

In some embodiments, the autoimmune disease or inflammatory disease is chosen from multiple sclerosis, systemic scleroderma, inflammatory bowel diseases, Crohn's disease, ulcerative colitis, psoriasis, atopic dermatitis, asthma, chronic obstructive pulmonary disease, Behcet's disease, rheumatoid arthritis, spinal arthritis, osteoarthritis, systemic juvenile idiopathic arthritis (SoJIA), ischemia reperfusion injury of parenchymatous organs, organ-graft rejection, septicemia, systemic inflammatory response syndrome, systemic lupus erythematosus and autoimmune nephritis.

The compound of formula (I) or a pharmaceutically acceptable salt thereof described herein can be used to achieve a beneficial therapeutic or prophylactic effect, for example, in subjects with neurodegenerative disease.

The term "neurodegenerative diseases" refers to degenerative diseases or disorders of the nervous system caused by neuronal degeneration and apoptosis. Examples of neurodegenerative diseases include, but are not limited to: Parkinson's disease (PD), multiple system atrophy, Alzheimer's disease (AD), frontotemporal lobar dementia, Huntington's disease (HD), corticobasal degeneration, spinocerebellar ataxia, amyotrophic lateral sclerosis (ALS), spinal muscular atrophy (SMA), hereditary motor and sensory neuropathy (CMT), etc.

The compound of formula (I) or a pharmaceutically acceptable salt thereof described herein can be used to achieve a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies. The term "cancer" encompasses diseases of skin, tissues, organs, bone, cartilage, blood, and vessels. The term "cancer" encompasses primary cancer, and further metastatic cancer.

Non-limiting examples of solid tumors include pancreatic cancer; bladder cancer; colorectal cancer; breast cancer, including metastatic breast cancer; prostate cancer, including androgen-dependent and androgen-independent prostate cancer; testicular cancer; renal cancer, including, e.g., metastatic renal cell carcinoma; urothelial carcinoma; liver cancer; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; endometrial cancer; gastric cancer; esophageal cancer; head and neck cancer, including, e.g., squamous cell carcinoma of the head and neck; skin cancer, including, e.g., melanoma and basal carcinoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; sarcoma, including, e.g., Kaposi's sarcoma; adrenal carcinoma; mesothelial carcinoma; choriocarcinoma; muscle carcinoma; connective tissue carcinoma; and thyroid carcinoma.

Non-limiting examples of hematologic malignancies include acute myelogenous leukemia (AML); chronic myelogenous leukemia (CML), including accelerated phase CML and CML blastic phase (CML-BP); acute lymphocytic leukemia (ALL); chronic lymphocytic leukemia (CLL); Hodgkin's lymphoma; non-Hodgkin's lymphoma (NHL); follicular lymphoma; mantle cell lymphoma (MCL); B-cell lymphoma; T-cell lymphoma; diffuse large B-cell lymphoma (DLBCL); multiple myeloma (MM); Waldenstrom's macroglobulinemia; myelodysplastic syndrome (MDS), including refractory anemia (RA), refractory anemia with ringed siderblast (RARS), refractory anemia with excess blast (RAEB) and refractory anemia with excess blast in transformation (RAEB-T); and myeloproliferative syndrome.

In addition, the compound of formula (I) (e.g., the compound of formula (I-1) or a compound of any of the examples as described herein) or a pharmaceutically acceptable salt thereof described herein can be administered in combination with additional therapeutic agents, for treating the autoimmune disease, inflammatory disease or cancer. The additional therapeutic agents may be administered separately with the compound of formula (I) or a pharmaceutically acceptable salt thereof described herein or included with such an ingredient in a pharmaceutical composition according to the disclosure, such as a fixed-dose combination drug product. In some embodiments, the additional therapeutic agents are those that are known or discovered to be effective in the treatment of a disease partially or completely mediated by RIPK1, such as another RIPK1 inhibitor or a compound active against another target associated with the particular disease. The combination may serve to increase efficacy (e.g., by including in the combination a compound potentiating the potency or effectiveness of the compound of formula (I) or a pharmaceutically acceptable salt thereof described herein), decrease one or more side effects, or decrease the required dose of the compound of formula (I) or a pharmaceutically acceptable salt thereof described herein.

In some embodiments, the compound of formula (I) (e.g., the compound of formula (I-1) or a compound of any of the examples as described herein) or a pharmaceutically acceptable salt thereof described herein can be administered in combination with anti-inflammatory agents.

Examples of anti-inflammatory agent include, but are not limited to, adrenocortical hormones (such as fluticasone propionate, beclometasone dipropionate, momestasone furoate, triamcinolone acetonide or budesonide), disease modifying agents (such as antimalarial drugs, methotrexate, sulfasalazine, masalazine, azathioprine, 6-mercaptopurine, metronidazole, D-penicillamine), non-steroidal anti-inflammatory drugs (such as acetaminophen, aspirin, sodium salicylate, cromoglycate sodium, magnesium salicylate, choline magnesium trisalicylate, salsalate, ibuprofen, naproxen, diclofenac, diflunisal, etodolac, fenoprofen calcium, flurbiprofen, piroxicam, indomethacin, ketoprofen, ketorolac tromethamine, meclofenamic acid, meclofenamate sodium, mefenamic acid, nabumetone, oxaprozin, phenyl butyl nitrone (PBN), sulindac or tolmetin), COX-2 inhibitors, cytokine synthesis/release inhibitors (such as anti-cytokine antibody, anti-cytokine receptor antibody, etc.).

In some embodiments, the compound of formula (I) (e.g., the compound of formula (I-1) or a compound of any of the examples as described herein) or a pharmaceutically acceptable salt thereof described herein can be administered in combination with anti-neoplastic agents. The term "anti-neoplastic agent" as used herein refers to any agent that is administered to a subject suffering from cancer for the purposes of treating the cancer, includes, but is not limited to a radiotherapeutic agent, a chemotherapeutic agent, an immunotherapeutic agent, a targeted therapeutic agent, and the like.

Non-limiting examples of chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; nucleoside mimetics (e.g., 5-fluorouracil, capecitabine, gemcitabine, fludarabine, cytarabine, azacitidine, mercaptopurine, thioguanine, pentostatin, and hydroxyurea); paclitaxel, docetaxel, and related analogs; vincristine, vinblastin, and related analogs; thalidomide and related analogs (e.g., CC-5013 and CC-4047).

Non-limiting examples of the immunotherapeutic agents or the targeted therapeutic agents include MEK inhibitor, RAF inhibitor, mTOR inhibitor, PAK inhibitor, CDK inhibitor, VEGFR inhibitor, PARP inhibitor, ERBB inhibitor, PI3K inhibitor, AKT inhibitor, IDO inhibitor, A2AR inhibitor, autophagy inhibitor, immune checkpoint inhibitor, such as PD-1 inhibitor, PD-L1 inhibitor, etc. For example, Trametinib, Cobimetinib, Vemurafenib, Dabrafenib, Rapamycin, Temsirolimus, Everolimus, Palbociclib, Ribociclib, Fruquintinib, Olaparib, Niraparib, Neratinib, Chloroquine, Hydroxychloroquine, LXH254, Selumetinib, LY3214996, Abemaciclib, P1446A-05 (Voruciclib), LGX818 (Encorafenib), ARRY-162 (Binimetinib), Gefitinib, Imatinib mesylate, Cetuximab, Trastuzumab, Rituximab, Panitumumab, BYL719 (Alpelisib), Bevacizumab, Pembrolizumab, Atezolizumab, PDR001 (Spartalizumab), Durvalumab, Nivolumab, Avelumab, Libtayo (Cemiplimab), Tislelizumab, JS001, Sintilimab, Camrelizumab and the like.

EXAMPLES

The examples below are intended to be purely exemplary and should not be considered to be limiting in any way. Efforts have been made to ensure the accuracy with respect to numbers used (e.g., amounts, temperature, etc.), but the POSITA should understand that some experimental errors and deviations should be accounted for. Unless indicated otherwise, parts are parts by weight, temperature is in degrees Centigrade, and pressure is at or near atmospheric. All MS data were determined by Agilent 6120 or Agilent 1100. All NMR data were generated using a Varian 400 MR machine. All reagents, except intermediates, used in this invention are commercially available. All compound names except the reagents are generated by Chemdraw 18.2.

If there is any atom with empty valence(s) in any one of the structures disclosed herein, the empty balance(s) is (are) the hydrogen atom(s) which is (are) omitted for convenience purpose.

In the present application, in the case of inconsistency of the name and structure of a compound, when the two of which are both given for the compound, it is subject to the structure of the compound, unless the context shows that the structure of the compound is incorrect and the name is correct.

In the following examples, the abbreviations are used:

AcOH Acetic acid
$AgNO_3$ Silver nitrate
$BF_3OEt_2$ Boron trifluoride diethyl etherate
$CDCl_3$ Deuterated chloroform
$Cs_2CO_3$ Cesium carbonate
$Cu(OAc)_2$ Copper acetate
DBU 1,8-diazabicyclo-undec-7-ene
DCM or $CH_2Cl_2$ Dichloromethane
DCE 1,2-dichloroethane
DIEA N,N-diisopropylethylamine
DIAD Diisopropyl azodicarboxylate
DEA Diethylamine
DMF N,N-dimethylformamide
DMSO Dimethyl sulfoxide
EA Ethyl acetate
EtOH Ethanol
HATU O-(7-azabenzotriazole-1-yl)-N, N, N', N'-tetramethyluronium hexafluorophosphate
IPA Isopropanol
$K_2CO_3$ Potassium carbonate
KOAc Potassium acetate
LiOH Lithium hydroxide
MeOH Methanol
MeCN Acetonitrile
MeI Iodomethane
MeONa Sodium methoxide
NaOH Sodium hydroxide
NCS N-chlorosuccinimide
$NH_2NH_2$ Hydrazine
$NH_4SO_2O_8$ Ammonium persulphate
NMP N-methylpyrrolidone
$Pd(dppf)Cl_2$ [1,1'-bis(diphenylphosphino) ferrocene]palladium dichloride
$Pd(PPh_3)_4$ Tetra(triphenylphosphine)palladium
$PPh_3$ Triphenylphosphine
PE Petroleum ether
$POCl_3$ Phosphorus oxychloride
Pyridine Pyridine
$SOCl_2$ Thionyl chloride
$Ti(i\text{-}PrO)_4$ Titanium tetraisopropoxide
THF Tetrahydrofuran
TEA Triethylamine
TFA Trifluoroacetic acid
Tol Toluene
TLC Thin-layer chromatography
p-TLC Preparative thin-layer chromatography
$Zn(CN)_2$ Zinc cyanide

Example 1. Preparation of Intermediates and Compounds

Intermediate 1

5-chloro-4-isobutylpyrimidine-2-carboxylic acid

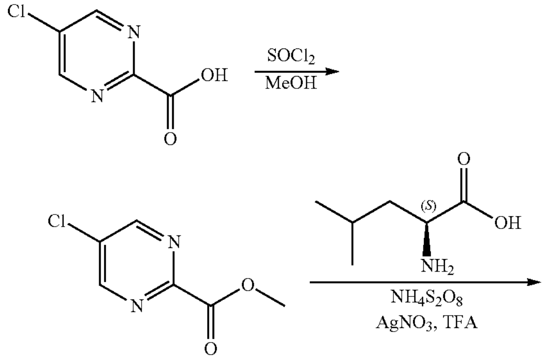

-continued

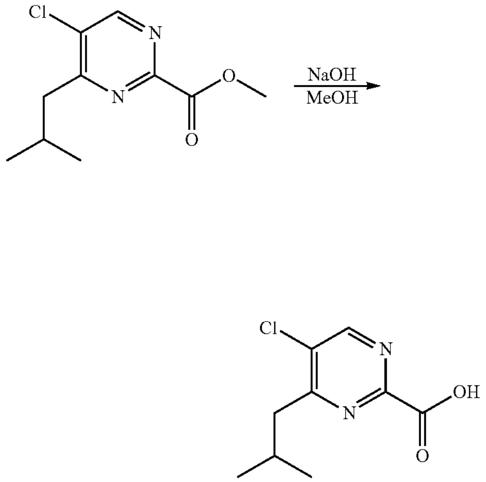

(A) methyl 5-chloropyrimidine-2-carboxylate

Methyl 5-chloropyrimidine-2-carboxylate (500 mg, 3.15 mmol) was dissolved in MeOH (20 mL), then $SOCl_2$ (0.5 mL) was added slowly. The solution was warmed to 80° C. and reacted overnight. TLC (PE:EA=5:1) showed that the reaction was completed. After cooling, the reaction solution was concentrated under reduced pressure and the residue was purified by flash column chromatography (eluting with gradient MeOH/$H_2O$=0%-100%) to give 500 mg of the product.

(B) methyl 5-chloro-4-isobutylpyrimidine-2-carboxylate

Methyl 5-chloropyrimidine-2-carboxylate (500 mg, 2.90 mmol), L-leucine (760 mg, 5.80 mmol) and $NH_4S_2O_8$ (3.04 g, 14.49 mmol) were dissolved in a mixed solvent of DCE (10 mL) and $H_2O$ (9 mL), then TFA (218 uL, 2.9 mmol) was added. The mixture was stirred at room temperature for about 1 minute. A solution of 2 mol/L $AgNO_3$ in $H_2O$ (1.45 mL, 2.90 mmol) was added in one portion. The mixture was warmed to 80° C. and reacted for 24 hours. After the reaction was completed, the reaction solution was cooled and concentrated under reduced pressure, and the residue was purified by flash column chromatography (eluting with gradient MeOH/$H_2O$=0%-100%) to give 80 mg of product. MS (m/z)=229 $[M+H]^+$.

(C) 5-chloro-4-isobutylpyrimidine-2-carboxylic acid

Methyl 5-chloro-4-isobutylpyrimidine-2-carboxylate (80 mg, 0.35 mmol) was dissolved in MeOH (5 mL), 2 mol/L NaOH in $H_2O$ (1.0 mL, 2.0 mmol) was added. The solution was reacted at room temperature for 2 hours. After the reaction was completed, 2 mol/L HCl aqueous solution was added until pH was about 7. The mixed solution was concentrated under reduced pressure, and the residue was purified by flash column chromatography (eluting with gradient MeOH/$H_2O$=0%-100%) to give 70 mg of the product. MS (m/z)=215 $[M+H]^+$.

Intermediate 2

5-bromo-2,3-dimethylpyrimidin-4(3H)-one

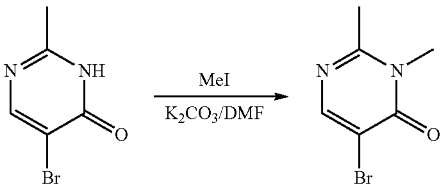

The mixture of 5-bromo-2-methylpyrimidin-4(3H)-one (756 mg, 4 mmol), iodomethane (568 mg, 4 mmol), and potassium carbonate (828 mg, 6 mmol) in DMF (5 mL) was stirred at room temperature under nitrogen atmosphere for 2 hours. After the reaction was completed, water (10 mL) was added to the reaction system, and the mixture was extracted with ethyl acetate (10 mL×3). The organic layer was washed with brine, dried over anhydrous sodium sulfate, filtered and concentrated. The residue was purified by column chromatography (eluting with gradient PE/EA=10%-50%) to obtain 500 mg of the product as pale yellow solid. MS (m/z)=203 $[M+H]^+$.

The following intermediates were prepared according to the procedure of Intermediate 2 using the corresponding materials and reagents under appropriate conditions that will be recognized by one skilled in the art.

| Intermediate No. | Structural formula | MS $(M + H)^+$ |
|---|---|---|
| 3 | 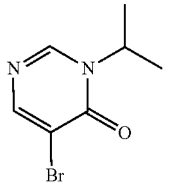 | 216.9 |
| 4 | 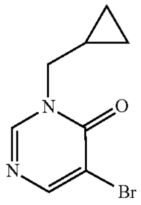 | 229, 231 $[M + 2H]^+$ |
| 5 | 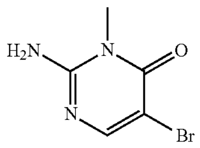 | 203.9 |
| 36 | 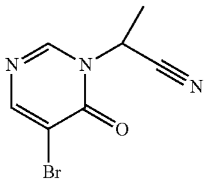 | 227.8, 229.8 $[M + 2H]^+$ |

Intermediate 6

(1-methyl-6-oxo-1,6-dihydropyrimidin-5-yl)boronic acid

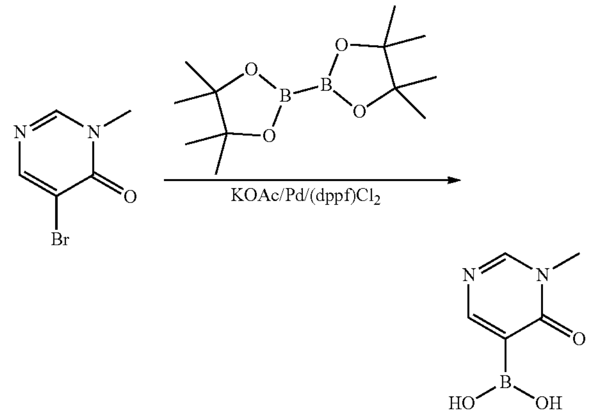

The mixture of 5-bromo-3-methylpyrimidin-4(3H)-one (1 g, 5.29 mmol), bis(pinacolato)diboron (2.02 g, 7.94 mmol), KOAc (1.56 g, 15.87 mmol), and Pd(dppf)$Cl_2$ (194 mg, 0.26 mmol) in dioxane (30 mL) was stirred at 120° C. under nitrogen atmosphere for 2 hours. The solvent was removed. The residue was purified by flash column chromatography (eluting with gradient MeOH/$H_2O$ (+0.1% HCOOH)=10%-80%) to give 525 mg of the product as white solid. MS (m/z)=155 $[M+H]^+$.

Intermediate 7

1-benzyl-1H-1,2,4-triazole-3-carboxylic acid

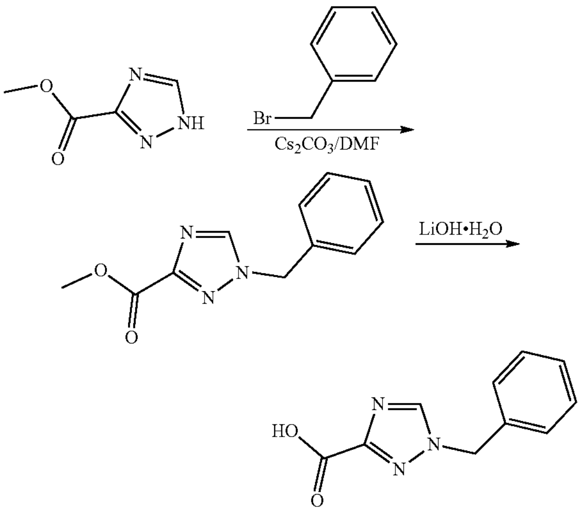

(A) methyl 1-benzyl-1H-1,2,4-triazole-3-carboxylate

The mixture of methyl 1H-1,2,4-triazole-3-carboxylate (2 g, 15.7 mmol), (bromomethyl)benzene (2 g, 15.7 mmol), and $Cs_2CO_3$ (7.68 g, 15.7 mmol) in DMF (100 mL) was stirred at room temperature under nitrogen atmosphere for 5 hours. After the reaction was completed, water (20 mL) was added to the reaction system, and the mixture was extracted with ethyl acetate (20 mL×3). The organic layer was washed with brine, dried over anhydrous sodium sulfate, filtered and concentrated. The residue was purified by column chromatography (eluting with gradient PE/EA=10%-80%) to obtain 0.8 g of product as white solid. MS (m/z)=218 $[M+H]^+$.

(B) 1-benzyl-1H-1,2,4-triazole-3-carboxylic acid

Methyl 1-benzyl-1H-1,2,4-triazole-3-carboxylate (0.8 g, 3.68 mmol) was dissolved in THF (20 mL), then a solution of LiOH (0.46 g, 11.04 mmol) in water (5 mL) was added. The mixture was stirred at room temperature for 1 hour and then THF was removed. 2N HCl was added to adjust pH=6. Then the solid was collected by filtration. The solid was washed with ice water 3 times. The filter cake was dried to afford 0.5 g of the product. MS (m/z)=204 $[M+H]^+$.

Intermediate 8 ethyl 5-phenyl-6,7-dihydro-5H-pyrrolo[1,2-b][1,2,4]triazole-2-carboxylate

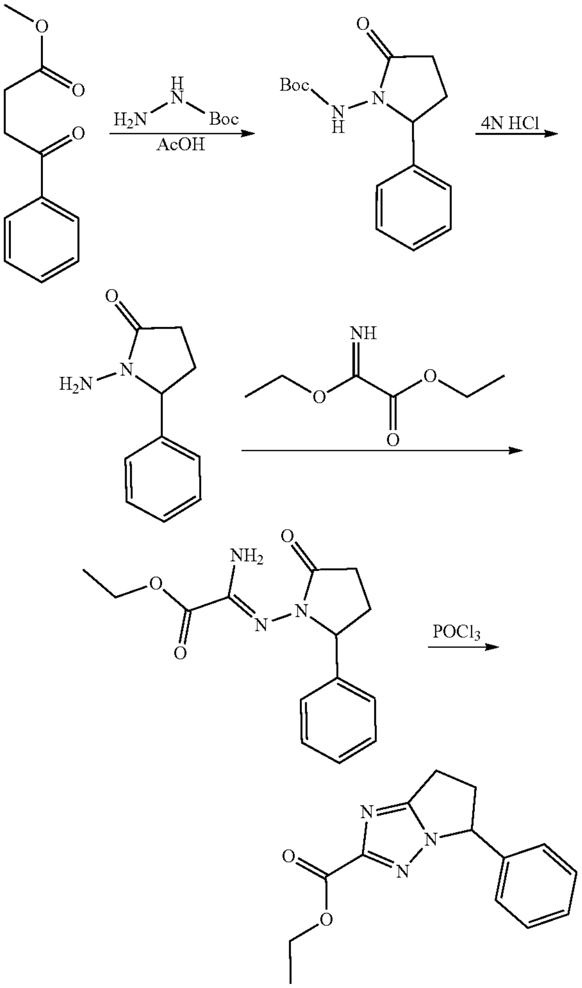

(A) tert-butyl (2-oxo-5-phenylpyrrolidin-1-yl)carbamate

To a solution of methyl 4-oxo-4-phenylbutanoate (5 g, 26.03 mmol) in AcOH (15 mL) was added tert-butyl hydrazinecarboxylate (5.15 g, 39.04 mmol) at room temperature. The reaction mixture was reacted at 40° C. overnight, then sodium cyanoborohydride (2.45 g, 39.04 mmol) was added, and the mixture was reacted at the temperature for 4 hours. After the reaction was completed, the mixture was cooled to room temperature and concentrated under reduced pressure. The residue was purified by flash column chromatography (eluting with gradient $MeOH/H_2O$=0%-100%) to give 4.2 g of target product. MS (m/z)=221 $[M-56]^+$.

(B) 1-amino-5-phenylpyrrolidin-2-one

To a solution of tert-butyl (2-oxo-5-phenylpyrrolidin-1-yl)carbamate (4.2 g, 15.20 mmol) in MeOH (10 mL) was added 4N HCl (11.4 mL, 45.61 mmol) at room temperature. The reaction mixture was reacted at 50° C. for 2 hours. After the reaction was completed, the mixture was cooled to room temperature and concentrated under reduced pressure to give 3.1 g of the target product. MS (m/z)=177 $[M+H]^+$.

(C) ethyl (Z)-2-amino-2-((2-oxo-5-phenylpyrrolidin-1-yl)imino)acetate

To a solution of 1-amino-5-phenylpyrrolidin-2-one (2.5 g, 14.20 mmol) in EtOH (10 mL) was added ethyl 2-ethoxy-2-imino-acetate (6.17 g, 42.6 mmol) at room temperature. The reaction mixture was heated to reflux and reacted for 8 hours. After the reaction was completed, the mixture was cooled to room temperature and concentrated under reduced pressure. The residue was purified by flash column chromatography (eluting with gradient $MeOH/H_2O$=0%-100%) to give 3.2 g of the target product. MS (m/z)=276 $[M+H]^+$.

(D) ethyl 5-phenyl-6,7-dihydro-5H-pyrrolo[1,2-b][1,2,4]triazole-2-carboxylate

To a solution of ethyl (Z)-2-amino-2-((2-oxo-5-phenylpyrrolidin-1-yl)imino)acetate (3.2 g, 11.63 mmol) in DCE (10 mL) was added $POCl_3$ (3 mL) at room temperature. The reaction mixture was heated to 100° C. and reacted for 8 hours. After the reaction was completed, the mixture was cooled to room temperature and concentrated under reduced pressure. The residue was purified by flash column chromatography (eluting with gradient $MeOH/H_2O$=0%-100%) to give 1.8 g of the target product. MS (m/z)=258 $[M+H]^+$.

Intermediate 9

5-bromo-3-cyclopropylpyrimidin-4(3H)-one

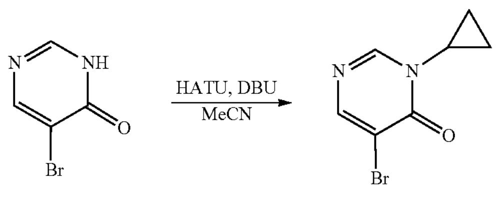 [SMILES: "MeCN" ; O=c1[nH]cncc1Br ; O=c1c(Br)cncn1C1CC1]

To a solution of 5-bromopyrimidin-4(3H)-one (500 mg, 2.86 mmol), cyclopropanamine (136 mg, 2.38 mmol), and DBU (534 mg, 3.57 mmol) in MeCN (10 mL) was added HATU (1.2 g, 3.09 mmol). The reaction mixture was heated to 45° C. and reacted for 20 hours. After concentration under reduced pressure, the residue was purified by flash column chromatography (eluting with gradient $MeOH/H_2O$=0%-100%) to give 200 mg of the target product. MS (m/z)=216 $[M+H]^+$.

The following intermediates were prepared according to the procedure of Intermediate 9 using the corresponding materials and reagents under appropriate conditions that will be recognized by one skilled in the art.

| Intermediate No. | Structural formula | MS $(M + H)^+$ |
|---|---|---|
| 10 | 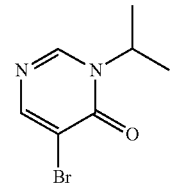 | 217.0 |
| 11 | 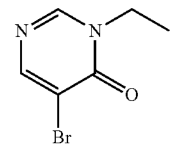 | 202.9 |
| 12 | 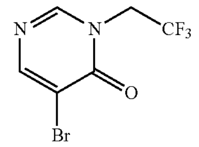 [SMILES: O=c1c(Br)cncn1CC(F)(F)F] | 256.9 |
| 13 | 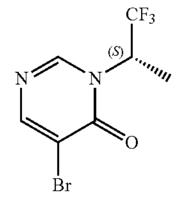 | 270.9 |
| 14 | 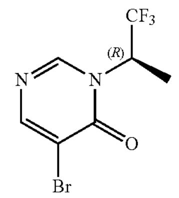 | 270.9 |
| 15 | 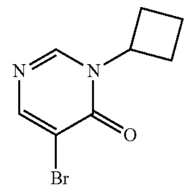 [SMILES: O=c1c(Br)cncn1C1CCC1] | 230.9 |
| 16 | 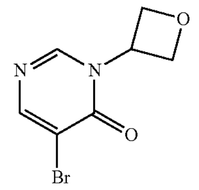 [SMILES: O=c1c(Br)cncn1C1COC1] | 231.0 |

-continued
| Intermediate No. | Structural formula | MS (M + H)+ |
|---|---|---|
| 17 | 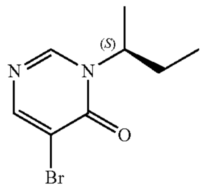 | 231.0 |
| 18 | 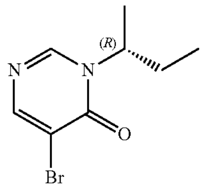 | 231.0 |
| 19 | 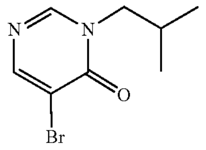 | 230.9 |
| 44 | 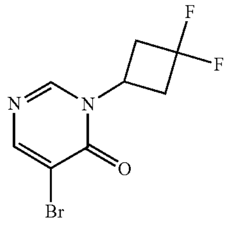 | 264.9, 266.9 [M + 2H]+ |
| 45 | 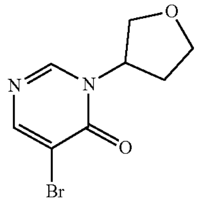 | 246.0, 248.0 [M + 2H]+ |
| 46 | 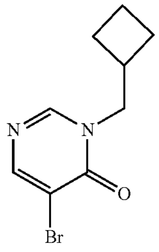 | 243.0, 245.0 [M + 2H]+ |
| 47 | 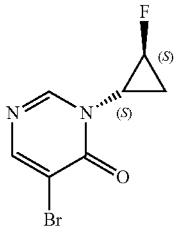 | 233.0, 235.0 [M + 2H]+ |
-continued
| Intermediate No. | Structural formula | MS (M + H)+ |
|---|---|---|
| 48 | 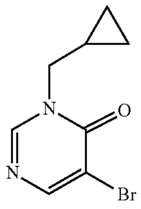 | 229, 231 [M + 2H]+ |
| 49 | 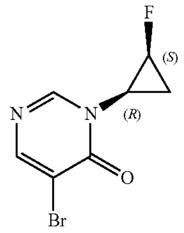 | 233.0, 235.0 [M + 2H]+ |
| 50 | 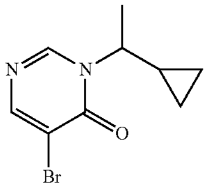 | 243.2, 245.2 [M + 2H]+ |
| 51 | 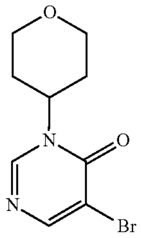 | 259.0, 261.0 [M + 2H]+ |
| 52 | 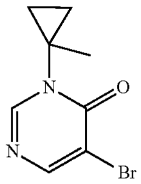 | 228.9, 230.9 [M + 2H]+ |
| 53 | 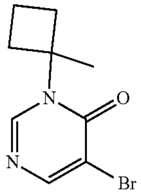 | 243.0, 245.0 [M + 2H]+ |
| 54 | 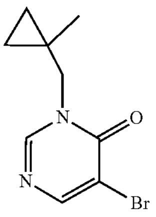 | 243.0, 245.0 [M + 2H]+ |

-continued

| Intermediate No. | Structural formula | MS $(M + H)^+$ |
|---|---|---|
| 55 | 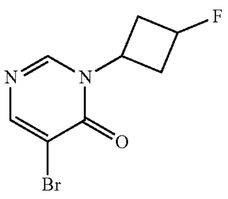 [SMILES: O=c1c(Br)cncn1C1CC(F)C1] | 247.0, 249.0 $[M + 2H]^+$ |

Intermediate 20 lithium 5-phenyl-6,7-dihydro-5H-pyrrolo[1,2-b][1,2,4]triazole-2-carboxylate

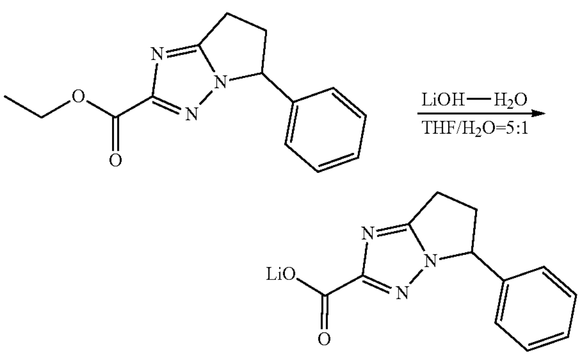

To a solution of ethyl 5-phenyl-6,7-dihydro-5H-pyrrolo[1,2-b][1,2,4]triazole-2-carboxylate (100 mg, 0.39 mmol) in THF (4 mL) was added the solution of lithium hydroxide monohydrate (49 mg, 1.17 mmol) in water (0.8 mL). The reaction mixture was reacted at room temperature for 2 hours. After concentration under reduced pressure, the residue was purified by flash column chromatography (eluting with gradient MeOH/$H_2O$=0%-100%) to give 92 mg of the target product. MS (m/z)=230 $[M-Li+2H]^+$.

The following intermediate was prepared according to the procedure of Intermediate 20 using Intermediate 7(A) as the raw material under appropriate conditions that will be recognized by one skilled in the art.

| Intermediate | Structural formula | MS $(M + H)^+$ |
|---|---|---|
| 21 | 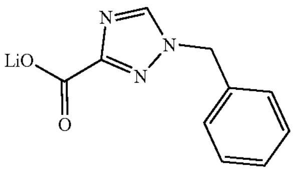 | 204.0 $[M - Li + 2H]^+$ |

Intermediate 22 lithium 5-(2,6-difluorobenzyl)-4H-1,2,4-triazole-3-carboxylate

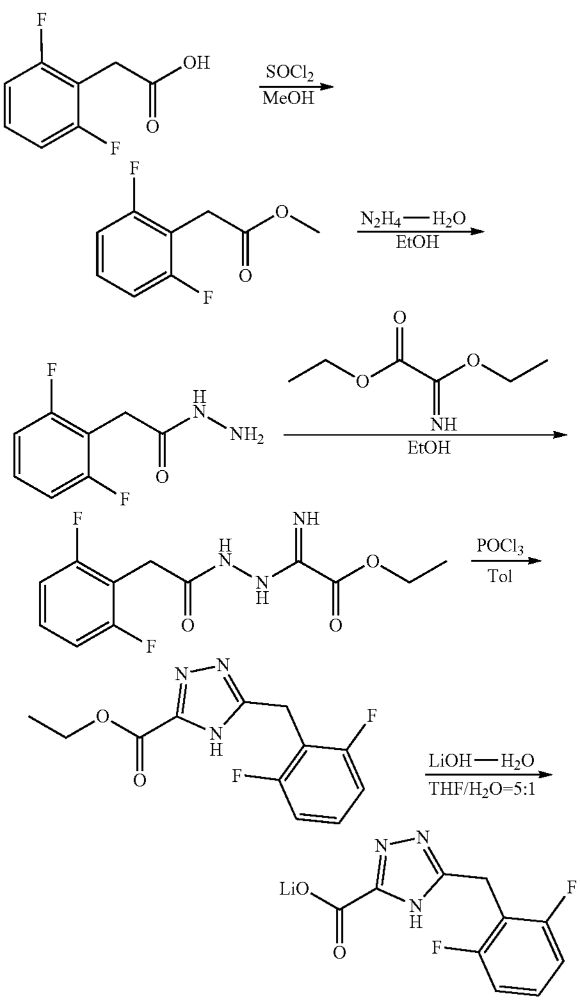

(A) methyl 2-(2,6-difluorophenyl)acetate

To a solution of 2-(2,6-difluorophenyl)acetic acid (1.0 g, 5.81 mmol) in methanol (15 mL) was added $SOCl_2$ (2 mL). The reaction mixture was heated to 50° C. and reacted for 2 hours, then concentrated under reduced pressure to give 1.08 g of the crude product. MS (m/z)=187 $[M+H]^+$.

(B) 2-(2,6-difluorophenyl)acetohydrazide

The mixture of methyl 2-(2,6-difluorophenyl)acetate (1.08 g, 5.81 mmol) and hydrazine hydrate (2 mL) in EtOH (10 mL) was heated to 70° C. and reacted for 4 hours, then cooled to room temperature. The precipitated solid was filtered and dried to give 700 mg of the target product. MS (m/z)=187 $[M+H]^+$.

(C) ethyl 2-(2-(2-(2,6-difluorophenyl)acetyl)hydrazineyl)-2-iminoacetate

The mixture of 2-(2,6-difluorophenyl)acetohydrazide (500 mg, 2.69 mmol) and ethyl 2-ethoxy-2-iminoacetate (390 mg, 2.69 mmol) in EtOH (10 mL) was heated to 70° C. and reacted for 4 hours, then cooled to room temperature. The precipitated solid was filtered and dried to give 730 mg of the target product. MS (m/z)=286 $[M+H]^+$.

(D) ethyl 5-(2,6-difluorobenzyl)-4H-1,2,4-triazole-3-carboxylate

To a solution of ethyl 2-(2-(2-(2,6-difluorophenyl)acetyl) hydrazineyl)-2-iminoacetate (315 mg, 1.10 mmol) in toluene (5 mL) was added $POCl_3$ (2 mL) dropwise. The reaction mixture was refluxed overnight. After concentration under reduced pressure, the residue was purified by flash column chromatography (eluting with gradient $MeOH/H_2O$=0%-100%) to give 235 mg of the target product. MS (m/z)=268 $[M+H]^+$.

(E) lithium 5-(2,6-difluorobenzyl)-4H-1,2,4-triazole-3-carboxylate

The target product was prepared according to the procedure of Intermediate 20 using ethyl 5-(2,6-difluorobenzyl)-4H-1,2,4-triazole-3-carboxylate as the raw material. MS (m/z)=240 $[M-Li+2H]^+$.

Intermediate 23

1-phenyl-1H-pyrazolo[3,4-d]pyrimidine-6-carboxylic acid

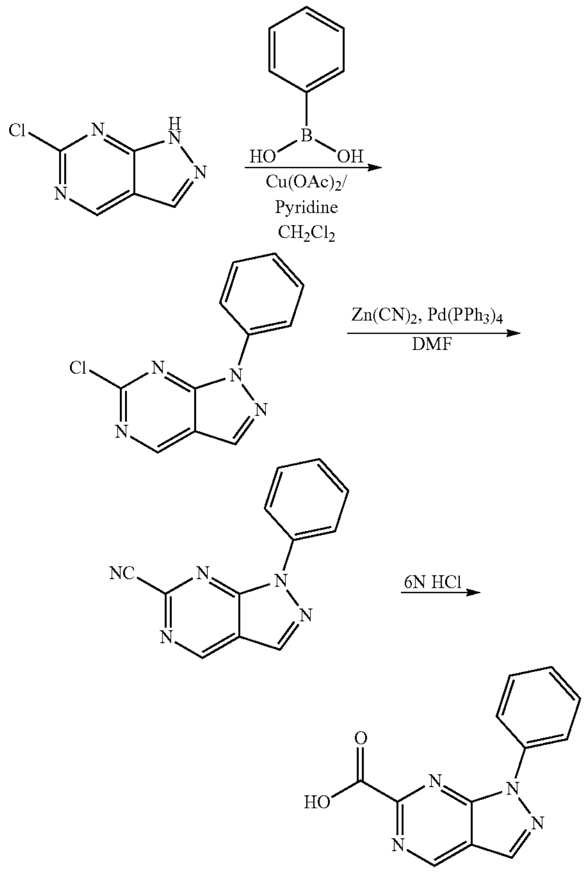

(A) 6-chloro-1-phenyl-1H-pyrazolo[3,4-d]pyrimidine

The mixture of 6-chloro-1H-pyrazolo[3,4-d]pyrimidine (1.6 g, 10.1 mmol), phenylboronic acid (2.5 g, 20.2 mmol), $Cu(OAc)_2$ (2.7 g, 15.2 mmol), and pyridine (1.6 g, 20.2 mmol) in DCE (15 mL) was heated to 80° C. and reacted overnight. After concentration under reduced pressure, the residue was purified by flash column chromatography (eluting with gradient $MeOH/H_2O$=0%-100%) to give 377 mg of the target product. MS (m/z)=231 $[M+H]^+$.

(B) 1-phenyl-1H-pyrazolo[3,4-d]pyrimidine-6-carbonitrile

The mixture of 6-chloro-1-phenyl-1H-pyrazolo[3,4-d]pyrimidine (377 mg, 1.63 mmol), $Zn(CN)_2$ (125 mg, 1.06 mmol), and $Pd(PPh_3)_4$ (94 mg, 0.082 mmol) in DMF (5 mL) was heated to 100° C. and reacted overnight. After concentration under reduced pressure, the residue was purified by flash column chromatography (eluting with gradient PE/EA=100%-0%) to give 335 mg of target product. MS (m/z)=222 $[M+H]^+$.

(C) 1-phenyl-1H-pyrazolo[3,4-d]pyrimidine-6-carboxylic acid

The mixture of 1-phenyl-1H-pyrazolo[3,4-d]pyrimidine-6-carbonitrile (335 mg, 1.52 mmol) in 6N HCl (2 mL) was heated to 100° C. and reacted for 4 hours. After concentration under reduced pressure, the residue was purified by flash column chromatography (eluting with gradient $MeOH/H_2O$=0%-100%) to give 36 mg of the target product. MS (m/z)=241 $[M+H]^+$.

Intermediate 26

1-(4-bromo-3-chlorophenyl)cyclopropan-1-amine

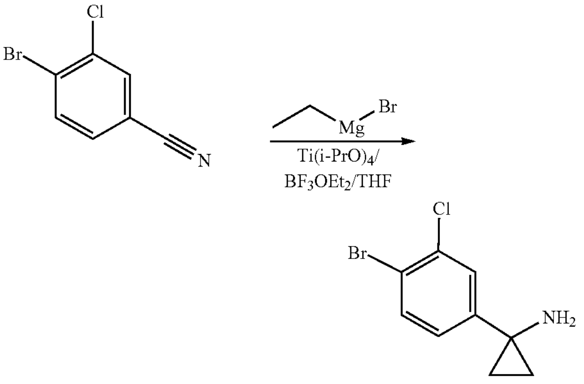

A solution of 4-bromo-3-chlorobenzonitrile (2 g, 9.3 mmol) and Titanium tetraisopropoxide (3.9 g, 13.95 mmol) in THF (40 mL) was stirred at room temperature under nitrogen atmosphere for 10 minutes. Ethylmagnesium bromide (6.2 mL, 18.6 mmol) was added at 0° C., and the mixture was stirred at 0° C. for 30 minutes, and then stirred at room temperature for 1 hour. A boron trifluoride diethyl etherate solution (2.64 g, 18.6 mmol) was added and stirred for 30 minutes, then diluted HCl (3 mL, 3 mmol) was added and stirred for 30 minutes. Then NaOH solution (10 mL, 20 mmol) was added, the mixture was extracted with ethyl acetate (50 mL×3). The organic phase was combined, washed with saturated brine (50 mL), concentrated under reduced pressure, and the residue was purified by flash column chromatography (eluting with gradient MeOH/$H_2O$ (+0.5% HCOOH)=0%-100%) to give 400 mg of the title product. MS (m/z)=246 $[M+H]^+$, 248 $[M+2H]^+$.

The following intermediates were prepared according to the procedure of Intermediate 26 using the corresponding materials and reagents under appropriate conditions that will be recognized by one skilled in the art.

| Intermediate No. | Structural formula | MS $(M + H)^+$ |
|---|---|---|
| 27 | 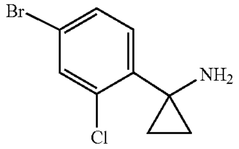 [SMILES: NC1(c2ccc(Br)cc2Cl)CC1] | 246, 248 $[M + 2H]^+$ |
| 28 | 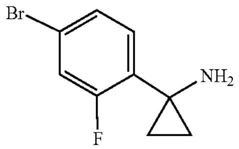 [SMILES: NC1(c2ccc(Br)cc2F)CC1] | 230, 232 $[M + 2H]^+$ |
| 29 | 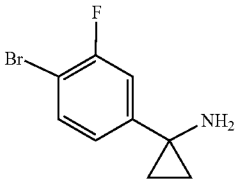 [SMILES: NC1(c2ccc(Br)c(F)c2)CC1] | 230, 232 $[M + 2H]^+$ |
| 56 | 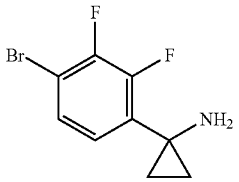 [SMILES: NC1(c2ccc(Br)c(F)c2F)CC1] | 248, 250 $[M + 2H]^+$ |
| 57 | 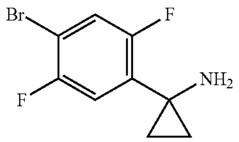 [SMILES: NC1(c2cc(F)c(Br)cc2F)CC1] | 248, 250 $[M + 2H]^+$ |
| 58 | 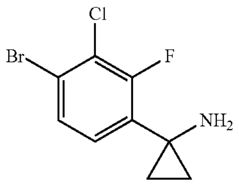 [SMILES: NC1(c2ccc(Br)c(Cl)c2F)CC1] | 264, 266 $[M + 2H]^+$ |
| 59 | 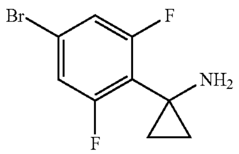 [SMILES: NC1(c2c(F)cc(Br)cc2F)CC1] | 248, 250 $[M + 2H]^+$ |

Intermediate 30

5-benzylisoxazole-3-carboxylic acid

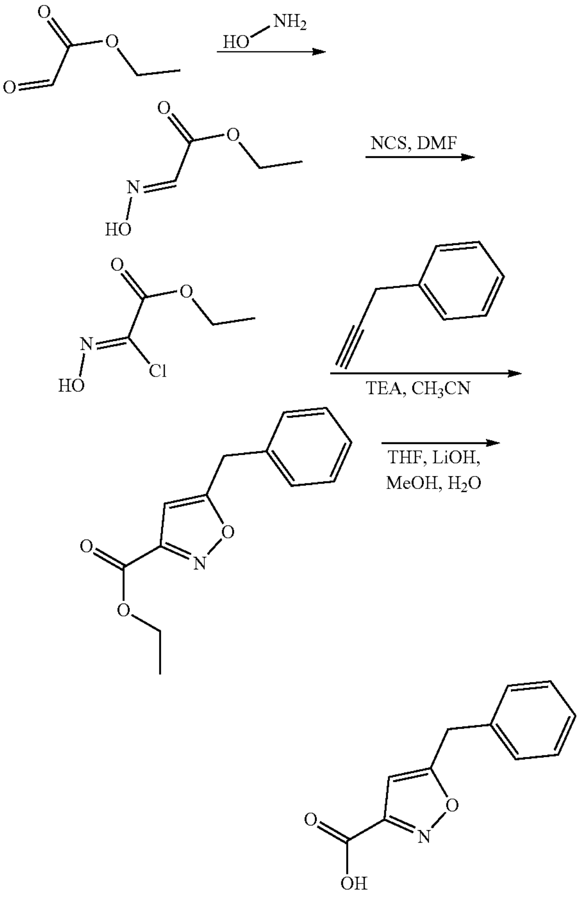

(A) ethyl (E)-2-(hydroxyimino)acetate

To a solution of ethyl 2-oxoacetate (30 mL, 587.7 mmol) in EtOH (100 mL) was added hydroxylamine (77.5 g, 1175.4 mmol, 50% in Tol) at 0° C. and then the mixture was reacted at room temperature for 2 hours. LC-MS showed that the reaction was completed. The mixture was quenched with water and the aqueous phase was extracted with ethyl acetate (150 mL×2). The organic phase was combined, washed with brine solution, dried over anhydrous sodium sulfate and concentrated under reduced pressure to give 20.62 g of the crude product. MS (m/z)=118 $[M+H]^+$.

(B) ethyl (Z)-2-chloro-2-(hydroxyimino)acetate

To a solution of ethyl (E)-2-(hydroxyimino)acetate (20.62 g, 176.3 mmol) in DMF (20 mL) was added NCS (27 g, 176.3 mmol) at 0° C. and then stirred at room temperature for 16 hours. The mixture was quenched with water and the aqueous phase was extracted with ethyl acetate (150 mL×2). The organic layer was combined, dried over anhydrous sodium sulfate and concentrated under reduced pressure. The residue was purified by flash column chromatography (eluting with gradient PE/EA=100%-0%) to give 16.8 g of the title product. MS (m/z)=152 $[M+H]^+$.

(C) ethyl 5-benzylisoxazole-3-carboxylate

To a solution of ethyl (Z)-2-chloro-2-(hydroxyimino) acetate (1.5 g, 9.9 mmol) in MeCN (20 mL) was added prop-2-yn-1-ylbenzene (576 mg, 4.96 mmol) and TEA (1.2 g, 11.88 mmol) at room temperature and then reacted at 90° C. under nitrogen atmosphere for 6 hours. The mixture was concentrated under reduced pressure and the residue was purified by flash column chromatography (eluting with gradient PE/EA=100%-0%) to give 100 mg of the title product. MS (m/z)=232 [M+H]$^+$.

(D) 5-benzylisoxazole-3-carboxylic acid

To a solution of ethyl 5-benzylisoxazole-3-carboxylate (100 mg, 0.432 mmol) in THF (2 mL), MeOH (0.5 mL) and water (0.5 mL) was added lithium hydroxide monohydrate (54 mg, 1.296 mmol). The mixture was stirred at room temperature for 1 hour. LC-MS showed that the reaction was completed. Then the mixture was concentrated under reduced pressure, adjusted pH to 7 with 1N diluted HCl, and the solid was precipitated, and filtered to give 40 mg of the product. MS (m/z)=204 [M+H]$^+$.

Intermediate 31

5-benzyloxazole-2-carboxylic acid

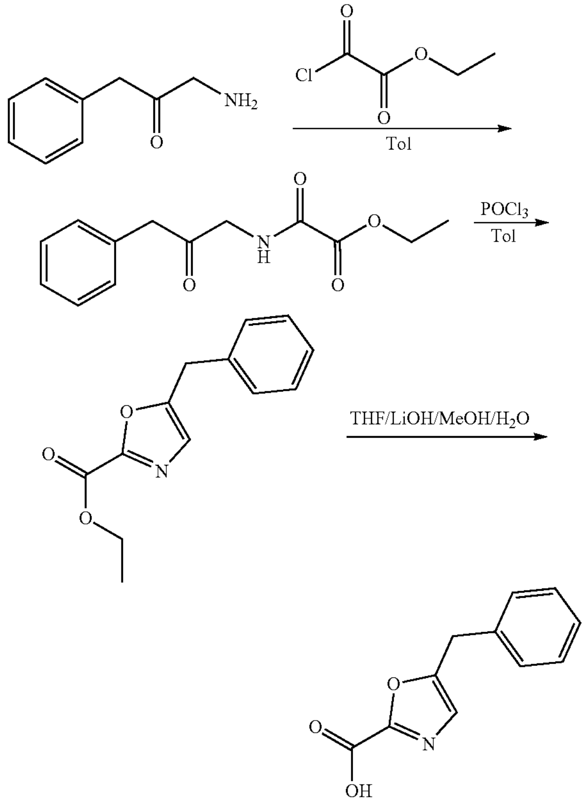

(A) ethyl 2-oxo-2-((2-oxo-3-phenylpropyl)amino) acetate

To a solution of 1-amino-3-phenylpropan-2-one (500 mg, 3.35 mmol) in toluene (20 mL) was added ethyl 2-chloro-2-oxoacetate (905 mg, 6.70 mmol) at room temperature and then the mixture was reacted at 90° C. under nitrogen atmosphere for 2 hours. The mixture was quenched with ice water and the aqueous phase was extracted with ethyl acetate (20 mL×2). The organic layer was combined, dried over anhydrous sodium sulfate and concentrated under reduced pressure. The residue was purified by flash column chromatography (eluting with gradient PE/EA=100%-0%) to give 650 mg of the title product. MS (m/z)=250 [M+H]$^+$.

(B) Ethyl 5-benzyloxazole-2-carboxylate

To a solution of ethyl 2-oxo-2-((2-oxo-3-phenylpropyl) amino)acetate (650 mg, 2.6 mmol) in toluene (20 mL) was added $POCl_3$ (2000 mg, 13 mmol) and the mixture was reacted at 120° C. for 5 hours. The mixture was quenched with ice water and the aqueous phase was extracted with ethyl acetate (20 mL×2). The organic layer was combined, dried over anhydrous sodium sulfate and concentrated under reduced pressure. The residue was purified by flash column chromatography (eluting with gradient PE/EA=100%-0%) to give 530 mg of the title product. MS (m/z)=232 [M+H]$^+$.

(C) 5-benzyloxazole-2-carboxylic acid

The product was prepared according to the procedure of Intermediate 30 (D) using ethyl 5-benzyloxazole-2-carboxylate as the raw material. MS (m/z)=204 [M+H]$^+$.

Intermediate 32 lithium 5-benzyl-1,3,4-oxadiazole-2-carboxylate

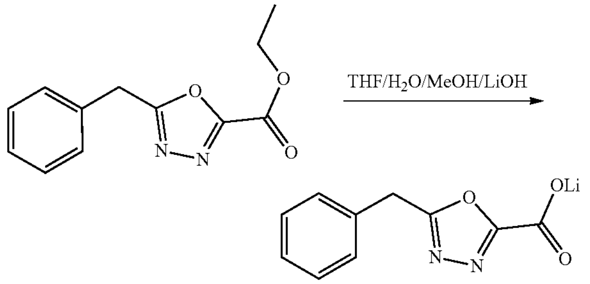

To a solution of ethyl 5-benzyl-1,3,4-oxadiazole-2-carboxylate (70 mg, 0.301 mmol) in THF (2 mL), MeOH (0.5 mL) and $H_2O$ (0.5 mL) was added lithium hydroxide monohydrate (50 mg, 1.206 mmol). The mixture was reacted at 60° C. for 1 hour. Then the mixture was concentrated under reduced pressure and used for next step reaction without further purification. MS (m/z)=205 [M+H]$^+$.

Intermediate 33 lithium 5-benzyl-1,2,4-oxadiazole-3-carboxylate

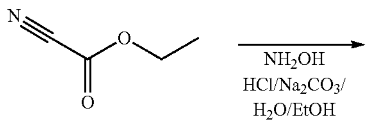

-continued

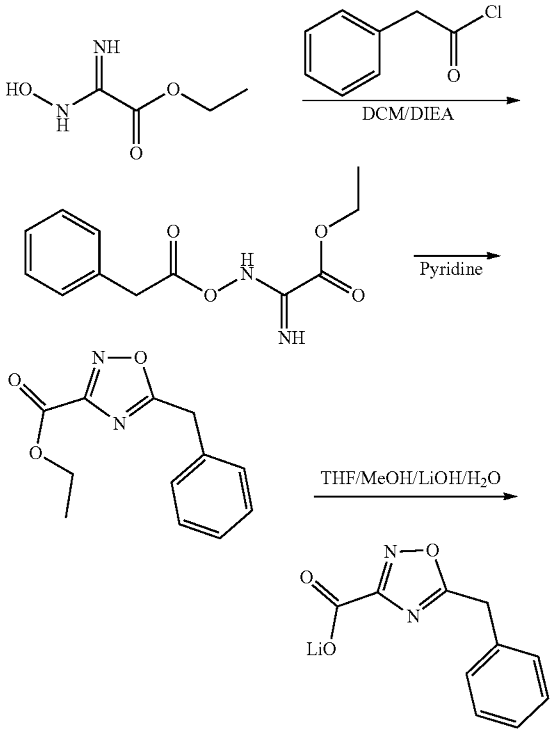

(A) ethyl 2-(hydroxyamino)-2-iminoacetate

To a solution of ethyl carbonocyanidate (2 g, 20 mmol) in EtOH (20 mL) was added hydroxylamine hydrochloride (2 g, 30 mmol) and sodium carbonate (1.63 g, 15.4 mmol), and the mixture was reacted at room temperature for 2 hours. The mixture was quenched with ice water and the aqueous phase was extracted with DCM (50 mL×2). The organic layer was combined, washed with brine solution, dried over anhydrous sodium sulfate and concentrated under reduced pressure to give 2.3 g of the title product. MS (m/z)=133 $[M+H]^+$.

(B) ethyl 2-imino-2-((2-phenylacetoxy)amino)acetate

To a solution of ethyl 2-(hydroxyamino)-2-iminoacetate (2.3 g, 18 mmol) in DCM (20 mL) was added DIEA (4.6 g, 36 mmol) and 2-phenylacetyl chloride (2.7 g, 18 mmol) at −15° C. The reaction mixture was reacted at room temperature overnight and then quenched with ice water. The solid was precipitated, filtered and dried to give 1.68 g of the title product. MS (m/z)=251$[M+H]^+$.

(C) Ethyl 5-benzyl-1,2,4-oxadiazole-3-carboxylate

A solution of ethyl 2-imino-2-((2-phenylacetoxy)amino) acetate (800 mg, 3.2 mmol) in pyridine (10 mL) was reacted at 80° C. under nitrogen atmosphere for 6 hours. The mixture was concentrated under reduced pressure and the residue was purified by flash column chromatography (eluting with gradient PE/EA=100%-0%) to give 600 mg of the title product. MS (m/z)=233 $[M+H]^+$.

(D) lithium 5-benzyl-1,2,4-oxadiazole-3-carboxylate

To a solution of ethyl 5-benzyl-1,2,4-oxadiazole-3-carboxylate (600 mg, 2.58 mmol) in THF (10 mL), MeOH (2 mL) and water (2 mL) was added lithium hydroxide monohydrate (325 mg, 7.74 mmol). The mixture was reacted at room temperature for 1 hour. Then the mixture was concentrated under reduced pressure and the residue (500 mg) was used for next step reaction without further purification. MS (m/z)=205 $[M+H]^+$.

Intermediate 34 lithium 1-(1-phenylethyl)-1H-1,2,4-triazole-3-carboxylate

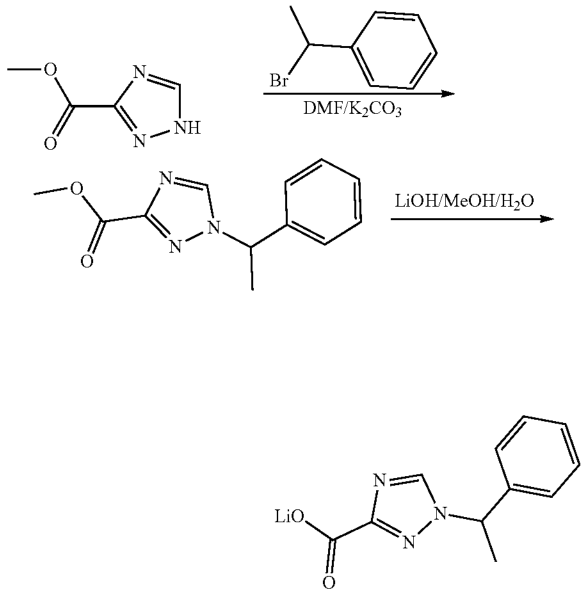

(A) methyl 1-(1-phenylethyl)-1H-1,2,4-triazole-3-carboxylate

To a solution of methyl 1H-1,2,4-triazole-3-carboxylate (1 g, 7.87 mmol) in DMF (10 mL) was added (1-bromoethyl)benzene (1737 mg, 9.44 mmol) and potassium carbonate (2.17 g, 15.74 mmol). The mixture was reacted at room temperature for 16 hours. The mixture was concentrated under reduced pressure and the residue was purified by flash column chromatography (eluting with gradient MeOH/$H_2O$ (+0.5% HCOOH)=0%-100%) to give 1.5 g of the title product. MS (m/z)=232 $[M+H]^+$.

(B) lithium 1-(1-phenylethyl)-1H-1,2,4-triazole-3-carboxylate

To a solution of methyl 1-(1-phenylethyl)-1H-1,2,4-triazole-3-carboxylate (1.5 g, 6.493 mmol) in MeOH (10 mL) and water (2 mL) was added lithium hydroxide monohydrate (817 mg, 19.47 mmol). The mixture was reacted at room temperature for 1 hour. The mixture was concentrated under reduced pressure and the residue was purified by flash column chromatography (eluting with gradient MeOH/$H_2O$=0%-100%) to give 1.22 g of the title product. MS (m/z)=218 $[M+H]^+$.

Intermediate 35 lithium 5-(1-phenylethyl)-4H-1,2,4-triazole-3-carboxylate

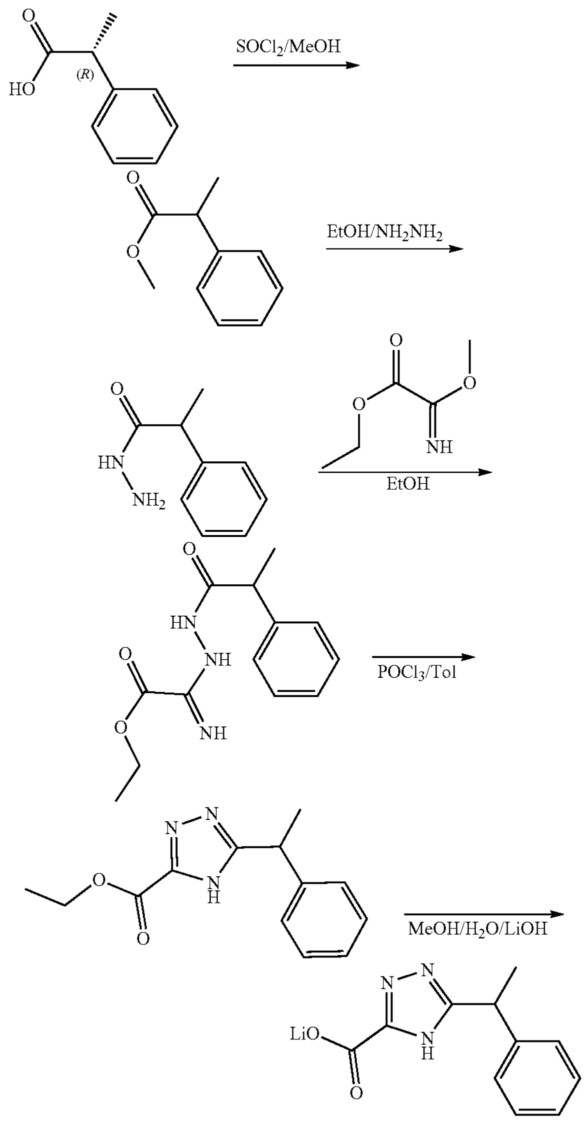

(A) methyl 2-phenylpropanoate

To a solution of (R)-2-phenylpropanoic acid (1.95 g, 12.98 mmol) in MeOH (20 mL) was added $SOCl_2$ (2 mL) at 0° C. The mixture was reacted at room temperature for 2 hours. Then the mixture was concentrated under reduced pressure and the residue (2.18 g) was used for next step reaction without further purification. MS (m/z)=165 [M+H]+.

(B) 2-phenylpropanehydrazide

To a solution of methyl 2-phenylpropanoate (2.18 g, 12.98 mmol) in EtOH (20 mL) was added hydrazine hydrate (5 mL) at 0° C. The mixture was reacted at 80° C. for 2 hours. The mixture was concentrated under reduced pressure and the residue was purified by flash column chromatography (eluting with gradient MeOH/$H_2O$=0%-100%) to give 1.96 g of the title product. MS (m/z)=165 [M+H]+.

(C) ethyl 2-imino-2-(2-(2-phenylpropanoyl)hydrazineyl)acetate

A mixture of 2-phenylpropanehydrazide (900 mg, 5.48 mmol) and ethyl 2-imino-2-methoxyacetate (1435 mg, 10.96 mmol) in EtOH (20 mL) was reacted at 80° C. under nitrogen atmosphere for 2 hours. The mixture was cooled to room temperature, and the solid was precipitated, filtered and dried to give 1.4 g of the product. MS (m/z)=264 [M+H]+.

(D) ethyl 5-(1-phenylethyl)-4H-1,2,4-triazole-3-carboxylate

To a solution of ethyl 2-imino-2-(2-(2-phenylpropanoyl)hydrazineyl)acetate (1.4 g, 5.32 mmol) in toluene (20 mL) was added $POCl_3$ (10 mL). The mixture was reacted at 120° C. for 24 hours. The mixture was concentrated under reduced pressure and the residue was purified by flash column chromatography (eluting with gradient MeOH/$H_2O$ (+0.5% HCOOH)=0%-100%) to give 563 mg of the title product. MS (m/z)=246 [M+H]+.

(E) lithium 5-(1-phenylethyl)-4H-1,2,4-triazole-3-carboxylate

The title product was prepared according to the procedure of Intermediate 34 (B) using ethyl 5-(1-phenylethyl)-4H-1,2,4-triazole-3-carboxylate as the raw material. MS (m/z)=218 [M+H]+.

Intermediate 37 and Intermediate 38

(R)-ethyl 5-phenyl-6,7-dihydro-5H-pyrrolo[1,2-b][1,2,4]triazole-2-carboxylate and (S)-ethyl 5-phenyl-6,7-dihydro-5H-pyrrolo[1,2-b][1,2,4]triazole-2-carboxylate

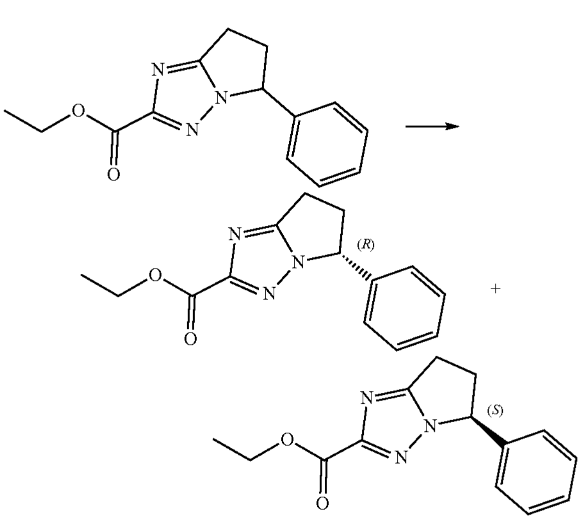

The racemic compound was resolved by chiral HPLC to provide the optically pure enantiomers Intermediate 37 and Intermediate 38 (HPLC conditions: column: AD-H 4.6×150 mm; mobile phase: n-hexane/EtOH=70/30; flow rate=0.5 mL/min; detector: UV 254 nm). The first eluent (Intermediate 37, Rf=3.651 min) was 100% ee, MS (m/z): 258 $[M+H]^+$. The second eluent (Intermediate 38, Rf=4.350 min) was 99.98% ee, MS (m/z): 258 $[M+H]^+$.

Intermediate 39

1-(1-cyclopropylethyl)-1H-pyrazolo[3,4-d]pyrimidine-6-carboxylic acid

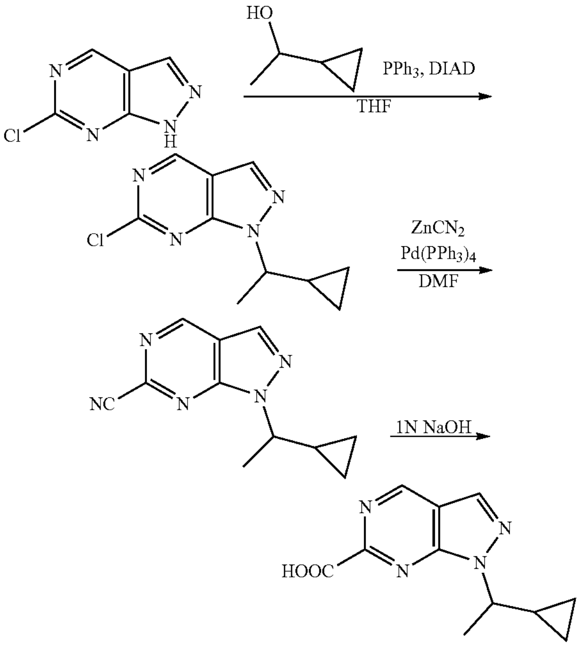

(A) 6-chloro-1-(1-cyclopropylethyl)-1H-pyrazolo[3,4-d]pyrimidine 6-chloro-1H-pyrazolo[3,4-d]pyrimidine (800 mg, 5.2 mmol), 1-cyclopropylethane-1-ol (1.3 g, 15.6 mmol) and triphenylphosphine (2.0 g, 7.8 mmol) were dissolved in tetrahydrofuran (10 mL), then DIAD (1.6 mL) was slowly added, then the mixture was warmed to 60° C. and reacted overnight. The reaction solution was concentrated under reduced pressure and the residue was purified by flash column chromatography (eluting with gradient PE/EA=100%-0%) to give 420 mg of the title product. MS (m/z)=223 $[M+H]^+$.

(B) 1-(1-cyclopropylethyl)-1H-pyrazolo[3,4-d]pyrimidine-6-carbonitrile

A mixture of 6-chloro-1-(1-cyclopropylethyl)-1H-pyrazolo[3,4-d]pyrimidine (420 mg, 1.88 mmol), zinc cyanide (120 mg, 1.13 mmol) and $Pd(PPh_3)$ 4 (220 mg, 0.188 mmol) in DMF (5 mL) was heated to 110° C. and reacted for 1.5 hours. The mixture was concentrated under reduced pressure and the residue was purified by flash column chromatography (eluting with gradient PE/EA=100%-0%) to give 310 mg of the product. MS (m/z)=214 $[M+H]^+$.

(C) 1-(1-cyclopropylethyl)-1H-pyrazolo[3,4-d]pyrimidine-6-carboxylic acid

A mixture of 1-(1-cyclopropylethyl)-1H-pyrazolo[3,4-d]pyrimidine-6-carbonitrile (310 mg, 1.45 mmol) in 1N sodium hydroxide (7 mL) was heated to 110° C. and reacted for 1.5 hours. The reaction solution was cooled, and the pH was adjusted to 4 with 1N hydrochloric acid, After concentration under reduced pressure, the residue was purified by flash column chromatography (eluting with gradient MeOH/$H_2O$=0%-100%) to give 377 mg of the target product. MS (m/z)=233 $[M+H]^+$.

The following intermediates were prepared according to the procedure of Intermediate 39 using the corresponding materials and reagents under appropriate conditions that will be recognized by one skilled in the art.

| Intermediate No. | Structural formula | MS $(M + H)^+$ |
|---|---|---|
| 40 | 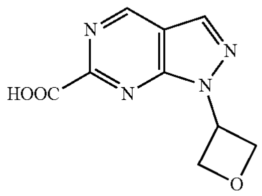 [SMILES: O=C(O)c1ncc2cnn(C3COC3)c2n1] | 221 |
| 41 | 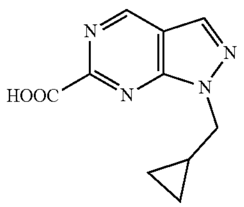 [SMILES: O=C(O)c1ncc2cnn(CC3CC3)c2n1] | 219 |

Intermediate 42

1-(cyclobutylmethyl)-1H-pyrazolo[3,4-d]pyrimidine-6-carboxylic acid

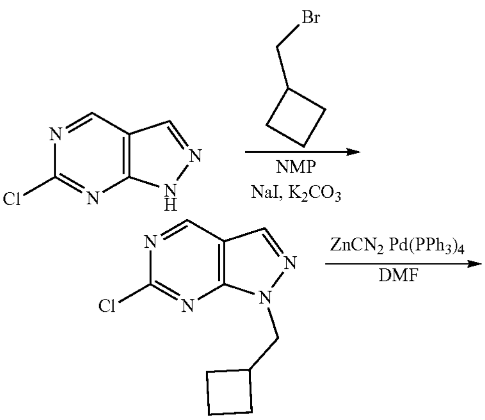

-continued

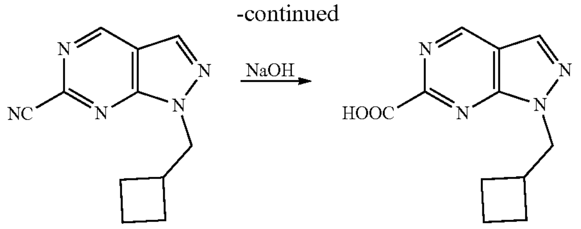

(A) 6-chloro-1-(cyclobutylmethyl)-1H-pyrazolo[3,4-d]pyrimidine 6-chloro-1H-pyrazolo[3,4-d]pyrimidine (500 mg, 3.23 mmol), (bromo methyl)cyclobutane (965 mg, 6.46 mmol), potassium carbonate (890 mg, 6.46 mmol) and sodium iodide (970 mg, 6.46 mmol) were dissolved in NMP (5 mL), the mixture was heated to 60° C. and reacted overnight. The reaction solution was cooled, to which water was added, and extracted with ethyl acetate, then the ethyl acetate extract was concentrated in vacuum, the residue was purified by flash column chromatography (eluting with gradient PE/EA=100%-0%), to give 310 mg of the product. MS (m/z)=223 $[M+H]^+$.

(B) 1-(cyclobutylmethyl)-1H-pyrazolo[3,4-d]pyrimidine-6-carbonitrile

The title product was prepared according to the procedure of intermediate 39(B) using 6-chloro-1-(cyclobutylmethyl)-1H-pyrazolo[3,4-d]pyrimidine as the raw material. MS (m/z)=214 $[M+H]^+$.

(C) 1-(cyclobutylmethyl)-1H-pyrazolo[3,4-d]pyrimidine-6-carboxylic acid

The title product was prepared according to the procedure of intermediate 39(C) using 1-(cyclobutylmethyl)-1H-pyrazolo[3,4-d]pyrimidine-6-carbonitrile as the raw material. MS (m/z)=233 $[M+H]^+$.

Intermediate 43

1-(pyridin-2-yl)-1H-pyrazolo[3,4-d]pyrimidine-6-carboxylic acid

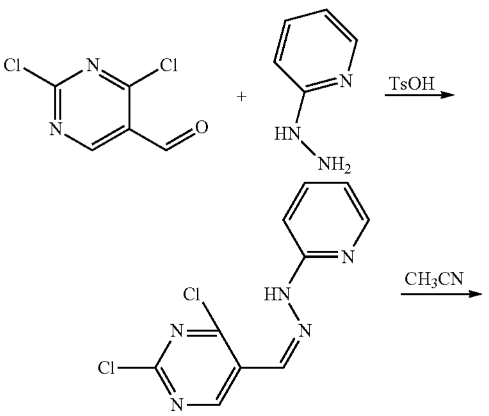

-continued

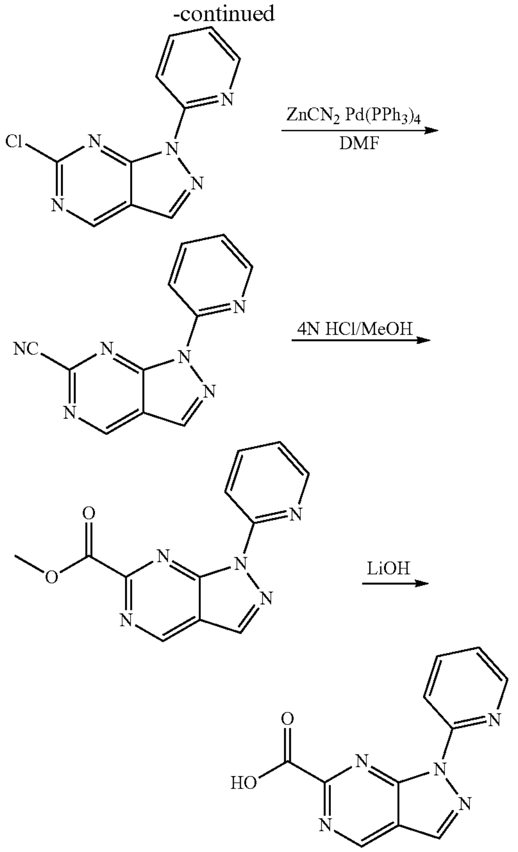

(A) (Z)-2,4-dichloro-5-((2-(pyridin-2-yl)hydrazineylidene)methyl)pyrimidine 2,4-dichloropyrimidine-5-formaldehyde (500 mg, 2.8 mmol), 2-hydrazinopyridine (310 mg, 2.8 mmol) and p-toluenesulfonic acid (540 mg, 2.8 mmol) were dissolved in DMF (5 mL), the mixture was reacted at room temperature for 2 hours, then water (20 mL) and saturated sodium bicarbonate solution (10 mL) were added. The mixture was filtered to give 610 mg of product, which was directly used in the next step. MS (m/z)=268 $[M+H]^+$.

(B) 6-chloro-1-(pyridin-2-yl)-1H-pyrazolo[3,4-d]pyrimidine (Z)-2,4-dichloro-5-((2-(pyridin-2-yl)hydrazineylidene)methyl)pyrimidine (1.4 g, 5.2 mmol) was dissolved in acetonitrile (30 mL), the mixture was heated to 140° C. and reacted under microwave for 3 hours. After concentration under reduced pressure, the residue was purified by flash column chromatography (eluting with gradient MeOH/$H_2O$=0%-100%) to give 125 mg of product. MS (m/z)=232 $[M+H]^+$.

(C) 1-(pyridin-2-yl)-1H-pyrazolo[3,4-d]pyrimidine-6-carbonitrile

A mixture of 6-chloro-1-(pyridin-2-yl)-1H-pyrazolo[3,4-d]pyrimidine (125 mg, 0.54 mmol), zinc cyanide (35 mg, 0.32 mmol) and $Pd(PPh_3)$ 4 (65 mg, 0.054 mmol) in DMF (5 mL) was heated to 110° C. and reacted for 1.5 hours. After concentration under reduced pressure, the residue was purified by flash column chromatography (eluting with gradient PE/EA=100%-0%) to give 121 mg of the product. MS (m/z)=223 $[M+H]^+$.

(D) methyl 1-(pyridin-2-yl)-1H-pyrazolo[3,4-d]pyrimidine-6-carboxylate 1-(pyridin-2-yl)-1H-pyrazolo[3,4-d]pyrimidine-6-carbonitrile (121 mg, 0.5 mmol) was dissolved in MeOH (5 mL), 4N hydrochloric acid in methanol solution (2.5 mL) was added. The mixture was reacted at 20° C. for 20 hours, and then reacted at 50° C. for 3 hours. After cooling and concentration under reduced pressure, the residue was purified by flash column chromatography (eluting with gradient $MeOH/H_2O$=0%-100%) to give 50 mg of the product. MS (m/z)=256 $[M+H]^+$.

(E) 1-(pyridin-2-yl)-1H-pyrazolo[3,4-d]pyrimidine-6-carboxylic acid

Methyl 1-(pyridin-2-yl)-1H-pyrazolo[3,4-d]pyrimidine-6-carboxylate (50 mg, 0.22 mmol) was dissolved in tetrahydrofuran/water (5 mL/1 mL), $LiOH \cdot H_2O$ (50 mg, 1.10 mmol) was added, and the mixture was reacted at 25° C. for 2 hours. After concentration under reduced pressure, the pH of the reaction solution was adjusted to 4 by adding 2N hydrochloric acid solution, and same was extracted with ethyl acetate (3×10 mL). The ethyl acetate layer was concentrated, and the residue was purified by flash column chromatography (eluting with gradient $MeOH/H_2O$=0%-100%) to give 45 mg of the product. MS (m/z)=242 $[M+H]^+$.

Compound 1

1-isopropyl-N-(1-(4-(1-methyl-6-oxo-1,6-dihydropyrimidin-5-yl)phenyl)cyclopropyl)-1H-pyrazolo[3,4-d]pyrimidine-6-carboxamide

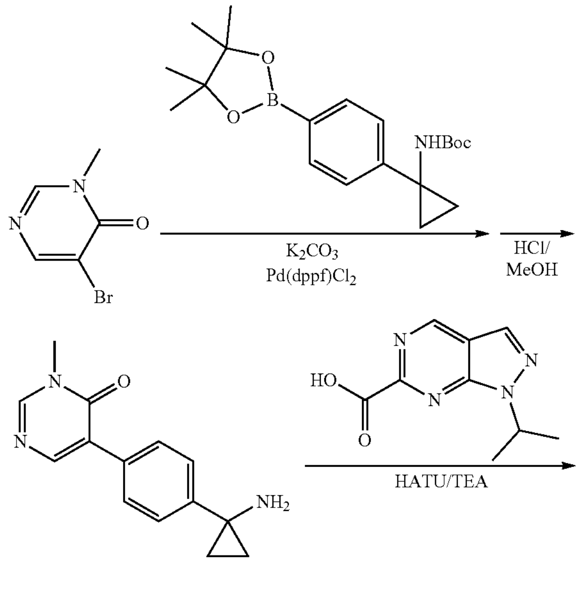

-continued

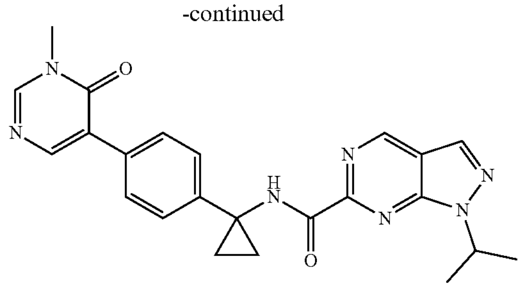

(A) 5-(4-(1-aminocyclopropyl)phenyl)-3-methylpyrimidin-4(3H)-one

The mixture of 5-bromo-3-methylpyrimidin-4(3H)-one (63 mg, 0.33 mmol), tert-butyl (1-(4-(4,4,5,5-tetramethyl-1,3,2-dioxaborolan-2-yl)phenyl)cyclopropyl)carbamate (143 mg, 0.40 mmol), $K_2CO_3$ (137 mg, 0.99 mmol), and Pd(dppf) $Cl_2$ (12 mg, 0.02 mmol) in 10 mL of dioxane and water (3:1) was stirred at 120° C. for 5 hours. The solvent was removed, and the residue was purified by flash column chromatography (eluting with gradient $MeOH/H_2O$ (+0.1% HCOOH)=10%-80%) to give the crude product. To the crude product was added 2N HCl in MeOH (10 mL) at room temperature. The mixture was stirred for 2 hours. Then the solvent was removed to obtain 65 mg of the product as pale yellow solid. MS (m/z)=242 $[M+H]^+$.

(B) 1-isopropyl-N-(1-(4-(1-methyl-6-oxo-1,6-dihydropyrimidin-5-yl)phenyl)cyclopropyl)-1H-pyrazolo[3,4-d]pyrimidine-6-carboxamide The mixture of 5-(4-(1-aminocyclopropyl)phenyl)-3-methylpyrimidin-4(3H)-one (65 mg, 0.27 mmol), 1-isopropyl-1H-pyrazolo[3,4-d]pyrimidine-6-carboxylic acid (56 mg, 0.27 mmol), HATU (123 mg, 0.32 mmol), and TEA (82 mg, 0.81 mmol) in DCM (5 mL) was stirred at room temperature under nitrogen atmosphere for 2 hours. The solvent was removed. The residue was purified by flash column chromatography (eluting with gradient $MeOH/H_2O$ (+0.1% HCOOH)=10%-80%) to obtain 90 mg of the product as white solid. MS (m/z)=430 $[M+H]^+$.

1H NMR (400 MHz, DMSO) δ 9.71 (s, 1H), 9.41 (s, 1H), 8.47 (d, J=0.4 Hz, 1H), 8.44 (s, 1H), 8.07 (s, 1H), 7.61-7.56 (m, 2H), 7.28-7.24 (m, 2H), 5.34-5.24 (m, 1H), 3.44 (s, 3H), 1.50 (d, J=6.7 Hz, 6H), 1.36-1.28 (m, 4H).

The following compounds were prepared according to the procedure of Compound 1 using the corresponding intermediates and reagents under appropriate conditions that will be recognized by one skilled in the art.

| Compound | Structure | ¹H-NMR | MS | Intermediates used |
|---|---|---|---|---|
| 2 | 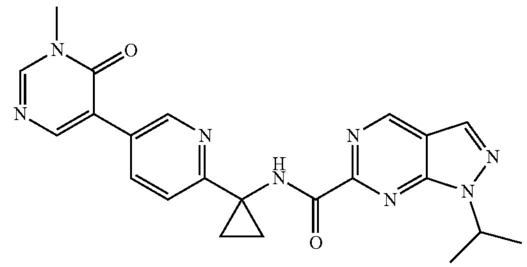 | $^1$H NMR (400 MHz, DMSO) δ 9.80 (s, 1H), 9.45 (s, 1H), 8.76-8.71 (m, 1H), 8.49 (s, 2H), 8.19 (s, 1H), 8.02-7.93 (m, 1H), 7.46-7.38 (m, 1H), 5.40-5.23 (m, 1H), 3.47 (s, 3H), 1.62-1.58 (m, 2H), 1.52 (d, J = 6.7 Hz, 6H), 1.38-1.33 (m, 2H). | 431 | |
| 3 | 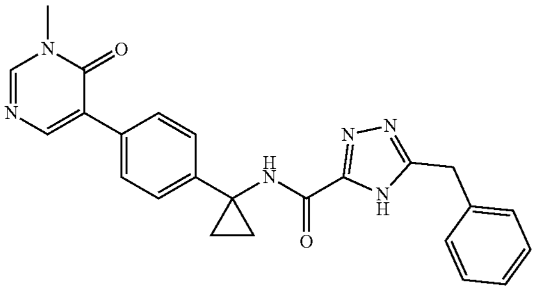 [SMILES: Cn1cncc(-c2ccc(C3(NC(=O)c4nnc(Cc5ccccc5)[nH]4)CC3)cc2)c1=O] | $^1$H NMR (400 MHz, DMSO) δ 9.13 (s, 1H), 8.44 (s, 1H), 8.06 (s, 1H), 7.60-7.53 (m, 2H), 7.31-7.23 (m, 4H), 7.22-7.16 (m, 3H), 4.05 (s, 2H), 3.45 (s, 3H), 1.29-1.20 (m, 4H). | 427 | |
| 4 | 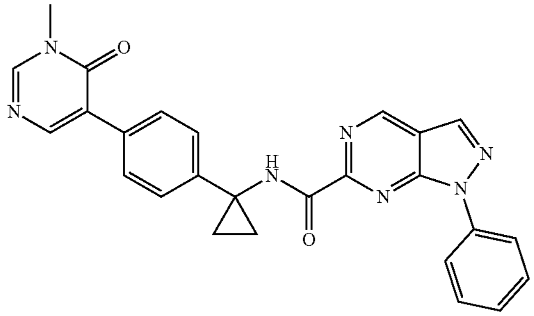 [SMILES: Cn1cncc(-c2ccc(C3(NC(=O)c4ncc5cnn(-c6ccccc6)c5n4)CC3)cc2)c1=O] | $^1$H NMR (400 MHz, DMSO) δ 9.73 (s, 1H), 9.58 (s, 1H), 8.76 (s, 1H), 8.45 (s, 1H), 8.28 (d, J = 7.7 Hz, 2H), 8.09 (s, 1H), 7.68-7.57 (m, 4H), 7.43 (t, J = 7.5 Hz, 1H), 7.30 (d, J = 8.4 Hz, 2H), 3.46 (s, 3H), 1.50-1.28 (m, 4H). | 464 | 23 |
| 5 | 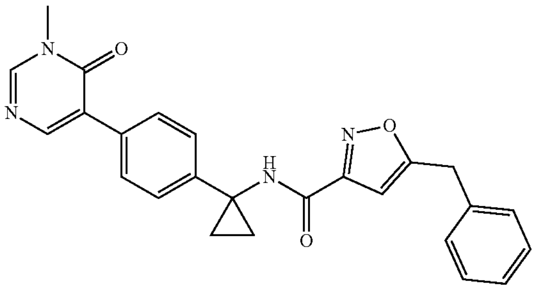 [SMILES: Cn1cncc(-c2ccc(C3(NC(=O)c4cc(Cc5ccccc5)on4)CC3)cc2)c1=O] | $^1$H NMR (400 MHz, DMSO) δ 9.46 (s, 1H), 8.44 (s, 1H), 8.07 (s, 1H), 7.60-7.55 (m, 2H), 7.36-7.24 (m, 5H), 7.22-7.17 (m, 2H), 6.53 (s, 1H), 4.19 (s, 2H), 3.45 (s, 3H), 1.25 (s, 4H). | 427 | 30 |
| 6 | 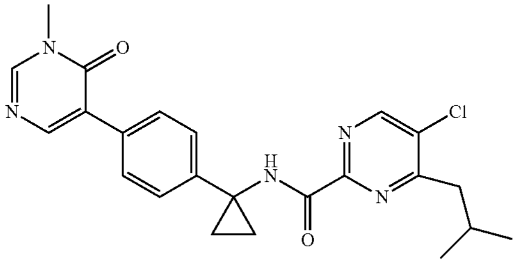 [SMILES: CC(C)Cc1nc(C(=O)NC2(c3ccc(-c4cncn(C)c4=O)cc3)CC2)ncc1Cl] | $^1$H NMR (400 MHz, $CD_3OD$) δ 8.84 (s, 1H), 8.37 (s, 1H), 8.06 (s, 1H), 7.64-7.54 (m, 2H), 7.41-7.28 (m, 2H), 3.57 (s, 3H), 2.91 (d, J = 7.3 Hz, 2H), 2.40-2.25 (m, 1H), 1.61-1.37 (m, 5H), 0.99 (d, J = 6.7 Hz, 6H). | 438 | 1 |

-continued
| Compound | Structure | $^1$H-NMR | MS | Intermediates used |
|---|---|---|---|---|
| 7 | 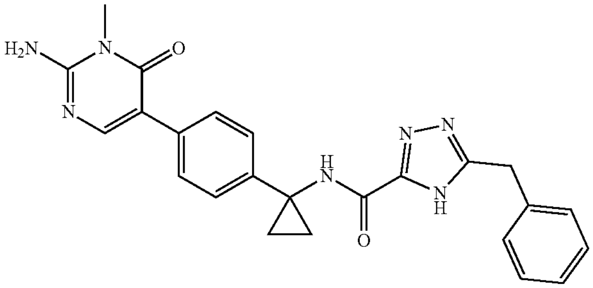 [SMILES: Cn1c(N)ncc(-c2ccc(C3(NC(=O)c4nnc(Cc5ccccc5)[nH]4)CC3)cc2)c1=O] | $^1$H NMR (400 MHz, DMSO) δ 9.21 (s, 1H), 7.75 (s, 1H), 7.46 (d, J = 8.4 Hz, 2H), 7.33-7.15 (m, 7H), 7.12 (d, J = 8.4 Hz, 2H), 4.07 (s, 2H), 3.30 (s, 3H), 1.25-1.16 (m, 4H). | 442 | 5 |
| 8 | 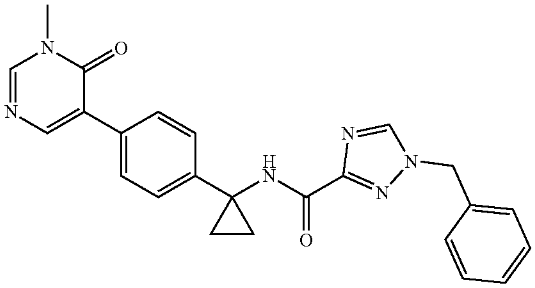 [SMILES: Cn1cncc(-c2ccc(C3(NC(=O)c4ncn(Cc5ccccc5)n4)CC3)cc2)c1=O] | $^1$H NMR (400 MHz, DMSO) δ 9.24 (s, 1H), 8.79 (s, 1H), 8.43 (s, 1H), 8.06 (s, 1H), 7.69-7.47 (m, 2H), 7.47-7.24 (m, 5H), 7.24-7.07 (m, 2H), 5.46 (s, 2H), 3.45 (s, 3H), 1.36-1.10 (m, 4H). | 427 | 21 |
| 9 | 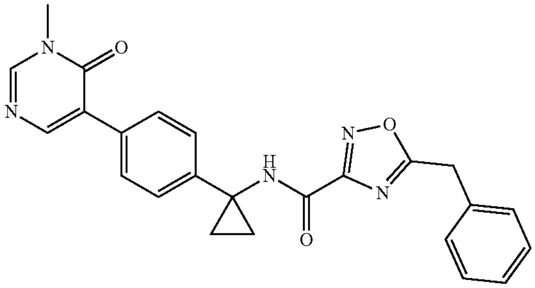 [SMILES: Cn1cncc(-c2ccc(C3(NC(=O)c4noc(Cc5ccccc5)n4)CC3)cc2)c1=O] | $^1$H NMR (400 MHz, DMSO) δ 9.77 (s, 1H), 8.44 (s, 1H), 8.08 (s, 1H), 7.69-7.48 (m, 2H), 7.48-7.26 (m, 5H), 7.25-7.12 (m, 2H), 4.42 (s, 2H), 3.45 (s, 3H), 1.35-1.17 (m, 4H). | 428 | 33 |
| 10 | 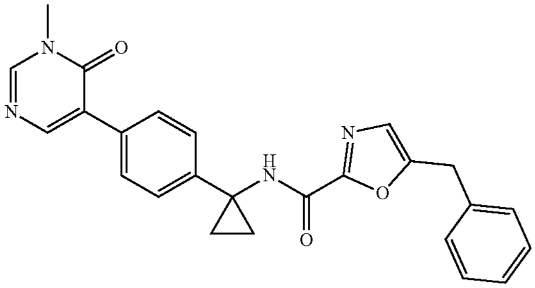 [SMILES: Cn1cncc(-c2ccc(C3(NC(=O)c4ncc(Cc5ccccc5)o4)CC3)cc2)c1=O] | $^1$H NMR (400 MHz, DMSO) δ 9.61 (s, 1H), 8.44 (s, 1H), 8.07 (s, 1H), 7.57 (d, J = 8.1 Hz, 2H), 7.39-7.21 (m, 5H), 7.18 (d, J = 8.2 Hz, 2H), 7.13 (d, J = 0.8 Hz, 1H), 4.11 (s, 2H), 3.45 (s, 3H), 1.29-1.21 (m, 4H). | 427 | 31 |
| 11 | 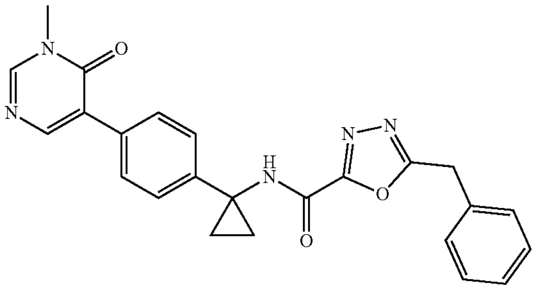 [SMILES: Cn1cncc(-c2ccc(C3(NC(=O)c4nnc(Cc5ccccc5)o4)CC3)cc2)c1=O] | $^1$H NMR (400 MHz, DMSO) δ 10.04 (s, 1H), 8.45 (s, 1H), 8.08 (s, 1H), 7.58 (d, J = 8.1 Hz, 2H), 7.43-7.25 (m, 5H), 7.21 (d, J = 8.1 Hz, 2H), 4.35 (s, 2H), 3.45 (s, 3H), 1.33-1.23 (m, 4H). | 428 | 32 |

-continued
| Compound | Structure | $^1$H-NMR | MS | Intermediates used |
|---|---|---|---|---|
| 12 | 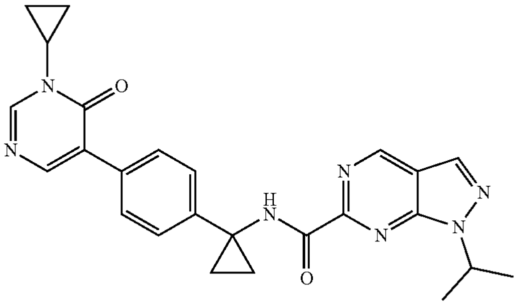 [SMILES: CC(C)n1ncc2cnc(C(=O)NC3(c4ccc(-c5cncn(C6CC6)c5=O)cc4)CC3)nc21] | $^1$H NMR (400 MHz, $CDCl_3$) δ 9.19 (s, 1H), 8.84 (s, 1H), 8.23 (s, 1H), 8.12 (s, 1H), 7.98 (s, 1H), 7.60 (d, J = 8.3 Hz, 2H), 7.44 (d, J = 8.3 Hz, 2H), 5.52-5.40 (m, 1H), 3.32-3.20 (m, 1H), 1.59 (d, J = 6.7 Hz, 6H), 1.50-1.42 (m, 4H), 1.23-1.18 (m, 2H), 0.96-0.90 (m, 2H). | 456 | 9 |
| 13 | 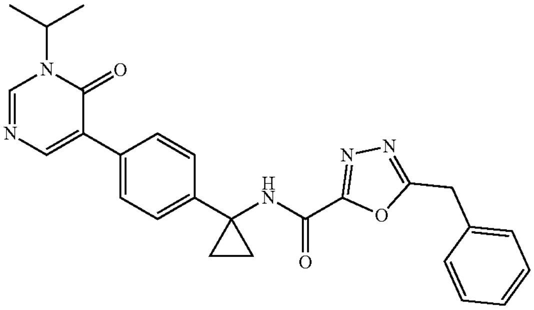 [SMILES: CC(C)n1cncc(-c2ccc(C3(NC(=O)c4nnc(Cc5ccccc5)o4)CC3)cc2)c1=O] | $^1$H NMR (400 MHz, $CDCl_3$) δ 8.15 (s, 1H), 7.98 (s, 1H), 7.77 (s, 1H), 7.62-7.56 (m, 2H), 7.39-7.35 (m, 2H), 7.35-7.26 (m, 5H), 5.21-5.07 (m, 1H), 4.25 (s, 2H), 1.48 (d, J = 6.9 Hz, 6H), 1.42-1.37 (m, 4H). | 456 | 10, 32 |
| 14 | 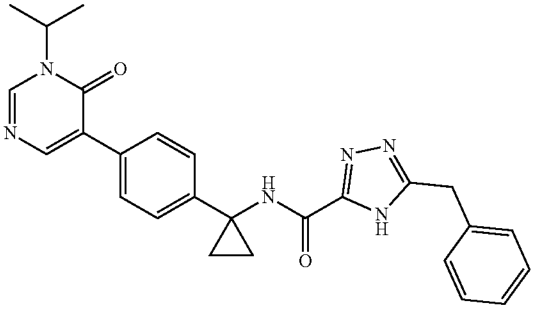 [SMILES: CC(C)n1cncc(-c2ccc(C3(NC(=O)c4nnc(Cc5ccccc5)[nH]4)CC3)cc2)c1=O] | $^1$H NMR (400 MHz, $CDCl_3$) δ 8.15 (s, 1H), 7.98-7.90 (m, 2H), 7.54 (d, J = 8.3 Hz, 2H), 7.32 (d, J = 8.3 Hz, 2H), 7.26-7.20 (m, 5H), 5.23-5.08 (m, 1H), 4.16 (s, 2H), 1.47 (d, J = 6.9 Hz, 6H), 1.41-1.32 (m, 4H). | 457 | 10 |
| 15 | 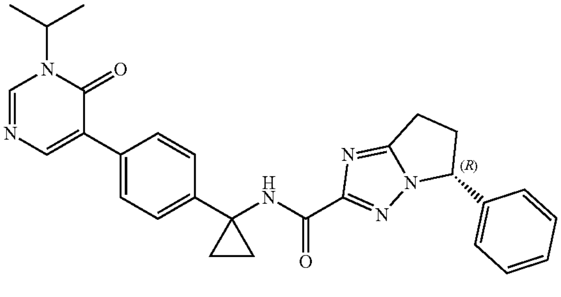 | $^1$H NMR (400 MHz, $CDCl_3$) δ 8.13 (s, 1H), 7.97 (s, 1H), 7.71 (s, 1H), 7.60-7.53 (m, 2H), 7.39-7.33 (m, 5H), 7.14-7.09 (m, 2H), 5.48-5.40 (m, 1H), 5.21-5.10 (m, 1H), 3.28-2.97 (m, 3H), 2.73-2.62 (m, 1H), 1.47 (d, J = 6.8 Hz, 6H), 1.43-1.34 (m, 4H). | 481 | 10, 37 or 38 |
| | & | | | |
| 16 | 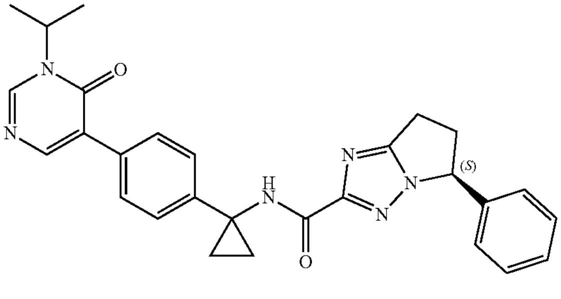 | $^1$H NMR (400 MHz, $CDCl_3$) δ 8.14 (s, 1H), 7.98 (s, 1H), 7.70 (s, 1H), 7.59-7.54 (m, 2H), 7.39-7.33 (m, 5H), 7.14-7.09 (m, 2H), 5.50-5.39 (m, 1H), 5.23-5.09 (m, 1H), 3.29-2.97 (m, 3H), 2.74-2.60 (m, 1H), 1.47 (d, J = 6.9 Hz, 6H), 1.44-1.35 (m, 4H). | 481 | 10, 37 or 38 |

-continued
| Compound | Structure | $^1$H-NMR | MS | Intermediates used |
|---|---|---|---|---|
| 17 | 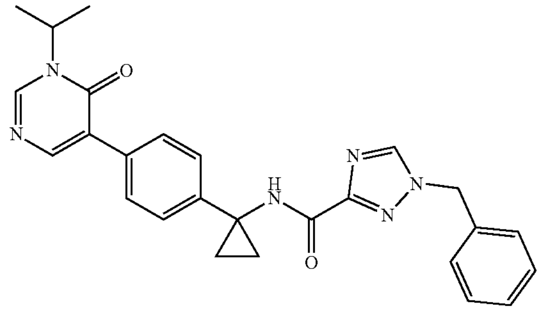 [SMILES: CC(C)n1cncc(-c2ccc(C3(NC(=O)c4ncn(Cc5ccccc5)n4)CC3)cc2)c1=O] | $^1$H NMR (400 MHz, $CDCl_3$) δ 8.14 (s, 1H), 7.99 (s, 2H), 7.76 (s, 1H), 7.57 (d, J = 8.2 Hz, 2H), 7.42-7.36 (m, 5H), 7.34-7.26 (m, 2H), 5.38 (s, 2H), 5.21-5.10 (m, 1H), 1.47 (d, J = 6.9 Hz, 6H), 1.46-1.35 (m, 4H). | 455 | 10, 21 |
| 18 | 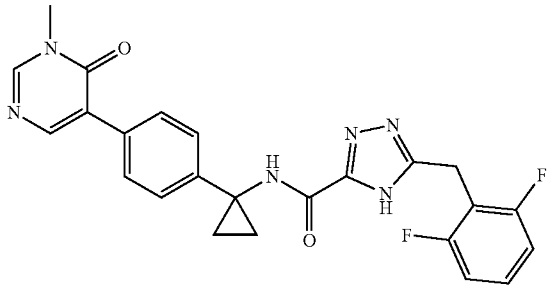 [SMILES: Cn1cncc(-c2ccc(C3(NC(=O)c4nnc(Cc5c(F)cccc5F)[nH]4)CC3)cc2)c1=O] | $^1$H NMR (400 MHz, $CD_3OD$) δ 8.37 (s, 1H), 8.05 (s, 1H), 7.59-7.54 (m, 2H), 7.37-7.28 (m, 3H), 7.05-6.95 (m, 2H), 4.20 (s, 2H), 3.56 (s, 3H), 1.39-1.33 (m, 4H). | 463 | 22 |
| 19 | 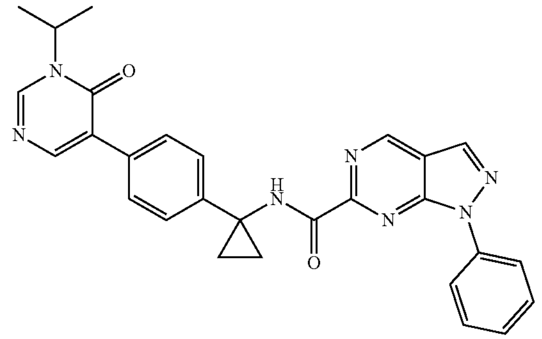 [SMILES: CC(C)n1cncc(-c2ccc(C3(NC(=O)c4ncc5cnn(-c6ccccc6)c5n4)CC3)cc2)c1=O] | $^1$H NMR (400 MHz, $CDCl_3$) δ 9.32 (s, 1H), 8.79 (s, 1H), 8.41 (s, 1H), 8.27 (d, J = 7.8 Hz, 2H), 8.13 (s, 1H), 7.98 (s, 1H), 7.61-7.54 (m, 4H), 7.45 (d, J = 8.4 Hz, 2H), 7.39 (t, J = 7.4 Hz, 1H), 5.20-5.10 (m, 1H), 1.49-1.45 (m, 10H). | 492 | 10, 23 |
| 22 | 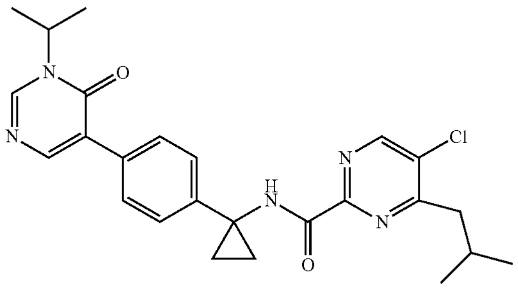 [SMILES: CC(C)Cc1nc(C(=O)NC2(c3ccc(-c4cncn(C(C)C)c4=O)cc3)CC2)ncc1Cl] | $^1$H NMR (400 MHz, $CDCl_3$) δ 8.70 (s, 1H), 8.50 (s, 1H), 8.13 (s, 1H), 7.98 (s, 1H), 7.58 (d, J = 8.4 Hz, 2H), 7.40 (d, J = 8.4 Hz, 2H), 5.22-5.10 (m, 1H), 2.86 (d, J = 7.2 Hz, 2H), 2.29 (m, 1H), 1.50-1.40 (m, 10H), 0.98 (d, J = 6.7 Hz, 6H). | 466 | 10, 1 |
| 59 | 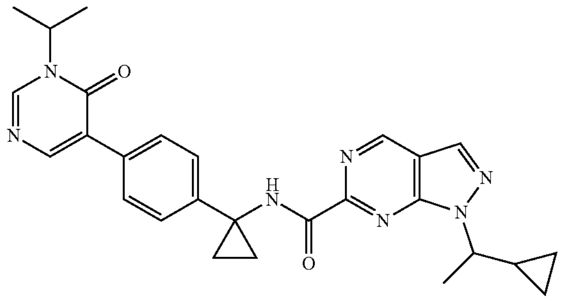 [SMILES: CC(C)n1cncc(-c2ccc(C3(NC(=O)c4ncc5cnn(C(C)C6CC6)c5n4)CC3)cc2)c1=O] | $^1$H NMR (400 MHz, $CD_3OD$): δ 9.34 (s, 1H), 8.47-8.34 (m, 2H), 8.02 (s, 1H), 7.61-7.53 (m, 2H), 7.41-7.35 (m, 2H), 5.12-5.00 (m, 1H), 4.65-4.48 (m, 1H), 1.74-1.64 (m, 3H), 1.55-1.45 (m, 9H), 1.44-1.41 (m, 2H), 0.76-0.59 (m, 1H), 0.56-0.44 (m, 1H), 0.41-0.30 (m, 2H). | 484 | 10, 39 |

-continued
| Compound | Structure | $^1$H-NMR | MS | Intermediates used |
|---|---|---|---|---|
| 60 | 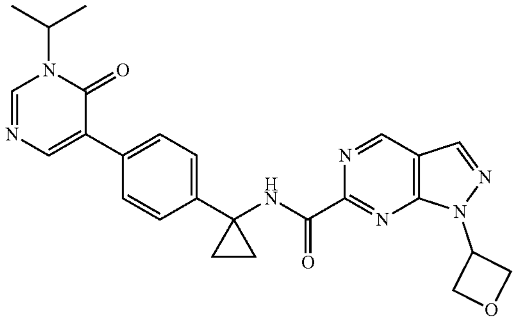 [SMILES: CC(C)n1cncc(-c2ccc(C3(NC(=O)c4ncc5cnn(C6COC6)c5n4)CC3)cc2)c1=O] | $^1$H NMR (400 MHz, $CD_3OD$): δ 9.35 (s, 1H), 8.59-8.46 (m, 1H), 8.41 (s, 1H), 8.06-7.95 (m, 1H), 7.59-7.50 (m, 2H), 7.42-7.32 (m, 2H), 6.45-6.28 (m, 1H), 5.24-5.17 (m, 2H), 5.15-5.09 (m, 2H), 5.08-4.99 (m, 1H), 1.49-1.44 (m, 8H), 1.43-1.41 (m, 2H). | 472 | 10, 40 |
| 61 | 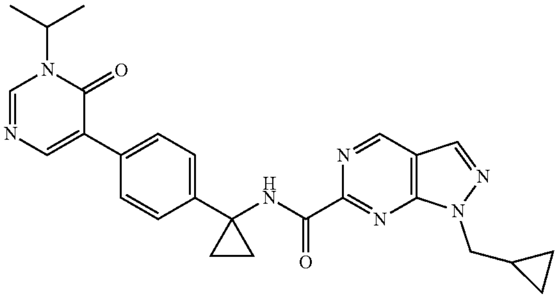 [SMILES: CC(C)n1cncc(-c2ccc(C3(NC(=O)c4ncc5cnn(CC6CC6)c5n4)CC3)cc2)c1=O] | $^1$H NMR (400 MHz, $CD_3OD$): δ 9.32 (s, 1H), 8.43 (s, 1H), 8.35 (s, 1H), 8.00 (s, 1H), 7.63-7.47 (m, 2H), 7.39-7.24 (m, 2H), 5.17-5.01 (m, 1H), 4.51-4.36 (m, 2H), 1.63-1.35 (m, 11H), 0.57-0.41 (m, 4H). | 470 | 10, 41 |
| 62 | 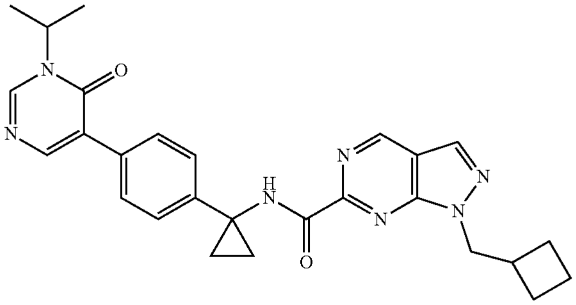 [SMILES: CC(C)n1cncc(-c2ccc(C3(NC(=O)c4ncc5cnn(CC6CCC6)c5n4)CC3)cc2)c1=O] | $^1$H NMR (400 MHz, $CD_3OD$): δ 9.32 (s, 1H), 8.42 (s, 1H), 8.33 (s, 1H), 8.01 (s, 1H), 7.63-7.51 (m, 2H), 7.46-7.28 (m, 2H), 5.15-4.99 (m, 1H), 4.67-4.53 (m, 2H), 3.04-2.85 (m, 1H), 2.09-1.80 (m, 7H), 1.52-1.40 (m, 9H). | 484 | 10, 42 |
| 63 | 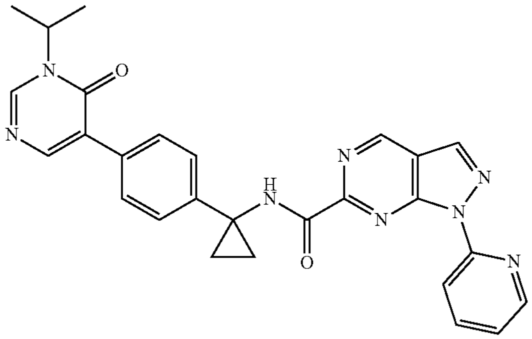 [SMILES: CC(C)n1cncc(-c2ccc(C3(NC(=O)c4ncc5cnn(-c6ccccn6)c5n4)CC3)cc2)c1=O] | $^1$H NMR (400 MHz, $CD_3OD$): δ 9.48 (s, 1H), 8.64 (s, 1H), 8.62-8.57 (m, 1H), 8.54 (s, 0.36H), 8.41 (s, 1H), 8.39-8.33 (m, 1H), 8.12-8.03 (m, 1H), 7.98 (s, 1H), 7.58-7.49 (m, 2H), 7.47-7.40 (m, 1H), 7.38-7.30 (m, 2H), 5.10-4.99 (m, 1H), 1.47-1.45 (m, 6H), 1.43-1.38 (m, 2H), 1.30-1.25 (m, 2H). | 493 | 10, 43 |

-continued

| Compound | Structure | $^1$H-NMR | MS | Intermediates used |
|---|---|---|---|---|
| 64 | 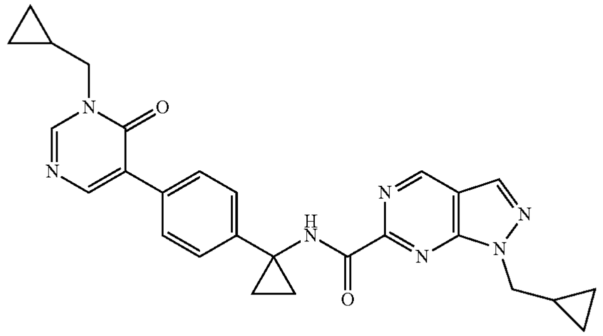 [SMILES: O=C(NC1(c2ccc(-c3cncn(CC4CC4)c3=O)cc2)CC1)c1ncc2cnn(CC3CC3)c2n1] | $^1$H NMR (400 MHz, $CD_3OD$) δ 9.35 (s, 1H), 8.41 (s, 1H), 8.37 (s, 1H), 8.05 (s, 1H), 7.58 (d, J = 8.1 Hz, 2H), 7.38 (d, J = 8.2 Hz, 2H), 4.47 (d, J = 7.1 Hz, 2H), 3.88 (d, J = 7.1 Hz, 2H), 1.46-1.39 (m, 4H), 1.34-1.22 (m, 2H), 0.61-0.57 (m, 2H), 0.56-0.47 (m, 4H), 0.45-0.42 (m, 2H). | 482 | 41, 48 |

Compound 23

N-(1-(3-fluoro-4-(1-methyl-6-oxo-1,6-dihydropyrimidin-5-yl)phenyl)cyclopropyl)-1-isopropyl-1H-pyrazolo[3,4-d]pyrimidine-6-carboxamide

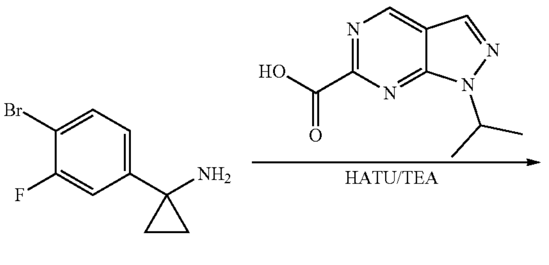

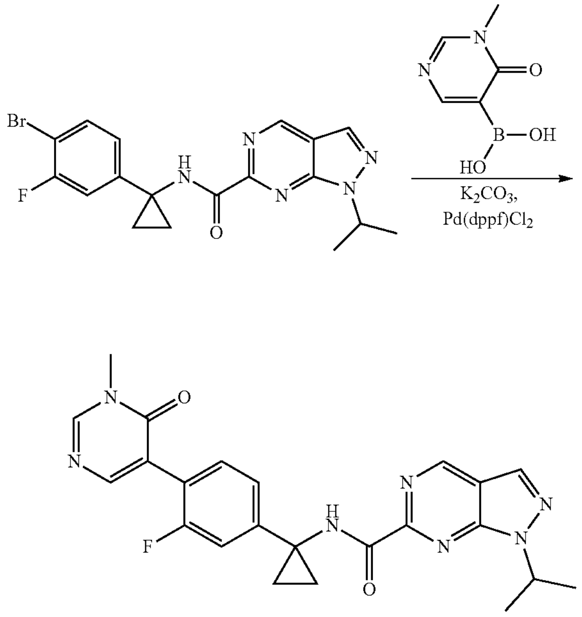

(A) N-(1-(4-bromo-3-fluorophenyl)cyclopropyl)-1-isopropyl-1H-pyrazolo[3,4-d]pyrimidine-6-carboxamide The mixture of 1-(4-bromo-3-fluorophenyl)cyclopropan-1-amine (100 mg, 0.43 mmol), 1-isopropyl-1H-pyrazolo[3,4-d]pyrimidine-6-carboxylic acid (90 mg, 0.43 mmol), HATU (196 mg, 0.52 mmol), and TEA (130 mg, 0.52 mmol) in DCM (10 mL) was stirred at room temperature under nitrogen atmosphere for 2 hours. The solvent was removed. The residue was purified by flash column chromatography (eluting with gradient MeOH/$H_2O$ (+0.1% HCOOH)=10%-80%) to obtain 100 mg of the product as white solid. MS (m/z)=419 [M+H]$^+$.

(B) N-(1-(3-fluoro-4-(1-methyl-6-oxo-1,6-dihydropyrimidin-5-yl)phenyl)cyclopropyl)-1-isopropyl-1H-pyrazolo[3,4-d]pyrimidine-6-carboxamide The mixture of N-(1-(4-bromo-3-fluorophenyl)cyclopropyl)-1-isopropyl-1H-pyrazolo[3,4-d]pyrimidine-6-carboxamide (100 mg, 0.24 mmol), (1-methyl-6-oxo-1,6-dihydropyrimidin-5-yl)boronic acid (38 mg, 0.24 mmol), $K_2CO_3$ (100 mg, 0.72 mmol), and Pd(dppf)$Cl_2$ (12 mg, 0.02 mmol) in 10 mL of dioxane/$H_2O$ (3:1) was stirred at 120° C. under nitrogen atmosphere for 5 hours. The solvent was removed, and the residue was purified by flash column chromatography (eluting with gradient MeOH/$H_2O$ (+0.1% HCOOH)=10%-80%) to give the crude product. The crude product was purified by Pre-TLC (DCM/MeOH=15/1) to give 50 mg of the product as white solid. MS (m/z)=448 [M+H]$^+$.

$^1$H NMR (400 MHz, DMSO) δ 9.76 (s, 1H), 9.43 (d, J=1.8 Hz, 1H), 8.48 (d, J=5.4 Hz, 2H), 7.97 (s, 1H), 7.36 (t, J=7.9 Hz, 1H), 7.12-7.08 (m, 2H), 5.35-5.24 (m, 1H), 3.45 (s, 3H), 1.51 (d, J=6.7 Hz, 6H), 1.40-1.34 (m, 4H).

The following compounds were prepared according to the procedure of Compound 23 using the corresponding intermediates and reagents under appropriate conditions that will be recognized by one skilled in the art.

| Compound | Structure | $^1$H-NMR | MS | Intermediates used |
|---|---|---|---|---|
| 24 | 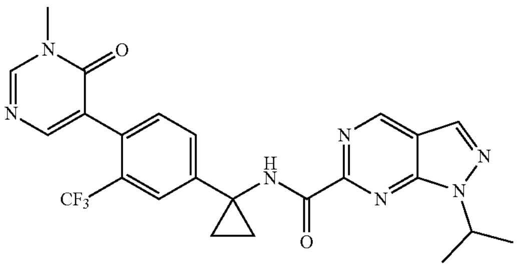 [SMILES: CC(C)n1ncc2cnc(C(=O)NC3(c4ccc(-c5cncn(C)c5=O)c(C(F)(F)F)c4)CC3)nc21] | $^1$H NMR (400 MHz, DMSO) δ 9.84 (s, 1H), 9.42 (s, 1H), 8.49 (d, J = 10.3 Hz, 2H), 7.80 (s, 1H), 7.68 (s, 1H), 7.56 (d, J = 8.1 Hz, 1H), 7.30 (d, J = 8.1 Hz, 1H), 5.38-5.20 (m, 1H), 3.44 (s, 3H), 1.51 (d, J = 6.7 Hz, 6H), 1.42-1.38 (m, 4H). | 498 | 6 |
| 25 | 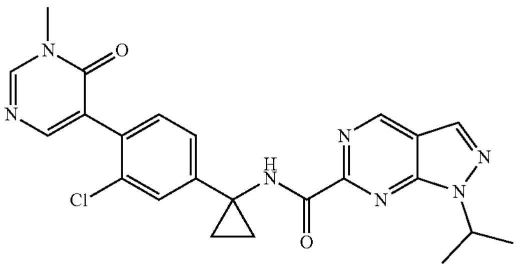 [SMILES: CC(C)n1ncc2cnc(C(=O)NC3(c4ccc(-c5cncn(C)c5=O)c(Cl)c4)CC3)nc21] | $^1$H NMR (400 MHz, DMSO) δ 9.77 (s, 1H), 9.42 (s, 1H), 8.49 (d, J = 12.0 Hz, 2H), 7.89 (s, 1H), 7.39 (d, J = 1.2 Hz, 1H), 7.30-7.21 (m, 2H), 5.34-5.23 (m, 1H), 3.45 (s, 3H), 1.51 (d, J = 6.7 Hz, 6H), 1.40-1.33 (m, 4H). | 464 | 6, 26 |
| 26 | 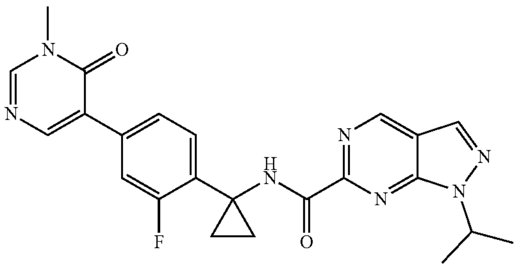 [SMILES: CC(C)n1ncc2cnc(C(=O)NC3(c4ccc(-c5cncn(C)c5=O)cc4F)CC3)nc21] | $^1$H NMR (400 MHz, DMSO) δ 9.49 (s, 1H), 9.38 (s, 1H), 8.46 (d, J = 11.9 Hz, 2H), 8.18 (s, 1H), 7.67-7.60 (m, 1H), 7.55-7.45 (m, 2H), 5.29-5.20 (m, 1H), 3.46 (s, 3H), 1.49 (d, J = 6.7 Hz, 6H), 1.32-1.27 (m, 4H). | 448 | 6, 28 |
| 27 | 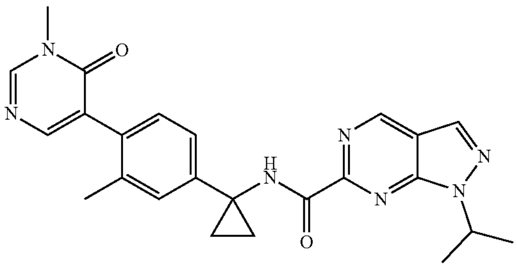 [SMILES: Cc1cc(C2(NC(=O)c3ncc4cnn(C(C)C)c4n3)CC2)ccc1-c1cncn(C)c1=O] | $^1$H NMR (400 MHz, DMSO) δ 9.66 (s, 1H), 9.42 (s, 1H), 8.52-8.45 (m, 2H), 7.81 (s, 1H), 7.14-7.10 (m, 2H), 7.07-7.00 (m, 1H), 5.34-5.25 (m, 1H), 3.45 (s, 3H), 2.09 (s, 3H), 1.51 (d, J = 6.7 Hz, 6H), 1.34-1.27 (m, 4H). | 444 | 6 |
| 48 | 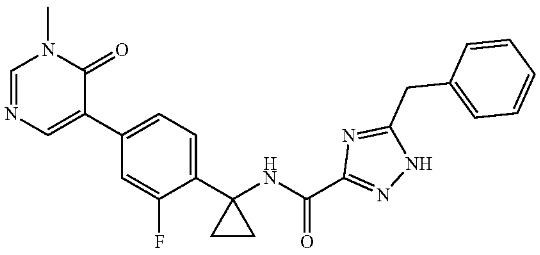 [SMILES: Cn1cncc(-c2ccc(C3(NC(=O)c4n[nH]c(Cc5ccccc5)n4)CC3)c(F)c2)c1=O] | $^1$H NMR (400 MHz, $CDCl_3$) δ 8.06 (s, 1H), 7.95 (s, 1H), 7.74-7.63 (m, 3H), 7.56-7.47 (m, 3H), 5.46 (d, J = 5.9 Hz, 1H), 5.43-5.37 (m, 1H), 5.36 (s, 2H), 1.38 (d, J = 6.8 Hz, 3H). | 445 | 6, 28 |

Compound 28

1-isopropyl-N-(1-(4-(1-methyl-6-oxo-1,6-dihydropyrimidin-5-yl)phenyl)cyclopropyl)-1H-pyrazolo[4,3-c]pyridine-6-carboxamide

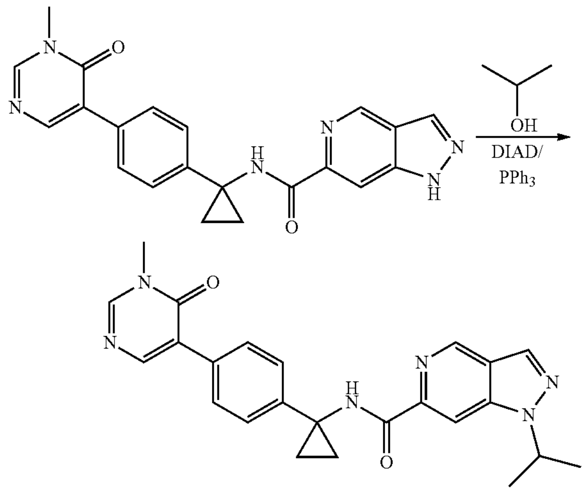

To a solution of N-(1-(4-(1-methyl-6-oxo-1,6-dihydropyrimidin-5-yl)phenyl)cyclopropyl)-1H-pyrazolo[4,3-c]pyridine-6-carboxamide (this compound was prepared according to the procedure of Compound 1 using 5-bromo-3-methylpyrimidin-4(3H)-one, tert-butyl (1-(4-(4,4,5,5-tetramethyl-1,3,2-dioxaborolan-2-yl)phenyl)cyclopropyl) carbamate and 1H-pyrazolo[4,3-c]pyridine-6-carboxylic acid as the raw materials) (60.0 mg, 0.16 mmol) and isopropanol (18.6 mg, 0.31 mmol) in a mixed solvent of DCM (4 mL) and THF (4 mL) was added DIAD (62.6 mg, 0.31 mmol) and $PPh_3$ (81.2 mg, 0.31 mmol). The reaction mixture was reacted at room temperature overnight. The mixture was concentrated under reduced pressure, and the residue was purified by flash column chromatography (eluting with gradient MeOH/$H_2O$=10%-100%) to give 35 mg of the title product. MS (m/z)=429 $[M+H]^+$.

$^1H$ NMR (400 MHz, DMSO) δ 9.51 (s, 1H), 9.19-9.09 (m, 1H), 8.43 (s, 1H), 8.41 (s, 1H), 8.31 (s, 1H), 8.07 (s, 1H), 7.57 (d, J=8.3 Hz, 2H), 7.24 (d, J=8.3 Hz, 2H), 5.35-4.97 (m, 1H), 3.45 (s, 3H), 1.48 (d, J=6.6 Hz, 6H), 1.41-1.26 (m, 4H).

Compound 29

1-isopropyl-N-(1-(4-(1-isopropyl-6-oxo-1,6-dihydropyrimidin-5-yl)phenyl)cyclopropyl)-1H-pyrazolo[3,4-d]pyrimidine-6-carboxamide

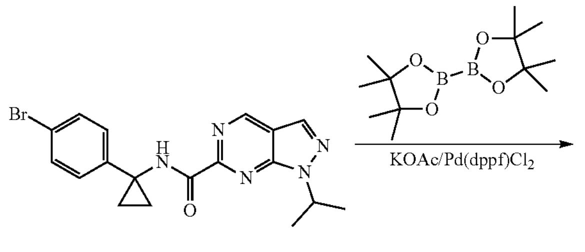

-continued

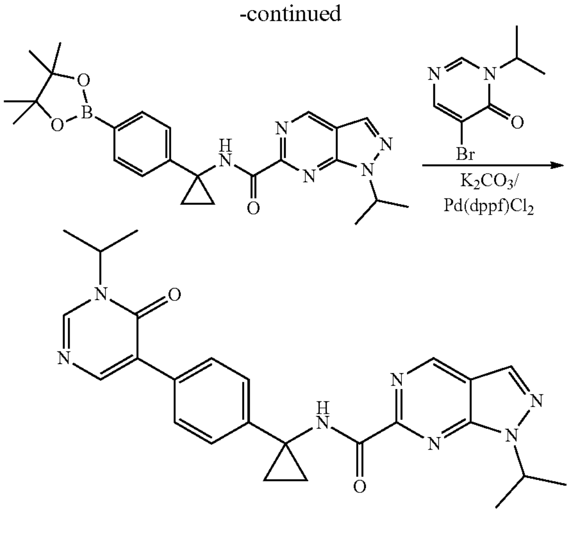

(A) 1-isopropyl-N-(1-(4-(4,4,5,5-tetramethyl-1,3,2-dioxaborolan-2-yl)phenyl)cyclopropyl)-1H-pyrazolo[3,4-d]pyrimidine-6-carboxamide The mixture of N-(1-(4-bromophenyl)cyclopropyl)-1-isopropyl-1H-pyrazolo[3,4-d]pyrimidine-6-carboxamide (this compound was prepared according to the procedure of Compound 23(A) using 1-(4-bromophenyl)cyclopropan-1-amine and 1-isopropyl-1H-pyrazolo[3,4-d]pyrimidine-6-carboxylic acid as the raw materials) (1 g, 2.5 mmol), Bis(pinacolato)diboron (952 mg, 3.75 mmol), KOAc (735 mg, 7.5 mmol), and Pd(dppf)$Cl_2$ (92 mg, 0.13 mmol) in dioxane (30 mL) was stirred at 120° C. under nitrogen atmosphere for 5 hours. The solvent was removed. The residue was purified by flash column chromatography (eluting with gradient MeOH/$H_2O$ (+0.1% HCOOH)=10%-80%) to give 800 mg of the product as yellow solid. MS (m/z)=448 $[M+H]^+$.

(B) 1-isopropyl-N-(1-(4-(1-isopropyl-6-oxo-1,6-dihydropyrimidin-5-yl)phenyl)cyclopropyl)-1H-pyrazolo[3,4-d]pyrimidine-6-carboxamide To a solution of 1-isopropyl-N-(1-(4-(4,4,5,5-tetramethyl-1,3,2-dioxaborolan-2-yl)phenyl)cyclopropyl)-1H-pyrazolo[3,4-d]pyrimidine-6-carboxamide (120 mg, 0.27 mmol) and 5-bromo-3-isopropylpyrimidin-4(3H)-one (59 mg, 0.27 mmol) in a mixed solvent of dioxane (10 mL) and water (2 mL) was added Pd(dppf)$Cl_2$ (20 mg, 0.027 mmol) and potassium carbonate (112 mg, 0.81 mmol) under nitrogen atmosphere. The reaction mixture was heated to reflux and reacted for 2 hours, and then cooled to room temperature. The mixture was concentrated under reduced pressure, and the residue was purified by flash column chromatography (eluting with MeOH/$H_2O$(+0.5% HCOOH)=60%:40%) to give 23 mg of the product as pale yellow solid. MS (m/z)=458.2 $[M+H]^+$.

$^1H$ NMR (400 MHz, DMSO) δ 9.72 (s, 1H), 9.43 (s, 1H), 8.53 (s, 1H), 8.48 (s, 1H), 8.07 (s, 1H), 7.58 (d, J=8.3 Hz, 2H), 7.27 (d, J=8.3 Hz, 2H), 5.38-5.26 (m, 1H), 5.03-4.90 (m, 1H), 1.51 (d, J=6.7 Hz, 6H), 1.39 (d, J=6.9 Hz, 6H), 1.34 (d, J=8.4 Hz, 4H).

The following compounds were prepared according to the procedure of Compound 29 using the corresponding intermediates and reagents under appropriate conditions that will be recognized by one skilled in the art.

| Compound | Structure | $^1$H-NMR | MS | Intermediates used |
|---|---|---|---|---|
| 30 | 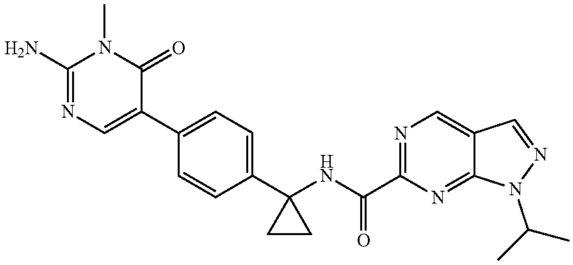 [SMILES: CC(C)n1ncc2cnc(C(=O)NC3(c4ccc(-c5cnc(N)n(C)c5=O)cc4)CC3)nc21] | $^1$H NMR (400 MHz, DMSO) δ 9.68 (s, 1H), 9.44 (s, 1H), 8.49 (s, 1H), 7.79 (s, 1H), 7.52 (d, J = 8.4 Hz, 2H), 7.22 (d, J = 8.6 Hz, 4H), 5.37-5.26 (m, 1H), 3.32 (s, 3H), 1.53 (d, J = 6.7 Hz, 6H), 1.31 (d, J = 12.5 Hz, 4H). | 445 | 5 |
| 31 | 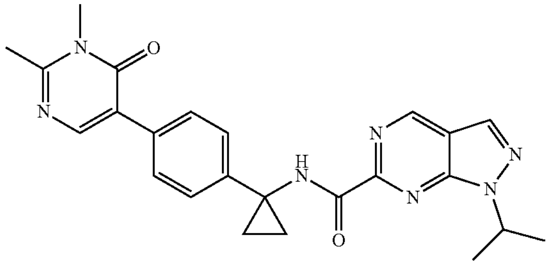 [SMILES: Cc1ncc(-c2ccc(C3(NC(=O)c4ncc5cnn(C(C)C)c5n4)CC3)cc2)c(=O)n1C] | $^1$H NMR (400 MHz, DMSO) δ 9.72 (s, 1H), 9.44 (s, 1H), 8.50 (s, 1H), 8.00 (s, 1H), 7.59 (d, J = 8.4 Hz, 2H), 7.29 (d, J = 8.4 Hz, 2H), 5.41-5.23 (m, 1H), 3.50 (s, 3H), 2.52 (s, 3H), 1.53 (d, J = 6.7 Hz, 6H), 1.41-1.29 (m, 4H). | 444 | 2 |
| 32 | 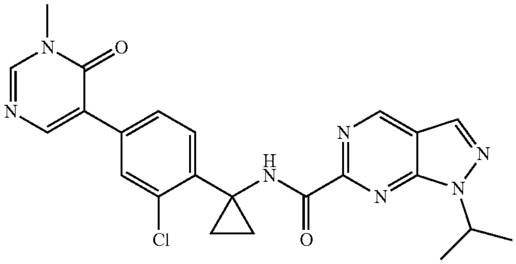 [SMILES: CC(C)n1ncc2cnc(C(=O)NC3(c4ccc(-c5cncn(C)c5=O)cc4Cl)CC3)nc21] | $^1$H NMR (400 MHz, $CD_3OD$) δ 9.25 (s, 1H), 8.36 (s, 1H), 8.30 (s, 1H), 8.06 (s, 1H), 7.84 (d, J = 8.0 Hz, 1H), 7.72 (d, J = 1.4 Hz, 1H), 7.58-7.47 (m, 1H), 5.40-5.27 (m, 1H), 3.53 (s, 3H), 1.53 (d, J = 6.7 Hz, 6H), 1.44-1.29 (m, 4H). | 464 | 27 |
| 33 | 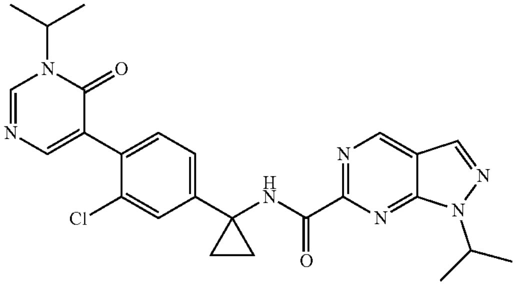 [SMILES: CC(C)n1cncc(-c2ccc(C3(NC(=O)c4ncc5cnn(C(C)C)c5n4)CC3)cc2Cl)c1=O] | $^1$H NMR (400 MHz, $CD_3OD$) δ 9.34 (s, 1H), 8.50 (s, 1H), 8.37 (s, 1H), 7.89 (s, 1H), 7.50 (s, 1H), 7.35-7.25 (m, 2H), 5.52-5.39 (m, 1H), 5.08-4.99 (m, 1H), 1.58 (d, J = 6.4 Hz, 6H), 1.49 (d, 6H), 1.47-1.43 (m, 4H). | 492 | 10, 26 |
| 34 | 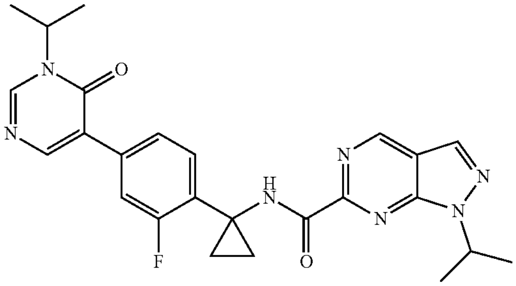 [SMILES: CC(C)n1cncc(-c2ccc(C3(NC(=O)c4ncc5cnn(C(C)C)c5n4)CC3)c(F)c2)c1=O] | $^1$H NMR (400 MHz, $CD_3OD$) δ 9.28 (s, 1H), 8.44 (s, 1H), 8.33 (s, 1H), 8.07 (s, 1H), 7.78-7.69 (m, 1H), 7.45 (d, J = 11.9 Hz, 1H), 7.38 (d, J = 7.5 Hz, 1H), 5.47-5.33 (m, 1H), 5.13-5.02 (m, 1H), 1.54 (d, J = 5.7 Hz, 6H), 1.47 (d, J = 6.1 Hz, 6H), 1.41-1.36 (m, 4H). | 476 | 10, 28 |

-continued

| Compound | Structure | $^{1}$H-NMR | MS | Intermediates used |
|---|---|---|---|---|
| 35 | 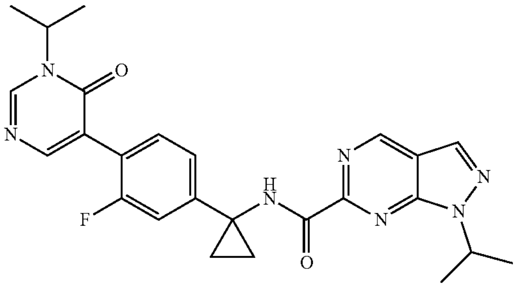 [SMILES: CC(C)n1cncc(-c2ccc(C3(NC(=O)c4ncc5cnn(C(C)C)c5n4)CC3)cc2F)c1=O] | $^{1}$H NMR (400 MHz, $CD_3OD$) δ 9.34 (s, 1H), 8.48 (s, 1H), 8.37 (s, 1H), 7.97 (s, 1H), 7.46-7.34 (m, J = 7.5 Hz, 1H), 7.21-7.13 (m, J = 8.5 Hz, 2H), 5.53-5.39 (m, 1H), 5.08-4.99 (m, 1H), 1.57 (d, J = 6.3 Hz, 6H), 1.49 (d, 6H), 1.47-1.40 (m, 4H). | 476 | 10, 29 |
| 36 | 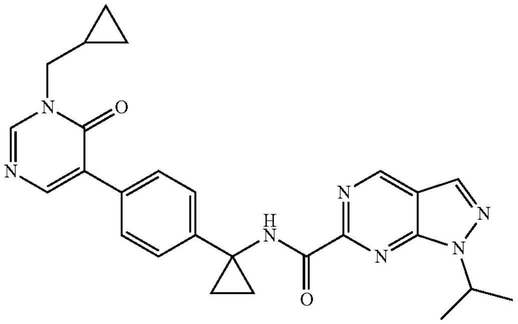 [SMILES: CC(C)n1ncc2cnc(C(=O)NC3(c4ccc(-c5cncn(CC6CC6)c5=O)cc4)CC3)nc21] | $^{1}$H NMR (400 MHz, $CD_3OD$) δ 9.33 (s, 1H), 8.39 (s, 1H), 8.36 (s, 1H), 8.04 (s, 1H), 7.58 (d, J = 7.8 Hz, 2H), 7.38 (d, J = 7.8 Hz, 2H), 5.51-5.33 (m, 1H), 3.87 (d, J = 7.1 Hz, 2H), 1.56 (d, J = 6.5 Hz, 6H), 1.49-1.40 (m, 4H), 1.36-1.27 (m, 1H), 0.63-0.52 (m, 2H), 0.47-0.35 (m, 2H). | 470 | 4 |
| 37 | 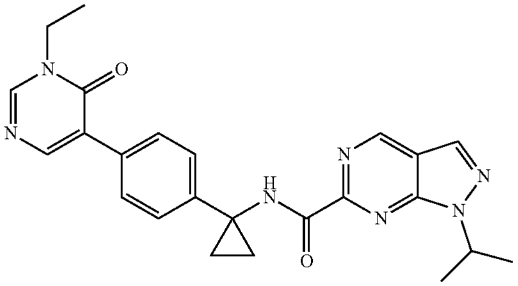 [SMILES: CCn1cncc(-c2ccc(C3(NC(=O)c4ncc5cnn(C(C)C)c5n4)CC3)cc2)c1=O] | $^{1}$H NMR (400 MHz, $CDCl_3$) δ 9.19 (s, 1H), 8.83 (s, 1H), 8.22 (s, 1H), 8.08 (s, 1H), 7.99 (s, 1H), 7.59 (d, J = 7.7 Hz, 2H), 7.44 (d, J = 7.6 Hz, 2H), 5.52-5.41 (m, 1H), 4.03 (q, J = 7.1 Hz, 2H), 1.58 (d, J = 6.5 Hz, 6H), 1.49-1.40 (m, 7H). | 444 | 11 |
| 38 | 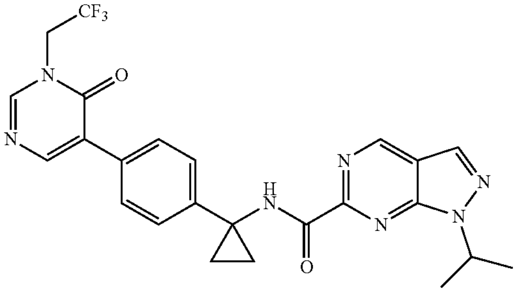 [SMILES: CC(C)n1ncc2cnc(C(=O)NC3(c4ccc(-c5cncn(CC(F)(F)F)c5=O)cc4)CC3)nc21] | $^{1}$H NMR (400 MHz, $CDCl_3$) δ 9.19 (s, 1H), 8.83 (s, 1H), 8.23 (s, 1H), 8.08 (s, 1H), 8.00 (s, 1H), 7.58 (d, J = 7.5 Hz, 2H), 7.44 (d, J = 7.8 Hz, 2H), 5.52-5.39 (m, 1H), 4.66 (q, J = 8.5 Hz, 2H), 1.59 (d, J = 6.6 Hz, 6H), 1.52-1.43 (m, 4H). | 498 | 12 |
| 39 | 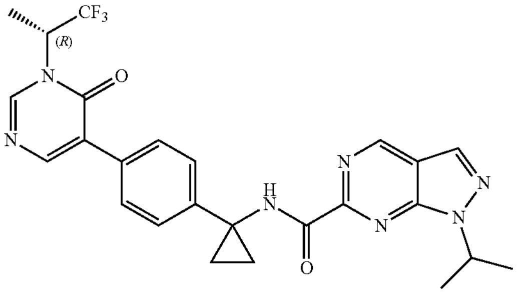 | $^{1}$H NMR (400 MHz, $CDCl_3$) δ 9.19 (s, 1H), 8.84 (s, 1H), 8.23 (s, 1H), 8.17 (s, 1H), 7.99 (s, 1H), 7.57 (d, J = 7.5 Hz, 2H), 7.45 (d, J = 7.5 Hz, 2H), 5.96-5.85 (m, 1H), 5.52-5.39 (m, 1H), 1.69 (d, J = 7.4 Hz, 3H), 1.59 (d, J = 6.6 Hz, 6H), 1.51-1.42 (m, 4H). | 512 | 14 |

-continued

| Compound | Structure | $^1$H-NMR | MS | Intermediates used |
|---|---|---|---|---|
| 40 | 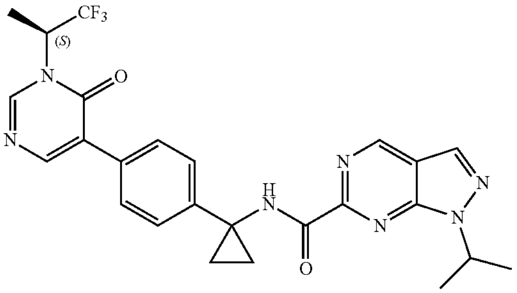 | $^1$H NMR (400 MHz, $CDCl_3$) δ 9.19 (s, 1H), 8.84 (s, 1H), 8.23 (s, 1H), 8.17 (s, 1H), 7.99 (s, 1H), 7.57 (d, J = 8.0 Hz, 2H), 7.45 (d, J = 8.1 Hz, 2H), 5.97-5.84 (m, 1H), 5.53-5.40 (m, 1H), 1.69 (d, J = 7.3 Hz, 3H), 1.59 (d, J = 6.7 Hz, 6H), 1.52-1.43 (m, 4H). | 512 | 13 |
| 41 | 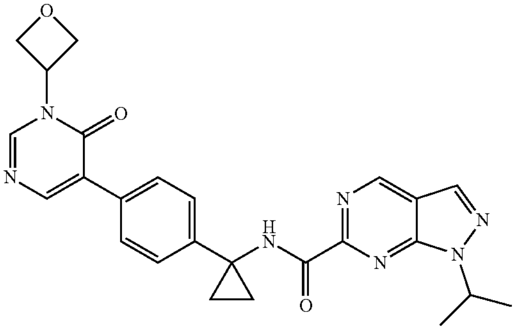 [SMILES: CC(C)n1ncc2cnc(C(=O)NC3(c4ccc(-c5cncn(C6COC6)c5=O)cc4)CC3)nc21] | $^1$H NMR (400 MHz, DMSO) δ 9.72 (s, 1H), 9.42 (s, 1H), 8.47 (s, 1H), 8.46 (s, 1H), 8.13 (s, 1H), 7.58 (d, J = 8.3 Hz, 2H), 7.27 (d, J = 8.4 Hz, 2H), 5.44 (p, J = 7.4 Hz, 1H), 5.35-5.24 (m, 1H), 4.86 (dt, J = 18.7, 7.2 Hz, 4H), 1.51 (d, J = 6.7 Hz, 6H), 1.37-1.29 (m, 4H). | 472 | 16 |
| 42 | 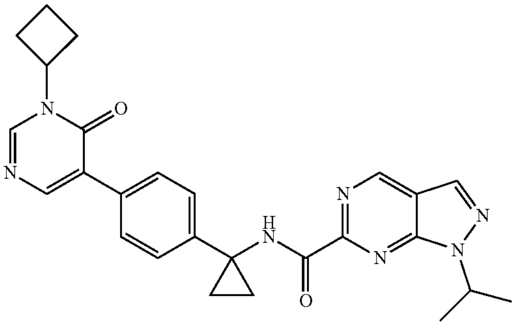 [SMILES: CC(C)n1ncc2cnc(C(=O)NC3(c4ccc(-c5cncn(C6CCC6)c5=O)cc4)CC3)nc21] | $^1$H NMR (400 MHz, DMSO) δ 9.73 (s, 1H), 9.42 (s, 1H), 8.50 (s, 1H), 8.47 (s, 1H), 8.08 (s, 1H), 7.57 (d, J = 8.4 Hz, 2H), 7.26 (d, J = 8.4 Hz, 2H), 5.30 (dt, J = 13.3, 6.6 Hz, 1H), 4.98-4.80 (m, 1H), 2.41-2.32 (m, 4H), 1.83-1.73 (m, 2H), 1.50 (d, J = 6.7 Hz, 6H), 1.37-1.29 (m, 4H). | 470 | 15 |
| 43 | 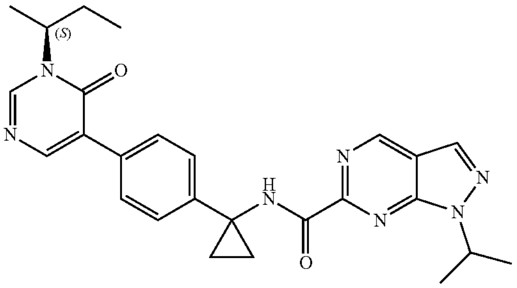 | $^1$H NMR (400 MHz, DMSO) δ 9.73 (s, 1H), 9.42 (s, 1H), 8.48 (d, J = 1.4 Hz, 2H), 8.07 (s, 1H), 7.58 (d, J = 8.4 Hz, 2H), 7.27 (d, J = 8.4 Hz, 2H), 5.38-5.19 (m, 1H), 4.79-4.72 (m, 1H), 1.84-1.71 (m, 2H), 1.50 (d, J = 6.7 Hz, 6H), 1.37 (d, J = 6.9 Hz, 3H), 1.33 (d, J = 9.4 Hz, 4H), 0.78 (t, J = 7.4 Hz, 3H). | 472 | 17 |
| 44 | 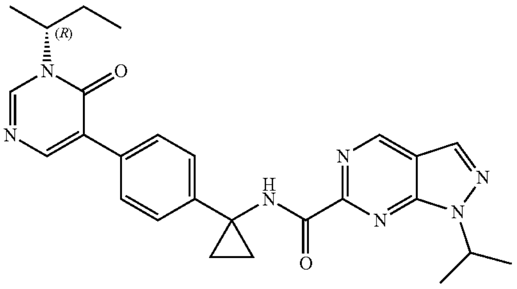 | $^1$H NMR (400 MHz, DMSO) δ 9.73 (s, 1H), 9.42 (s, 1H), 8.48 (d, J = 1.1 Hz, 2H), 8.07 (s, 1H), 7.58 (d, J = 8.4 Hz, 2H), 7.27 (d, J = 8.4 Hz, 2H), 5.38-5.21 (m, 1H), 4.87-4.69 (m, 1H), 1.85-1.70 (m, 2H), 1.50 (d, J = 6.7 Hz, 6H), 1.37 (d, J = 6.9 Hz, 3H), 1.33 (d, J = 9.4 Hz, 4H), 0.78 (t, J = 7.4 Hz, 3H). | 472 | 18 |

-continued
| Compound | Structure | $^1$H-NMR | MS | Intermediates used |
|---|---|---|---|---|
| 45 | 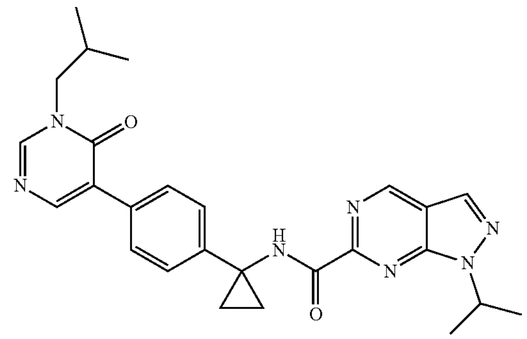 [SMILES: CC(C)Cn1cncc(-c2ccc(C3(NC(=O)c4ncc5cnn(C(C)C)c5n4)CC3)cc2)c1=O] | $^1$H NMR (400 MHz, DMSO) δ 9.73 (s, 1H), 9.42 (s, 1H), 8.47 (s, 1H), 8.42 (s, 1H), 8.08 (s, 1H), 7.58 (d, J = 8.3 Hz, 2H), 7.27 (d, J = 8.3 Hz, 2H), 5.42-5.17 (m, 1H), 3.76 (d, J = 7.3 Hz, 2H), 2.06 (dt, J = 13.7, 6.7 Hz, 1H), 1.50 (d, J = 6.6 Hz, 6H), 1.33 (d, J = 9.3 Hz, 4H), 0.85 (d, J = 6.7 Hz, 6H). | 472 | 19 |
| 46 | 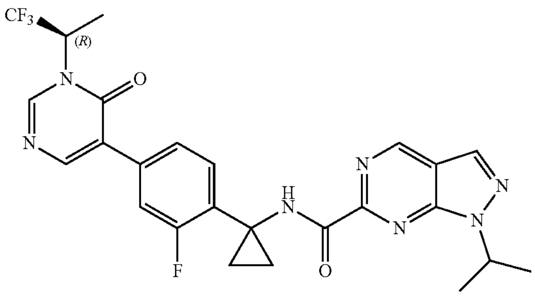 | $^1$H NMR (400 MHz, $CDCl_3$) δ 9.15 (s, 1H), 8.87 (s, 1H), 8.23-8.14 (m, 2H), 8.01 (s, 1H), 7.89-7.79 (m, 1H), 7.41 (d, J = 11.8 Hz, 1H), 7.31 (d, J = 8.0 Hz, 1H), 5.98-5.78 (m, 1H), 5.53-5.32 (m, 1H), 1.71-1.67 (d, J = 7.3 Hz, 3H), 1.56 (d, J = 5.4 Hz, 6H), 1.41-1.33 (m, 4H). | 530 | 14, 28 |
| 47 | 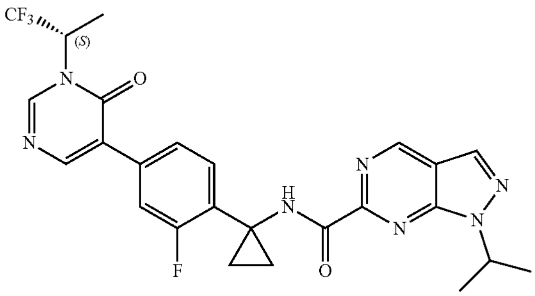 | $^1$H NMR (400 MHz, $CDCl_3$) δ 9.20 (s, 1H), 8.89 (s, 1H), 8.26-8.19 (m, 2H), 8.02 (s, 1H), 7.86-7.72 (m, 1H), 7.39 (d, J = 11.0 Hz, 1H), 7.29 (d, J = 7.6 Hz, 1H), 5.95-5.82 (m, 1H), 5.48-5.35 (m, 1H), 1.70 (d, J = 7.3 Hz, 3H), 1.56 (d, J = 6.6 Hz, 6H), 1.40-1.32 (m, 4H). | 530 | 13, 28 |
| 65 | 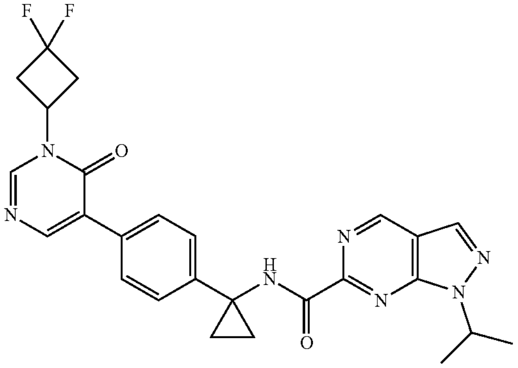 [SMILES: CC(C)n1ncc2cnc(C(=O)NC3(c4ccc(-c5cncn(C6CC(F)(F)C6)c5=O)cc4)CC3)nc21] | $^1$H NMR (400 MHz, $CD_3OD$) δ 9.34 (s, 1H), 8.36 (d, J = 4.9 Hz, 2H), 8.06 (s, 1H), 7.58 (d, J = 8.1 Hz, 2H), 7.38 (d, J = 8.1 Hz, 2H), 5.57-5.39 (m, 1H), 4.74-4.69 (m, 1H), 3.27-3.17 (m, 2H), 3.16-3.08 (m, 2H), 1.58 (d, J = 6.6 Hz, 6H), 1.46-1.44 (m, 4H). | 506 | 44 |

-continued
| Compound | Structure | $^1$H-NMR | MS | Intermediates used |
|---|---|---|---|---|
| 66 | 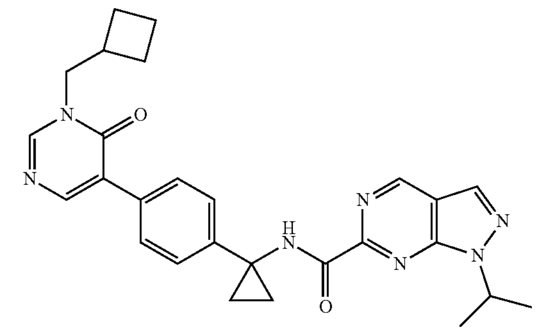 [SMILES: CC(C)n1ncc2cnc(C(=O)NC3(c4ccc(-c5cncn(CC6CCC6)c5=O)cc4)CC3)nc21] | $^1$H NMR (400 MHz, $CDCl_3$) δ 9.17 (s, 1H), 8.83 (s, 1H), 8.20 (s, 1H), 7.99 (d, J = 26.6 Hz, 2H), 7.56 (d, J = 8.0 Hz, 2H), 7.41 (d, J = 8.1 Hz, 2H), 5.46-5.40 (m, 1H), 3.96 (d, J = 7.2 Hz, 2H), 2.82-2.75 (m, 1H), 2.12-1.99 (m, 2H), 1.89-1.85 (m, 2H), 1.80-1.73 (m, 2H), 1.55 (d, J = 6.6 Hz, 6H), 1.48-1.36 (m, 4H). | 484 | 46 |
| 67 | 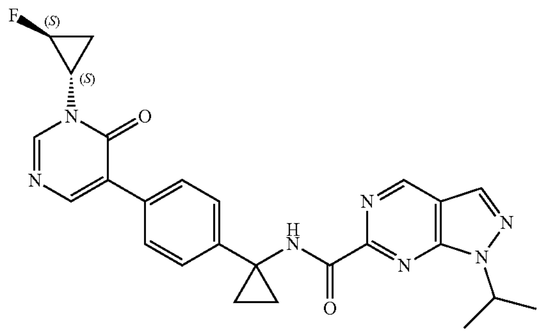 | $^1$H NMR (400 MHz, $CD_3OD$) δ 9.34 (s, 1H), 8.54 (s, 1H), 8.37 (s, 1H), 8.24 (s, 1H), 8.02 (s, 1H), 7.59 (d, J = 8.5 Hz, 2H), 7.39 (d, J = 8.6 Hz, 2H), 5.51-5.40 (m, 1H), 4.99-4.89 (m, 1H), 4.85-4.78 (m, 1H), 3.70-3.60 (m, 1H), 1.81-1.70 (m, 1H), 1.58 (d, J = 6.7 Hz, 6H), 1.49-1.41 (m, 4H). | 474 | 47 |
| 68 | 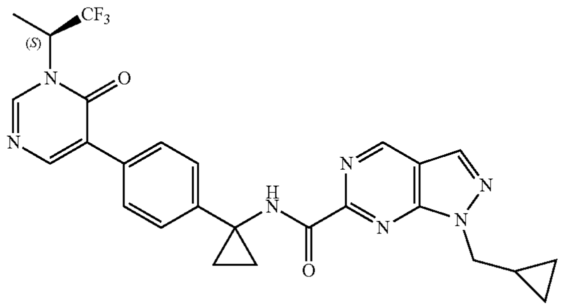 | $^1$H NMR (400 MHz, $CDCl_3$) δ 9.22 (s, 1H), 8.82 (s, 1H), 8.23 (s, 1H), 8.16 (s, 1H), 7.99 (s, 1H), 7.57 (d, J = 8.2 Hz, 2H), 7.44 (d, J = 8.3 Hz, 2H),5.93-5.88 (m, 1H), 4.45 (d, J = 7.3 Hz, 2H), 1.68 (d, J = 7.4 Hz, 3H), 1.54-1.41 (m, 4H), 0.88-0.85 (m, 1H), 0.61-0.56 (m, 2H), 0.53-0.49 (m, 2H). | 524 | 13, 41 |
| 69 | 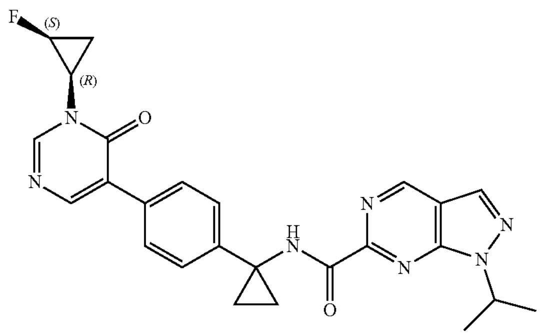 | $^1$H NMR (400 MHz, $CD_3OD$) δ 9.33 (s, 1H), 8.37 (s, 1H), 8.36 (s, 1H), 8.05 (s, 1H), 7.58 (d, J = 8.3 Hz, 2H), 7.37 (d, J = 8.3 Hz, 2H), 5.48-5.41 (m, 1H), 5.05-5.02 (m, 1H), 4.92-4.87 (m, 1H), 1.64-1.59 (m, 1H), 1.57 (d, J = 6.6 Hz, 6H), 1.54-1.48 (m, 1H), 1.48-1.40 (m, 4H). | 474 | 49 |

-continued

| Compound | Structure | $^1$H-NMR | MS | Intermediates used |
| --- | --- | --- | --- | --- |
| 70 | 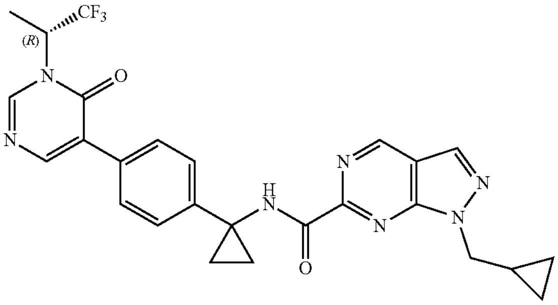 | $^1$H NMR (400 MHz, $CDCl_3$) δ 9.21 (s, 1H), 8.82 (s, 1H), 8.23 (s, 1H), 8.16 (s, 1H), 7.99 (s, 1H), 7.57 (d, J = 8.0 Hz, 2H), 7.44 (d, J = 8.2 Hz, 2H),5.92-5.88 (m, 1H), 4.45 (d, J = 7.6 Hz, 2H), 1.68 (d, J = 7.3 Hz, 3H), 1.47-1.44 (m, 4H), 0.89-0.85 (m, 1H), 0.61-0.57 (m, 2H), 0.52-0.48 (m, 2H). | 524 | 14, 41 |
| 71 | 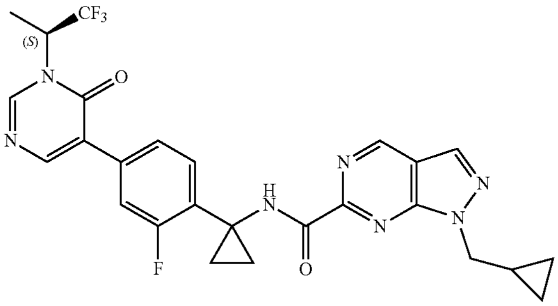 | $^1$H NMR (400 MHz, $CDCl_3$) δ 9.17 (s, 1H), 8.87 (s, 1H), 8.19 (s, 2H), 8.01 (s, 1H), 7.82 (s, 1H), 7.41 (d, J = 11.8 Hz, 1H), 7.31 (d, J = 7.5 Hz, 1H),5.90-5.86 (m, 1H), 4.43 (d, J = 6.8 Hz, 2H), 1.69 (d, J = 7.1 Hz, 3H), 1.40-1.35 (m, 4H), 0.88-0.84 (m, 1H), 0.59-0.55 (m, 2H), 0.50-0.46 (m, 2H). | 542 | 13, 28, 41 |
| 72 | 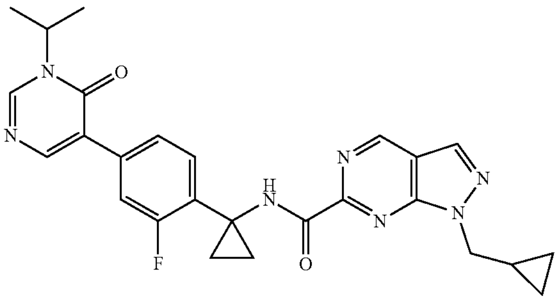 [SMILES: CC(C)n1cncc(-c2ccc(C3(NC(=O)c4ncc5cnn(CC6CC6)c5n4)CC3)c(F)c2)c1=O] | $^1$H NMR (400 MHz, $CDCl_3$): δ 9.18 (s, 1H), 8.86 (s, 1H), 8.20 (s, 1H), 8.15 (s, 1H), 7.99 (s, 1H), 7.84-7.74 (m, 1H), 7.48-7.40 (m, 1H), 7.34-7.29 (m, 1H), 5.20-5.05 (m, 1H), 4.51-4.35 (m, 2H), 1.48-1.46 (m, 6H), 1.41-1.34 (m, 5H), 0.61-0.45 (m, 4H). | 488 | 10, 28, 41 |
| 73 | 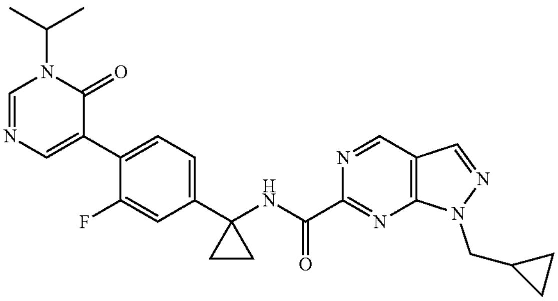 [SMILES: CC(C)n1cncc(-c2ccc(C3(NC(=O)c4ncc5cnn(CC6CC6)c5n4)CC3)cc2F)c1=O] | $^1$H NMR (400 MHz, $CD_3OD$): δ 9.36 (s, 1H), 8.48 (s, 1H), 8.37 (s, 1H), 8.00-7.95 (m, 1H), 7.44-7.37 (m, 1H), 7.22-7.11 (m, 2H), 5.11-4.96 (m, 1H), 5.12-4.96 (m, 2H), 1.50-1.45 (m, 11H), 0.56-0.50 (m, 4H). | 488 | 10, 29, 41 |
| 74 | 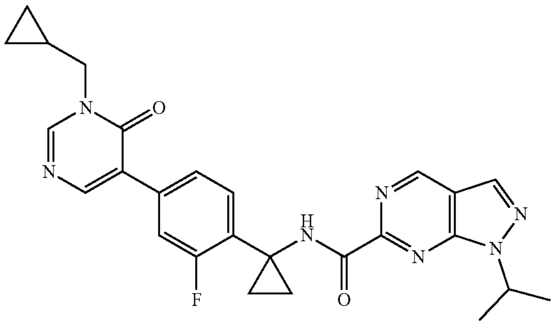 [SMILES: CC(C)n1ncc2cnc(C(=O)NC3(c4ccc(-c5cncn(CC6CC6)c5=O)cc4F)CC3)nc21] | $^1$H NMR (400 MHz, $CDCl_3$) δ 9.15 (s, 1H), 8.87 (s, 1H), 8.19 (s, 1H), 8.16 (s, 1H), 8.02 (s, 1H), 7.82 (t, J = 8.0 Hz, 1H), 7.48-7.41 (m, 1H), 7.36-7.30 (m, 1H), 5.48-5.35 (m, 1H), 3.83 (d, J = 7.2 Hz, 2H), 1.56 (d, J = 6.7 Hz, 6H), 1.41-1.33 (m, 4H), 1.30-1.24 (m, 1H), 0.69-0.63 (m, 2H), 0.43-0.38 (m, 2H). | 488 | 28, 48 |

-continued
| Compound | Structure | $^1$H-NMR | MS | Intermediates used |
|---|---|---|---|---|
| 75 | 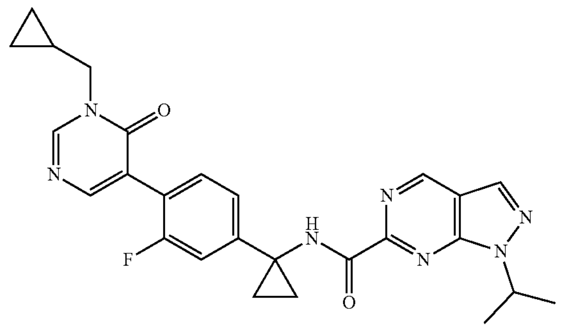 [SMILES: CC(C)n1ncc2cnc(C(=O)NC3(c4ccc(-c5cncn(CC6CC6)c5=O)c(F)c4)CC3)nc21] | $^1$H NMR (400 MHz, $CDCl_3$) δ 9.19 (s, 1H), 8.82 (s, 1H), 8.23 (s, 1H), 8.18 (s, 1H), 8.01-7.95 (m, 1H), 7.44 (t, J = 7.8 Hz, 1H), 7.20-7.15 (m, 2H), 5.52-5.40 (m, 1H), 3.83 (d, J = 7.2 Hz, 2H), 1.58 (d, J = 6.7 Hz, 6H), 1.51-1.42 (m, 4H), 1.32-1.25 (m, 1H), 0.68-0.63 (m, 2H), 0.43-0.39 (m, 2H). | 488 | 29, 48 |
| 76 | 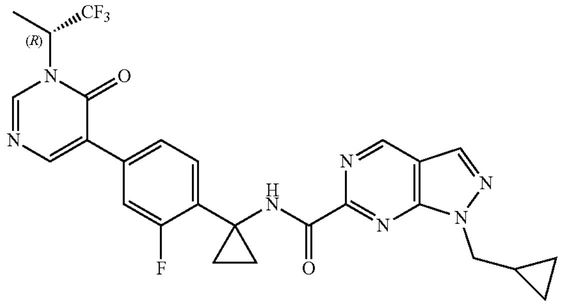 | $^1$H NMR (400 MHz, $CDCl_3$) δ 9.17 (s, 1H), 8.87 (s, 1H), 8.20-8.19 (m, 1H), 8.18 (s, 1H), 8.01 (s, 1H), 7.82 (t, J = 8.0 Hz, 1H), 7.41 (dd, J = 11.7, 1.6Hz, 1H), 7.31 (dd, J = 8.0, 1.7 Hz, 1H), 5.97-5.79 (m, 1H), 4.42 (d, J = 7.2 Hz, 2H), 1.69 (d, J = 7.4 Hz, 3H), 1.40-1.36 (m, 5H), 0.60-0.53 (m, 2H), 0.51-0.45 (m, 2H). | 542 | 14, 28, 41 |
| 77 | 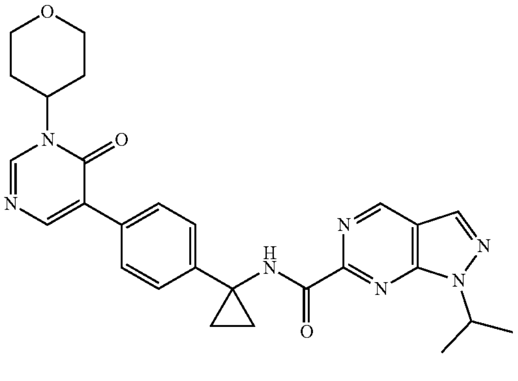 [SMILES: CC(C)n1ncc2cnc(C(=O)NC3(c4ccc(-c5cncn(C6CCOCC6)c5=O)cc4)CC3)nc21] | $^1$H NMR (400 MHz, $CD_3OD$) δ 9.34 (s, 1H), 8.43 (s, 1H), 8.37 (s, 1H), 8.03 (s, 1H), 7.58 (d, J = 8.4 Hz, 2H), 7.39 (d, J = 8.4 Hz, 2H), 5.51-5.40 (m, 1H), 4.98-4.92 (m, 1H), 4.10-4.04 (m, 2H), 3.60-3.53 (m, 2H), 2.14-2.06 (m, 2H), 1.92-1.87 (m, 2H), 1.57 (d, J = 6.7 Hz, 6H), 1.48-1.42 (m, 4H). | 500 | 51 |
| 78 | 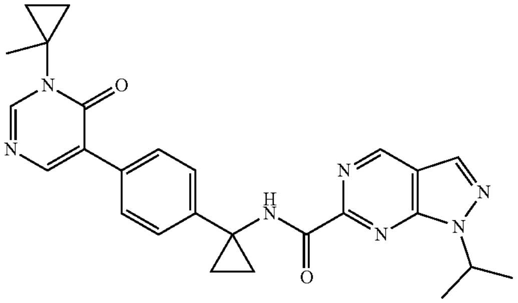 [SMILES: CC(C)n1ncc2cnc(C(=O)NC3(c4ccc(-c5cncn(C6(C)CC6)c5=O)cc4)CC3)nc21] | $^1$H NMR (400 MHz, $CD_3OD$) δ 9.34 (s, 1H), 8.45 (s, 1H), 8.37 (s, 1H), 8.01 (s, 1H), 7.58 (d, J = 8.0 Hz, 2H), 7.39 (d, J = 8.1 Hz, 2H), 5.54-5.38 (m, 1H), 1.58 (d, J = 6.6 Hz, 6H), 1.53 (s, 3H), 1.48-1.45 (m, 2H), 1.44-1.40 (m, 2H), 1.15-1.10 (m, 2H), 1.06-1.03 (m, 2H). | 470 | 52 |

-continued
| Compound | Structure | $^1$H-NMR | MS | Intermediates used |
|---|---|---|---|---|
| 79 | 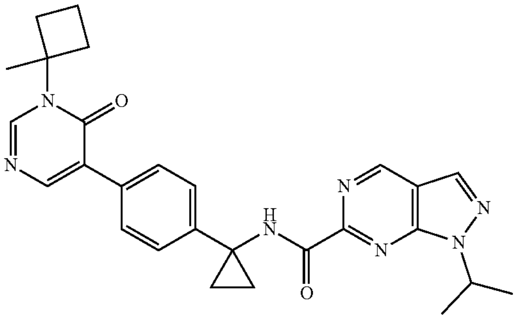 [SMILES: CC(C)n1ncc2cnc(C(=O)NC3(c4ccc(-c5cncn(C6(C)CCC6)c5=O)cc4)CC3)nc21] | $^1$H NMR (400 MHz, $CD_3OD$) δ 9.33 (s, 1H), 8.36 (s, 1H), 8.17 (s, 1H), 8.01 (s, 1H), 7.59-7.51 (m, 2H), 7.41-7.33 (m, 2H), 5.48-5.39 (m, 1H), 2.65-2.50 (m, 2H), 2.45-2.35 (m, 2H), 2.06-1.95 (m, 1H), 1.90-1.81 (m, 1H), 1.68 (s, 3H), 1.56 (d, J = 4.6 Hz, 6H), 1.49-1.40 (m, 4H). | 484 | 53 |
| 86 | 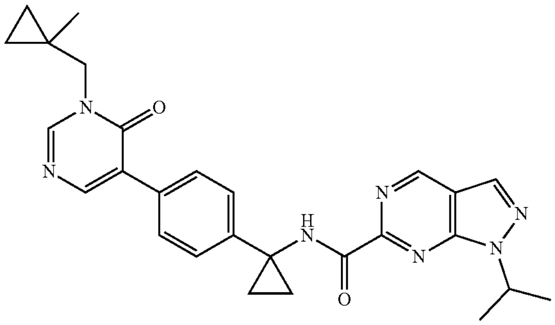 [SMILES: CC(C)n1ncc2cnc(C(=O)NC3(c4ccc(-c5cncn(CC6(C)CC6)c5=O)cc4)CC3)nc21] | $^1$H NMR (400 MHz, $CD_3OD$) δ 9.33 (s, 1H), 8.37 (s, 1H), 8.35 (s, 1H), 8.02 (s, 1H), 7.57 (d, J = 8.4 Hz, 2H), 7.38 (d, J = 8.5 Hz, 2H), 5.51-5.37 (m, 1H), 3.97 (s, 2H), 1.56 (d, J = 6.7 Hz, 6H), 1.47-1.40 (m, 4H), 1.04 (s, 3H), 0.72-0.69 (m, 2H), 0.42-0.36 (m, 2H). | 484 | 54 |
| 91 | 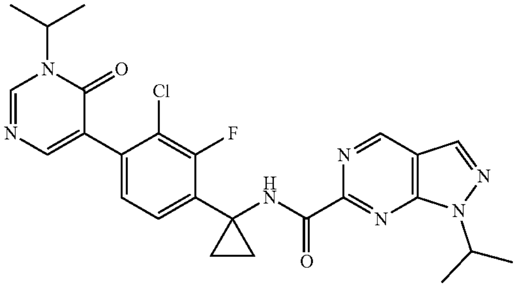 [SMILES: CC(C)n1cncc(-c2ccc(C3(NC(=O)c4ncc5cnn(C(C)C)c5n4)CC3)c(F)c2Cl)c1=O] | 1H NMR (400 MHz, $CD_3OD$): δ 9.29 (s, 1H), 8.53 (s, 1H), 8.34 (s, 1H), 7.90 (s, 1H), 7.76-7.58 (m, 1H), 7.22-7.00 (m, 1H), 5.50-5.32 (m, 1H), 5.11-4.95 (m, 1H), 1.60-1.52 (m, 6H), 1.51-1.45 (m, 6H), 1.43-1.32 (m, 4H). | 510 | 10, 58 |
| 92 | 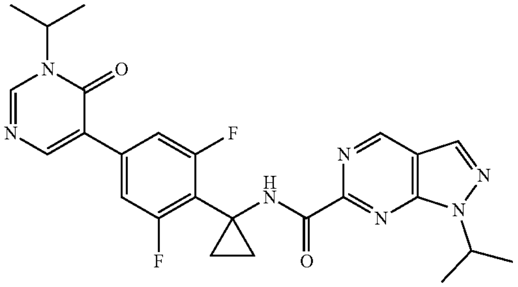 [SMILES: CC(C)n1cncc(-c2cc(F)c(C3(NC(=O)c4ncc5cnn(C(C)C)c5n4)CC3)c(F)c2)c1=O] | 1H NMR (400 MHz, $CDCl_3$): δ 9.19 (s, 1H), 8.79 (s, 1H), 8.23 (s, 1H), 8.12 (s, 1H), 7.97 (s, 1H), 7.60-7.54 (m, 2H), 7.48-7.40 (m, 2H), 5.20-5.08 (m, 1H), 4.58-4.41 (m, 1H), 1.67-1.62 (m, 3H), 1.49-1.39 (m, 12H), 0.74-0.63 (m, 1H), 0.48-0.30 (m, 3H). | 494 | 10, 59 |
| 93 | 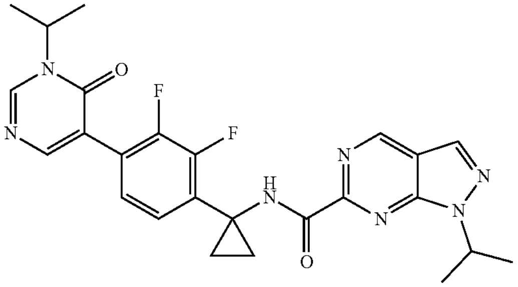 [SMILES: CC(C)n1cncc(-c2ccc(C3(NC(=O)c4ncc5cnn(C(C)C)c5n4)CC3)c(F)c2F)c1=O] | 1H NMR (400 MHz, $CDCl_3$) δ 9.15 (s, 1H), 8.86 (s, 1H), 8.19 (s, 1H), 8.18 (s, 1H), 7.93 (s, 1H), 7.58 (t, J = 7.4 Hz, 1H), 7.15 (t, J = 7.2 Hz, 1H), 5.50-5.36 (m, 1H), 5.19-5.03 (m, 1H), 1.56 (d, J = 6.9 Hz, 6H), 1.47 (d, J = 6.9 Hz, 6H), 1.41-1.34 (m, 4H). | 494 | 10, 56 |

-continued

| Compound | Structure | $^1$H-NMR | MS | Intermediates used |
|---|---|---|---|---|
| 94 | 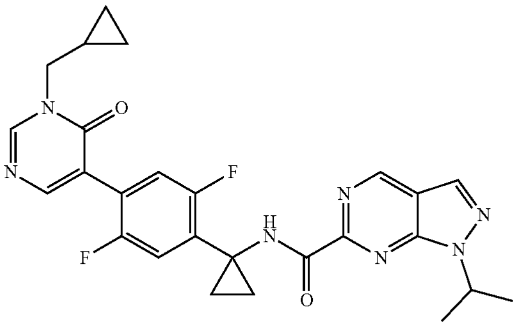 [SMILES: CC(C)n1ncc2cnc(C(=O)NC3(c4cc(F)c(-c5cncn(CC6CC6)c5=O)cc4F)CC3)nc21] | 1H NMR (400 MHz, $CDCl_3$) δ 9.15 (s, 1H), 8.85 (s, 1H), 8.19 (s, 2H), 8.02 (d, J = 1.8 Hz, 1H), 7.59-7.53 (m, 1H), 7.33-7.25 (m, 1H), 5.49-5.36 (m, 1H), 3.82 (d, J = 7.2 Hz, 2H), 1.56 (d, J = 6.7 Hz, 6H), 1.41-1.31 (m, 4H), 1.30-1.22 (m, 1H), 0.65 (q, J = 5.5 Hz, 2H), 0.40 (q, J = 5.2 Hz, 2H). | 506 | 48, 57 |
| 95 | 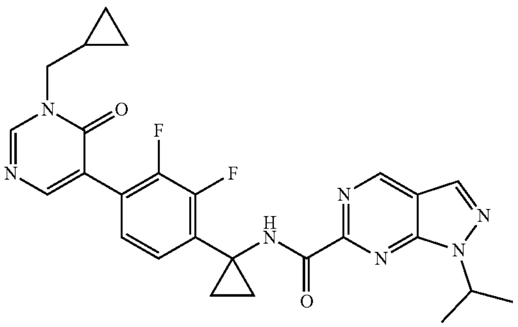 [SMILES: CC(C)n1ncc2cnc(C(=O)NC3(c4ccc(-c5cncn(CC6CC6)c5=O)c(F)c4F)CC3)nc21] | 1H NMR (400 MHz, $CDCl_3$) δ 9.15 (d, J = 0.6 Hz, 1H), 8.87 (s, 1H), 8.21 (s, 1H), 8.20 (s, 1H), 7.96 (s, 1H), 7.56-7.57 (m, 1H), 7.23-7.10 (m, 1H), 5.49-5.35 (m, 1H), 3.83 (d, J = 7.2 Hz, 2H), 1.56 (d, J = 6.5 Hz, 6H), 1.46-1.33 (m, 4H), 1.33-1.20 (m, 1H), 0.70-0.60 (m, 2H), 0.45-0.37 (m, 2H). | 506 | 48, 56 |

Compound 53 and Compound 54

(S)—N-(1-(4-(1-methyl-6-oxo-1,6-dihydropyrimidin-5-yl)phenyl)cyclopropyl)-5-phenyl-6,7-dihydro-5H-pyrrolo[1,2-b][1,2,4]triazole-2-carboxamide and (R)—N-(1-(4-(1-methyl-6-oxo-1,6-dihydropyrimidin-5-yl)phenyl)cyclopropyl)-5-phenyl-6,7-dihydro-5H-pyrrolo[1,2-b][1,2,4]triazole-2-carboxamide

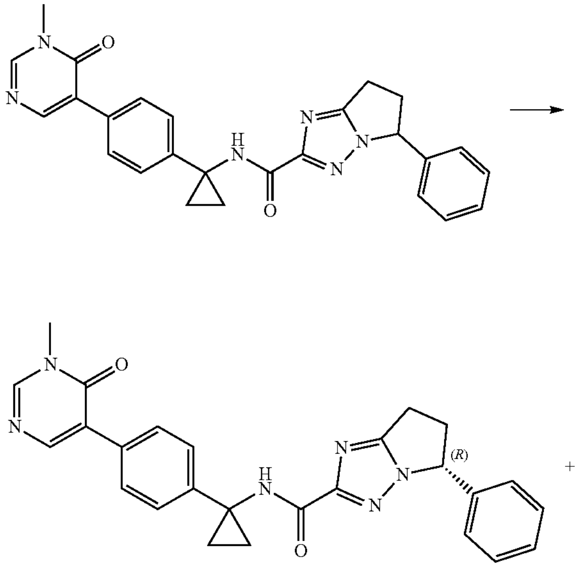

-continued

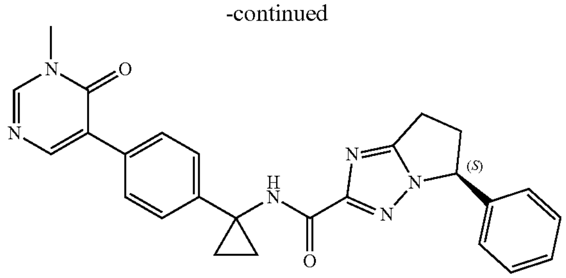

The racemic compound N-(1-(4-(1-methyl-6-oxo-1,6-dihydropyrimidin-5-yl)phenyl)cyclopropyl)-5-phenyl-6,7-dihydro-5H-pyrrolo[1,2-b][1,2,4]triazole-2-carboxamide (this compound was prepared according to the procedure of Compound 1 using 5-bromo-3-methylpyrimidin-4(3H)-one, tert-butyl (1-(4-(4,4,5,5-tetramethyl-1,3,2-dioxaborolan-2-yl)phenyl)cyclopropyl)carbamate and Intermediate 20 as the raw materials) was resolved by chiral HPLC to provide the optically pure enantiomers Compound 53 and Compound 54 (HPLC conditions: column: OJ-H 4.6×150 mm; mobile phase: n-hexane/EtOH=60/40; flow rate=0.5 mL/min; detector: UV 254 nm). The first eluent (Compound 53, Rf=3.028 min) was 100% ee, MS (m/z): 453 $[M+H]^+$. The second eluent (Compound 54, Rf=4.915 min) was 99.78% ee, MS (m/z): 453 $[M+H]^+$.

Compound 53: $^1$H NMR (400 MHz, $CDCl_3$) δ: 8.09 (s, 1H), 8.00 (s, 1H), 7.71 (s, 1H), 7.61-7.54 (m, 2H), 7.39-7.32 (m, 5H), 7.16-7.08 (m, 2H), 5.48-5.40 (m, 1H), 3.57 (s, 3H), 3.29-2.95 (m, 3H), 2.76-2.59 (m, 1H), 1.45-1.34 (m, 4H).

Compound 54: $^1$H NMR (400 MHz, $CDCl_3$) δ: 8.09 (s, 1H), 8.00 (s, 1H), 7.71 (s, 1H), 7.61-7.55 (m, 2H), 7.39-7.31

(m, 5H), 7.18-7.06 (m, 2H), 5.51-5.39 (m, 1H), 3.56 (s, 3H), 3.28-2.97 (m, 3H), 2.74-2.60 (m, 1H), 1.44-1.34 (m, 4H).

Compound 55 and Compound 56

(R)—N-(1-(4-(1-methyl-6-oxo-1,6-dihydropyrimidin-5-yl)phenyl)cyclopropyl)-1-(1-phenyl ethyl)-1H-1,2,4-triazole-3-carboxamide and (S)—N-(1-(4-(1-methyl-6-oxo-1,6-dihydropyrimidin-5-yl)phenyl)cyclopropyl)-1-(1-phenylethyl)-1H-1,2,4-triazole-3-carboxamide

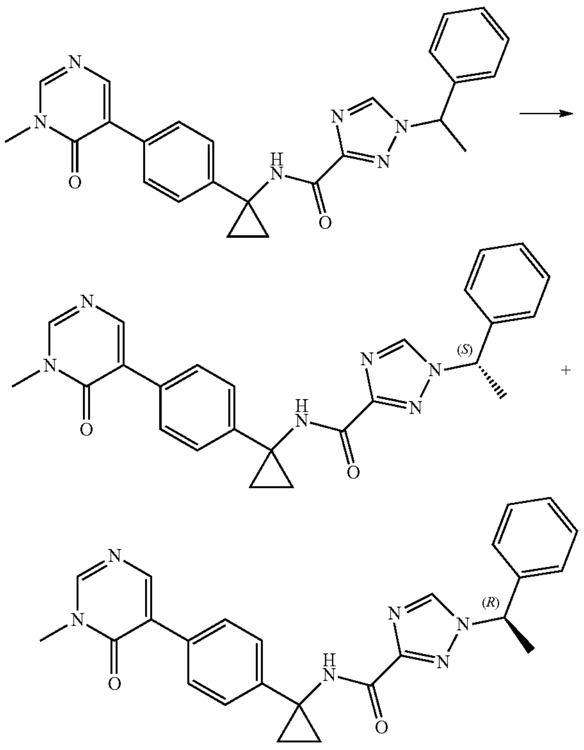

The racemic compound N-(1-(4-(1-methyl-6-oxo-1,6-dihydropyrimidin-5-yl)phenyl)cyclopropyl)-1-(1-phenylethyl)-1H-1,2,4-triazole-3-carboxamide (this compound was prepared according to the procedure of Compound 1 using 5-bromo-3-methylpyrimidin-4(3H)-one, tert-butyl (1-(4-(4,4,5,5-tetramethyl-1,3,2-dioxaborolan-2-yl)phenyl)cyclopropyl)carbamate and Intermediate 34 as the raw materials) was resolved by chiral HPLC to provide the optically pure enantiomers Compound 55 and Compound 56 (HPLC conditions: column: Daicel OJ 4.6×150 mm; mobile phase: n-hexaneisopropanol (0.1% diethylamine)=60/40; flow rate=0.5 mL/min; detector: UV 254 nm). The first eluent (Compound 55, Rf=4.676 min) was 99.85% ee, MS (m/z): 441 $[M+H]^+$. The second eluent (Compound 56, Rf=5.955 min) was 99.89% ee, MS (m/z): 441 $[M+H]^+$.

Compound 55: $^1H$ NMR (400 MHz, $CD_3OD$) δ 8.54 (s, 1H), 8.36 (s, 1H), 8.04 (s, 1H), 7.59-7.53 (m, 2H), 7.35 (d, J=4.4 Hz, 4H), 7.33-7.27 (m, 3H), 5.83-5.68 (m, J=7.1 Hz, 1H), 3.55 (s, 3H), 1.93 (d, J=7.1 Hz, 3H), 1.39-1.33 (m, 4H).

Compound 56: $^1H$ NMR (400 MHz, $CD_3OD$) δ 8.55 (s, 1H), 8.36 (s, 1H), 8.04 (s, 1H), 7.59-7.54 (m, 2H), 7.35 (d, J=3.7 Hz, 4H), 7.33-7.29 (m, 3H), 5.82-5.66 (m, 1H), 3.55 (s, 3H), 1.93 (d, J=7.1 Hz, 3H), 1.39-1.34 (m, 4H).

Compound 57 and Compound 58

(R)—N-(1-(4-(1-methyl-6-oxo-1,6-dihydropyrimidin-5-yl)phenyl)cyclopropyl)-5-(1-phenylethyl)-4H-1,2,4-triazole-3-carboxamide and (S)—N-(1-(4-(1-methyl-6-oxo-1,6-dihydropyrimidin-5-yl)phenyl)cyclopropyl)-5-(1-phenylethyl)-4H-1,2,4-triazole-3-carboxamide

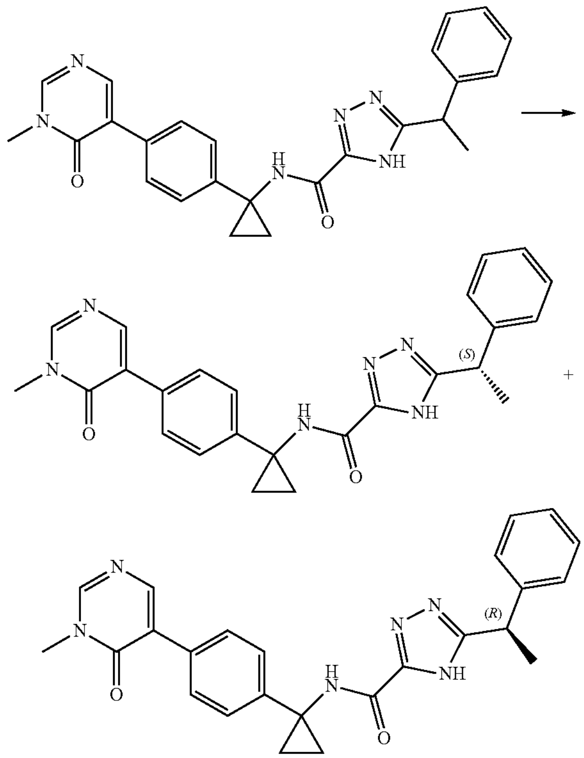

The racemic compound N-(1-(4-(1-methyl-6-oxo-1,6-dihydropyrimidin-5-yl)phenyl)cyclopropyl)-5-(1-phenylethyl)-4H-1,2,4-triazole-3-carboxamide (this compound was prepared according to the procedure of Compound 1 using 5-bromo-3-methylpyrimidine-4(3H)-one, tert-butyl (1-(4-(4,4,5,5-tetramethyl-1,3,2-dioxaborolan-2-yl)phenyl)cyclopropyl)carbamate and Intermediate 35 as the raw materials) was resolved by chiral HPLC to provide the optically pure enantiomers Compound 57 and Compound 58 (HPLC conditions: column: Daicel OJ 4.6×150 mm; mobile phase: n-hexane/ethanol (0.1% diethylamine)=60:40; flow rate: 0.5 mL/minute; detector: UV 254 nm). The first eluent (Compound 57, Rf=6.485 min) was 100% ee, MS (m/z): 441 $[M+H]^+$. The second eluent (Compound 58, Rf=6.979 min) was 99.90% ee, MS (m/z): 441 $[M+H]^+$.

Compound 57: $^1H$ NMR (400 MHz, DMSO) δ 9.26 (s, 1H), 8.44 (s, 1H), 8.06 (s, 1H), 7.58-7.54 (m, 2H), 7.35-7.26 (m, 4H), 7.26-7.14 (m, 3H), 4.38-4.21 (m, 1H), 3.45 (s, 3H), 1.61 (d, J=7.2 Hz, 3H), 1.28-1.22 (m, 4H)

Compound 58: $^1H$ NMR (400 MHz, DMSO) δ 9.24 (s, 1H), 8.44 (s, 1H), 8.06 (s, 1H), 7.62-7.53 (m, 2H), 7.35-7.26 (m, 4H), 7.26-7.13 (m, 3H), 4.36-4.25 (m, 1H), 3.45 (s, 3H), 1.61 (d, J=7.2 Hz, 3H), 1.28-1.22 (m, 4H).

Compound 80 and Compound 81

(R)-1-i-propyl-N-(1-(4-(6-oxo-1-(tetrahydrofuran-3-yl)-1,6-dihydropyrimidin-5-yl)phenyl)cyclopropyl)-1H-pyrazolo[3,4-d]pyrimidine-6-carboxamide and (S)-1-i-propyl-N-(1-(4-(6-oxo-1-(tetrahydrofuran-3-yl)-1,6-dihydropyrimidin-5-yl)phenyl)cyclopropyl)-1H-pyrazolo[3,4-d]pyrimidine-6-carboxamide

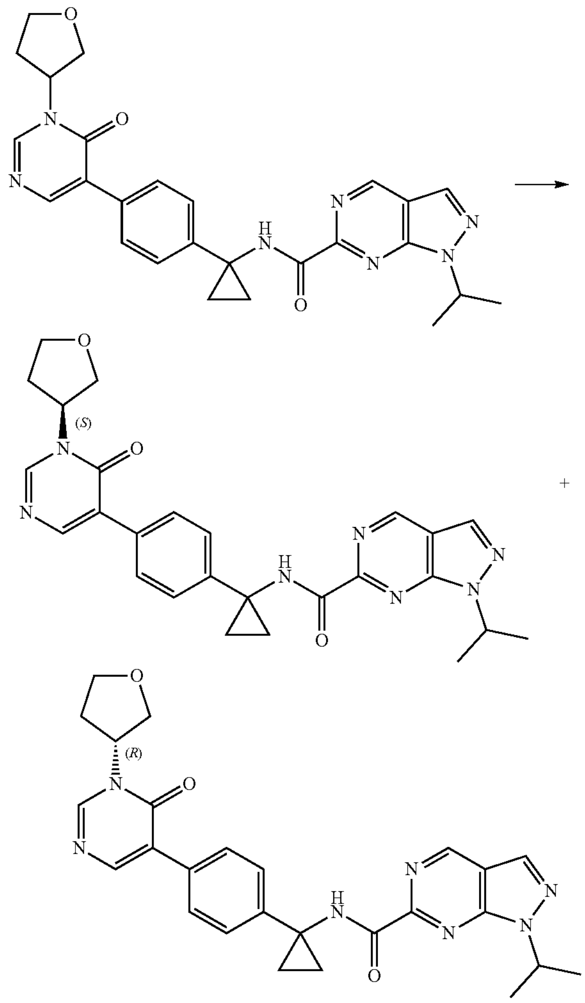

The racemic compound 1-i-propyl-N-(1-(4-(6-oxo-1-(tetrahydrofuran-3-yl)-1,6-dihydropyrimidin-5-yl)phenyl)cyclopropyl)-1H-pyrazolo[3,4-d]pyrimidine-6-carboxamide (this compound was prepared according to the procedure of Compound 29 using 1-(4-bromophenyl)cyclopropan-1-amine, 1-i-propyl-1H-pyrazolo[3,4-d]pyrimidine-6-carboxylic acid and Intermediate 45 as the raw materials) was resolved by chiral HPLC to provide the optically pure enantiomers Compound 80 and Compound 81 (HPLC conditions: column: AD-H 4.6×50 mm; mobile phase: $CO_2$:IPA (0.1% DEA)=60:40; flow rate: 4 mL/minute; detector: UV 254 nm). The first eluent (Compound 80, Rf=2.933 min) was 100% ee, MS (m/z): 486.2 $[M+H]^+$. The second eluent (Compound 81, Rf=3.691 min) was 99.17% ee, MS (m/z): 486.2 $[M+H]^+$.

Compound 80: $^1H$ NMR (400 MHz, $CDCl_3$) δ 9.19 (s, 1H), 8.83 (s, 1H), 8.25 (s, 1H), 8.23-8.20 (m, 1H), 7.98 (s, 1H), 7.59-7.54 (m, 2H), 7.47-7.41 (m, 2H), 5.59-5.50 (m, 1H), 5.51-5.41 (m, 1H), 4.18 (td, J=8.6, 6.1 Hz, 1H), 4.13-4.06 (m, 1H), 3.98-3.84 (m, 2H), 2.61 (dtd, J=14.5, 8.7, 6.0 Hz, 1H), 2.14-2.04 (m, 1H), 1.57 (s, 6H), 1.49 (dd, J=7.1, 5.5 Hz, 2H), 1.45-1.41 (m, 2H).

Compound 81: $^1H$ NMR (400 MHz, $CDCl_3$) δ 9.19 (s, 1H), 8.83 (s, 1H), 8.25 (s, 1H), 8.22 (d, J=0.4 Hz, 1H), 8.00-7.96 (m, 1H), 7.58-7.55 (m, 2H), 7.46-7.43 (m, 2H), 5.58-5.51 (m, 1H), 5.52-5.41 (m, 1H), 4.18 (td, J=8.6, 6.0 Hz, 1H), 4.09 (d, J=11.3 Hz, 1H), 3.98-3.86 (m, 2H), 2.61 (dtd, J=14.5, 8.7, 6.1 Hz, 1H), 2.08 (ddd, J=16.5, 11.1, 5.0 Hz, 1H), 1.59 (s, 6H), 1.49 (dd, J=7.2, 5.5 Hz, 2H), 1.44 (d, J=4.5 Hz, 2H).

Compound 82 and Compound 83

(R)—N-(1-(4-(1-(1-cyanoethyl)-6-oxo-1,6-dihydropyrimidin-5-yl)phenyl)cyclopropyl)-1-i-propyl-1H-pyrazolo[3,4-d]pyrimidine-6-carboxamide and (S)—N-(1-(4-(1-(1-cyanoethyl)-6-oxo-1,6-dihydropyrimidin-5-yl)phenyl)cyclopropyl)-1-i-propyl-1H-pyrazolo[3,4-d]pyrimidine-6-carboxamide

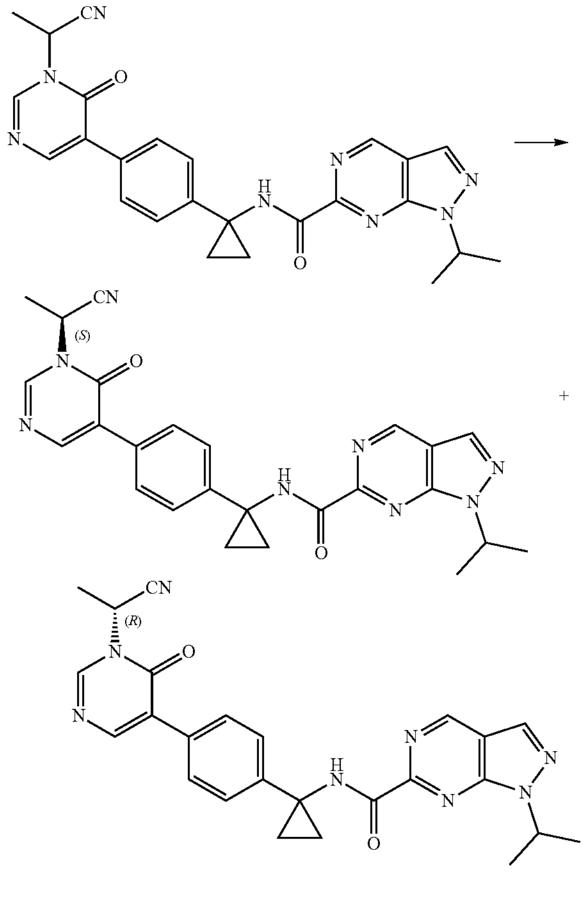

The racemic compound N-(1-(4-(1-(1-cyanoethyl)-6-oxo-1,6-dihydropyrimidin-5-yl)phenyl)cyclopropyl)-1-i-propyl-1H-pyrazolo[3,4-d]pyrimidine-6-carboxamide (this compound was prepared according to the procedure of Compound 29 using 1-(4-bromophenyl)cyclopropan-1-amine, 1-i-propyl-1H-pyrazolo[3,4-d]pyrimidine-6-carboxylic acid and Intermediate 36 as the raw materials) was resolved by chiral HPLC to provide the optically pure enantiomers Compound 82 and Compound 83 (HPLC conditions: column: AD-H 4.6×50 mm; mobile phase: $CO_2$:IPA (0.1% DEA)=60/40; flow rate: 4 mL/minute; detector: UV 254 nm). The first eluent (Compound 82, Rf=1.554 min) was 100% ee, MS (m/z): 469.2 $[M+H]^+$. The second eluent (Compound 83, Rf=2.063 min) was 99.88% ee, MS (m/z): 469.2 $[M+H]^+$.

Compound 82: $^1$H NMR (400 MHz, $CDCl_3$) δ 9.21 (s, 1H), 8.85 (s, 1H), 8.36 (s, 1H), 8.23 (s, 1H), 8.03 (s, 1H), 7.55 (d, J=8.2 Hz, 2H), 7.43 (d, J=8.1 Hz, 2H), 5.98-5.84 (m, 1H), 5.55-5.40 (m, 1H), 1.81 (d, J=7.1 Hz, 3H), 1.58 (d, J=6.6 Hz, 6H), 1.51-1.43 (m, 4H).

Compound 83: $^1$H NMR (400 MHz, $CDCl_3$) δ 9.19 (s, 1H), 8.84 (s, 1H), 8.34 (s, 1H), 8.23 (s, 1H), 8.02 (s, 1H), 7.55 (d, J=8.3 Hz, 2H), 7.44 (d, J=8.3 Hz, 2H), 5.90 (q, J=7.0 Hz, 1H), 5.45 (dt, J=13.1, 6.6 Hz, 1H), 1.81 (d, J=7.1 Hz, 3H), 1.58 (d, J=6.7 Hz, 6H), 1.52-1.42 (m, 4H).

Compound 84 and Compound 85

(R)—N-(1-(4-(1-(1-cyclopropylethyl)-6-oxo-1,6-dihydropyrimidin-5-yl)phenyl)cyclopropyl)-1-i-propyl-1H-pyrazolo[3,4-d]pyrimidine-6-carboxamide and (S)—N-(1-(4-(1-(1-cyclopropylethyl)-6-oxo-1,6-dihydropyrimidin-5-yl)phenyl)cyclopropyl)-1-i-propyl-1H-pyrazolo[3,4-d]pyrimidine-6-carboxamide

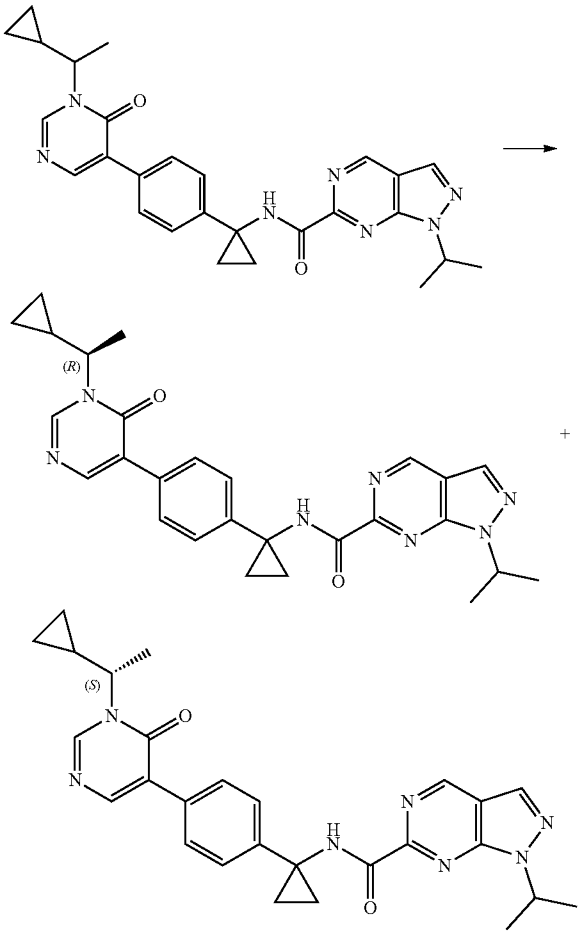

The racemic compound N-(1-(4-(1-(1-cyclopropylethyl)-6-oxo-1,6-dihydropyrimidin-5-yl)phenyl)cyclopropyl)-1-i-propyl-1H-pyrazolo[3,4-d]pyrimidine-6-carboxamide (this compound was prepared according to the procedure of Compound 29 using 1-(4-bromophenyl)cyclopropan-1-amine, 1-i-propyl-1H-pyrazolo[3,4-d]pyrimidine-6-carboxylic acid and Intermediate 50 as the raw materials) was resolved by chiral HPLC to provide the optically pure enantiomers Compound 84 and Compound 85 (HPLC conditions: column: IG-H 4.6×150 mm; mobile phase: ethanol: acetonitrile=90/10; flow rate: 0.5 mL/minute; detector: UV 254 nm). The first eluent (Compound 84, Rf=21.601 min) was 100% ee, MS (m/z): 484.2 $[M+H]^+$. The second eluent (Compound 85, Rf=27.267 min) was 100% ee, MS (m/z): 484.2 $[M+H]^+$.

Compound 84: $^1$H NMR (400 MHz, $CD_3OD$) δ 9.33 (s, 1H), 8.57 (s, 1H), 8.36 (s, 1H), 8.03 (s, 1H), 7.57 (d, J=8.4 Hz, 2H), 7.38 (d, J=8.4 Hz, 2H), 5.47-5.40 (1H), 4.16-4.08 (m, 1H), 1.56 (d, J=6.7 Hz, 6H), 1.52 (d, J=6.8 Hz, 3H), 1.46-1.40 (m, 4H), 0.91-0.72 (m, 2H), 0.60-0.42 (m, 2H), 0.31-0.25 (m, 1H).

Compound 85: $^1$H NMR (400 MHz, $CD_3OD$) δ 9.34 (s, 1H), 8.57 (s, 1H), 8.36 (s, 1H), 8.04 (s, 1H), 7.57 (d, J=8.4 Hz, 2H), 7.39 (d, J=8.4 Hz, 2H), 5.48-5.41 (m, 1H), 4.16-4.09 (m, 1H), 1.57 (d, J=6.7 Hz, 6H), 1.53 (d, J=6.8 Hz, 3H), 1.45 (d, J=11.8 Hz, 4H), 0.98-0.73 (m, 2H), 0.60-0.44 (m, 2H), 0.32-0.26 (td, J=9.7, 5.1 Hz, 1H).

Compound 87 and Compound 88

N-(1-(4-(1-(trans-3-fluorocyclobutyl)-6-oxo-1,6-dihydropyrimidin-5-yl)phenyl)cyclopropyl)-1-i-propyl-1H-pyrazolo[3,4-d]pyrimidine-6-carboxamide and N-(1-(4-(1-(cis-3-fluorocyclobutyl)-6-oxo-1,6-dihydropyrimidin-5-yl)phenyl)cyclopropyl)-1-i-propyl-1H-pyrazolo[3,4-d]pyrimidine-6-carboxamide

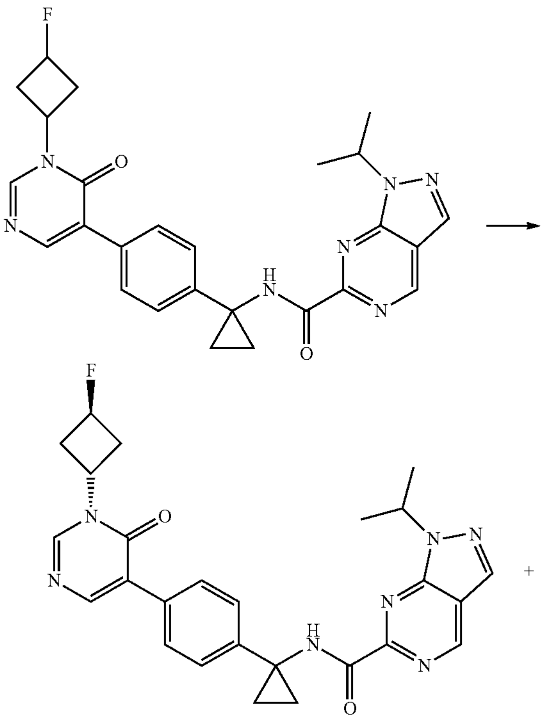

-continued

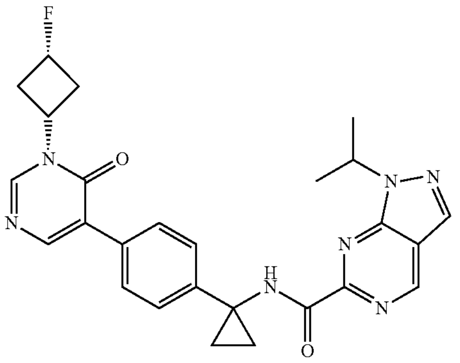

The compound N-(1-(4-(1-(3-fluorocyclobutyl)-6-oxo-1,6-dihydropyrimidin-5-yl)phenyl)cyclopropyl)-1-i-propyl-1H-pyrazolo[3,4-d]pyrimidine-6-carboxamide (this compound was prepared according to the procedure of Compound 29 using 1-(4-bromophenyl)cyclopropan-1-amine, 1-i-propyl-1H-pyrazolo[3,4-d]pyrimidine-6-carboxylic acid and Intermediate 55 as the raw materials) was resolved by chiral HPLC to provide Compound 87 and Compound 88 (HPLC conditions: column: OD-H 4.6×50 mm; Mobile phase: $CO_2$:IPA (0.1% DEA)=60:40; flow rate: 4 mL/minute; detector: UV 254 nm). The first eluent (Compound 87, Rf=14.930 min) was 100% ee, MS (m/z): 488.2 $[M+H]^+$. The second eluent (Compound 88, Rf=21.254 min) was 100% ee, MS (m/z): 488.2 $[M+H]^+$.

Compound 87: 1H NMR (400 MHz, $CD_3OD$) δ 9.32 (s, 1H), 8.35 (s, 1H), 8.32 (s, 1H), 8.02 (s, 1H), 7.55 (d, J=8.4 Hz, 2H), 7.36 (d, J=8.4 Hz, 2H), 5.51-5.39 (m, 1H), 5.37-5.20 (m, 1H), 5.19-5.12 (m, 1H), 2.92-2.73 (m, 4H), 1.56 (d, J=6.7 Hz, 6H), 1.47-1.40 (m, 4H).

Compound 88: 1H NMR (400 MHz, $CD_3OD$) δ 9.33 (s, 1H), 8.38 (s, 1H), 8.36 (s, 1H), 8.05 (s, 1H), 7.57 (d, J=8.5 Hz, 2H), 7.37 (d, J=8.6 Hz, 2H), 5.48-5.39 (m, 1H), 5.07-4.90 (m, 1H), 4.45-4.34 (m, 1H), 3.08-2.98 (m, 2H), 2.67-2.52 (m, 2H), 1.57 (d, J=6.7 Hz, 6H), 1.47-1.41 (m, 4H).

Compound 89 and Compound 90

(R)-1-(1-cyclopropylethyl)-N-(1-(4-(1-i-propyl-6-oxo-1,6-dihydropyrimidin-5-yl)phenyl)cyclopropyl)-1H-pyrazolo[3,4-d]pyrimidine-6-carboxamide and (S)-1-(1-cyclopropylethyl)-N-(1-(4-(1-i-propyl-6-oxo-1,6-dihydropyrimidin-5-yl)phenyl)cyclopropyl)-1H-pyrazolo[3,4-d]pyrimidine-6-carboxamide

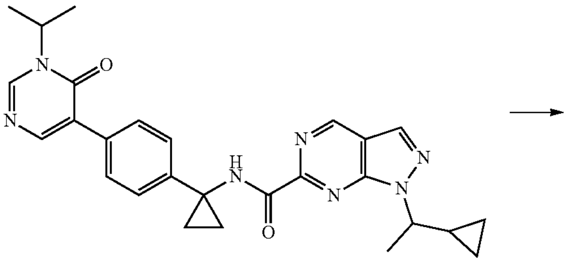

-continued

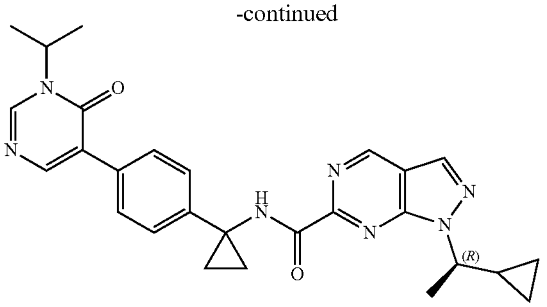

+

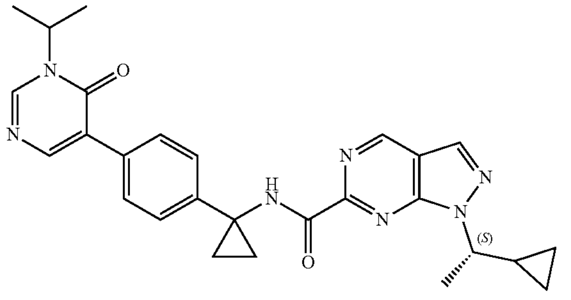

The racemic compound 1-(1-cyclopropylethyl)-N-(1-(4-(1-i-propyl-6-oxo-1,6-dihydropyrimidin-5-yl)phenyl)cyclopropyl)-1H-pyrazolo[3,4-d]pyrimidine-6-carboxamide (namely, Compound 59) was resolved by chiral HPLC to provide the optically pure enantiomers Compound 89 and Compound 90 (HPLC conditions: column: AS-H 4.6×15 mm; Mobile phase: $CO_2$:ETOH (0.1% DEA)=70:30; flow rate: 2.5 mL/minute; detector: UV 254 nm). The first eluent (Compound 89, Rf=3.919 minute min) was 100% ee, MS (m/z): 484.2 $[M+H]^+$. The second eluent (Compound 90, Rf=4.260 min) was 100% ee, MS (m/z): 484.2 $[M+H]^+$.

Compound 89: $^1H$ NMR (400 MHz, $CDCl_3$) δ 9.19 (s, 1H), 8.79 (s, 1H), 8.23 (s, 1H), 8.12 (s, 1H), 7.97 (s, 1H), 7.60-7.54 (m, 2H), 7.48-7.40 (m, 2H), 5.20-5.08 (m, 1H), 4.58-4.41 (m, 1H), 1.67-1.62 (m, 3H), 1.49-1.39 (m, 11H), 0.74-0.63 (m, 1H), 0.48-0.30 (m, 3H).

Compound 90: $^1H$ NMR (400 MHz, $CDCl_3$) δ 9.19 (s, 1H), 8.80 (s, 1H), 8.23 (s, 1H), 8.13 (s, 1H), 7.97 (s, 1H), 7.61-7.53 (m, 2H), 7.49-7.37 (m, 2H), 5.26-5.03 (m, 1H), 4.69-4.36 (m, 1H), 1.69-1.65 (m, 3H), 1.50-1.44 (m, 9H), 1.43-1.39 (m, 2H), 0.73-0.69 (m, 1H), 0.46-0.31 (m, 3H).

Example 2. RIPK1 Kinase Activity Assay

1. Reagents and Materials

RIPK1 recombination protein: synthesized by Shanghai Medicilon Inc. under the commission by Hutchison MediPharma Limited (50 g of cell pellet was resuspended in 250 mL of lysis buffer (50 mM Tris, pH 7.5, 250 mM NaCl, 1 mM DTT, protease inhibitor 1:50), the cells were ultrasonically lysed using a sonicator (the power set to 4) on ice for 3×30 minutes; then centrifugation was carried out at 4° C., at 15,000 g for 30 minutes to clarify the suspension, the soluble pellet was resuspended into 10 mL of glutathione agarose, and incubated at 4° C. for 2 hours; then the beads were loaded into the column and washed with lysis buffer (no protease inhibitors) to baseline, and eluted with 20 mM of reduced glutathione (50 mM Tris, pH 8). The fractions identified by SDS-PAGE as containing the protein of interest were collected (10 mL of total volume), concentrated to about 5 mL and loaded into 300 mL superdex75 column (GE Healthcare) equilibrated with buffer (50 mM Tris, pH 7.5, 150 mM NaCl, 1 mM DTT, 10% glycerol, pH 7.5). RIP1 protein was eluted as a dimer from the superdex75 column. The protein concentration was determined by the Bradford assay using BSA as the standard. The yield was 12.5 mg at 0.63 mg/mL. The protein was aliquoted and frozen at −80° C. for later use.

The sequence of the RIPK1 recombinant protein was:

```
  1 MHHHHHHHHH HSPILGYWKI KGLVQPTRLL LEYLEEKYEE HLYERDEGDK

 51 WRNKKFELGL EFPNLPYYID GDVKLTQSMA IIRYIADKHN MLGGCPKERA

101 EISMLEGAVL DIRYGVSRIA YSKDFETLKV DFLSKLPEML KMFEDRLCHK

151 TYLNGDHVTH PDFMLYDALD VVLYMDPMCL DAFPKLVCFK KRIEAIPQID

201 KYLKSSKYIA WPLQGWQATF GGGDHPPKSD LVPRGSENLY FQGMQPDMSL

251 NVIKMKSSDF LESAELDSGG FGKVSLCFHR TQGLMIMKTV YKGPNCIEHN

301 EALLEEAKMM NRLRHSRVVK LLGVIIEEGK YSLVMEYMEK GNLMHVLKAE

351 MSTPLSVKGR IILEIIEGMC YLHGKGVIHK DLKPENILVD NDFHIKIADL

401 GLASFKMWSK LNNEEHNELR EVDGTAKKNG GTLYYMAPEH LNDVNAKPTE

451 KSDVYSFAVV LWAIFANKEP YENAICEQQL IMCIKSGNRP DVDDITEYCP

501 REIISLMKLC WEANPEARPT FPGIEEKFRP FYLSQLEESV EEDVKSLKKE

551 YSNENAVVKR MQSLQLDCVA VPSSRSNSAT EQPGSLHSSQ GLGMGPVEES

601 WFAPSLEHPQ EENEPSLQ
```

ADP-Glo Kinase Kit: Promega, Cat #V9102;

384-well microplate (White, Flat bottom, Polystyrene): Corning, Cat #3574;

96-well microplate (V-bottom, Polystyrene): Thermo Scientific Nunc, Cat #277143;

Envision multi-mode plate reader: PerkinElmer;

Mixmate Shaker: Eppendorf;

TS-2102 shaking incubator: TENSUC.

2. Methods (1) Principle:

ADP-Glo Kinase kit can be used to measure ADP level in kinase activity assay so as to distinguish the inhibitory effects of different compounds on RIPK1 kinase activity. The ADP-Glo assay was usually divided into three steps. Firstly, the kinase converted ATP to ADP and phosphorylated the substrate at the same time; secondly, ATP digestion reagent was added to degrade all ATP in the reaction system; finally, a detection reagent was added to reduce ADP to ATP, and energy from ATP was transferred to fluorescein which thus emitting a chemical luminescence that can be detected. Assay procedure can refer to manufacture's technical manual.

(2) Reagent Preparation:

1.33× kinase buffer: 5× kinase buffer stock (250 mM of NaCl, 150 mM of $MgCl_2$, 2.5 mg/ml BSA (bovine serum albumin), 0.1% CHAPS (3-[(3-cholamidopropyl)-dimethyl-ammonio]-1-propane sulfonate), and 5 mM of dithiothreitol) was diluted with water to 1.33× kinase buffer;

RIPK1 enzyme solution: the kinase was dissolved in 1.33× kinase buffer to make 40 nM as the final working concentration;

ATP solution: 10 mM ATP stock solution in water was dissolved in 1.33× kinase buffer to make 10 μM as the final working concentration;

4× compound preparation: the compound was diluted in a 3-fold gradient, and finally 4% DMSO aqueous solution containing different concentrations of the compound was obtained. The final concentrations of the test compound were 10, 3.33, 1.11, 0.37, 0.12, 0.04, 0.014, and 0.005 μM.

(3) Specific Steps of the Experiment:

The assay set up two control groups, one was 100% inhibition group (no enzyme treatment), another was 0% inhibition group (no inhibitor treatment), each control group contained 8 replicate wells. 2.5 μl of serially diluted compound was added to each well of a 384-well plate, with double replicate wells, and 4% DMSO solution was added to control wells. Then 5 μl of RIPK1 enzyme solution was added to each well except 100% inhibition control, 5 ul of buffer was added to 100% inhibition control, after that, 2.5 μl of ATP solution was added to all wells, the plate was vibrated at 1000 rpm for 30 seconds to perform transient centrifuge; finally the 384-well assay plate was put in the shaking incubator, and incubated at room temperature for 3 hours. After the enzymatic reaction was completed, 5 μl of ATP depletion reagent was added to each well, the mixture was centrifuged transiently, then the 384-well assay plate was put in the shaking incubator, and incubated at room temperature for 1 hour. 5 μl of ADP detection reagent was added to each well, and the mixture was centrifuged transiently, and incubated at room temperature for 0.5 hour.

3. Detecting

The 384-well plate was taken out and the signal value of each well was determined using the Envision multi-mode plate reader.

4. Calculating

The mean of the signal values of the 100% inhibition group and the 0% inhibition group was used as the reference value, the inhibition rate of each concentration of every compound was calculated according to the signal value of each well, and the $IC_{50}$ value was processed by model 205 in XL-Fit 5.3 software (ID Business Solutions Limited).

The inhibition rate was calculated following the formula as below:

Inhibition rate (%)=100%×(mean signal value of 0% inhibition group−signal value of testing well)/(mean signal value of 0% inhibition group−mean signal value of 100% inhibition group)

5. Test Results

| Compound No. | $IC_{50}$ (μM) | Compound No. | $IC_{50}$ (μM) | Compound No. | $IC_{50}$ (μM) | Compound No. | $IC_{50}$ (μM) |
|---|---|---|---|---|---|---|---|
| 1 | 0.028 | 23 | 0.049 | 43 | 0.032 | 67 | 0.049 |
| 2 | 0.063 | 24 | 0.089 | 44 | 0.037 | 68 | 0.043 |
| 3 | 0.035 | 25 | 0.053 | 45 | 0.040 | 69 | 0.021 |
| 4 | 0.026 | 26 | 0.022 | 46 | 0.035 | 70 | 0.051 |
| 5 | 0.057 | 27 | 0.046 | 47 | 0.029 | 71 | 0.110 |
| 6 | 0.056 | 28 | 0.095 | 48 | 0.053 | 72 | 0.065 |
| 7 | 0.039 | 29 | 0.019 | 53 | 0.121 | 73 | 0.052 |
| 8 | 0.022 | 30 | 0.035 | 54 | 0.027 | 74 | 0.062 |
| 9 | 0.037 | 31 | 0.432 | 55 | 0.023 | 75 | 0.051 |
| 10 | 0.026 | 32 | 82.5@3 μM* | 56 | 0.189 | 76 | 0.051 |
| 11 | 0.038 | 33 | 0.059 | 57 | 0.531 | 77 | 0.042 |
| 12 | 0.009 | 34 | 0.065 | 58 | 0.139 | 78 | 0.033 |
| 13 | 0.022 | 35 | 0.047 | 59 | 0.026 | 80 | 0.042 |
| 14 | 0.018 | 36 | 0.042 | 60 | 0.059 | 81 | 0.039 |
| 15 | 0.030 | 37 | 0.041 | 61 | 0.014 | 82 | 0.051 |
| 16 | 0.025 | 38 | 0.048 | 62 | 0.021 | 83 | 0.047 |
| 17 | 0.015 | 39 | 0.059 | 63 | 0.037 | 84 | 0.045 |
| 18 | 0.038 | 40 | 0.052 | 64 | 0.017 | 85 | 0.030 |
| 19 | 0.071 | 41 | 0.061 | 65 | 0.036 | 79 | 0.021 |
| 22 | 0.055 | 42 | 0.056 | 66 | 0.048 | 86 | 0.014 |
| 87 | 0.041 | 90 | 0.054 | 93 | 0.035 | | |
| 88 | 0.041 | 91 | 0.072 | 94 | 0.027 | | |
| 89 | 0.048 | 92 | 0.104 | 95 | 0.028 | | |

*: Inhibition rate at the compound concentration of 3 μM

Example 3. U937 Cell Viability Assay

1. Reagents and Materials

U937 cell line (human histiocytic lymphoma cell line): purchased from ATCC (American Type Culture Collection) Cell Bank, cultured in a 5% $CO_2$, 37° C. incubator, and RPMI 1640 medium which contains L-glutamine, 1.5 g/L sodium bicarbonate, 2.383 g/L HEPES solution, 0.11 g/L sodium pyruvate and 4.5 g/L glucose, plus 10% fetal bovine serum (FBS) was used.

RPMI 1640 medium: GIBCO, Cat #A10491-01;

Fetal bovine serum (FBS): GIBCO, Cat #10099-141C;

Dimethyl sulfoxide (DMSO): Sigma, Cat #D2650;

Recombinant Human TNF-alpha Protein (hTNF-α): R&D system, Cat #210-TA-100;

Pan-Caspase inhibitor (Z-VAD-FMK): Selleckchem, Cat #S7023;

CellTiter-Glo 2.0 Cell Viability Assay kit: Promega, Cat #G9242;

Microwell plate reader: Envision, Perkin Elmer;

96-well plate: Corning, Cat #3917.

2. Methods

The U937 cells at the logarithmic phase were taken out, centrifuged to remove the medium, washed with PRMI 1640 medium containing 1% FBS, and diluted with 1% FBS-containing RPMI 1640 medium to $2.5\times10^5$ cells/ml, inoculated at 70 μL/well into a 96-well plate, i.e., $1.75\times10^4$ cells/well. The plate was cultured in a 5% $CO_2$, 37° C. cell incubator. After incubating for 1 hour, the test compound was diluted to the corresponding concentrations using DMSO with 3-fold serial dilution, then the corresponding concentration of DMSO diluted solution was diluted into 1% FBS-containing RPMI 1640 medium, and 10 μL/well of the diluted test compound with different concentrations (final concentration of test compound was 1.0, 0.333, 0.111, 0.037, 0.012, 0.004, 0.0014 and 0.0005 μM, while final concentration of DMSO was 0.3%) or 10 μL/well control solution (3% DMSO) were added to the cell culture system respectively, with the total volume being 80 μL/well; Then 10 μL of Z-VAD-FMK solution diluted with 1% FBS-containing RPMI 1640 medium (final concentration of 50 μM) or 10 μL of control solution (2.5% DMSO) was added to each well, with the total volume being 90 μL/well. The plate was incubated in a 5% $CO_2$, 37° C. cell culture incubator for 1 hour.

After being cultured for 1 hour, 10 μL of human recombinant TNF-α protein diluted with 1% FBS-containing RPMI 1640 medium (final concentration of 0.1 μg/mL) or 10 μL/well control solution (1% FBS-containing RPMI 1640 medium) was added to each well. The plate was incubated in a 5% $CO_2$, 37° C. cell culture incubator for 20 hours.

The cell culture plate was taken out from the incubator, and left to stand at room temperature for 30 minutes. Meanwhile, CellTiter-Glo viability assay kit was put from freezer to room temperature, and 50 μL of CellTiter-Glo reagent was added to all wells, the plate was shaken for 1 minutes, protected from light at room temperature for 10 minutes then read the plate on Envision to get the luminescence signal.

3. Detecting

The 96-well plate in the dark was taken out, and the chemiluminescence was determined using the Envision microwell plate reader as the signal value of each well.

The mean signal value of the wells of the mixed solution of recombinant human TNF-alpha protein (final concentration of 0.1 μg/mL) and Pan-Caspase inhibitor (final concentration of 50 μM) was used as the lower value, and the mean signal value of the wells without stimulation was used as the upper value. According to the signal value of each well, the inhibition rate of each concentration of every compound was calculated, and the $IC_{50}$ value of compound was obtained by Model 205 in XL-Fit 5.3 software (ID Business Solutions Limited).

The inhibition rate was calculated following the formula as below:

Inhibition rate %=[(Luminescence readout of treated compound−Luminescence readout of positive control)/(Luminescence readout of negative control−Luminescence readout of positive control)]×100%, wherein Luminescence readout of treated compound: referred to the signal value of U937 cells treated with recombinant human TNF-alpha protein, Pan-Caspase inhibitor and test compound.

Luminescence readout of positive control: referred to the signal value of U937 cells treated with recombinant human TNF-alpha protein, Pan-Caspase inhibitor and no compound.

Luminescence readout of negative control: referred to the signal value of U937 cells without any special treatment.

4. Test Results

| Compound No. | $IC_{50}$ (μM) | Compound No. | $IC_{50}$ (μM) | Compound No. | $IC_{50}$ (μM) | Compound No. | $IC_{50}$ (μM) |
|---|---|---|---|---|---|---|---|
| 1 | 0.021 | 23 | 0.057 | 45 | 0.002 | 72 | 0.002 |
| 2 | 0.170 | 24 | 0.161 | 46 | 0.002 | 73 | 0.002 |
| 3 | 0.021 | 25 | 0.032 | 47 | 0.002 | 74 | 0.001 |
| 4 | 0.017 | 26 | 0.012 | 48 | 0.039 | 75 | 0.002 |
| 5 | 0.024 | 27 | 0.102 | 53 | 0.554 | 76 | 0.003 |
| 6 | 0.021 | 28 | 0.135 | 54 | 0.012 | 77 | 0.010 |
| 7 | 0.068 | 29 | 0.003 | 55 | 0.007 | 78 | 0.008 |
| 8 | 0.014 | 30 | 0.008 | 59 | 0.003 | 80 | 0.009 |
| 9 | 0.052 | 33 | 0.010 | 60 | 0.066 | 81 | 0.008 |
| 10 | 0.008 | 34 | 0.007 | 61 | 0.003 | 82 | 0.018 |
| 11 | 0.139 | 35 | 0.011 | 62 | 0.002 | 83 | 0.017 |
| 12 | 0.018 | 36 | 0.003 | 63 | 0.051 | 84 | 0.001 |
| 13 | 0.004 | 37 | 0.014 | 64 | 0.002 | 85 | 0.002 |
| 14 | 0.003 | 38 | 0.013 | 65 | 0.007 | 79 | 0.002 |
| 15 | 0.020 | 39 | 0.006 | 66 | 0.003 | 86 | 0.001 |
| 16 | 0.002 | 40 | 0.012 | 67 | 0.091 | 87 | 0.011 |
| 17 | 0.001 | 41 | 0.064 | 68 | 0.006 | 88 | 0.011 |
| 18 | 0.082 | 42 | 0.007 | 69 | 0.009 | 89 | 0.005 |
| 19 | 0.003 | 43 | 0.002 | 70 | 0.002 | 90 | 0.004 |
| 22 | 0.003 | 44 | 0.002 | 71 | 0.003 | 91 | 0.011 |
| 92 | 0.100 | 93 | 0.006 | 94 | 0.003 | 95 | 0.003 |

According to the assay described above, the compounds of the present invention showed good potency in inhibiting the U937 cell line necroptosis.

Example 4. L929 Cell Viability Assay

1. Reagents and Materials

L929 cell line (mouse fibroblastoma cell line): purchased from ATCC (American Type Culture Collection) Cell Bank, cultured in 5% $CO_2$, 37° C. incubator, and MEM medium which contains L-Glutamine, with 10% FBS was used.

MEM medium: GIBCO, Cat #11095080;

Fetal bovine serum (FBS): GIBCO, Cat #10099-141C;

Dimethyl sulfoxide (DMSO): Sigma, Cat #D2650;

0.25% Trypsin-EDTA: GIBCO, Cat #25200072;

Recombinant Mouse TNF-alpha Protein (mTNF-α): R&D system, Cat #410-MT-050;

Pan-Caspase inhibitor (Z-VAD-FMK): Selleckchem, Cat #S7023;

CellTiter-Glo 2.0 Cell Viability Assay kit: Promega, Cat #G9242;

Microwell plate reader: Envision, Perkin Elmer;

96-well plate: Corning, Cat #3917.

2. Methods

The L929 cells at the logarithmic phase were taken out, and the supernatant was discarded. After trypsinization and cell shedding, 10% FBS-containing medium was added for neutralization, and the supernatant was discarded after centrifugation. The cells were re-suspended using 10% FBS-containing medium, adjusted to $7\times10^4$ cells/ml, added to 96-well microplate at 70 μL/well, i.e., $4.9\times10^3$ cells/well. Then the plate was incubated in a 5% $CO_2$, 37° C. cell incubator overnight.

After incubating overnight, the 96-well plate was taken out, the medium was discarded, and the plate was washed with 1% FBS-containing MEM medium. Then 1% FBS-containing MEM medium was added at 70 μL/well, and the plate was cultured in a 5% $CO_2$, 37° C. cell incubator. After incubating for 1 hour, the test compound was diluted to the corresponding concentrations using DMSO with 3-fold serial dilution, then the corresponding concentration of DMSO diluted solution was diluted into 1% FBS-containing MEM medium, and 10 μL/well of the diluted test compound with different concentrations (final concentrations of test compound were 10, 3.33, 1.11, 0.37, 0.12, 0.04, 0.014 and 0.005 μM, while final concentration of DMSO was 0.3%) or 10 μL/well control solution (3% DMSO) were added to the cell culture system respectively, with the total volume being 80 μL/well. Then 10 μL of Z-VAD-FMK solution diluted with 1% FBS-containing MEM medium (final concentration of 5 μM) or 10 μL of control solution (2.5% DMSO) was added to each well, with the total volume being 90 μL/well. The plate was incubated in a 5% $CO_2$, 37° C. cell culture incubator for 1 hour.

After incubating for 1 hour, 10 μL of recombinant mouse TNF-α protein solution diluted with 1% FBS-containing MEM medium (final concentration of 0.1 μg/mL) or 10 μL control solution (1% FBS-containing MEM medium) was added to each well. The plate was incubated in a 5% $CO_2$, 37° C. cell culture incubator for 20 hours.

The cell culture plate was taken out from the incubator, and left to stand at room temperature for 30 minutes. Meanwhile, CellTiter-Glo viability assay kit was put from freezer to room temperature, and 50 μL of CellTiter-Glo reagent was added to all wells, the plate was shaken for 1 minutes, protected from light at room temperature for 10 minutes then read the plate on Envision to get the luminescence signal.

3. Detecting

The 96-well plate in the dark was taken out, and the chemiluminescence was determined using the Envision microwell plate reader as the signal value of each well.

The mean signal value of the wells of the mixed solution of recombinant mouse TNF-alpha protein (final concentration of 0.1 μg/mL) and Pan-Caspase inhibitor (final concentration of 5 μM) was used as the lower value, and the mean signal value of the wells without stimulation was used as the upper value. According to the signal value of each well, the inhibition rate of each concentration of every compound was calculated, and the $IC_{50}$ value of compound was obtained by Model 205 in XL-Fit 5.3 software (ID Business Solutions Limited).

The inhibition rate was calculated following the formula as below:

Inhibition rate %=[(Luminescence readout of treated compound−Luminescence readout of positive control)/(Luminescence readout of negative control−Luminescence readout of positive control)]×100%, wherein Luminescence readout of treated compound: referred to the signal value of L929 cells treated with recombinant mouse TNF-alpha protein, Pan-Caspase inhibitor and test compound.

Luminescence readout of positive control: referred to the signal value of L929 cells treated with recombinant mouse TNF-alpha protein, Pan-Caspase inhibitor and no compound.

Luminescence readout of negative control: referred to the signal value of L929 cells without any special treatment.

4. Test Results

RPMI 1640 medium: L-Glutamine, 1.5 g/L $NaHCO_3$, 2.383 g/L HEPES solution, 0.11 g/L sodium pyruvate and 4.5 g/L Glucose; Gibco, catalog: A10491-01;

Dimethyl sulfoxide (DMSO): Sigma, catalog: D2650;

Recombinant Human TNF-alpha Protein (hTNF-α): R&D system, catalog: 210-TA-100;

Pan-Caspase inhibitor (Z-VAD-FMK): Selleckchem, catalog: S7023;

Smac Mimetic-164 (SM-164): APEXBIO, catalog: A8815;

Human IL-1 beta/IL-1F2 Quantikine ELISA Kit: R&D systems, catalog: SLB50;

Envision Multimode Microplate Reader: PerkinElmer;

96-well clear flat bottom TC-treated culture microplate: Falcon, catalog: 353072;

96-well Microplate (U bottom): Corning, catalog: 3799.

2. Assay Protocol Human whole blood was anti-coagulated with heparin and used in human whole blood assay immediately. Fresh heparinized human whole blood was diluted with an equal volume of RPMI 1640 medium, aliquoted the diluted blood into 96-well plate, 90 μL each well.

Compound preparation: dilute the compound stock using DMSO and perform 3-fold serial dilution to 8-points. Then transfer the diluted compounds to RPMI 1640 medium and mix.

Compound treatment and stimulation: transfer 5 μL of the diluted compound to appropriate wells of the plate. The final concentration of the compound was 1.0, 0.333, 0.111, 0.037, 0.012, 0.004, 0.0014 and 0.0005 μM, and each well contained 0.3% DMSO. For positive and negative control wells, add 5 μL of RPMI 1640 medium with 3% DMSO. And incubate the plate at 5% $CO_2$, 37° C. for 1 hour.

| Compound No. | $IC_{50}$ (μM) | Compound No. | $IC_{50}$ (μM) | Compound No. | $IC_{50}$ (μM) | Compound No. | $IC_{50}$ (μM) |
|---|---|---|---|---|---|---|---|
| 1 | 1.252 | 25 | 7.603 | 54 | 0.578 | 77 | 0.151 |
| 2 | 7.453 | 26 | 0.846 | 55 | 0.259 | 78 | 0.044 |
| 3 | 4.275 | 28 | 5.699 | 59 | 0.017 | 80 | 0.297 |
| 4 | 0.721 | 29 | 0.034 | 60 | 9.077 | 81 | 0.258 |
| 5 | 2.503 | 30 | 2.586 | 61 | 0.048 | 82 | 0.359 |
| 6 | 0.299 | 33 | 0.665 | 62 | 0.027 | 83 | 0.199 |
| 8 | 1.762 | 34 | 0.078 | 63 | 9.424 | 84 | 0.007 |
| 9 | 2.814 | 35 | 0.154 | 64 | 0.079 | 85 | 0.013 |
| 10 | 0.676 | 36 | 0.084 | 65 | 0.861 | 79 | 0.010 |
| 11 | 9.124 | 37 | 0.186 | 66 | 0.053 | 86 | 0.019 |
| 12 | 1.018 | 38 | 0.152 | 67 | 5.650 | 87 | 0.393 |
| 13 | 0.195 | 39 | 0.059 | 68 | 0.032 | 88 | 0.335 |
| 14 | 0.181 | 40 | 0.109 | 69 | 0.098 | 89 | 0.038 |
| 15 | 2.365 | 41 | 1.97 | 70 | 0.012 | 90 | 0.012 |
| 16 | 0.007 | 42 | 0.119 | 71 | 0.020 | 91 | 0.786 |
| 17 | 0.025 | 43 | 0.016 | 72 | 0.016 | 92 | 3.131 |
| 18 | 1.719 | 44 | 0.028 | 73 | 0.041 | 93 | 0.148 |
| 19 | 0.061 | 45 | 0.058 | 74 | 0.030 | 94 | 0.050 |
| 22 | 0.028 | 46 | 0.019 | 75 | 0.041 | 95 | 0.145 |
| 23 | 2.705 | 47 | 0.024 | 76 | 0.032 | | |

According to the assay described above, the compounds of the present invention showed good efficacy in inhibiting the L929 cell necroptosis.

Example 5. Effect of the Compound of the Present Invention on TNF-α Induced IL-1β in Human Whole Blood 1. Reagents and Materials Human blood samples were collected by venipuncture from healthy volunteers, with signed consent from each volunteer before blood collection;

Then 5 μL of the mixture of stimuli (TNF-α, Z-VAD-FMK and SM-164) was added with the final concentration of 20 μM, 1 μM and 0.01 μg/mL except negative control wells. The negative control wells were added same volume of RPMI 1640 medium.

After incubation 6 hours in a 37° C./5% $CO_2$ incubator, each well was added with 100 μL of PBS, and centrifuged at 4000 rmp for 10 minutes. The 110 μL of supernatant per well was collected, and stored at −80° C. for ELISA.

3. Detection

Prepared 100 μL of IL-1β standards (in duplicate) in designated wells. ELISA was operated according to manufacturer's instruction. In the end, measured the ELISA plate absorbance at 450 nm/570 nm using Envision.

4. Data Calculation

Inhibition rates of compounds on TNF-α, Z-VAD-FMK and SM-164 induced IL-1β Production in human whole blood were calculated as follows:

IL-1β level was calculated with IL-1β standard curve (standard curve fitting equation is four parameters logistic model)

$$\text{Inhibition rate } \% = \frac{IL\text{-}1\beta\ \text{level}_{stimulated} - IL\text{-}1\beta\ \text{level}_{compound}}{IL\text{-}1\beta\ \text{level}_{stimulated} - IL\text{-}1\beta\ \text{level}_{non\text{-}stimulated}} \times 100$$

IL-1β $\text{level}_{stimulated}$: the concentration of IL-1β in the positive control wells which added TNF-α, Z-VAD-FMK, SM-164 and no compound;

IL-1β $\text{level}_{non\text{-}stimulated}$: the concentration of IL-1β in the negative control wells without the treatment of TNF-α, Z-VAD-FMK, SM-164 and compound;

IL-1β $\text{level}_{compound}$: the concentration of IL-1β in the wells with the treatment of TNF-α, Z-VAD-FMK, SM-164 and compound.

The $IC_{50}$ value of compound is determined with XLFit 5 software (ID Business Solutions Limited).

5. Results

| Compound | $IC_{50}$ (μM) | Compound | $IC_{50}$ (μM) | Compound | $IC_{50}$ (μM) | Compound | $IC_{50}$ (μM) |
|---|---|---|---|---|---|---|---|
| 29 | 0.004 | 60 | 0.010 | 72 | 0.039 | 85 | 0.005 |
| 36 | 0.004 | 61 | 0.011 | 73 | 0.021 | 86 | 0.013 |
| 41 | 0.018 | 64 | 0.012 | 74 | 0.013 | 89 | 0.018 |
| 46 | 0.006 | 68 | 0.043 | 75 | 0.011 | 90 | 0.007 |
| 47 | 0.009 | 70 | 0.008 | 76 | 0.009 | | |
| 59 | 0.004 | 71 | 0.038 | 84 | 0.005 | | |

According to the assay described above, the test compounds showed good potency in inhibiting TNF-α, Z-VAD-FMK and SM-164 induced IL-1β Production in human whole blood.

Example 6. In Vivo Target Inhibition of RIPK1 of the Compound of the Present Invention in Mouse SIRS Model Objective: To evaluate the in vivo efficacy of the compound of the present invention on TNF-α+zVAD-FMK induced hypothermia in the mice Systemic Inflammatory Response Syndrome (SIRS) model.

Methods: Before the model induction, C57BL/6 mice (male, 6-8 weeks, purchased from Shanghai Lingchang Biotechnology) were grouped randomly by body weight. Each group was orally administered with vehicle, positive compound 1 mg/kg (GSK-547) and different doses of the compound of the present invention (the test compound), respectively, according to the grouping table (Table 1).

TABLE 1

Grouping information for the IVTI study

| Group | Dose (mg/kg) | Number of animals in each group | Vehicle | Model induction | Read outs |
|---|---|---|---|---|---|
| Control | — | 6 | 0.5% CMC, pH 2.1 | zVAD-FMK(16.7 mg/kg) TNF-α (0.325 mg/kg) + zVAD-FMK(16.7 mg/kg) with i.v. injection, 0.5 h post compound dosing | Temperature measured 3 h post model induction Serum cytokine/chemokine tested 3 h post model induction Survival observation |
| Vehicle | — | 6 | | | |
| GSK-547-1 | 1 | 6 | | | |
| Test Compound-0.01 | 0.01 | 6 | | | |
| Test Compound-0.03 | 0.03 | 6 | | | |
| Test Compound-0.1 | 0.1 | 6 | | | |
| Test Compound-0.3 | 0.3 | 6 | | | |
| Test Compound-1 | 1 | 6 | | | |

After 30 minutes of oral dosing, mice were injected intravenously with zVAD-FMK (eybridge, Lot #S02910-074-01) (16.7 mg/kg) or TNF-α (Novoprotein Scientific, Cat #CF09)+zVAD-FMK (0.325 mg/kg+16.7 mg/kg) in phosphate-buffered saline (PBS) pH 7.2 and contained 2.5% DMSO. Body temperature was measured 3 hours post the model induction by rectal probe. And the cytokine and chemokine levels in the plasma were detected 3 hours post the model induction by ELISA. All the animals were monitored the survival status until 72 hours after the model induction.

Result:

To investigate the in vivo efficacy of the compound of the present invention in TNF-induced SIRS, mice were pretreated with the compound of the present invention. The test compound could protect mice from hypothermia induced by TNF-α in a dose-dependent manner. Mortality and systemic inflammation could be decreased by the test compound pretreatment.

Example 7. In Vivo Efficacy of the Compound of the Present Invention on the Model of Bovine Type II Collagen Induced Arthritis in DBA1 Mice Objective:

To investigate in vivo efficacy of the compound of the present invention on the model of bovine type II collagen induced arthritis in DBA1 mice Animals:

DBA1 mice, male, 7-9 weeks old, 18-20 g, provided by Vital River Laboratory Animal Technology Co., Ltd. (Peking, P.R. China).

Methods:

Bovine type II collagen (CII, Chondrex. Cat: 20021) were dissolved in 100 mM HOAc (SPGC Sinopharm Chemical Reagent Co., Ltd (Shanghai, P.R. China), Cat: 10000218.) at 8 mg/ml and stored by stirring in 4° C. over night. 8 mg/ml Type II collagen was mixed with equal volume of CFA (Sigma, Cat #: F5881) and made an emulsion on ice using a high-speed homogenizer (FLUKO Equipment Shanghai Co., Ltd.).

Before immunization, five mice were randomly grouped as normal (naive) group. The other mice were anaesthetized with intraperitoneal injection of isoflurane, and injected subcutaneously at the base of the tail with 0.05 ml of the emulsion (4 mg/ml CII/CFA), about 1.5-2 cm from the body on day 0 and day 21.

After the symptoms of arthritis showed in mouse model at Day 24 post the first immunization, mice challenged with CII/CFA were randomly grouped and administrated as the Table 2. The YiSaiPu (Sunshine Guojian Pharmaceutical (Shanghai) Co, Ltd)-treated group was intraperitoneally injected every other day (qod), while the control group and the compound of the present invention (the test compound)-treated group was orally administrated daily.

TABLE 2

Grouping and dosing regimen

| Group | Dose (mg/kg) | Number of animals in each group | Model induction | Vehicle | Route | Dose | Dose volumes |
|---|---|---|---|---|---|---|---|
| Vehicle | — | 10 | 200 μg CII + 25 μg CFA/mouse emulsion on day0 and 21 | 0.5%CMC, pH = 2.1 | p.o., bid | after arthritis onset day 24-44 | 10 mL/kg BW |
| Test compound | 15 | 10 | | | | | |
| YiSaiPu | 25 | 10 | | Saline | i.p., qod | | |
| Naive | — | 5 | — | — | — | — | — |

The severity of arthritic symptoms of four paws in arthritis mice was scored every other day after arthritis onset, as following criteria:

0, No evidence of erythema and swelling;

1, Erythema and mild swelling confined to hemed-foot (tarsals) or ankle joint;

2, Erythema and mild swelling extending from the ankle to the mid-foot;

3, Erythema and moderate swelling extending from the ankle to the metatarsal joints;

4, Erythema and severe swelling encompass the ankle, foot, and digits.

The severity of arthritis was determined by the sum of the scores from four paws. Score=sum of separate score of four paws.

Repeated One-Way ANOVA followed by Dunnett's test was used to calculate the differences between vehicle and compound treated groups by JMP.

The arthritic score of each animal prior to dosing was considered as the baseline (or 100% of achievable inhibition of inflammation). Arthritic score change (SC) in each mouse was calculated according to the equation, wherein ScoreD24 was the score at the starting day to dose and ScoreDt is the score at dosing day Dt:

$$SCDt = ScoreDt - ScoreD24.$$

Area under the curve (AUC) of score was calculated from score change in each mouse based on Trapezoidal rule:

$$AUC_{score} = \tfrac{1}{2}\times(SCDt+SCD(t-2))\times(Dt-D(t-2))+\tfrac{1}{2}\times(SCD(t-2)+SCD(t-4))\times(D(t-2)-D(t-4))+\ldots+\tfrac{1}{2}\times(SCD26+SCD24)\times(D26-D24)$$

The effects of treatment on arthritic score change were calculated based on AUC values. Percent inhibition of AUC was calculated using the following formula:

$$\text{Inhibition Rate }(\%)=(AUC_{vehicie}-AUC_{treatment})/(AUC_{vehicle})\times 100\%.$$

Result:

Immunization of the mice challenged with bovine Collagen II developed severe inflammation and edema in the paws. The arthritic score was measured by visual scoring to evaluate the in vivo efficacy of the test compound on this model.

Vehicle treatment in this study resulted in a progressive increase in arthritis score. The treatment was initiated from day 24 post immunization. Treatment of YiSaiPu, a positive control, at 25 mg/kg QOD from day 24 to the end, significantly blocked arthritis compared with vehicle control. And the test compound at 15 mg/kg could ameliorate the paw swelling as well.

The entire content of all patents and non-patent documents listed herein are incorporated into herein by reference, as if their respective content are listed one by one.

Although specific embodiments and examples are provided herein to illustrate the present invention, same are not intended to limit the scope of the present invention. Based on the present disclosure, a person skilled in the art would have been able to arrive, in an obvious way, at other modifications or equivalent solutions without departing from the spirit of the present invention, and these modifications and equivalent solutions are all within the scope of the present invention.

The invention claimed is:

1. A compound of formula (I):

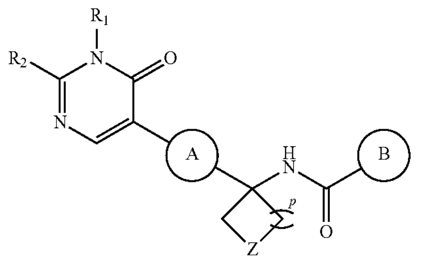

(I)

or a pharmaceutically acceptable salt thereof, or a solvate, a racemic mixture, an enantiomer, a diastereomer or a tautomer thereof, wherein $R_1$ is hydrogen, $C_{1-6}$ alkyl, $C_{1-6}$ haloalkyl, cyano-substituted $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl or —($C_{1-6}$ alkylene)$_n$-5-6 membered heteroaryl; wherein the $C_{3-6}$ cycloalkyl, phenyl, 4-6 membered heterocyclyl and 5-6 membered heteroaryl are each optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl) and —N($C_{1-6}$ alkyl)$_2$;

$R_2$ is hydrogen, halogen, —CN, —$NH_2$, $C_{1-6}$ alkyl, $C_{1-6}$ haloalkyl, —O($C_{1-6}$ alkyl), —O($C_{1-6}$ haloalkyl), —NH ($C_{1-6}$ alkyl) or —N($C_{1-6}$ alkyl)$_2$;

Z is O, $NR_3$ or $CR_4R_5$;

$R_3$ is hydrogen or $C_{1-6}$ alkyl;

$R_4$ and $R_5$ are each independently chosen from: hydrogen, halogen, —CN, —OH, $C_{1-6}$ alkyl, $C_{1-6}$ haloalkyl, —O($C_{1-6}$ alkyl), —O($C_{1-6}$ haloalkyl) and $C_{3-6}$ cycloalkyl;

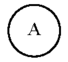

is phenyl or 5-6 membered heteroaryl, each of which is optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl) and —N($C_{1-6}$ alkyl)$_2$;

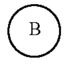

is 5-12 membered heteroaryl, which is optionally substituted with one or more groups independently chosen from: halogen, —CN, —OH, oxo, —$NH_2$, $C_{1-6}$ alkyl, $C_{1-6}$ haloalkyl, $C_{2-6}$ alkenyl, $C_{2-6}$ alkynyl, —O($C_{1-6}$ alkyl), —O($C_{1-6}$ haloalkyl), —NH($C_{1-6}$ alkyl), —N($C_{1-6}$ alkyl)$_2$, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more groups independently chosen from: halogen, —CN, —OH, —$NH_2$, $C_{1-6}$ alkyl, $C_{2-6}$ alkenyl, $C_{2-6}$ alkynyl, $C_{1-6}$ haloalkyl, —O($C_{1-6}$ alkyl), —O($C_{1-6}$ haloalkyl), —NH($C_{1-6}$ alkyl), —N($C_{1-6}$ alkyl)$_2$ and $C_{3-6}$ cycloalkyl;

n is 0 or 1;

and p is 0 or 1.

2. The compound of formula (I), or a pharmaceutically acceptable salt thereof, or a solvate, a racemic mixture, an enantiomer, a diastereomer or a tautomer thereof according to claim 1, wherein $R_1$ is $C_{1-6}$ alkyl, $C_{1-6}$ haloalkyl, cyano-substituted $C_{1-6}$ alkyl, —($C_{1-6}$ alkylene)$_n$-$C_{3-6}$ cycloalkyl or —($C_{1-6}$ alkylene)$_n$-4-6 membered heterocyclyl; wherein the $C_{3-6}$ cycloalkyl and 4-6 membered heterocyclyl are each optionally substituted with one or more groups independently chosen from: halogen and $C_{1-6}$ alkyl.

3. The compound of formula (I), or a pharmaceutically acceptable salt thereof, or a solvate, a racemic mixture, an enantiomer, a diastereomer or a tautomer thereof according to claim 2, wherein $R_1$ is $C_{1-6}$ alkyl.

4. The compound of formula (I), or a pharmaceutically acceptable salt thereof, or a solvate, a racemic mixture, an enantiomer, a diastereomer or a tautomer thereof according to claim 2, wherein $R_1$ is —($C_{1-6}$ alkylene)$_n$-$C_{3-6}$ cycloalkyl, wherein the $C_{3-6}$ cycloalkyl is optionally substituted with one or more halogen, and n is 0 or 1; or $R_1$ is 4-6 membered heterocyclyl, wherein the 4-6 membered heterocyclyl is oxetanyl, tetrahydrofuranyl or tetrahydropyranyl.

5. The compound of formula (I), or a pharmaceutically acceptable salt thereof, or a solvate, a racemic mixture, an enantiomer, a diastereomer or a tautomer thereof according to claim 1, wherein $R_2$ is hydrogen, —$NH_2$ or $C_{1-6}$ alkyl.

6. The compound of formula (I), or a pharmaceutically acceptable salt thereof, or a solvate, a racemic mixture, an enantiomer, a diastereomer or a tautomer thereof according to claim 1, wherein p is 0, and Z is $CH_2$.

7. The compound of formula (I), or a pharmaceutically acceptable salt thereof, or a solvate, a racemic mixture, an enantiomer, a diastereomer or a tautomer thereof according to claim 1, wherein

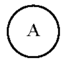

is phenyl or pyridyl, each of which is optionally substituted with one or more groups independently chosen from: halogen, $C_{1-6}$ alkyl, and $C_{1-6}$ haloalkyl.

8. The compound of formula (I), or a pharmaceutically acceptable salt thereof, or a solvate, a racemic mixture, an enantiomer, a diastereomer or a tautomer thereof according to claim 1, wherein

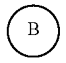

is 5-9 membered heteroaryl, which is optionally substituted with one or more groups independently chosen from: halogen, $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; and wherein the phenyl, $C_{3-6}$ cycloalkyl, 4-6 membered heterocyclyl and 5-6 membered heteroaryl are each optionally substituted with one or more halogen.

9. The compound of formula (I), or a pharmaceutically acceptable salt thereof, or a solvate, a racemic mixture, an enantiomer, a diastereomer or a tautomer thereof according to claim 1, wherein the compound of formula (I) is the compound of formula (I-1):

(I-1)

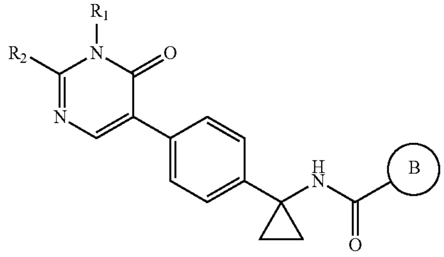

wherein $R_1$ is $C_{1-6}$ alkyl, $C_{1-6}$ haloalkyl, cyano-substituted $C_{1-6}$ alkyl, —($C_{1-6}$ alkylene)$_n$-$C_{3-6}$ cycloalkyl or —($C_{1-6}$ alkylene)$_n$-4-6 membered heterocyclyl; wherein the $C_{3-6}$ cycloalkyl and 4-6 membered heterocyclyl are each optionally substituted with one or more groups independently chosen from: halogen and $C_{1-6}$ alkyl;

$R_2$ is hydrogen, —$NH_2$ or $C_{1-6}$ alkyl;

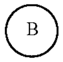

is 5-9 membered heteroaryl, which is optionally substituted with one or more groups independently chosen from: halogen, $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more halogen;

and n is 0 or 1.

10. The compound of formula (I), or a pharmaceutically acceptable salt thereof, or a solvate, a racemic mixture, an enantiomer, a diastereomer or a tautomer thereof according to claim 1, wherein

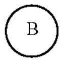

is triazolyl, oxazolyl, isoxazolyl, oxadiazolyl, pyrimidyl, pyrazolopyrimidyl, pyrazolopyridyl or dihydropyrrolotriazolyl, each of which is optionally substituted with one or more groups independently chosen from: halogen, $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more halogen.

11. The compound of formula (I), or a pharmaceutically acceptable salt thereof, or a solvate, a racemic mixture, an enantiomer, a diastereomer or a tautomer thereof according to claim 10, wherein

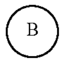

is chosen from

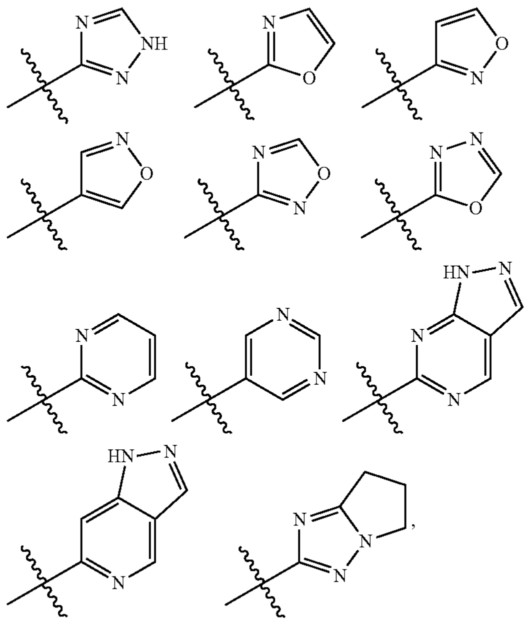

each of which is optionally substituted with one or more groups independently chosen from: halogen, $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; wherein the phenyl, $C_{3-6}$ cycloalkyl, 4-6 membered heterocyclyl and 5-6 membered heteroaryl are each optionally substituted with one or more halogen.

12. The compound of formula (I), or a pharmaceutically acceptable salt thereof, or a solvate, a racemic mixture, an enantiomer, a diastereomer or a tautomer thereof according to claim 11, wherein

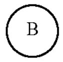 is 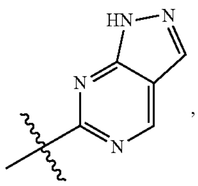, which is optionally substituted with one or more groups independently chosen from: $C_{1-6}$ alkyl, —($C_{1-6}$ alkylene)$_n$-$C_{3-6}$ cycloalkyl, —($C_{1-6}$ alkylene)$_n$-phenyl, —($C_{1-6}$ alkylene)$_n$-4-6 membered heterocyclyl and —($C_{1-6}$ alkylene)$_n$-5-6 membered heteroaryl; and wherein the $C_{3-6}$ cycloalkyl, 4-6 membered heterocyclyl and 5-6 membered heteroaryl are each optionally substituted with one or more halogen, and n is 0 or 1.

13. The compound of formula (I), or a pharmaceutically acceptable salt thereof, or a solvate, a racemic mixture, an enantiomer, a diastereomer or a tautomer thereof according to claim 12, wherein

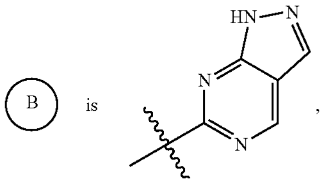

which is optionally substituted with one or more groups independently chosen from: $C_{1-6}$ alkyl;

or

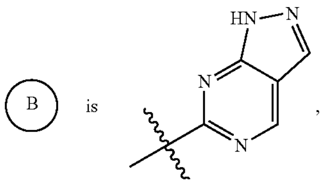

which is optionally substituted with one or more groups independently chosen from: —$(C_{1-6}$ alkylene$)_n$-$C_{3-6}$ cycloalkyl, wherein n is 0 or 1; wherein the $C_{3-6}$ cycloalkyl is optionally substituted with one or more halogen;

or

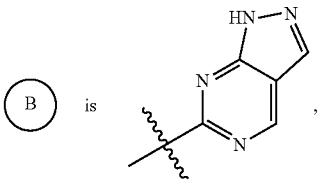

which is optionally substituted with one or more groups independently chosen from: —$(C_{1-6}$ alkylene$)_n$-phenyl, wherein n is 0 or 1;

or

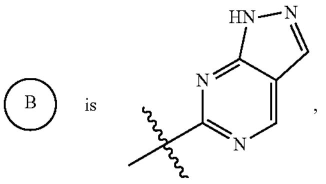

which is optionally substituted with one or more groups independently chosen from: 4-6 membered heterocyclyl; wherein the 4-6 membered heterocyclyl is oxetanyl;

or

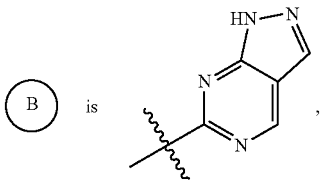

which is optionally substituted with one or more groups independently chosen from: 5-6 membered heteroaryl; wherein the 5-6 membered heteroaryl is pyridyl.

14. The compound of formula (I), or a pharmaceutically acceptable salt thereof according to claim 1, wherein the compound of formula (I) is chosen from Compounds 1-19, 22-48 and 53-95:

| Compound No. | Structure |
|---|---|
| 1 | 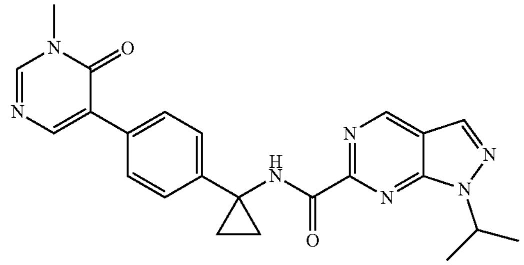 [SMILES: CC(C)n1ncc2cnc(C(=O)NC3(c4ccc(-c5cncn(C)c5=O)cc4)CC3)nc21] |

-continued
| Compound No. | Structure |
| --- | --- |
| 2 | 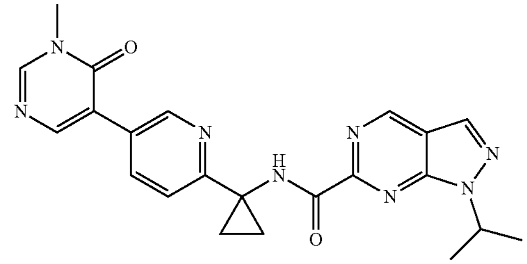 [SMILES: CC(C)n1ncc2cnc(C(=O)NC3(c4ccc(-c5cncn(C)c5=O)cn4)CC3)nc21] |
| 3 | 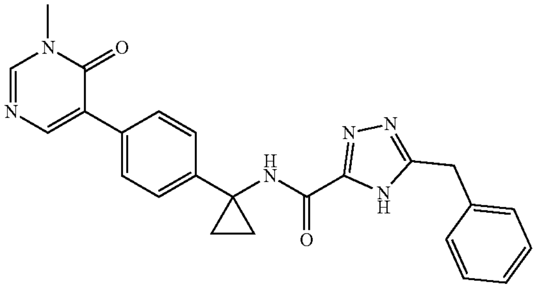 [SMILES: Cn1cncc(-c2ccc(C3(NC(=O)c4nnc(Cc5ccccc5)[nH]4)CC3)cc2)c1=O] |
| 4 | 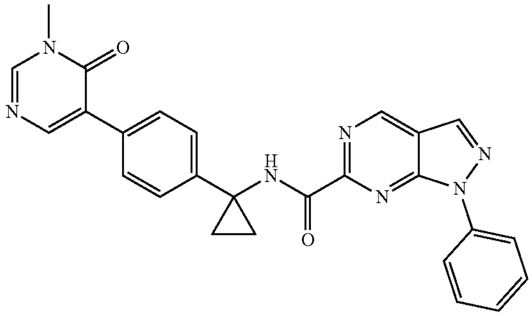 [SMILES: Cn1cncc(-c2ccc(C3(NC(=O)c4ncc5cnn(-c6ccccc6)c5n4)CC3)cc2)c1=O] |
| 5 | 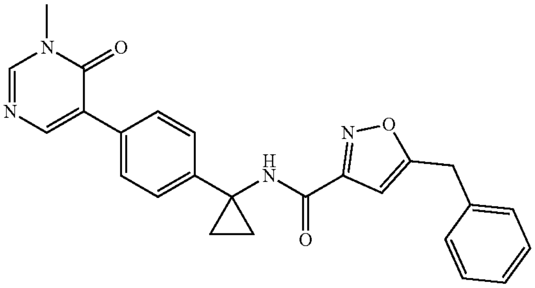 [SMILES: Cn1cncc(-c2ccc(C3(NC(=O)c4cc(Cc5ccccc5)on4)CC3)cc2)c1=O] |
| 6 | 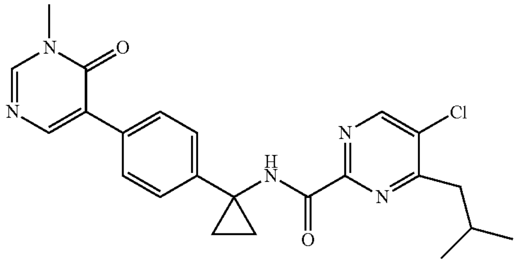 [SMILES: CC(C)Cc1nc(C(=O)NC2(c3ccc(-c4cncn(C)c4=O)cc3)CC2)ncc1Cl] |

-continued
| Compound No. | Structure |
|---|---|
| 7 | 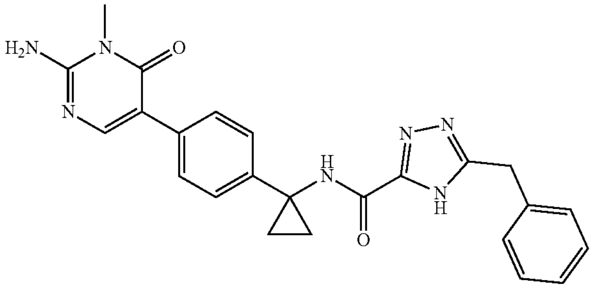 [SMILES: Cn1c(N)ncc(-c2ccc(C3(NC(=O)c4nnc(Cc5ccccc5)[nH]4)CC3)cc2)c1=O] |
| 8 | 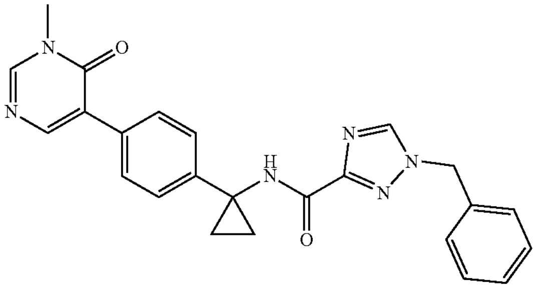 [SMILES: Cn1cncc(-c2ccc(C3(NC(=O)c4ncn(Cc5ccccc5)n4)CC3)cc2)c1=O] |
| 9 | 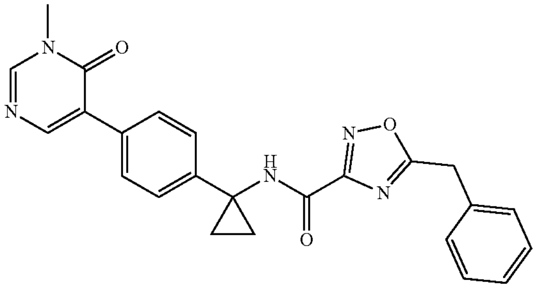 [SMILES: Cn1cncc(-c2ccc(C3(NC(=O)c4noc(Cc5ccccc5)n4)CC3)cc2)c1=O] |
| 10 | 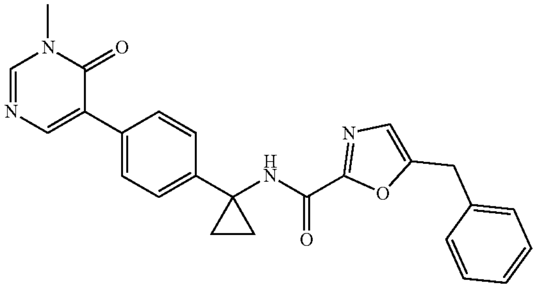 [SMILES: Cn1cncc(-c2ccc(C3(NC(=O)c4ncc(Cc5ccccc5)o4)CC3)cc2)c1=O] |
| 11 | 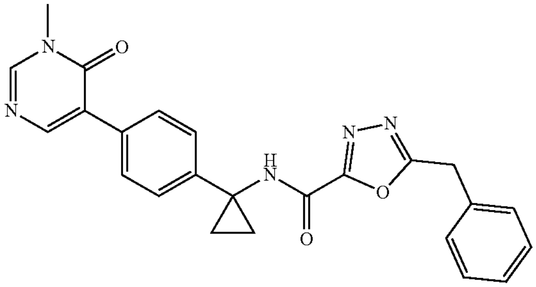 [SMILES: Cn1cncc(-c2ccc(C3(NC(=O)c4nnc(Cc5ccccc5)o4)CC3)cc2)c1=O] |

-continued
| Compound No. | Structure |
|---|---|
| 12 | 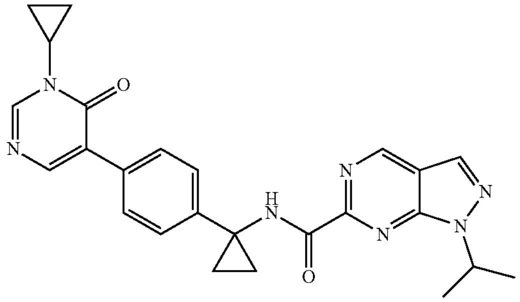 [SMILES: CC(C)n1ncc2cnc(C(=O)NC3(c4ccc(-c5cncn(C6CC6)c5=O)cc4)CC3)nc21] |
| 13 | 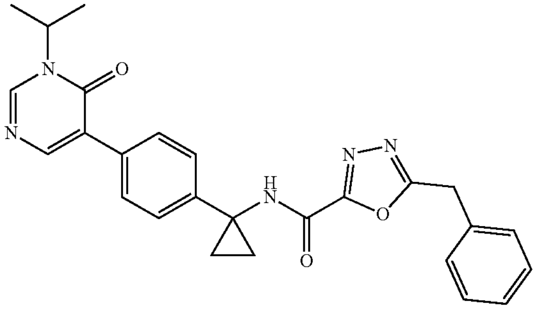 [SMILES: CC(C)n1cncc(-c2ccc(C3(NC(=O)c4nnc(Cc5ccccc5)o4)CC3)cc2)c1=O] |
| 14 | 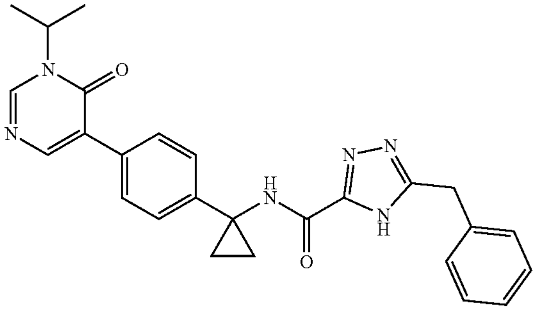 [SMILES: CC(C)n1cncc(-c2ccc(C3(NC(=O)c4nnc(Cc5ccccc5)[nH]4)CC3)cc2)c1=O] |
| 15 and 16 | 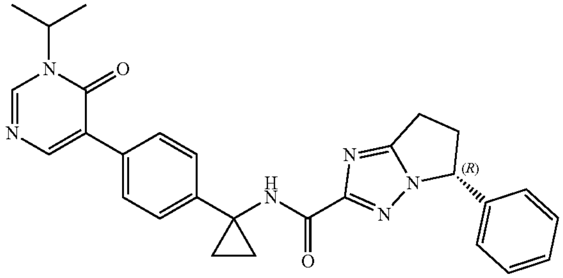 and 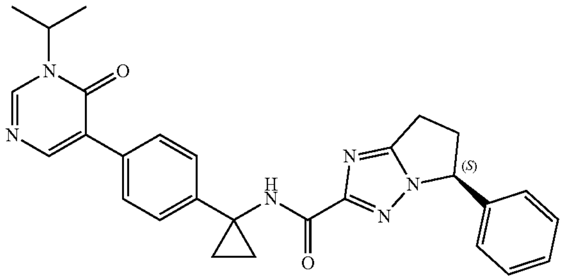 |

-continued
| Compound No. | Structure |
|---|---|
| 17 | 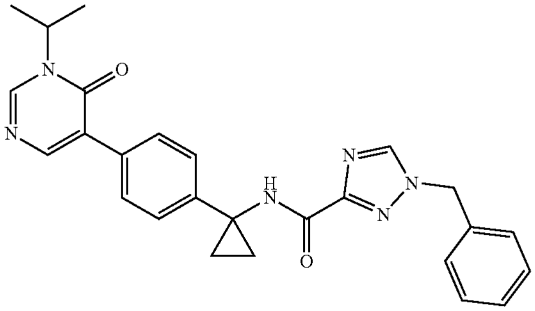 [SMILES: CC(C)n1cncc(-c2ccc(C3(NC(=O)c4ncn(Cc5ccccc5)n4)CC3)cc2)c1=O] |
| 18 | 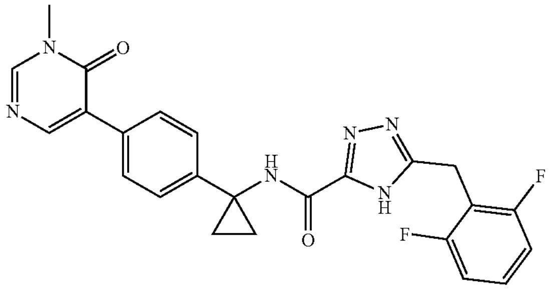 [SMILES: Cn1cncc(-c2ccc(C3(NC(=O)c4nnc(Cc5c(F)cccc5F)[nH]4)CC3)cc2)c1=O] |
| 19 | 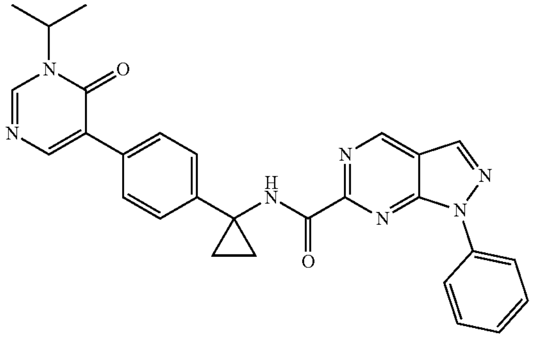 [SMILES: CC(C)n1cncc(-c2ccc(C3(NC(=O)c4ncc5cnn(-c6ccccc6)c5n4)CC3)cc2)c1=O] |
| 22 | 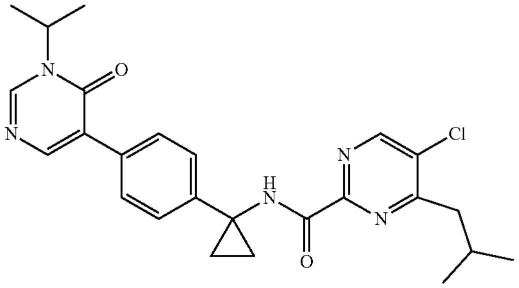 [SMILES: CC(C)Cc1nc(C(=O)NC2(c3ccc(-c4cncn(C(C)C)c4=O)cc3)CC2)ncc1Cl] |
| 23 | 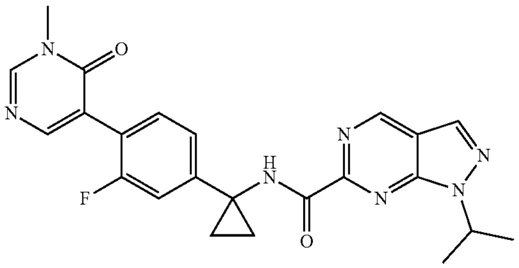 [SMILES: CC(C)n1ncc2cnc(C(=O)NC3(c4ccc(-c5cncn(C)c5=O)c(F)c4)CC3)nc21] |

-continued
| Compound No. | Structure |
|---|---|
| 24 | 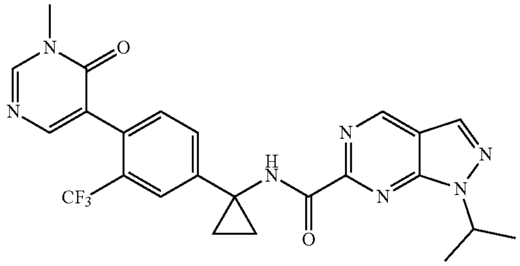 [SMILES: CC(C)n1ncc2cnc(C(=O)NC3(c4ccc(-c5cncn(C)c5=O)c(C(F)(F)F)c4)CC3)nc21] |
| 25 | 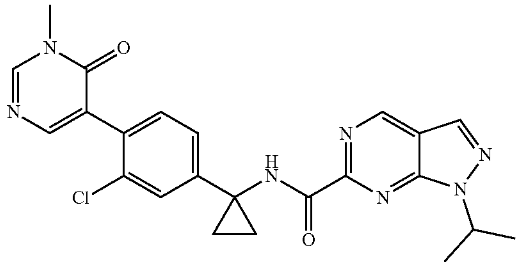 [SMILES: CC(C)n1ncc2cnc(C(=O)NC3(c4ccc(-c5cncn(C)c5=O)c(Cl)c4)CC3)nc21] |
| 26 | 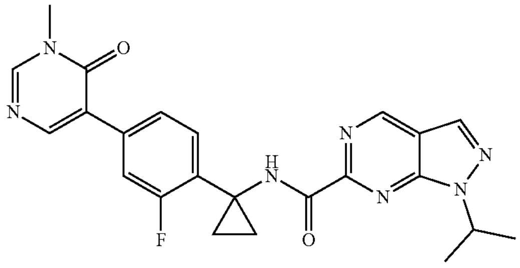 [SMILES: CC(C)n1ncc2cnc(C(=O)NC3(c4ccc(-c5cncn(C)c5=O)cc4F)CC3)nc21] |
| 27 | 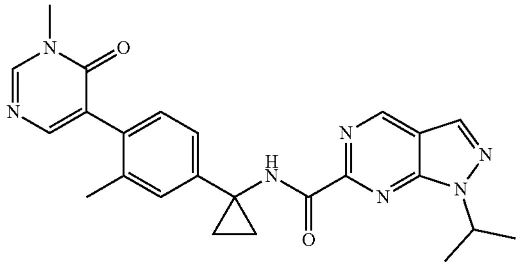 [SMILES: Cc1cc(C2(NC(=O)c3ncc4cnn(C(C)C)c4n3)CC2)ccc1-c1cncn(C)c1=O] |
| 28 | 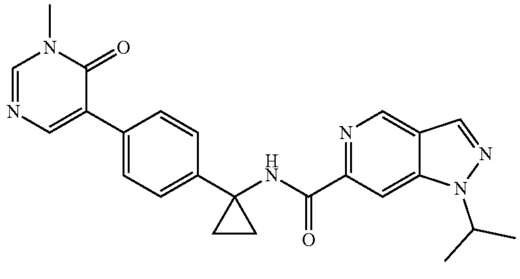 [SMILES: CC(C)n1ncc2cnc(C(=O)NC3(c4ccc(-c5cncn(C)c5=O)cc4)CC3)cc21] |

-continued
| Compound No. | Structure |
|---|---|
| 29 | 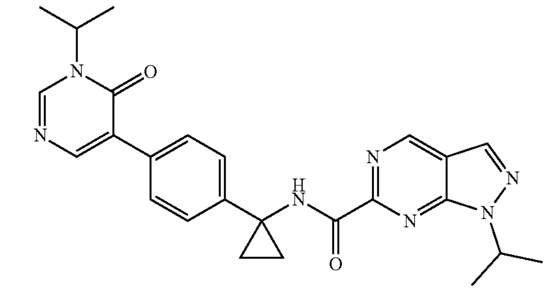 [SMILES: CC(C)n1cncc(-c2ccc(C3(NC(=O)c4ncc5cnn(C(C)C)c5n4)CC3)cc2)c1=O] |
| 30 | 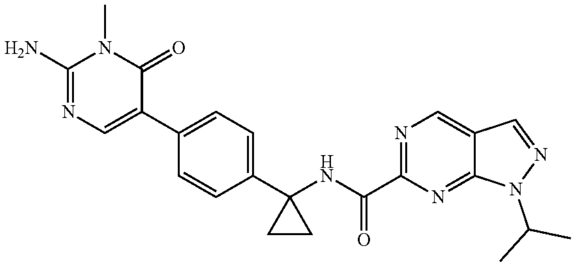 [SMILES: CC(C)n1ncc2cnc(C(=O)NC3(c4ccc(-c5cnc(N)n(C)c5=O)cc4)CC3)nc21] |
| 31 | 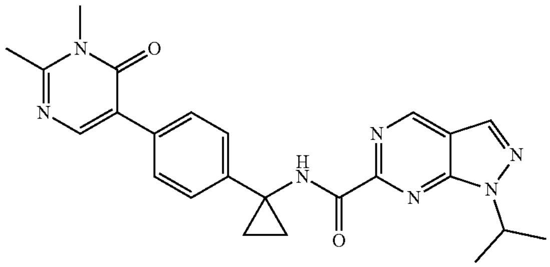 [SMILES: Cc1ncc(-c2ccc(C3(NC(=O)c4ncc5cnn(C(C)C)c5n4)CC3)cc2)c(=O)n1C] |
| 32 | 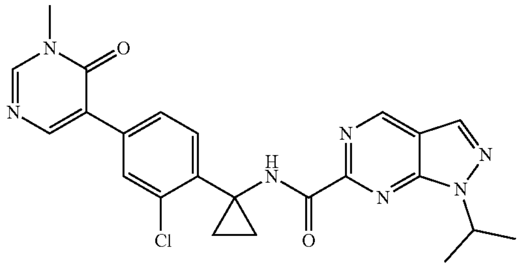 [SMILES: CC(C)n1ncc2cnc(C(=O)NC3(c4ccc(-c5cncn(C)c5=O)cc4Cl)CC3)nc21] |
| 33 | 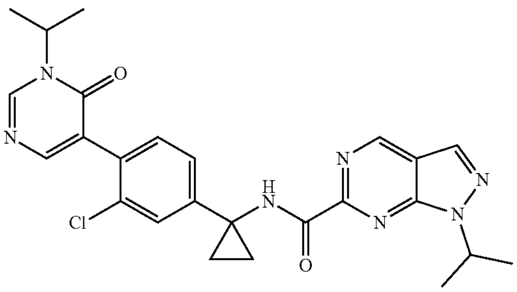 [SMILES: CC(C)n1cncc(-c2ccc(C3(NC(=O)c4ncc5cnn(C(C)C)c5n4)CC3)cc2Cl)c1=O] |

-continued
| Compound No. | Structure |
|---|---|
| 34 | 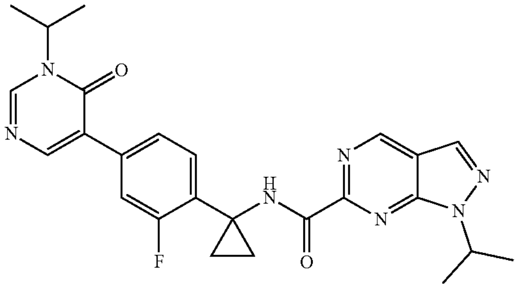 [SMILES: CC(C)n1cncc(-c2ccc(C3(NC(=O)c4ncc5cnn(C(C)C)c5n4)CC3)c(F)c2)c1=O] |
| 35 | 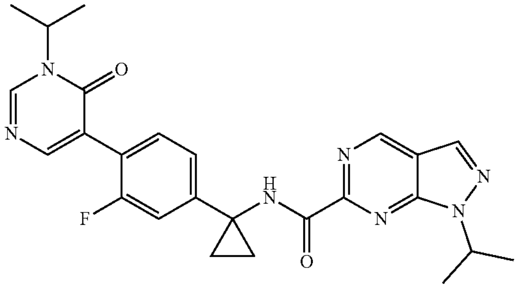 [SMILES: CC(C)n1cncc(-c2ccc(C3(NC(=O)c4ncc5cnn(C(C)C)c5n4)CC3)cc2F)c1=O] |
| 36 | 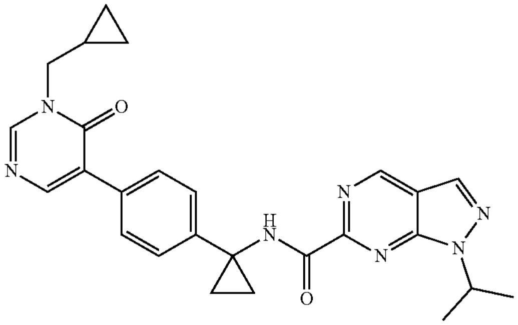 [SMILES: CC(C)n1ncc2cnc(C(=O)NC3(c4ccc(-c5cncn(CC6CC6)c5=O)cc4)CC3)nc21] |
| 37 | 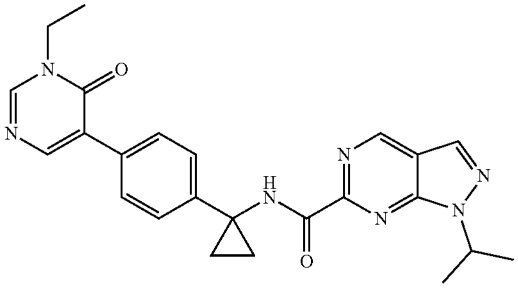 [SMILES: CCn1cncc(-c2ccc(C3(NC(=O)c4ncc5cnn(C(C)C)c5n4)CC3)cc2)c1=O] |
| 38 | 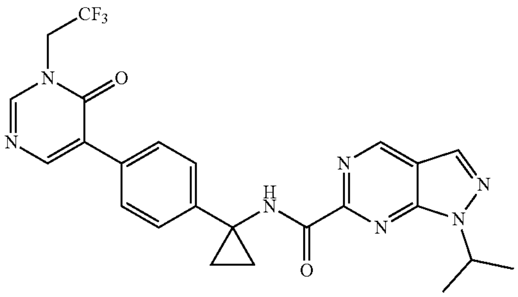 [SMILES: CC(C)n1ncc2cnc(C(=O)NC3(c4ccc(-c5cncn(CC(F)(F)F)c5=O)cc4)CC3)nc21] |

-continued
| Compound No. | Structure |
| --- | --- |
| 39 | 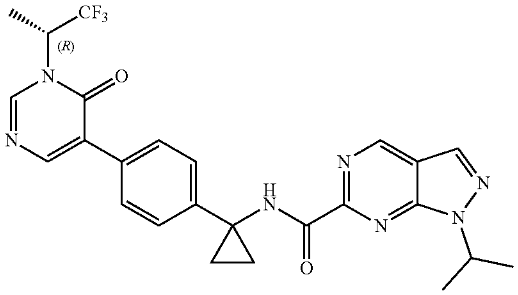 |
| 40 | 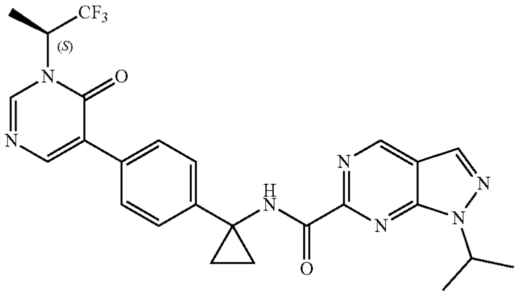 |
| 41 | 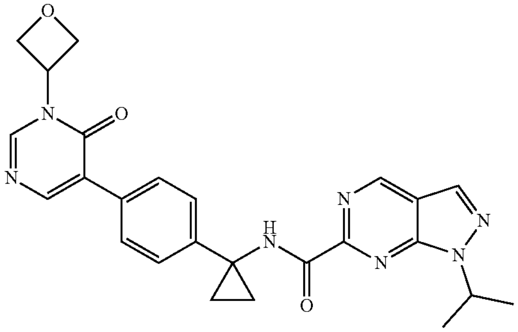 [SMILES: CC(C)n1ncc2cnc(C(=O)NC3(c4ccc(-c5cncn(C6COC6)c5=O)cc4)CC3)nc21] |
| 42 | 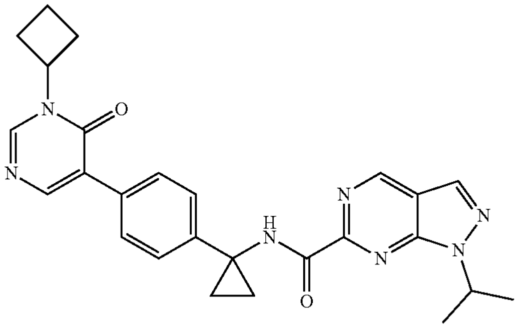 [SMILES: CC(C)n1ncc2cnc(C(=O)NC3(c4ccc(-c5cncn(C6CCC6)c5=O)cc4)CC3)nc21] |
| 43 | 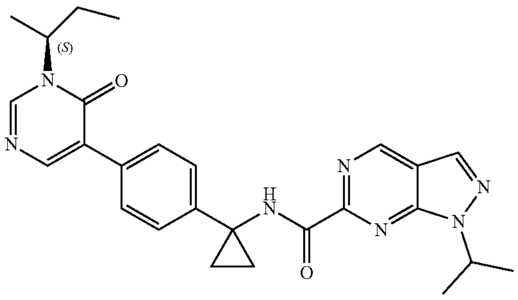 |

-continued
| Compound No. | Structure |
| --- | --- |
| 44 | 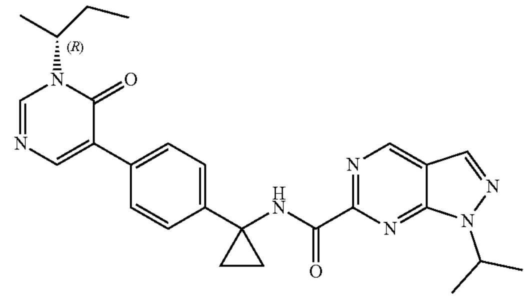 |
| 45 | 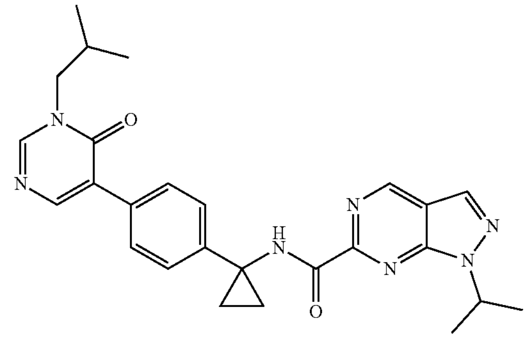 [SMILES: CC(C)Cn1cncc(-c2ccc(C3(NC(=O)c4ncc5cnn(C(C)C)c5n4)CC3)cc2)c1=O] |
| 46 | 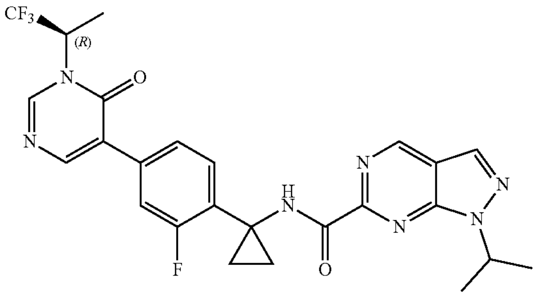 |
| 47 | 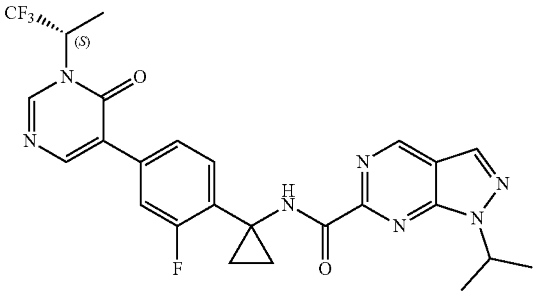 |
| 48 | 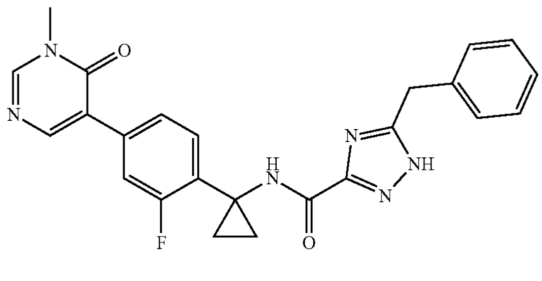 [SMILES: Cn1cncc(-c2ccc(C3(NC(=O)c4n[nH]c(Cc5ccccc5)n4)CC3)c(F)c2)c1=O] |

-continued
| Compound No. | Structure |
| --- | --- |
| 53 and 54 | 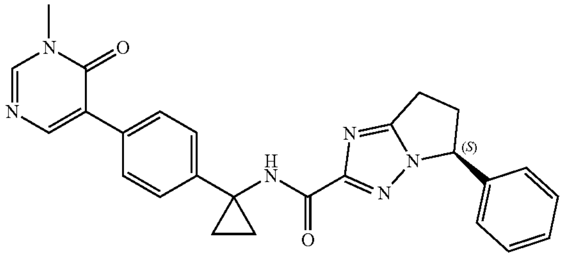<br>and<br>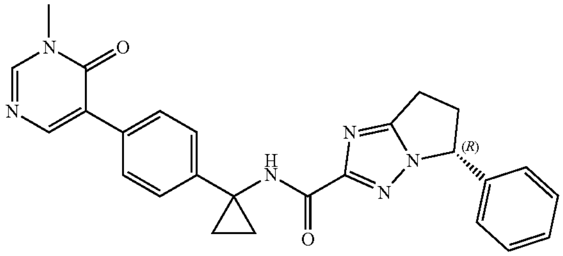 |
| 55 and 56 | 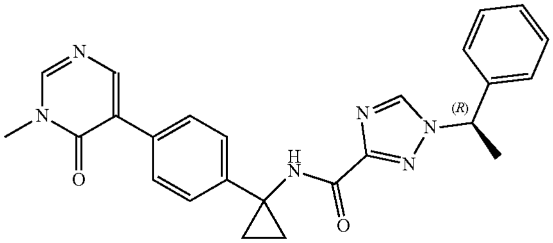<br>and<br>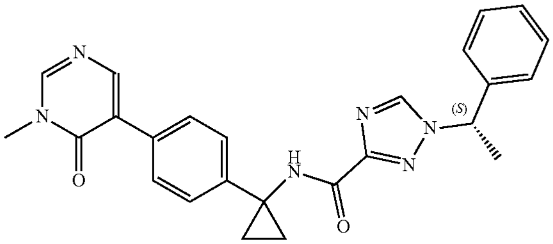 |
| 57 and 58 | 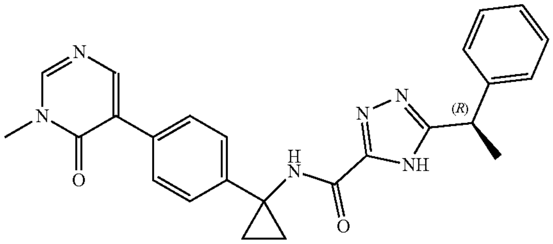 |

-continued
| Compound No. | Structure |
|---|---|
| | and<br>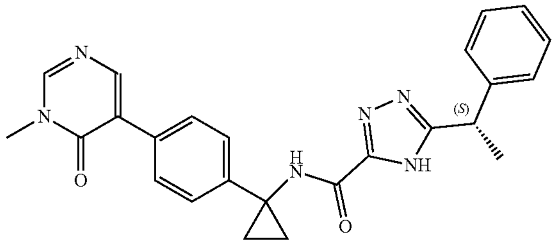 |
| 59 | 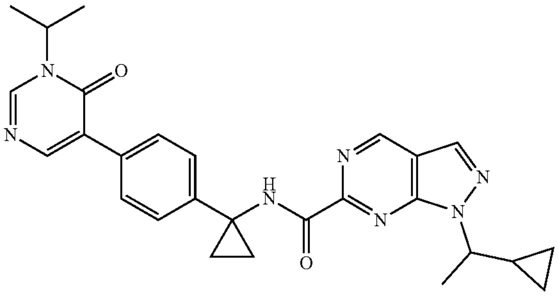 [SMILES: CC(C)n1cncc(-c2ccc(C3(NC(=O)c4ncc5cnn(C(C)C6CC6)c5n4)CC3)cc2)c1=O] |
| 60 | 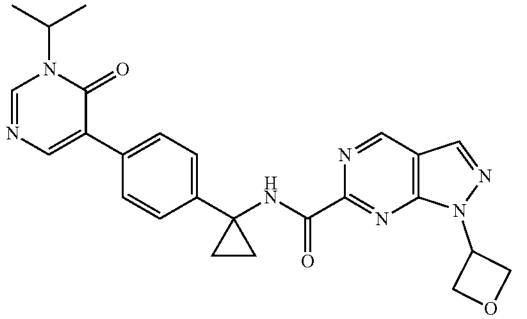 [SMILES: CC(C)n1cncc(-c2ccc(C3(NC(=O)c4ncc5cnn(C6COC6)c5n4)CC3)cc2)c1=O] |
| 61 | 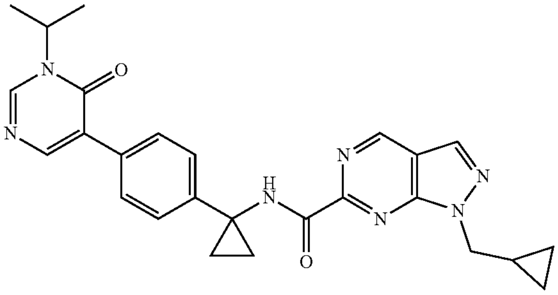 [SMILES: CC(C)n1cncc(-c2ccc(C3(NC(=O)c4ncc5cnn(CC6CC6)c5n4)CC3)cc2)c1=O] |
| 62 | 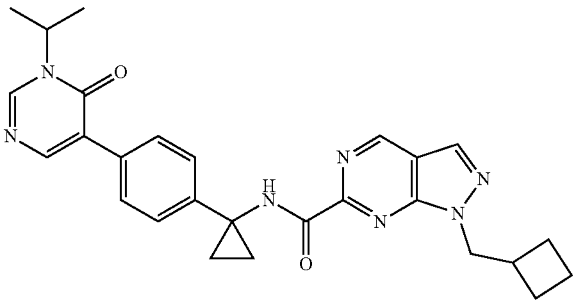 [SMILES: CC(C)n1cncc(-c2ccc(C3(NC(=O)c4ncc5cnn(CC6CCC6)c5n4)CC3)cc2)c1=O] |

-continued
| Compound No. | Structure |
|---|---|
| 63 | 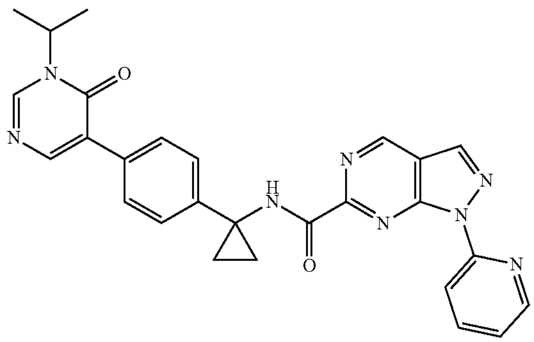 [SMILES: CC(C)n1cncc(-c2ccc(C3(NC(=O)c4ncc5cnn(-c6ccccn6)c5n4)CC3)cc2)c1=O] |
| 64 | 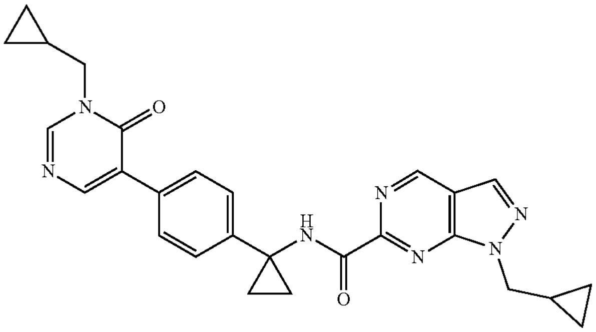 [SMILES: O=C(NC1(c2ccc(-c3cncn(CC4CC4)c3=O)cc2)CC1)c1ncc2cnn(CC3CC3)c2n1] |
| 65 | 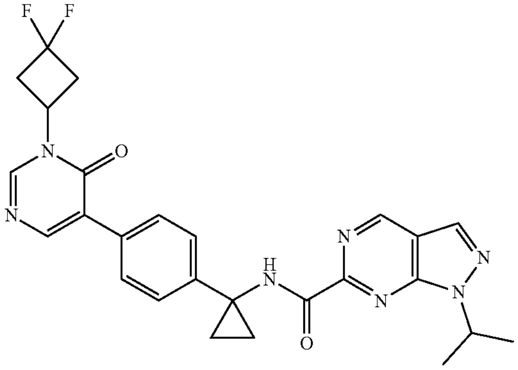 [SMILES: CC(C)n1ncc2cnc(C(=O)NC3(c4ccc(-c5cncn(C6CC(F)(F)C6)c5=O)cc4)CC3)nc21] |
| 66 | 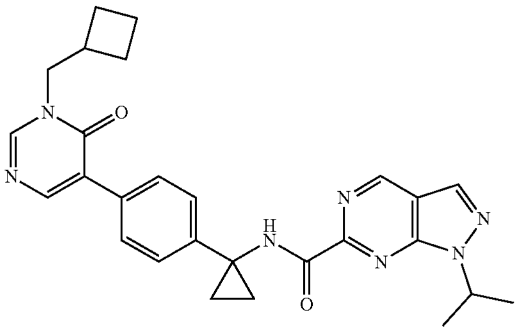 [SMILES: CC(C)n1ncc2cnc(C(=O)NC3(c4ccc(-c5cncn(CC6CCC6)c5=O)cc4)CC3)nc21] |

-continued
| Compound No. | Structure |
|---|---|
| 67 | 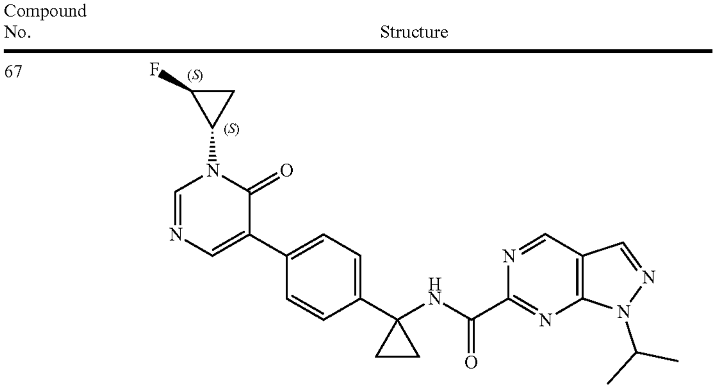 |
| 68 | 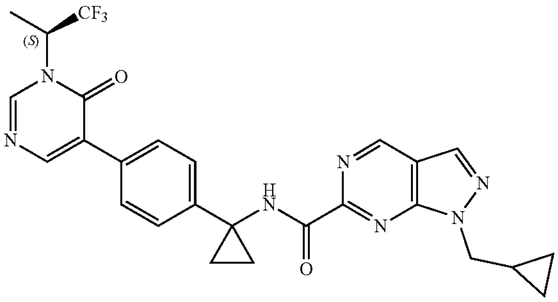 |
| 69 | 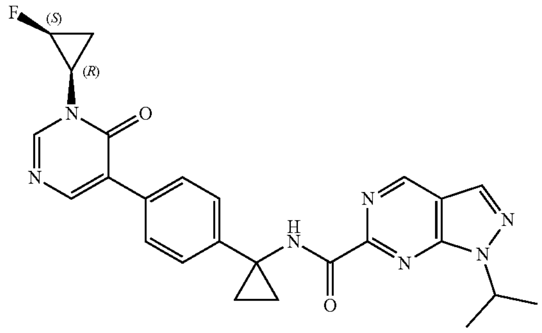 |
| 70 | 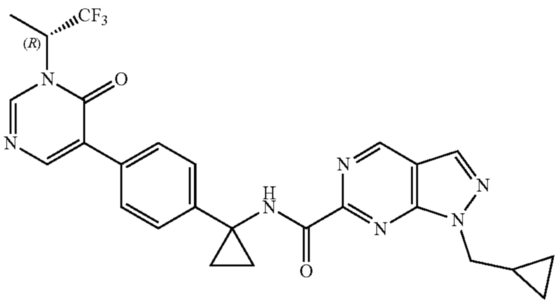 |
| 71 | 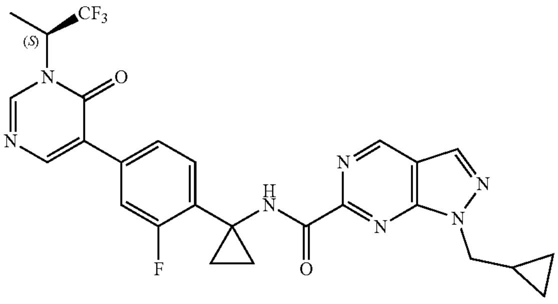 |

-continued
| Compound No. | Structure |
|---|---|
| 72 | 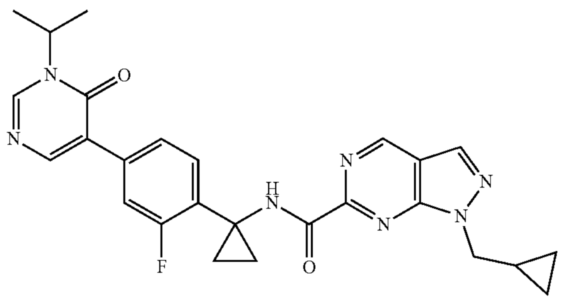 [SMILES: CC(C)n1cncc(-c2ccc(C3(NC(=O)c4ncc5cnn(CC6CC6)c5n4)CC3)c(F)c2)c1=O] |
| 73 | 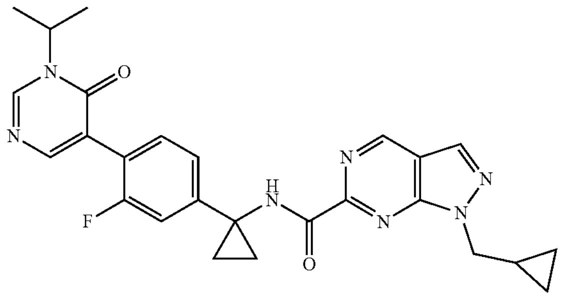 [SMILES: CC(C)n1cncc(-c2ccc(C3(NC(=O)c4ncc5cnn(CC6CC6)c5n4)CC3)cc2F)c1=O] |
| 74 | 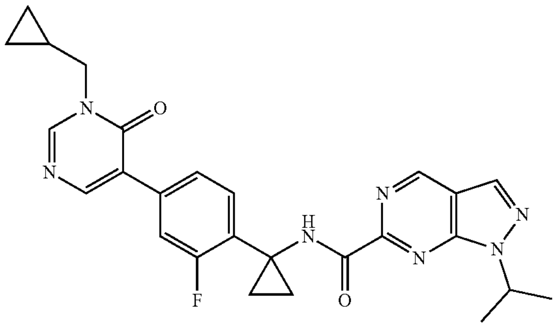 [SMILES: CC(C)n1ncc2cnc(C(=O)NC3(c4ccc(-c5cncn(CC6CC6)c5=O)cc4F)CC3)nc21] |
| 75 | 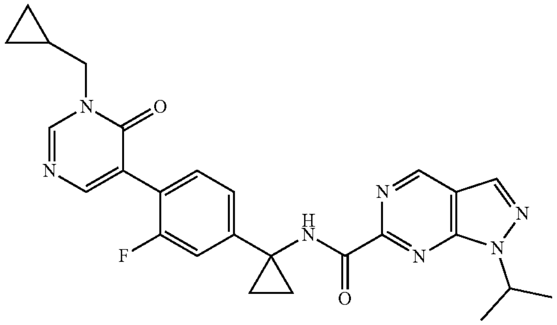 [SMILES: CC(C)n1ncc2cnc(C(=O)NC3(c4ccc(-c5cncn(CC6CC6)c5=O)c(F)c4)CC3)nc21] |
| 76 | 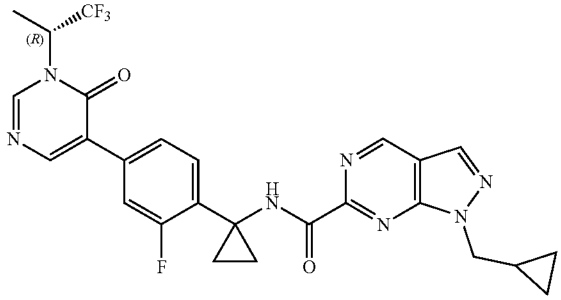 |

-continued
| Compound No. | Structure |
|---|---|
| 77 | 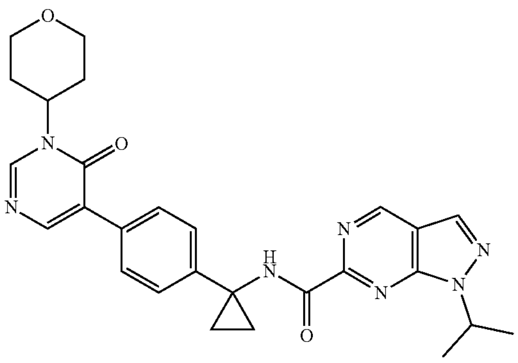 [SMILES: CC(C)n1ncc2cnc(C(=O)NC3(c4ccc(-c5cncn(C6CCOCC6)c5=O)cc4)CC3)nc21] |
| 78 | 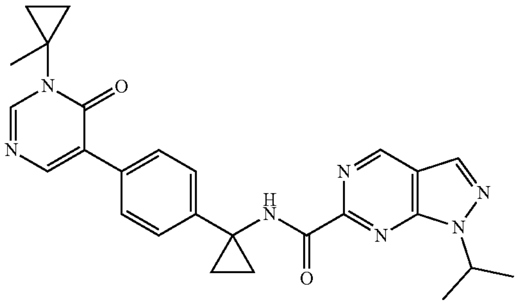 [SMILES: CC(C)n1ncc2cnc(C(=O)NC3(c4ccc(-c5cncn(C6(C)CC6)c5=O)cc4)CC3)nc21] |
| 79 | 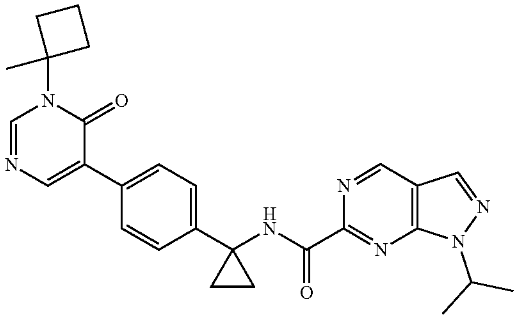 [SMILES: CC(C)n1ncc2cnc(C(=O)NC3(c4ccc(-c5cncn(C6(C)CCC6)c5=O)cc4)CC3)nc21] |
| 80 and 81 | 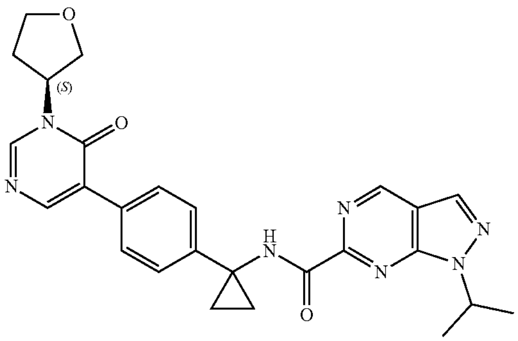 |

-continued
| Compound No. | Structure |
| --- | --- |
| | and |
| | 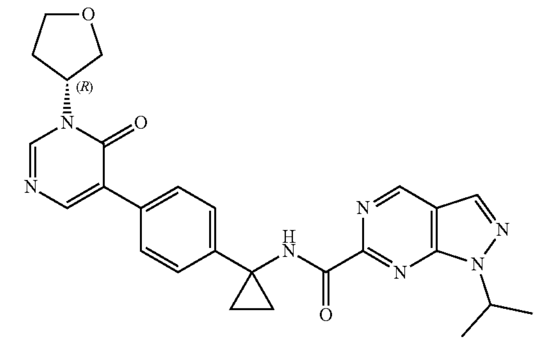 |
| 82 and 83 | 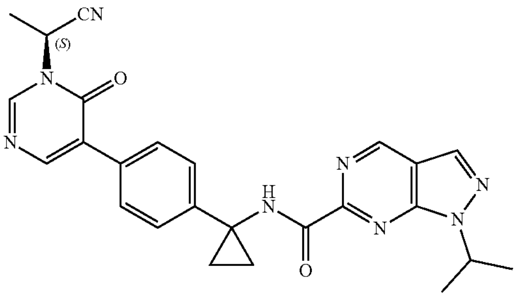 |
| | and |
| | 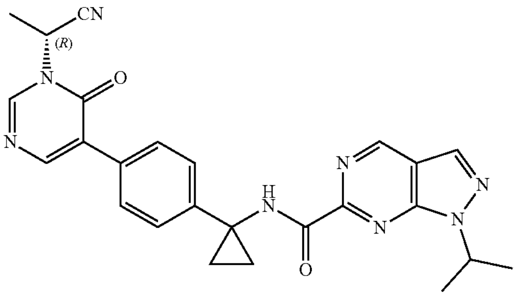 |
| 84 and 85 | 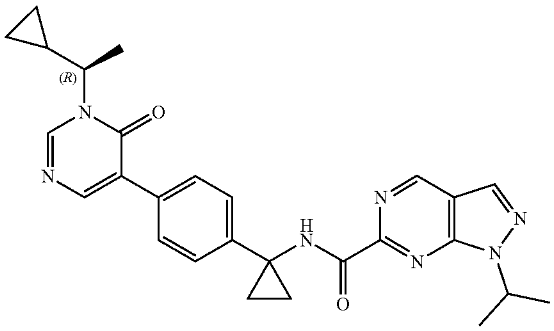 |

-continued
| Compound No. | Structure |
|---|---|
| | and |
| | 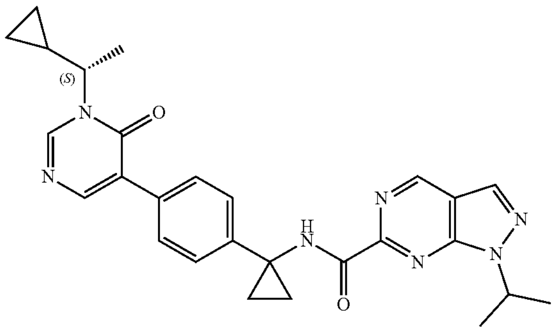 |
| 86 | 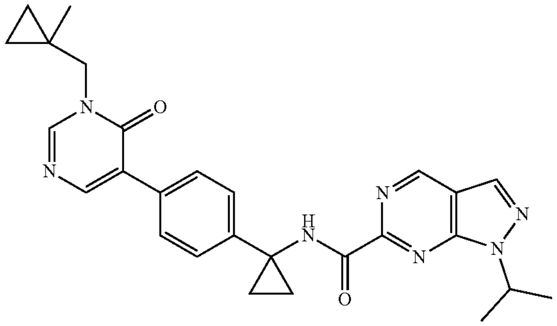 [SMILES: CC(C)n1ncc2cnc(C(=O)NC3(c4ccc(-c5cncn(CC6(C)CC6)c5=O)cc4)CC3)nc21] |
| 87 and 88 | 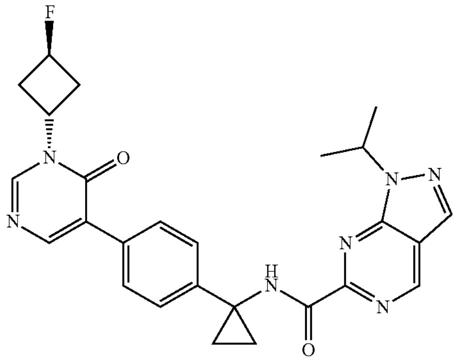 |
| | and |
| | 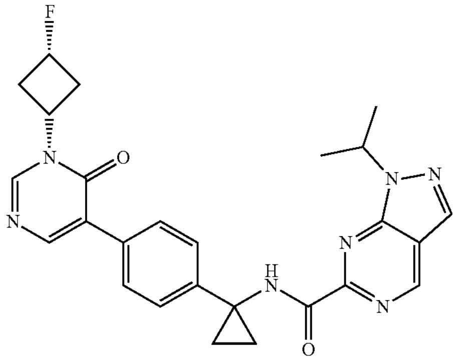 |

-continued
| Compound No. | Structure |
|---|---|
| 89 and 90 | 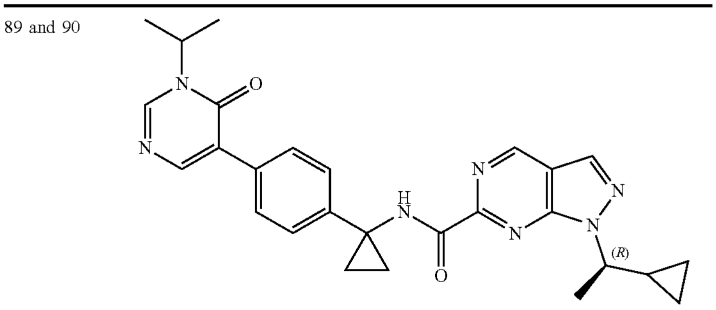 and 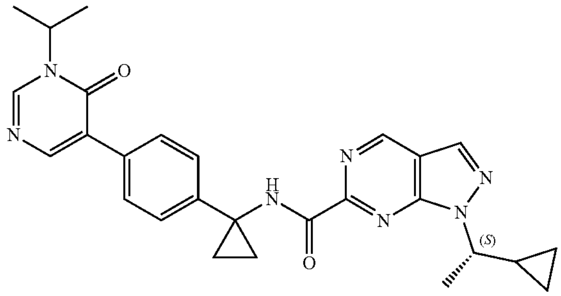 |
| 91 | 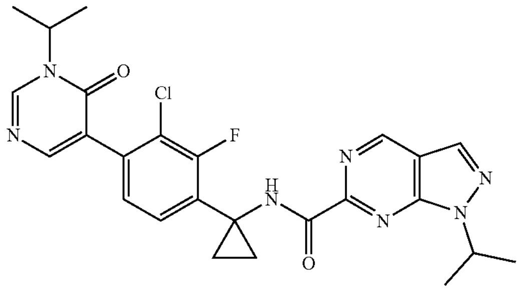 [SMILES: CC(C)n1cncc(-c2ccc(C3(NC(=O)c4ncc5cnn(C(C)C)c5n4)CC3)c(F)c2Cl)c1=O] |
| 92 | 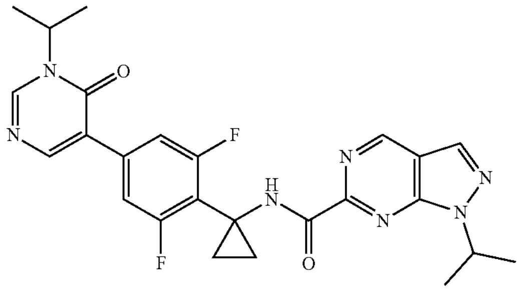 [SMILES: CC(C)n1cncc(-c2cc(F)c(C3(NC(=O)c4ncc5cnn(C(C)C)c5n4)CC3)c(F)c2)c1=O] |
| 93 | 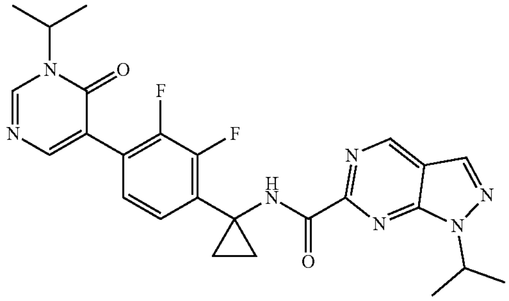 [SMILES: CC(C)n1cncc(-c2ccc(C3(NC(=O)c4ncc5cnn(C(C)C)c5n4)CC3)c(F)c2F)c1=O] |

-continued

| Compound No. | Structure |
| --- | --- |
| 94 | 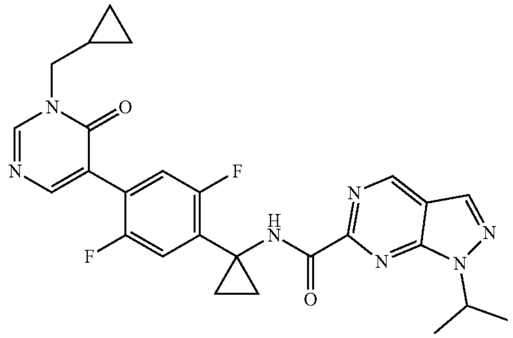 [SMILES: CC(C)n1ncc2cnc(C(=O)NC3(c4cc(F)c(-c5cncn(CC6CC6)c5=O)cc4F)CC3)nc21] |
| 95 | 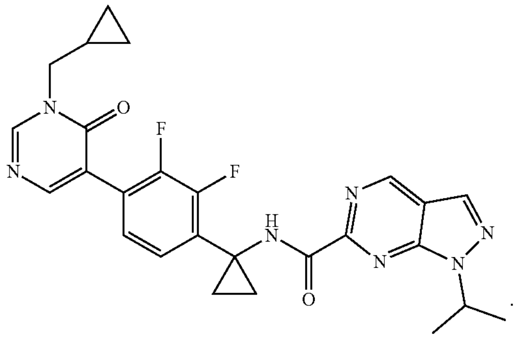 [SMILES: CC(C)n1ncc2cnc(C(=O)NC3(c4ccc(-c5cncn(CC6CC6)c5=O)c(F)c4F)CC3)nc21] |

15. A pharmaceutical composition, comprising the compound or a pharmaceutically acceptable salt thereof according to claim 1, and optionally comprising a pharmaceutically acceptable carrier.

16. A method of in vivo or in vitro inhibiting the activity of RIPK1, comprising contacting RIPK1 with an effective amount of the compound or a pharmaceutically acceptable salt thereof according to claim 1.

17. A method of treating a disease partially or completely mediated by RIPK1 in a subject, comprising administering to the subject an effective amount of the compound or a pharmaceutically acceptable salt thereof according to claim 1, wherein the disease is chosen from an autoimmune disease, an inflammatory disease, a neurodegenerative disease, and cancer.

18. A pharmaceutical combination, comprising the compound or a pharmaceutically acceptable salt thereof according to claim 1, and at least one additional therapeutic agent.

19. The pharmaceutical combination according to claim 18, wherein the therapeutic agent is an anti-inflammatory agent or an anti-neoplastic agent; and the anti-neoplastic agent is chosen from a radiotherapeutic agent, a chemotherapeutic agent, an immunotherapeutic agent, and a targeted therapeutic agent.

* * * * *